United States Patent
Dominguez et al.

(10) Patent No.: US 9,783,488 B2
(45) Date of Patent: Oct. 10, 2017

(54) HISTONE DEACETYLASE INHIBITORS AND COMPOSITIONS AND METHODS OF USE THEREOF

(71) Applicant: CHDI Foundation, Inc., New York, NY (US)

(72) Inventors: Celia Dominguez, Los Angeles, CA (US); Ignacio Muñoz-Sanjuán, Los Angeles, CA (US); Michel Maillard, Los Angeles, CA (US); Gilles Raphy, Saffron Walden (GB); Alan F. Haughan, Cambridge (GB); Christopher A. Luckhurst, Cambridge (GB); Rebecca E. Jarvis, Saffron Walden (GB); Roland W. Bürli, Hertfordshire (GB); Perla Breccia, Cambridge (GB); Grant Wishart, Saffron Walden (GB); Samantha J. Hughes, Saffron Walden (GB); Daniel R. Allen, Saffron Walden (GB); Stephen D. Penrose, Saffron Walden (GB)

(73) Assignee: CHDI Foundation, Inc., New York, NY (US)

( * ) Notice: Subject to any disclaimer, the term of this patent is extended or adjusted under 35 U.S.C. 154(b) by 14 days.

(21) Appl. No.: 14/776,280

(22) PCT Filed: Mar. 10, 2014

(86) PCT No.: PCT/US2014/022597
§ 371 (c)(1),
(2) Date: Sep. 14, 2015

(87) PCT Pub. No.: WO2014/159224
PCT Pub. Date: Oct. 2, 2014

(65) Prior Publication Data
US 2016/0039745 A1   Feb. 11, 2016

Related U.S. Application Data

(60) Provisional application No. 61/785,395, filed on Mar. 14, 2013.

(51) Int. Cl.
| | | |
|---|---|---|
| *A61K 31/133* | (2006.01) |
| *C07C 233/60* | (2006.01) |
| *C07D 263/56* | (2006.01) |
| *C07D 215/14* | (2006.01) |
| *C07D 231/12* | (2006.01) |
| *C07D 231/56* | (2006.01) |
| *C07D 333/54* | (2006.01) |
| *C07D 235/08* | (2006.01) |
| *C07D 239/26* | (2006.01) |
| *C07D 471/04* | (2006.01) |
| *C07D 265/36* | (2006.01) |

(Continued)

(52) U.S. Cl.
CPC .......... *C07C 233/60* (2013.01); *C07C 259/08* (2013.01); *C07D 209/46* (2013.01); *C07D 213/54* (2013.01); *C07D 213/56* (2013.01); *C07D 213/58* (2013.01); *C07D 215/06* (2013.01); *C07D 215/14* (2013.01); *C07D 231/12* (2013.01); *C07D 231/56* (2013.01); *C07D 235/06* (2013.01); *C07D 235/08* (2013.01); *C07D 239/26* (2013.01); *C07D 263/56* (2013.01); *C07D 263/57* (2013.01); *C07D 265/30* (2013.01); *C07D 265/36* (2013.01); *C07D 277/64* (2013.01); *C07D 277/66* (2013.01); *C07D 295/073* (2013.01); *C07D 307/79* (2013.01); *C07D 307/81* (2013.01); *C07D 311/96* (2013.01); *C07D 333/54* (2013.01); *C07D 401/12* (2013.01); *C07D 413/06* (2013.01); *C07D 471/04* (2013.01); *C07C 2601/08* (2017.05); *C07C 2601/14* (2017.05); *C07C 2601/18* (2017.05)

(58) Field of Classification Search
USPC .......................... 514/230.5, 236.5, 249, 256
See application file for complete search history.

(56) References Cited

U.S. PATENT DOCUMENTS

| | | |
|---|---|---|
| 4,003,859 A | 1/1977 | Reymore, Jr. et al. |
| 5,384,331 A | 1/1995 | Kogan et al. |

(Continued)

FOREIGN PATENT DOCUMENTS

| | | |
|---|---|---|
| EP | 1446155 | 2/2008 |
| WO | WO 2008/122115 | 10/2008 |

(Continued)

OTHER PUBLICATIONS

International Search Report and Written Opinion dated May 24, 2014 for PCT Application No. PCT/US2014/22597 (8 pages).
Database CAPLUS in STN, Acct. No. 1991:631727, Dang et al., Journal of the Chemical Society, Perkin Transactions 2: Physical Organic Chemistry (1972-1999) (1991), 5, pp. 721-734 (abstract).
Heinemann, B. Prophage Induction in Lysogenic *Escherichia coli* with Simple Hydroxylamine and Hydrazine Compounds. Applied Microbiology, vol. 21, No. 4, Apr. 1971, pp. 726-731.
International Search Report and Written Opinion dated Jul. 21, 2014 for PCT Application No. PCT/US2014/022567 (13 pages).

(Continued)

*Primary Examiner* — Pancham Bakshi
(74) *Attorney, Agent, or Firm* — Sheppard Mullin Richter & Hampton LLP

(57) ABSTRACT

Provided are certain histone deacetylase (HDAC) inhibitors of Formula I, compositions thereof, and methods of their use.

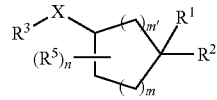

Formula I

43 Claims, No Drawings

(51) Int. Cl.

| | | |
|---|---|---|
| *C07D 277/64* | (2006.01) | |
| *C07D 295/073* | (2006.01) | |
| *C07D 213/54* | (2006.01) | |
| *C07D 213/56* | (2006.01) | |
| *C07D 307/79* | (2006.01) | |
| *C07C 259/08* | (2006.01) | |
| *C07D 209/46* | (2006.01) | |
| *C07D 213/58* | (2006.01) | |
| *C07D 215/06* | (2006.01) | |
| *C07D 235/06* | (2006.01) | |
| *C07D 263/57* | (2006.01) | |
| *C07D 265/30* | (2006.01) | |
| *C07D 277/66* | (2006.01) | |
| *C07D 307/81* | (2006.01) | |
| *C07D 311/96* | (2006.01) | |
| *C07D 401/12* | (2006.01) | |
| *C07D 413/06* | (2006.01) | |

(56) References Cited

U.S. PATENT DOCUMENTS

| | | |
|---|---|---|
| 2006/0019944 A1 | 1/2006 | Wu et al. |
| 2008/0269294 A1 | 10/2008 | Andrews et al. |
| 2009/0181943 A1* | 7/2009 | Tessier ............... C07C 259/06 514/211.13 |
| 2012/0121502 A1 | 5/2012 | Van Duzer et al. |
| 2014/0163009 A1 | 6/2014 | Luckhurst et al. |
| 2015/0203468 A1 | 7/2015 | Dominguez et al. |
| 2016/0024019 A1 | 1/2016 | Dominguez et al. |
| 2016/0031863 A1 | 2/2016 | Dominguez et al. |
| 2016/0031876 A1 | 2/2016 | Dominguez et al. |

FOREIGN PATENT DOCUMENTS

| | | |
|---|---|---|
| WO | WO 2012/103008 | 8/2012 |
| WO | WO 2015/187542 | 12/2015 |

OTHER PUBLICATIONS

International Search Report and Written Opinion dated Aug. 4, 2014 for PCT Application No. PCT/US2014/022550 (8 pages).
PubChem CID 21702499, Dec. 5, 2007, pp. 1-10 [online], [retrieved on Jun. 16, 2016]. Retrieved from the Internet <URL: https://pubchem.ncbi.nlm.nih.gov/summary/summary.cgi?cid=21702499>; p. 1, formula.
PubChem CID 331910, Mar. 26, 2005, pp. 1-14 [online], [retrieved on Jun. 16, 2016]. Retrieved from the Internet <URL: https://pubchem.ncbi.nlm.nih.gov/summary/summary.cgi?cid=331910>; p. 1, formula.
PubChem CID 57779614, Aug. 19, 2012, pp. 1-4 [online], [retrieved on Jun. 16, 2014]. Retrieved from the Internet <URL: https://pubchem.ncbi.nlm.nih.gov/summary/summary.cgi?cid=57779614&loc=ec_rcs>; p. 1, formula.
PubChem CID 59191078, Aug. 20, 2012, pp. 1-4 [online], [retrieved on Jun. 16, 2014]. Retrieved from the Internet <URL: https://pubchem.ncbi.nlm.nih.gov/summary/summary.cgi?cid=59191078&loc=ec_rcs >; p. 1, formula.
Wu Z, et al., A High-Affinity Fluorenone-Based Beta2-Adrenergic Receptor Antagonist with a Photoactivatable Pharmacophore, Biochemistry, vol. 39, No. 42, 2000, pp. 13044-13052 [online], [retrieved on Jun. 16, 2014). Retrieved from the IInternet<URL: http:[pubs.acs.org/doi/abs/1O. 1021/bi001342k?jornal1Code=bichaw><DOI:10. 1021/bi001342k>; abstract.
Database CAPLUS; Accession No. 1984: 185792, Tihanyi et al., HU 27601, 1980.
Extended European Search Report for EP 14775535.9 dated Aug. 26, 2016 (7 pages).
Extended European Search Report for EP 14775793.4 dated Jul. 6, 2016 (9 pages).

\* cited by examiner

HISTONE DEACETYLASE INHIBITORS AND COMPOSITIONS AND METHODS OF USE THEREOF

This application claims the benefit of priority under 35 U.S.C. §371 of PCT International Application No. PCT/US2014/022597, filed Mar. 10, 2014, which in turn claims the benefit of priority to U.S. provisional application No. 61/785,395, filed Mar. 14, 2013, which is incorporated herein by reference in its entirety.

Provided herein are certain histone deacetylase (HDAC) inhibitors, compositions thereof, and methods of their use.

Histone deacetylases (HDACs) are zinc-containing enzymes which catalyse the removal of acetyl groups from the ϵ-amino termini of lysine residues clustered near the amino terminus of nucleosomal histones. There are 11 known metal-dependent human histone deacetylases, grouped into four classes based on the structure of their accessory domains. Class I includes HDAC1, HDAC2, HDAC3, and HDAC8 and have homology to yeast RPD3. HDAC4, HDAC5, HDAC7, and HDAC9 belong to Class IIa and have homology to yeast HDAC1. HDAC6 and HDAC1 contain two catalytic sites and are classified as Class IIb, whereas HDAC11 has conserved residues in its catalytic center that are shared by both Class I and Class II deacetylases and is sometimes placed in Class IV.

Provided is a compound of Formula I, or a pharmaceutically acceptable salt thereof,

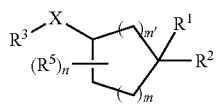

Formula I wherein:
$R^1$ is chosen from —C(O)NH(OH) and —N(OH)C(O)$R^4$;
$R^2$ is aryl, heteroaryl, and heterocycloalkyl, each of which is optionally substituted with 1 to 3 substituents independently chosen from halo, alkyl, cycloalkyl, haloalkyl, hydroxyl, alkoxy, and nitrile;
X is absent or X is chosen from —O—, —N$R^6$—, and —[C($R^7R^8$)]$_p$—;
$R^3$ is chosen from hydrogen, alkyl, cycloalkyl, heterocycloalkyl, aryl, heteroaryl, aralkyl, and heteroaralkyl, each of which is optionally substituted with 1 to 3 substituents independently chosen from halo, —CON$R^bR^c$, alkyl, alkyl substituted with —N$R^bR^c$, cycloalkyl, haloalkyl, hydroxyl, alkoxy, haloalkoxy, alkoxy substituted with —N$R^bR^c$, aryl, heteroaryl, and nitrile;
$R^4$ is chosen from hydrogen, lower alkyl and lower haloalkyl;
for each occurrence, $R^5$ is independently chosen from halo, lower alkyl, lower haloalkyl, and hydroxyl; or
$R^3$ taken together with $R_5$, and any intervening atoms, forms a 3- to 7-membered heterocycloalkyl or cycloalkyl ring;
m and m' are independently chosen from 1, 2, and 3, provided that m+m'≤4;
n is chosen from 0, 1, 2 and 3;
p is chosen from 1 and 2;
$R^6$ is chosen from hydrogen, lower alkyl, cycloalkyl, and lower haloalkyl; and
for each occurrence, $R^7$ and $R^8$ are each independently chosen from hydrogen, halo, lower alkyl, and lower haloalkyl, $R^b$ is chosen from H, $C_1$-$C_6$ alkyl, aryl, and heteroaryl; and
$R^c$ is chosen from hydrogen and $C_1$-$C_4$ alkyl; or
$R^b$ and $R^c$, and the nitrogen to which they are attached, form a heterocycloalkyl group; and
where for $R^b$ and $R^c$, each $C_1$-$C_6$ alkyl, cycloalkyl, aryl, heterocycloalkyl, and heteroaryl is unsubstituted or substituted with one or more substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —$C_1$-$C_4$ alkyl-O—$C_1$-$C_4$ alkyl, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

Also provided is a pharmaceutical composition comprising a compound, or a pharmaceutically acceptable salt thereof, described herein and at least one pharmaceutically acceptable excipient.

Also provided is a method of treating a condition or disorder mediated by at least one histone deacetylase in a subject in need of such a treatment which method comprises administering to the subject a therapeutically effective amount of a compound, or a pharmaceutically acceptable salt thereof, described herein.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, cyclopentenyl and cyclohexyl, as well as bridged, spirocyclic, and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge.

"Aryl" indicates an aromatic carbon ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl", as defined herein, regardless of the point of attachment (e.g., both quinolin-5-yl and quinolin-2-yl are heteroaryl groups). In some instances, aryl is phenyl or naphthyl. In certain instances, aryl is phenyl.

Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

The term "halo" includes fluoro, chloro, bromo, and iodo, and the term "halogen" includes fluorine, chlorine, bromine, and iodine.

"Heteroaryl" indicates an aromatic ring containing the indicated number of atoms (e.g., 5 to 12, or 5 to 1 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+$—$O^-$). Additionally, when sulfur is present in a heteroaryl ring, it may, where the nature of the adjacent atoms and groups permits, exist in an oxidized state (i.e., $S^+$—$O^-$ or $SO_2$). Heteroaryl groups may be monocyclic or polycyclic (e.g., bicyclic, tricyclic).

In some instances, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, spirocyclic, or tricyclic).

Examples of monocyclic heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl.

When nitrogen is present in a heterocycloalkyl ring, it may, where the nature of the adjacent atoms and groups permits, exist in an oxidized state (i.e., $N^+$—$O^-$). Examples include piperidinyl N-oxide and morpholinyl-N-oxide. Additionally, when sulfur is present in a heterocycloalkyl ring, it may, where the nature of the adjacent atoms and groups permits, exist in an oxidized state (i.e., $S^+$—$O^-$ or —$SO_2$—). Examples include thiomorpholine S-oxide and thiomorpholine S,S-dioxide.

In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). When nitrogen is present in a heterocycloalkenyl ring, it may, where the nature of the adjacent atoms and groups permits, exist in an oxidized state (i.e., $N^+$—$O^-$). Additionally, when sulfur is present in a heterocycloalkenyl ring, it may, where the nature of the adjacent atoms and groups permits, exist in an oxidized state (i.e., $S^+$—$O^-$ or —$SO_2$—). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl (including without limitation $C_1$-$C_4$ alkyl), cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from —$R^a$, —$OR^b$, —O($C_1$-$C_2$ alkyl) O— (e.g., methylenedioxy-), —$SR^b$, guanidine (—NHC(=NH)$NH_2$), guanidine wherein one or more of the guanidine hydrogens are replaced with a $C_1$-$C_4$ alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$, where $R^a$ is chosen from $C_1$-$C_6$ alkyl, cycloalkyl, aryl, heterocycloalkyl, and heteroaryl;

$R^b$ is chosen from H, $C_1$-$C_6$ alkyl, aryl, and heteroaryl; and $R^c$ is chosen from hydrogen and $C_1$-$C_4$ alkyl; or $R^b$ and $R^c$, and the nitrogen to which they are attached, form a heterocycloalkyl group; and where each $C_1$-$C_6$ alkyl, cycloalkyl, aryl, heterocycloalkyl, and heteroaryl is optionally substituted with one or more, such as one, two, or three, substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, such compounds include Z- and E-forms (or cis- and trans-forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, the term "salt" is intended to include all tautomeric forms and crystal forms of the compound.

"Pharmaceutically acceptable salts" include, but are not limited to salts with inorganic acids, such as hydrochloride, phosphate, diphosphate, hydrobromide, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—(CH$_2$)$_q$—COOH where q is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As used herein the terms "group", "radical" or "fragment" are synonymous and are intended to indicate functional groups or fragments of molecules attachable to a bond or other fragments of molecules.

The term "active agent" is used to indicate a compound or a pharmaceutically acceptable salt thereof which has biological activity. In some embodiments, an "active agent" is a compound or pharmaceutically acceptable salt thereof having pharmaceutical utility. For example an active agent may be an anti-neurodegenerative therapeutic.

The term "therapeutically effective amount" means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease responsive to inhibition of HDAC activity.

As used herein, the terms "histone deacetylase" and "HDAC" are intended to refer to anyone of a family of enzymes that remove N$^{68}$-acetyl groups from the ε-amino groups of lysine residues of a protein (for example, a histone, or tubulin). Unless otherwise indicated by context, the term "histone" is meant to refer to any histone protein, including H1, H2A, H2B, H3, H4, and H5, from any species.

In some embodiments, the histone deacetylase is a human HDAC, including, but not limited to, HDAC-4, HDAC-5, HDAC-6, HDAC-7, HDAC-9, and HDAC-10. In some embodiments, at least one histone deacetylase is selected from HDAC-4, HDAC-5, HDAC-7, and HDAC-9. In some embodiments, the histone deacetylase is a class IIa HDAC. In some embodiments, the histone deacetylase is HDAC-4. In some embodiments, the histone deacetylase is HDAC-5. In some embodiments, the histone deacetylase is derived from a protozoal or fungal source.

The terms "histone deacetylase inhibitor" and "inhibitor of histone deacetylase" are intended to mean a compound, or a pharmaceutically acceptable salt thereof, described herein which is capable of interacting with a histone deacetylase and inhibiting its enzymatic activity.

The term "a condition or disorder mediated by HDAC" or "a condition or disorder mediated by histone deacetylase" as used herein refers to a condition or disorder in which HDAC and/or the action of HDAC is important or necessary, e.g., for the onset, progress, expression, etc. of that condition, or a condition which is known to be treated by HDAC inhibitors (such as, e.g., trichostatin A).

The term "effect" describes a change or an absence of a change in cell phenotype or cell proliferation. "Effect" can also describe a change or an absence of a change in the catalytic activity of HDAC. "Effect" can also describe a change or an absence of a change in an interaction between HDAC and a natural binding partner.

The term "inhibiting histone deacetylase enzymatic activity" is intended to mean reducing the ability of a histone deacetylase to remove an acetyl group from a protein, such as but not limited to a histone or tubulin. The concentration of inhibitor which reduces the activity of a histone deacetylase to 50% of that of the uninhibited enzyme is determined as the IC$_{50}$ value. In some embodiments, such reduction of histone deacetylase activity is at least 50%, such as at least about 75%, for example, at least about 90%. In some embodiments, histone deacetylase activity is reduced by at least 95%, such as by at least 99%. In some embodiments, the compounds and pharmaceutical acceptable salts thereof described herein have an IC$_{50}$ value less than 100 nanomolar. In some embodiments, the compounds and pharmaceutical acceptable salts thereof described herein have an IC$_{50}$ value from 100 nanomolar to 1 micromolar. In some embodiments, the compounds and pharmaceutical acceptable salts thereof described herein have an IC$_{50}$ value from 1 to 25 micromolar.

In some embodiments, such inhibition is specific, i.e., the histone deacetylase inhibitor reduces the ability of a histone deacetylase to remove an acetyl group from a protein at a concentration that is lower than the concentration of the inhibitor that is required to produce another, unrelated biological effect. In some embodiments, the concentration of the inhibitor required for histone deacetylase inhibitory activity is at least 2-fold lower, such as at least 5-fold lower, for example, at least 10-fold lower, such as at least 20-fold lower than the concentration required to produce an unrelated biological effect.

"Treatment" or "treating" means any treatment of a disease state in a patient, including
a) preventing the disease, that is, causing the clinical symptoms of the disease not to develop;
b) inhibiting the disease;
c) slowing or arresting the development of clinical symptoms; and/or
d) relieving the disease, that is, causing the regression of clinical symptoms.

"Subject" or "patient" refers to an animal, such as a mammal, that has been or will be the object of treatment, observation or experiment. The methods described herein may be useful in both human therapy and veterinary applications. In some embodiments, the subject is a mammal; and in some embodiments the subject is human.

Provided is a compound of Formula I, or a pharmaceutically acceptable salt thereof,

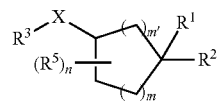

Formula I wherein:
$R^1$ is chosen from —C(O)NH(OH) and —N(OH)C(O)$R^4$;
$R^2$ is aryl, heteroaryl, and heterocycloalkyl, each of which is optionally substituted with 1 to 3 substituents independently chosen from halo, alkyl, cycloalkyl, haloalkyl, hydroxyl, alkoxy, and nitrile;
X is absent or X is chosen from —O—, —$NR^6$—, and —[C($R^7R^8$)]$_p$—;
$R^3$ is chosen from hydrogen, alkyl, cycloalkyl, heterocycloalkyl, aryl, heteroaryl, aralkyl, and heteroaralkyl, each of which is optionally substituted with 1 to 3 substituents independently chosen from halo, —CON$R^bR^c$, alkyl, alkyl substituted with —$NR^bR^c$, cycloalkyl, haloalkyl, hydroxyl, alkoxy, haloalkoxy, alkoxy substituted with —$NR^bR^c$, aryl, heteroaryl, and nitrile;
$R^4$ is chosen from hydrogen, lower alkyl and lower haloalkyl;
for each occurrence, $R^5$ is independently chosen from halo, lower alkyl, lower haloalkyl, and hydroxyl; or
$R^3$ taken together with $R_5$, and any intervening atoms, forms a 3- to 7-membered heterocycloalkyl or cycloalkyl ring;
m and m' are independently chosen from 1, 2, and 3, provided that m+m'≤4;
n is chosen from 0, 1, 2 and 3;
p is chosen from 1 and 2;
$R^6$ is chosen from hydrogen, lower alkyl, cycloalkyl, and lower haloalkyl; and
for each occurrence, $R^7$ and $R^8$ are each independently chosen from hydrogen, halo, lower alkyl, and lower haloalkyl,
$R^b$ is chosen from H, $C_1$-$C_6$ alkyl, aryl, and heteroaryl; and
$R^c$ is chosen from hydrogen and $C_1$-$C_4$ alkyl; or
$R^b$ and $R^c$, and the nitrogen to which they are attached, form a heterocycloalkyl group; and
where for $R^b$ and $R^c$, each $C_1$-$C_6$ alkyl, cycloalkyl, aryl, heterocycloalkyl, and heteroaryl is unsubstituted or substituted with one or more substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —$C_1$-$C_4$ alkyl-O—$C_1$-$C_4$ alkyl, —O$C_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2NH$($C_1$-$C_4$ alkyl), —$SO_2NH$(phenyl), —$NHSO_2$($C_1$-$C_4$ alkyl), —$NHSO_2$(phenyl), and —$NHSO_2$($C_1$-$C_4$ haloalkyl).

In some embodiments, the compound of Formula I is chosen from compounds of Formula II, Formula III, Formula IV, and Formula V.

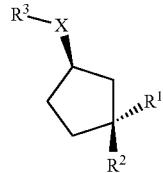

Formula II

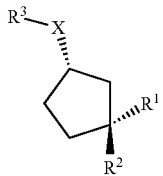

Formula III

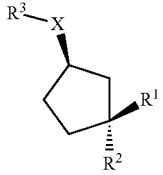

Formula IV

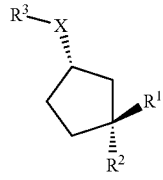

Formula V

In some embodiments, m is 1. In some embodiments, m is 2. In some embodiments, m is 3.

In some embodiments, m' is 1. In some embodiments, m' is 2. In some embodiments, m' is 3.

In some embodiments, $R^1$ is —C(O)NH(OH). In some embodiments, $R^1$ is —N(OH)C(O)$R^4$. In some embodiments, $R^4$ is chosen from hydrogen and lower alkyl. In some embodiments, $R^4$ is lower alkyl.

In some embodiments, n is 1. In some embodiments, n is 2. In some embodiments, n is 3.

In some embodiments, $R^5$ is independently chosen from halo and lower alkyl.

In some embodiments, n is 0.

In some embodiments, $R^2$ is phenyl optionally substituted with 1 to 3 substituents independently chosen from halo, alkyl, cycloalkyl, haloalkyl, hydroxyl, alkoxy, and nitrile. In some embodiments, $R^2$ is phenyl optionally substituted with 1 to 3 substituents independently chosen from halo, lower alkyl, and haloalkyl. In some embodiments, $R^2$ is chosen from 3,4-difluoro-2-methylphenyl, 3-fluoro-2-methylphenyl and 2-methylphenyl. In some embodiments, $R^2$ is chosen from 3-fluoro-2-methylphenyl and 2-methylphenyl. In some embodiments, $R^2$ is 3-fluoro-2-methylphenyl.

In some embodiments, $R^2$ is heteroaryl optionally substituted with 1 to 3 substituents independently chosen from halo, lower alkyl, and haloalkyl. In some embodiments, $R^2$ is pyridinyl optionally substituted with 1 to 3 substituents independently chosen from halo, lower alkyl, and haloalkyl. In some embodiments, $R^2$ is 2-methylpyridin-3-yl.

In some embodiments, p is 1. In some embodiments, p is 2.

In some embodiments, for each occurrence, R' and $R^8$ are each independently chosen from hydrogen, halo, and lower alkyl.

In some embodiments, X is absent. In some embodiments, X is —O—. In some embodiments, X is —$NR^6$—. In some embodiments, $R^6$ is hydrogen, lower alkyl, and cycloalkyl.

In some embodiments, $R^3$ is chosen from hydrogen, alkyl, cycloalkyl, heterocycloalkyl, aryl, heteroaryl, aralkyl, and heteroaralkyl, each of which is optionally substituted with 1 to 3 substituents independently chosen from halo, —$CONR^bR^c$, alkyl, alkyl substituted with —$NR^bR^c$, cycloalkyl, haloalkyl, hydroxyl, alkoxy, alkoxy substituted with —$NR^bR^c$, and nitrile.

In some embodiments, $R^3$ is aryl optionally substituted with 1 to 3 substituents independently chosen from halo, alkyl, cycloalkyl, haloalkyl, hydroxyl, alkoxy, and nitrile. In some embodiments, $R^3$ is chosen from phenyl, 2-methylphenyl, 3,4-dihydro-2H-benzo[b][1,4]oxazin-6-yl, 4,4-difluoro-1,2,3,4-tetrahydroquinolin-7-yl, and 4,4,8-trifluoro-1,2,3,4-tetrahydroquinolin-6-yl.

In some embodiments, $R^3$ is heteroaryl optionally substituted with 1 to 3 substituents independently chosen from halo, alkyl, cycloalkyl, haloalkyl, hydroxyl, alkoxy, and nitrile. In some embodiments, $R^3$ is chosen from 6-methylpyridin-3-yl, 5-fluoropyridin-3-yl, 5-(trifluoromethyl)pyrimidin-2-yl, 5-methylpyrimidin-2-yl, pyrimidin-2-yl, 2-(trifluoromethyl)pyrimidin-5-yl, 2-methylpyrimidin-5-yl, pyrimidin-5-yl, 2-(trifluoromethyl)pyrimidin-4-yl, 2-methylpyrimidin-4-yl, pyrimidin-4-yl, 6-(trifluoromethyl)pyridazin-4-yl, 6-methylpyridazin-4-yl, pyridazin-4-yl, 6-cyclopropylpyridazin-4-yl, pyrazin-2-yl, 5-(trifluoromethyl)pyrazin-2-yl, 5-methylpyrazin-2-yl, 3-cyclopropylpyrazin-2-yl, 1-(2,2,2-trifluoroethyl)-1H-pyrazol-4-yl, 2-cyclopropyloxazol-5-yl, 2-cyclopropylthiazol-5-yl, 2-methylbenzo[d]oxazol-5-yl, 1H-pyrrolo[2,3-b]pyridin-6-yl, imidazo[1,2-a]pyridin-7-yl, 1H-indazol-6-yl, and 2-oxo-1,2-dihydropyridin-3-yl.

In some embodiments, $R^3$ is heterocycloalkyl optionally substituted with 1 to 3 substituents independently chosen from halo, alkyl, cycloalkyl, haloalkyl, hydroxyl, alkoxy, aryl, heteroaryl, and nitrile. In some embodiments, $R^3$ is chosen from 1H-pyrrolo[3,4-c]pyridin-2(3H)-yl, 3,4-dihydroisoquinolin-2(1H-yl, 4-cyclopropylpiperazin-1-yl, 1-(2,2,2-trifluoroethyl)piperidin-4-yl, and 1-cyclopropylpiperidin-4-yl.

In some embodiments, $R^3$ taken together with $R_5$, and any intervening atoms, forms a 3- to 7-membered heterocycloalkyl or cycloalkyl ring. In some embodiments, $R^3$ taken together with $R_5$, and any intervening atoms, forms a 3- to 7-membered spirocycle.

Also provided is a compound chosen from
1-(3-fluoro-2-methylphenyl)-N-hydroxy-3-(pyridin-3-yl)cyclopentanecarboxamide,
1-(3-fluoro-2-methylphenyl)-N-hydroxy-3-(pyrimidin-5-yl)cyclopentanecarboxamide,
1-(3-fluoro-2-methylphenyl)-N-hydroxy-3-phenylcyclopentanecarboxamide,
1-(3-fluoro-2-methylphenyl)-N-hydroxy-3-(o-tolyl)cyclopentanecarboxamide,
1-(2,3-difluorophenyl)-N-hydroxycyclopentanecarboxamide,
1-(2,3-dihydrobenzofuran-7-yl)-N-hydroxycyclopentanecarboxamide
1-(3-chloro-2-methylphenyl)-N-hydroxycyclopentanecarboxamide,
1-(3-fluoro-2-methylphenyl)-N-hydroxycyclopentanecarboxamide,
1-(2-fluorophenyl)-N-hydroxycyclopentanecarboxamide,
1-(4-chlorophenyl)-N-hydroxycyclopentanecarboxamide,
N-Hydroxy-1-phenylcyclopentanecarboxamide,
1-(2-chloro-6-fluorophenyl)-N-hydroxycyclopentanecarboxamide,
N-hydroxy-1-(2-methoxyphenyl)cyclopentanecarboxamide,
N-hydroxy-1-o-tolylcyclopentanecarboxamide,
N-hydroxy-1-m-tolylcyclopentanecarboxamide,
1-(2-chlorophenyl)-N-hydroxycyclopentanecarboxamide,
1-phenyl-N-hydroxycyclohexylcarboxamide, and
N-hydroxy-1-phenylcycloheptanecarboxamide,
or a pharmaceutically acceptable salt thereof.

Also provided is a compound chosen from
(1S)-3-(1-(2-(diethylamino)ethyl)-1H-pyrazol-4-yl)-1-(3-fluoro-2-methylphenyl)-N-hydroxycyclopentanecarboxamide,
(1S)-1-(3-fluoro-2-methylphenyl)-N-hydroxy-3-(1-(2-(pyrrolidin-1-yl)ethyl)-1H-pyrazol-4-yl)cyclopentanecarboxamide,
(1S)-3-(1-(3-(diethylamino)propyl)-1H-pyrazol-4-yl)-1-(3-fluoro-2-methylphenyl)-N-hydroxycyclopentanecarboxamide,
(1S)-3-(1-(3-(cyclopropyl(ethyl)amino)-1,1,1-trifluoropropan-2-yl)-1H-pyrazol-4-yl)-1-(3-fluoro-2-methylphenyl)-N-hydroxycyclopentanecarboxamide,
(1S)-3-(3-(2-(diethylamino)ethoxy)-5-fluorophenyl)-1-(3-fluoro-2-methylphenyl)-N-hydroxycyclopentanecarboxamide,
(1S)-3-(3-((diethylamino)methyl)-5-fluorophenyl)-1-(3-fluoro-2-methylphenyl)-N-hydroxycyclopentanecarboxamide,
(1S)-1-(3-fluoro-2-methylphenyl)-N-hydroxy-3-(2-(pyrrolidin-1-yl)ethoxy)cyclopentanecarboxamide,
(1S)-1-(3-fluoro-2-methylphenyl)-3-(3-fluoro-5-(1-(pyrrolidin-1-yl)propan-2-yl)phenyl)-N-hydroxycyclopentanecarboxamide,
(1S)-3-(2-(2-(diethylamino)ethoxy)pyridin-4-yl)-1-(3-fluoro-2-methylphenyl)-N-hydroxycyclopentanecarboxamide,
(1S)-3-(5-(2-(diethylamino)ethoxy)pyridin-3-yl)-1-(3-fluoro-2-methylphenyl)-N-hydroxycyclopentanecarboxamide, and
(1S)-1-(3-fluoro-2-methylphenyl)-3-(5-fluoro-6-(2-(pyrrolidin-1-yl)ethoxy)pyridin-3-yl)-N-hydroxycyclopentanecarboxamide,
or a pharmaceutically acceptable salt thereof.

Also provided is a compound chosen from
1-(2-cyanophenyl)-N-hydroxycyclopentanecarboxamide;
1-(3-cyanophenyl)-N-hydroxycyclopentanecarboxamide;
1-(3,4-difluoro-2-methylphenyl)-N-hydroxycyclopentanecarboxamide;
1-(3,5-difluoro-2-methylphenyl)-N-hydroxycyclopentanecarboxamide;
1-(2-chloro-6-methylphenyl)-N-hydroxycyclopentanecarboxamide;
1-(2-ethylphenyl)-N-hydroxycyclopentanecarboxamide;
N-hydroxy-1-(3-methoxy-2-(trifluoromethyl)phenyl)cyclopentanecarboxamide;
N-hydroxy-1-(2-(trifluoromethyl)phenyl)cyclopentanecarboxamide;
1-(4-fluoro-2-methylphenyl)-N-hydroxycyclopentanecarboxamide;

1-(5-fluoro-2-methylphenyl)-N-hydroxycyclopentanecarboxamide;
1-(2-fluoro-6-methylphenyl)-N-hydroxycyclopentanecarboxamide;
1-(Benzo[b]thiophen-7-yl)-N-hydroxycyclopentanecarboxamide;
(1R,3S*)-1-(3-fluoro-2-methylphenyl)-3-(5-fluoropyridin-3-yl)-N-hydroxycyclopentanecarboxamide;
(1R,3R*)-1-(3-fluoro-2-methylphenyl)-3-(5-fluoropyridin-3-yl)-N-hydroxycyclopentanecarboxamide;
(1S,3R)-3-(5-fluoropyridin-3-yl)-N-hydroxy-1-phenylcyclopentanecarboxamide;
(1S,3S)-3-(5-fluoropyridin-3-yl)-N-hydroxy-1-phenylcyclopentanecarboxamide;
(1S,3R)-3-(2-cyclopropyl-5-fluoropyridin-3-yl)-1-(3-fluoro-2-methylphenyl)-N-hydroxycyclopentanecarboxamide;
(1S,3S*)-1-(3-fluoro-2-methylphenyl)-3-(5-fluoro-6-methoxypyridin-3-yl)-N-hydroxycyclopentanecarboxamide;
(1S,3R*)-1-(3-fluoro-2-methylphenyl)-3-(5-fluoro-6-methoxypyridin-3-yl)-N-hydroxycyclopentanecarboxamide;
(1S,3R*)-3-(1-(Difluoromethyl)-1H-pyrazol-4-yl)-1-(3-fluoro-2-methylphenyl)-N-hydroxy cyclopentane carboxamide;
(1S,3R*)-1-(3-fluoro-2-methylphenyl)-N-hydroxy-3-(1-(2-morpholinoethyl)-1H-pyrazol-4-yl)cyclopentanecarboxamide;
(1S,3R*)-1-(3-fluoro-2-methylphenyl)-3-(5-fluoro-6-(2-(pyrrolidin-1-yl)ethoxy)pyridin-3-yl)-N-hydroxycyclopentanecarboxamide;
(1S,3R*)-1-(3-fluoro-2-methylphenyl)-N-hydroxy-3-(1-methyl-1H-pyrazol-5-yl)cyclopentane carboxamide;
(1S,3S*)-1-(3-fluoro-2-methylphenyl)-N-hydroxy-3-(1-methyl-1H-pyrazol-5-yl)cyclopentanecarboxamide;
(1S,3R*)-3-(1-(2-(diethylamino)ethyl)-1H-pyrazol-4-yl)-1-(3-fluoro-2-methylphenyl)-N-hydroxycyclopentanecarboxamide;
N—((R)-1-(dipropylamino)propan-2-yl)-4-((1R*,3S)-3-(3-fluoro-2-methylphenyl)-3-(hydroxycarbamoyl)cyclopentyl)benzamide;
N—((R)-1-(dipropylamino)propan-2-yl)-4-((1S*,3S)-3-(3-fluoro-2-methylphenyl)-3-(hydroxycarbamoyl)cyclopentyl)benzamide;
(1S,3R*)-3-(1-(difluoromethyl)-1H-indazol-6-yl)-1-(3-fluoro-2-methylphenyl)-N-hydroxycyclopentanecarboxamide;
(1S,3S*)-3-(1-(difluoromethyl)-1H-indazol-6-yl)-1-(3-fluoro-2-methylphenyl)-N-hydroxycyclopentanecarboxamide;
(1S,3R*)-1-(3-fluoro-2-methylphenyl)-N-hydroxy-3-(1-methyl-1H-indazol-6-yl)cyclopentanecarboxamide;
(1S,3R*)-1-(3-fluoro-2-methylphenyl)-N-hydroxy-3-(imidazo[1,2-a]pyridin-7-yl)cyclopentanecarboxamide;
(1S,3S*)-1-(3-fluoro-2-methylphenyl)-N-hydroxy-3-(imidazo[1,2-a]pyridin-7-yl)cyclopentanecarboxamide;
(1S,3R*)-3-(2-cyclopropyl-1-oxoisoindolin-5-yl)-1-(3-fluoro-2-methylphenyl)-N-hydroxycyclopentanecarboxamide;
(1S,3R*)-1-(3-fluoro-2-methylphenyl)-N-hydroxy-3-(1-methyl-1H-indazol-7-yl)cyclopentanecarboxamide;
(1S,3R*)-3-(7-fluoro-1H-indazol-6-yl)-1-(3-fluoro-2-methylphenyl)-N-hydroxycyclopentanecarboxamide;
(1S,3R*)-3-(2-cyclopropylbenzo[d]oxazol-5-yl)-1-(3-fluoro-2-methylphenyl)-N-hydroxycyclopentanecarboxamide;
(1S,3R*)-1-(3-fluoro-2-methylphenyl)-N-hydroxy-3-(1-methyl-1H-indazol-5-yl)cyclopentanecarboxamide;
(1S,3S*)-1-(3-fluoro-2-methylphenyl)-N-hydroxy-3-(1-methyl-1H-indazol-5-yl)cyclopentanecarboxamide;
(1S,3R*)-3-(2-(difluoromethyl)-2H-indazol-6-yl)-1-(3-fluoro-2-methylphenyl)-N-hydroxycyclopentanecarboxamide;
(1S,3S*)-3-(2-(difluoromethyl)-2H-indazol-6-yl)-1-(3-fluoro-2-methylphenyl)-N-hydroxycyclopentanecarboxamide;
(1S,3R*)-3-(3-fluoro-1-methyl-1H-indazol-6-yl)-1-(3-fluoro-2-methylphenyl)-N-hydroxycyclopentanecarboxamide;
(1S,3S*)-3-(3-fluoro-1-methyl-1H-indazol-6-yl)-1-(3-fluoro-2-methylphenyl)-N-hydroxycyclopentanecarboxamide;
(1S,3R*)-1-(3-fluoro-2-methylphenyl)-N-hydroxy-3-(1-methyl-1H-benzo[d]imidazol-5-yl)cyclopentanecarboxamide;
(1S,3R*)-1-(3-fluoro-2-methylphenyl)-N-hydroxy-3-(1-methyl-1H-benzo[d]imidazol-6-yl)cyclopentanecarboxamide;
(1S,3S*)-1-(3-fluoro-2-methylphenyl)-N-hydroxy-3-(1-methyl-1H-benzo[d]imidazol-6-yl)cyclopentanecarboxamide;
(1S,3R*)-1-(3-fluoro-2-methylphenyl)-N-hydroxy-3-(1-methyl-1H-benzo[d]imidazol-6-yl)cyclopentanecarboxamide;
(1S,3S*)-1-(3-fluoro-2-methylphenyl)-N-hydroxy-3-(1-methyl-1H-benzo[d]imidazol-6-yl)cyclopentanecarboxamide;
(1S,3R*)-1-(3-fluoro-2-methylphenyl)-N-hydroxy-3-(2-(trifluoromethyl)-1H-benzo[d]imidazol-6-yl)cyclopentanecarboxamide;
(1S,3S*)-3-(benzo[d]thiazol-2-yl)-1-(3-fluoro-2-methylphenyl)-N-hydroxycyclopentanecarboxamide;
(1S,3R*)-3-(benzo[d]thiazol-2-yl)-1-(3-fluoro-2-methylphenyl)-N-hydroxycyclopentanecarboxamide;
(1S,3S*)-3-(2-cyclopropylbenzo[d]thiazol-6-yl)-1-(3-fluoro-2-methylphenyl)-N-hydroxycyclopentanecarboxamide;
(1S,3R*)-3-(2-cyclopropylbenzo[d]thiazol-6-yl)-1-(3-fluoro-2-methylphenyl)-N-hydroxycyclopentanecarboxamide;
(1S,3S*)-3-(2-cyclopropylbenzo[d]thiazol-5-yl)-1-(3-fluoro-2-methylphenyl)-N-hydroxycyclopentanecarboxamide;
(1S,3R*)-3-(2-cyclopropylbenzo[d]thiazol-5-yl)-1-(3-fluoro-2-methylphenyl)-N-hydroxycyclopentanecarboxamide;
(1S,3R)-3-(5-fluoro-1-methyl-1H-indazol-6-yl)-1-(3-fluoro-2-methylphenyl)-N-hydroxycyclopentanecarboxamide;
(1S,3S*)-3-(7-fluoro-1-methyl-1H-indazol-6-yl)-1-(3-fluoro-2-methylphenyl)-N-hydroxycyclopentanecarboxamide;
(1S,3R*)-3-(7-fluoro-1-methyl-1H-indazol-6-yl)-1-(3-fluoro-2-methylphenyl)-N-hydroxycyclopentanecarboxamide;
(1S,3S*)-1-(3-fluoro-2-methylphenyl)-N-hydroxy-3-(quinolin-6-yl)cyclopentanecarboxamide;
(1S,3R*)-1-(3-fluoro-2-methylphenyl)-N-hydroxy-3-(quinolin-6-yl)cyclopentanecarboxamide;
(1S,3R*)-1-(3,4-difluoro-2-methylphenyl)-N-hydroxy-3-(1-methyl-1H-indazol-6-yl)cyclopentanecarboxamide;
(1S,3R*)-1-(3-fluoro-2-methylphenyl)-N-hydroxy-3-(pyrrolidin-1-yl)cyclopentanecarboxamide;

(1S,3S*)-1-(3-fluoro-2-methylphenyl)-N-hydroxy-3-(pyrrolidin-1-yl)cyclopentanecarboxamide;
(1S,3R*)-1-(3-fluoro-2-methylphenyl)-N-hydroxy-3-morpholinocyclopentanecarboxamide;
(1S,3S*)-1-(3-fluoro-2-methylphenyl)-N-hydroxy-3-morpholinocyclopentanecarboxamide;
(1S,3R)-1-(3-fluoro-2-methylphenyl)-N-hydroxy-3-((1-methyl-1H-indazol-6-yl)oxy)cyclopentanecarboxamide;
(1S,3S)-1-(3-fluoro-2-methylphenyl)-N-hydroxy-3-((1-methyl-1H-indazol-6-yl)oxy)cyclopentanecarboxamide;
(1S,3R)-1-(3-fluoro-2-methylphenyl)-3-((5-fluoropyridin-3-yl)oxy)-N-hydroxycyclopentanecarboxamide;
(1S,3S)-1-(3-fluoro-2-methylphenyl)-3-((5-fluoropyridin-3-yl)oxy)-N-hydroxycyclopentanecarboxamide;
(1S,3R)-1-(3-fluoro-2-methylphenyl)-N-hydroxy-3-phenoxycyclopentanecarboxamide;
(1S,3S)-1-(3-fluoro-2-methylphenyl)-N-hydroxy-3-phenoxycyclopentanecarboxamide;
(1S,3S)-1-(3-fluoro-2-methylphenyl)-3-((4-fluorobenzyl)oxy)-N-hydroxycyclopentanecarboxamide;
1-phenyl-N-hydroxycyclohexylcarboxamide;
(1r,4r)-1-(3-fluoro-2-methylphenyl)-4-(5-fluoropyridin-3-yl)-N-hydroxycyclohexanecarboxamide;
(1s,4s)-1-(3-fluoro-2-methylphenyl)-4-(5-fluoropyridin-3-yl)-N-hydroxycyclohexanecarboxamide;
(1r,4r)-1-(3-fluoro-2-methylphenyl)-N-hydroxy-4-phenoxycyclohexanecarboxamide;
(1s,4s)-1-(3-fluoro-2-methylphenyl)-4-((4-fluorobenzyl)oxy)-N-hydroxycyclohexanecarboxamide;
(1s,4s)-1-(3-fluoro-2-methylphenyl)-N-hydroxy-4-(1-methyl-1H-indazol-6-yl)cyclohexanecarboxamide;
(1r,4r)-1-(3-fluoro-2-methylphenyl)-N-hydroxy-4-(1-methyl-1H-indazol-6-yl)cyclohexanecarboxamide;
(±)-2-(3-fluoro-2-methylphenyl)-N-hydroxy-8-oxaspiro[4.5]decane-2-carboxamide;
N-hydroxy-1-phenylcycloheptanecarboxamide; and
1-(3-fluoro-2-methylphenyl)-N-hydroxycycloheptanecarboxamide, or a pharmaceutically acceptable salt thereof.

Methods for obtaining the compounds, or pharmaceutically acceptable salts thereof, described herein will be apparent to those of ordinary skill in the art, suitable procedures being described, for example, in examples below, and in the references cited herein.

Also provided is a method for inhibiting at least one histone deacetylase. In some embodiments, the at least one histone deacetylase is a class IIa HDAC. In some embodiments, the at least one histone deacetylase is selected from HDAC-4, HDAC-5, HDAC-7, and HDAC-9. In some embodiments, the inhibition is in a cell. In some embodiments, the compound, or pharmaceutically acceptable salt thereof, described herein is selective for inhibiting at least one class II histone deacetylase. In some embodiments, the compound, or pharmaceutically acceptable salt thereof, described herein is a selective inhibitor of HDAC-4 and/or HDAC-5.

Also provided is a method of treating a condition or disorder mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a neurodegenerative pathology. Accordingly, also provided is a method of treating a neurodegenerative pathology mediated by HDAC in a subject in need of such a treatment, comprising administering to the subject a therapeutically effective amount of at least one compound, or pharmaceutically acceptable salt thereof, described herein.

In some embodiments, the neurodegenerative pathology is chosen from Alzheimer's disease, Parkinson's disease, neuronal intranuclear inclusion disease (NIID), Dentatorubral pallidolusyian atrophy (DRPLA), Friedreich's ataxia, Rubenstein-Taubi Syndrome, and polyglutamine diseases such as Huntington's disease; spinocerebellar ataxia 1 (SCA 1), spinocerebellar ataxia 7 (SCA 7), seizures, striatonigral degeneration, progressive supranuclear palsy, torsion dystonia, spasmodic torticollis, dyskinesis, familial tremor, Gilles de la Tourette syndrome, diffuse Lewy body disease, progressive supranuclear palsy, Pick's disease, primary lateral sclerosis, progressive neural muscular atrophy, spinal muscular atrophy, hypertrophic interstitial polyneuropathy, retinitis pigmentosa, hereditary optic atrophy, hereditary spastic paraplegia, Shy-Drager syndrome, Kennedy's disease, protein-aggregation-related neurodegeneration, Machado-Joseph's disease, spongiform encephalopathy, prion-related disease, multiple sclerosis (MS), progressive supranuclear palsy (Steel-Richardson-Olszewski disease), Hallervorden-Spatz disease, progressive familial myoclonic epilepsy, cerebellar degeneration, motor neuron disease, Werdnig-Hoffman disease, Wohlfart-Kugelberg-Welander disease, Charcot-Marie-Tooth disease, Dejerine-Sottas disease, retinitis pigmentosa, Leber's disease, progressive systemic sclerosis, dermatomyositis, and mixed connective tissue disease.

In some embodiments, the neurodegenerative pathology is an acute or chronic degenerative disease of the eye. Acute or chronic degenerative diseases of the eye include glaucoma, dry age-related macular degeneration, retinitis pigmentosa and other forms of heredodegenerative retinal disease, retinal detachment, macular pucker, ischemia affecting the outer retina, cellular damage associated with diabetic retinopathy and retinal ischemia, damage associated with laser therapy, ocular neovascular, diabetic retinopathy, rubeosis iritis, uveitis, Fuch's heterochromatic iridocyclitis, neovascular glaucoma, corneal neovascularization, retinal ischemia, choroidal vascular insufficiency, choroidal thrombosis, carotid artery ischemia, contusive ocular injury, retinopathy of prematurity, retinal vein occlusion, proliferative vitreoretinopathy, corneal angiogenesis, retinal microvasculopathy, and retinal eduema.

In some embodiments, the condition or disorder mediated by HDAC comprises a fibrotic disease such as liver fibrosis, cystic fibrosis, cirrhosis, and fibrotic skin diseases, e.g., hypertrophic scars, keloid, and Dupuytren's contracture. Accordingly, also provided is a method of treating a fibrotic disease mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a psychological disorder, such as depression, bipolar disease and dementia. In some embodiments, the condition or disorder mediated by HDAC comprises depression. Accordingly, also provided is a method of treating a psychological disorder, such as depression, mediated by HDAC in a subject in need of such a treatment, comprising administering to the subject a therapeutically effective amount of at least one compound, or pharmaceutically acceptable salt thereof, described herein. In some embodiments, the depression is chosen from major depressive disorder, and bipolar disorder.

In some embodiments, the condition or disorder mediated by HDAC comprises anxiety. Accordingly, also provided is a method of treating an anxiety mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises schizophrenia. Accordingly, also provided is a method of treating a schizophrenia mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a motor neuron disease, muscle atrophy/muscle wasting disorders, or amyotrophic lateral sclerosis (ALS). Accordingly, also provided is a method of treating a motor neuron disease, muscle atrophy/muscle wasting disorders, or amyotrophic lateral sclerosis (ALS) mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a cardiovascular condition. Accordingly, also provided is a method of treating a cardiovascular condition mediated by HDAC in a subject in need of such a treatment, comprising administering to the subject a therapeutically effective amount of at least one compound, or pharmaceutically acceptable salt thereof, described herein. In some embodiments, the cardiovascular condition is chosen from cardiomyopathy, cardiac hypertrophy, myocardial ischemia, heart failure, cardiac restenosis, and arteriosclerosis.

In some embodiments, the condition or disorder mediated by HDAC comprises cancer. Accordingly, also provided is a method of treating cancer mediated by HDAC in a subject in need of such a treatment, comprising administering to the subject a therapeutically effective amount of at least one compound, or pharmaceutically acceptable salt thereof, described herein. In some embodiments, the cancer is chosen from lymphoma, pancreatic cancer, colorectal cancer, hepatocellular carcinoma, Waldenstrom macroglobulinemia, hormone refractory cancer of the prostate, and leukaemia, breast cancer, lung cancer, ovarian cancer, prostate cancer, head and neck cancer, renal cancer, gastric cancer, brain cancer, B-cell lymphoma, peripheral T-cell lymphoma, and cutaneous T-cell lymphoma. In some further embodiments, the cancer is chosen from the following cancer types. Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma, cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma; and the sensitization of tumors to radiotherapy by administering the compound according to the invention before, during or after irradiation of the tumor for treating cancer.

In some embodiments, the condition or disorder mediated by HDAC comprises a condition or disorder treatable by immune modulation. Accordingly, also provided is a method of treating a condition or disorder treatable by immune modulation mediated by HDAC in a subject in need of such a treatment, comprising administering to the subject a therapeutically effective amount of at least one compound, or pharmaceutically acceptable salt thereof, described herein. In some embodiments, the condition or disorder treatable by immune modulation is chosen from asthma, irritable bowel syndrome, Crohn's disease, ulcerative colitis, bowel motility disorders, hypertension, rheumatoid arthritis, osteoarthritis, juvenile chronic arthritis, graft versus host disease, psoriasis, spondyloarthropathy, inflammatory bowel disease, alcoholic hepatitis, Sjogren's syndrome, ankylosing spondylitis, membranous glomerulopathy, discogenic pain, systemic lupus erythematosus, allergic bowel disease, coeliac disease, bronchitis, cystic fibrosis, rheumatoid spondylitis, osteoarthritis, uveitis, iritis, and conjunctivitis, ischemic bowel disease, psoriasis, eczema, dermatitis, septic arthritis, gout, pseudogout, juvenile arthritis, Still's disease, Henoch-Schonlein purpura, psoriatic arthritis, myalgia, reactive arthritis (Reiter's syndrome), hemochromatosis, Wegener's granulomatosis, familial Mediterranean fever (FMF), HBDS (hyperimmunoglobulinemia D and periodic fever syndrome), TRAPS (TNF-alpha receptor associated periodic fever syndrome), chronic obstructive pulmonary disease, neonatal-onset multisystem inflammatory disease (NO-MID), cryopyrin-associated periodic syndrome (CAPS), and familial cold autoinflammatory syndrome (FCAS).

In some embodiments, the condition or disorder mediated by HDAC comprises an allergic disease. Accordingly, also provided is a method of treating an allergic disease, mediated by HDAC in a subject in need of such a treatment, comprising administering to the subject a therapeutically effective amount of at least one compound, or pharmaceutically acceptable salt thereof, described herein. Allergic diseases include, but are not limited to, respiratory allergic diseases such as allergic rhinitis, hypersensitivity lung diseases, hypersensitivity pneumonitis, eosinophilic pneumonias, Loeffler's syndrome, chronic eosinophilic pneumonia, delayed-type hypersensitivity, interstitial lung diseases (ILD), idiopathic pulmonary fibrosis, polymyositis, dermatomyositis, systemic anaphylaxis, drug allergies (e.g., to penicillin or cephalosporins), and insect sting allergies.

In some embodiments, the condition or disorder mediated by HDAC comprises an infectious disease such as a fungal infection, bacterial infection, viral infection, and protozoal infection, e.g., malaria, giardiasis, leishmaniasis, Chaga's disease, dysentery, toxoplasmosis, and coccidiosis. In some embodiments, the condition or disorder mediated by HDAC comprises malaria. Accordingly, also provided is a method of treating an infectious disease, such as malaria, mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises autism or Rett syndrome. Accordingly, also provided is a method of treating autism or Rett syndrome mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a hematological disorder such as thalassemia, anemia, and sickle cell anemia. Accordingly, also provided is a method of treating a hematological disorder mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a metabolic disease such as prediabetes or diabetes (type I or II). Accordingly, also provided is a method of treating a metabolic disease, such as prediabetes or diabetes (type I or II), mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a disorder that may also be treated by progenitor/stem cell based therapies such as: disorders related to diabetes (organ failure, cirrhosis, and hepatitis); central nervous system (CNS) disorders associated with dysregulation of progenitor cells in the brain (e.g., post-traumatic stress disorder (PTSD); tumors (e.g., retinoblastomas); disorders affecting oligodendrycoyte progenitor cells (e.g., astrocytomas and ependimal cell tumors); multiple sclerosis; demyelinating disorders such as the leukodystrophies; neuropathies associated with white matter loss; and cerebellar disorders such as ataxia; and olfactory progenitor disorders (e.g., anosmic conditions). Accordingly, also provided is a method of treating a disorder that is mediated by HDAC in a subject in need of such a treatment, comprising administering to the subject a therapeutically effective amount of at least one compound, or pharmaceutically acceptable salt thereof, described herein, either before, during, or after a treatment with progenitor/stem cell based therapies.

In some embodiments, the condition or disorder mediated by HDAC comprises a disorder related to the proliferation of epithelial and mesenchymal cells (e.g., tumors, wound healing, and surgeries). Accordingly, also provided is a method of treating a disorder related to the proliferation of epithelial and mesenchymal cells that is mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a disorder related to the proliferation of bone progenitors (e.g., osteoblasts and osteoclasts), disorders related to hair and epidermal progenitors (e.g., hair loss, cutaneous tumors, skin regeneration, burns, and cosmetic surgery); and disorders related to bone loss during menopause. Accordingly, also provided is a method of treating disorders related to the proliferation of bone progenitors, disorders related to hair and epidermal progenitors, or disorders related to bone loss that are mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC is a viral disorder for which blood cells become sensitized to other treatments after HDAC inhibition, following administering to the subject a therapeutically effective amount of at least one compound, or pharmaceutically acceptable salt thereof, as described herein.

In some embodiments, the condition or disorder mediated by HDAC is an immune disorder that may be co-treated with TNFα or other immune modulators, upon administering to the subject a therapeutically effective amount of at least one compound, or pharmaceutically acceptable salt thereof, as described herein.

In some embodiments, the condition or disorder mediated by HDAC comprises a graft rejection or transplant rejection. Accordingly, also provided is a method of treating a disorder related to a graft rejection or a transplant rejection that is mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a blood pressure disorder related to nitric oxide (NO) regulation (e.g., hypertension, erectile dysfunction, asthma; and ocular disorders as glaucoma). Accordingly, also provided is a method of treating a blood pressure disorder related to nitric oxide (NO) regulation that is mediated by HDAC in a subject in need of such a treatment, comprising administering to the subject a therapeutically effective amount of at least one compound, or pharmaceutically acceptable salt thereof, described herein. In some embodiments, the condition or disorder is a cardiac hypertrophic disorder. Accordingly, also provided is a method of treating a cardiac hypertrophic disorder that is mediated by HDAC in a subject in need of such a treatment, comprising administering to the subject a therapeutically effective amount of at least one compound, or pharmaceutically acceptable salt thereof, described herein.

Also provided are methods of treatment in which at least one compound, or pharmaceutically acceptable salt thereof, described herein is the only active agent given to the subject and also includes methods of treatment in which at least one compound, or pharmaceutically acceptable salt thereof, described herein is given to the subject in combination with one or more additional active agents.

In general, the compounds, or pharmaceutically acceptable salts thereof, described herein will be administered in a therapeutically effective amount by any of the accepted modes of administration for agents that serve similar utilities. The actual amount of the compound, i.e., the active ingredient, will depend upon numerous factors such as the severity of the disease to be treated, the age and relative health of the subject, the potency of the compound used, the route and form of administration, and other factors well known to the skilled artisan. The drug can be administered at least once a day, such as once or twice a day.

In some embodiments, the compounds, or pharmaceutically acceptable salts thereof, described herein are administered as a pharmaceutical composition. Accordingly, provided are pharmaceutical compositions comprising at least one compound, or pharmaceutically acceptable salt thereof, described herein, together with at least one pharmaceutically acceptable vehicle chosen from carriers, adjuvants, and excipients.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the compound, or pharmaceutically acceptable salt thereof, is sufficient to provide a practical quantity of material for administration per unit dose of the compound, or pharmaceutically acceptable salt thereof.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound, or pharmaceutically acceptable salt thereof, described herein.

Effective concentrations of at least one compound, or pharmaceutically acceptable salt thereof, described herein are mixed with a suitable pharmaceutically acceptable vehicle. In instances in which the compound, or pharmaceutically acceptable salt thereof, exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate.

Upon mixing or addition of a compound, or pharmaceutically acceptable salt thereof, described herein, the resulting mixture may be a solution, suspension, emulsion or the like. The form of the resulting mixture depends upon a number of factors, including the intended mode of administration and the solubility of the compound, or pharmaceutically acceptable salt thereof, in the chosen vehicle. The effective concentration sufficient for ameliorating the symptoms of the disease treated may be empirically determined.

The compounds, or pharmaceutically acceptable salts thereof, described herein may be administered orally, topically, parenterally, intravenously, by intramuscular injection, by inhalation or spray, sublingually, transdermally, via buccal administration, rectally, as an ophthalmic solution, or by other means, in dosage unit formulations.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of at least one compound, or pharmaceutically acceptable salt thereof, described herein. In some embodiments, oral pharmaceutical compositions contain at least 5% (weight %) of at least one compound, or pharmaceutically acceptable salt thereof, described herein. Some embodiments contain from 25% to 50% or from 5% to 75% of at least one compound, or pharmaceutically acceptable salt thereof, described herein.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

The compound, or pharmaceutically acceptable salt thereof, described herein can be incorporated into oral liquid preparations such as aqueous or oily suspensions, solutions, emulsions, syrups, or elixirs, for example. Moreover, pharmaceutical compositions containing these at least one compound, or pharmaceutically acceptable salt thereof, can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, Avicel RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such pharmaceutical compositions may also be coated by conventional methods, typically with pH or time-dependent coatings, such that the compound, or pharmaceutically acceptable salt thereof, is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

The compound, or pharmaceutically acceptable salt thereof, described herein may be administered parenterally in a sterile medium. Parenteral administration includes subcutaneous injections, intravenous, intramuscular, intrathecal injection or infusion techniques. The compound, or pharmaceutically acceptable salt thereof, described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

The compound, or pharmaceutically acceptable salt thereof, described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

The compound, or pharmaceutically acceptable salt thereof, described herein may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Such solutions may be formulated as 0.01%-10% isotonic solutions, pH 5-7, with appropriate salts. The compound, or pharmaceutically acceptable salt thereof, described herein may also be formulated for transdermal administration as a transdermal patch.

Topical pharmaceutical compositions comprising at least one compound, or pharmaceutically acceptable salt thereof, described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows.

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The compound, or pharmaceutically acceptable salt thereof, described herein may also be topically administered in the form of liposome delivery systems, such as small unilamellar vesicles, large unilamellar vesicles, and multi-lamellar vesicles. Liposomes can be formed from a variety of phospholipids, such as cholesterol, stearylamine or phosphatidylcholines.

Other pharmaceutical compositions useful for attaining systemic delivery of the compound, or pharmaceutically acceptable salt thereof, include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the compound, or pharmaceutically acceptable salt thereof, described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of at least one compound, or pharmaceutically acceptable salt thereof, described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

Also provided are packaged pharmaceutical compositions. Such packaged compositions include a pharmaceutical composition comprising at least one compound, or pharmaceutically acceptable salt thereof, described herein, and instructions for using the composition to treat a subject (typically a human patient). In some embodiments, the instructions are for using the pharmaceutical composition to treat a subject suffering a condition or disorder mediated by HDAC. The packaged pharmaceutical composition can include providing prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the compound, or pharmaceutically acceptable salt thereof, can be administered alone, as mixtures, or in combination with other active agents.

The methods described herein include methods for treating Huntington's disease, including treating memory and/or cognitive impairment associated with Huntington's disease, comprising administering to a subject, simultaneously or sequentially, at least one compound, or pharmaceutically acceptable salt thereof, described herein and one or more additional agents used in the treatment of Huntington's disease such as, but not limited to, Amitriptyline, Imipramine, Despiramine, Nortriptyline, Paroxetine, Fluoxetine, Sertraline, Terabenazine, Haloperidol, Chlorpromazine, Thioridazine, Sulpride, Quetiapine, Clozapine, and Risperidone. In methods using simultaneous administration, the agents can be present in a combined composition or can be administered separately. As a result, also provided are pharmaceutical compositions comprising at least one compound, or pharmaceutically acceptable salt thereof, described herein and one or more additional pharmaceutical agents used in the treatment of Huntington's disease such as, but not limited to, Amitriptyline, Imipramine, Despiramine, Nortriptyline, Paroxetine, Fluoxetine, Sertraline, Terabenazine, Haloperidol, Chlorpromazine, Thioridazine, Sulpride, Quetiapine, Clozapine, and Risperidone. Similarly, also provided are packaged pharmaceutical compositions containing a pharmaceutical composition comprising at least one compound, or pharmaceutically acceptable salt thereof, described herein, and another composition comprising one or more additional pharmaceutical agents used in the treatment of Huntington's disease such as, but not limited to, Amitriptyline, Imipramine, Despiramine, Nortriptyline, Paroxetine, Fluoxetine, Sertraline, Terabenazine, Haloperidol, Chloropromazine, Thioridazine, Sulpride, Quetiapine, Clozapine, and Risperidone.

Also provided are methods for Alzheimer's disease, including treating memory and/or cognitive impairment associated with Alzheimer's disease, comprising administering to a subject, simultaneously or sequentially, at least one compound, or pharmaceutically acceptable salt thereof, described herein and one or more additional agents used in the treatment of Alzheimer's disease such as, but not limited to, Reminyl, Cognex, Aricept, Exelon, Akatinol, Neotropin, Eldepryl, Estrogen and Clioquinol. In methods using simultaneous administration, the agents can be present in a combined composition or can be administered separately. Also provided are pharmaceutical compositions comprising at least one compound, or pharmaceutically acceptable salt thereof, described herein, and one or more additional pharmaceutical agents used in the treatment of Alzheimer's disease such as, but not limited to, Reminyl, Cognex, Aricept, Exelon, Akatinol, Neotropin, Eldepryl, Estrogen and Clioquinol. Similarly, also provided are packaged pharmaceutical compositions containing a pharmaceutical composition comprising at least one compound, or pharmaceutically acceptable salt thereof, described herein, and another composition comprising one or more additional pharmaceutical agents used in the treatment of Alzheimer's disease such as, but not limited to Reminyl, Cognex, Aricept, Exelon, Akatinol, Neotropin, Eldepryl, Estrogen and Clioquinol.

Also provided are methods for treating cancer comprising administering to a subject, simultaneously or sequentially, at least one compound, or pharmaceutically acceptable salt thereof, described herein and one or more additional agents used in the treatment of cancer such as, but not limited to, the following categories of anti-tumor agents (i) other cell cycle inhibitory agents that work by the same or different mechanisms from those defined hereinbefore, for example cyclin dependent kinase (CDK) inhibitors, in particular CDK2 inhibitors;
(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example vascular endothelial growth factor, epithelial growth factor, platelet derived growth factor and hepatocyte growth factor such inhibitors include growth factor antibodies, growth factor receptor antibodies, tyrosine kinase inhibitors and serine/threonine kinase inhibitors);
(iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan);
(iv) antiangiogenic agents that work by different mechanisms from those defined hereinbefore (for example receptor tyrosine kinases like Tie-2, inhibitors of integrin α5β3 function, angiostatin, razoxin, thalidomide), and including vascular targeting agents; and
(v) differentiation agents (for example retinoic acid and vitamin D).

In methods using simultaneous administration, the agents can be present in a combined composition or can be administered separately. Also provided are pharmaceutical compositions comprising at least one compound, or pharmaceutically acceptable salt thereof, described herein, and one or more anti-tumor agent as described herein. Similarly, also provided are packaged pharmaceutical compositions containing a pharmaceutical composition comprising at least one compound, or pharmaceutically acceptable salt thereof, described herein, and another composition comprising one or more one or more anti-tumor agent as described herein. When used in combination with one or more additional pharmaceutical agent or agents, the described herein may be administered prior to, concurrently with, or following administration of the additional pharmaceutical agent or agents.

In some embodiments, the compounds, or pharmaceutically acceptable salts thereof, described herein, are administered in conjunction with surgery or radiotherapy, optionally in combination with one or more additional agents used in the treatment of cancer.

The dosages of the compounds described herein depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compound, or pharmaceutically acceptable salt thereof, described herein is typically administered at dosage levels and in a manner customary for HDAC inhibitors. For example, the compound, or pharmaceutically acceptable salt thereof, can be administered, in single or multiple doses, by oral administration at a dosage level of generally 0.001-100 mg/kg/day, for example, 0.01-100 mg/kg/day, such as 0.1-70 mg/kg/day, for example, 0.5-10 mg/kg/day. Unit dosage forms can contain generally 0.01-1000 mg of at least one compound, or pharmaceutically acceptable salt thereof, described herein, for example, 0.1-50 mg of at least one compound, or pharmaceutically acceptable salt thereof, described herein. For intravenous administration, the compounds can be administered, in single or multiple dosages, at a dosage level of, for example, 0.001-50 mg/kg/day, such as 0.001-10 mg/kg/day, for example, 0.01-1 mg/kg/day. Unit dosage forms can contain, for example, 0.1-10 mg of at least one compound, or pharmaceutically acceptable salt thereof, described herein.

A labeled form of a compound, or pharmaceutically acceptable salt thereof, described herein can be used as a diagnostic for identifying and/or obtaining compounds that have the function of modulating an activity of HDAC as described herein. The compound, or pharmaceutically acceptable salt thereof, described herein may additionally be used for validating, optimizing, and standardizing bioassays.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In carrying out the procedures of the methods described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

EXAMPLES

The compounds, or pharmaceutically acceptable salts thereof, compositions, and methods described herein are further illustrated by the following non-limiting examples.

As used herein, the following abbreviations have the following meanings. If an abbreviation is not defined, it has its generally accepted meaning.

Abbreviations
aq: Aqueous
DCM: Dichloromethane
DCE: Dichloroethane
DIPEA: Diisopropylethylamine
DME: Dimethoxyethane
DMF: Dimethylformamide
DMSO: Dimethylsulfoxide
d.r.: Diastereomeric ratio
ee: Enantiomeric excess
ES+: Electrospray Positive Ionisation
ES−: Electrospray Negative Ionisation
Et$_2$O: Diethyl ether
EtOAc: Ethyl acetate
FA: Formic acid
h: Hour
HPLC: High Performance Liquid Chromatography
i-hex: iso-Hexane
IPA: iso-propanol
LCMS: Liquid Chromatography Mass Spectrometry
LiHMDS: Lithium bis(trimethylsilyl)amide
M: Mass
MeCN: Acetonitrile
MeOH: Methanol
N/A: Not available
NaHMDS Sodium bis(trimethylsilyl)amide
NMP: N-Methyl pyrrolidinone
o-tolyl: 2-Methylphenyl
Pd/C: Palladium on carbon
Pd$_2$(dba)$_3$: Tris(dibenzylideneacetone)dipalladium(0)
Pd(dppf)Cl$_2$: [1,1'-Bis(diphenylphosphino)ferrocene]dichloropalladium(II) complex with DCM
Pd(PPh$_3$)$_4$: Tetrakis(triphenylphosphine)palladium(0)
RT: Retention time
r.t.: Room temperature
sat: Saturated
SFC: Supercritical fluid chromatography
TFFH: Tetramethylfluoroformamidinium hexafluorophosphate
THF: Tetrahydrofuran
Xantphos: 4,5-Bis(diphenylphosphino)-9,9-dimethylxanthene Analytical Conditions

| Analytical Condition | Method | Description |
|---|---|---|
| 10 cm_ESI_Formic_MeCN, 10 cm_ESCI_Formic_MeCN | 1 | Solvents: Acetonitrile (far UV grade) with 0.1% (v/v) formic acid. Water (high purity via PureLab Option unit) with 0.1% formic acid Column: Phenomenex Luna 5 µm C18 (2), 100 × 4.6 mm (Plus guard cartridge) Flow Rate: 2 mL/min gradient: A: Water/formic acid B: MeCN/formic acid |

| Time | A % | B % |
|---|---|---|
| 0.00 | 95 | 5 |
| 3.50 | 5 | 95 |
| 5.50 | 5 | 95 |
| 5.60 | 95 | 5 |
| 6.50 | 95 | 5 |

| Analytical Condition | Method | Description |
|---|---|---|
| 15 cm_Formic_Ascentis_HPLC_MeCN | 2 | Typical Injections 2-7 µL (concentration ~0.2-1.0 mg/mL) Solvents: Acetonitrile (Far UV grade) with 0.1% (V/V) formic acid Water (High purity via PureLab Ultra unit) with 0.1% formic acid Column: Supelco, Ascentis ® Express C18 or Hichrom Halo C18, 2.7 µm C18, 150 × 4.6 mm. Flow Rate: 1 mL/min gradient: A: Water/formic B: MeCN/formic |

| Time | A % | B % |
|---|---|---|
| 0.00 | 96 | 4 |
| 3.00 | 96 | 4 |
| 9.00 | 0 | 100 |
| 13.6 | 0 | 100 |
| 13.7 | 96 | 4 |
| 15 | 96 | 4 |

| Analytical Condition | Method | Description |
|---|---|---|
| 10 cm_Formic_ACE-AR_HPLC_CH3CN | 3 | Typical Injections 2-7 µL (concentration ~0.2-1 mg/mL) Solvents: Acetonitrile (Far UV grade) with 0.1% (V/V) formic acid Water (High purity via PureLab Ultra unit) with 0.1% formic acid Column: Hichrom ACE 3 C18-AR mixed mode column 100 × 4.6 mm Flow Rate: 1 mL/min gradient: A: Water/formic B: MeCN/formic |

| Time | A % | B % |
|---|---|---|
| 0.00 | 98 | 2 |
| 3.00 | 98 | 2 |
| 12.00 | 0 | 100 |
| 15.4 | 0 | 100 |
| 15.5 | 98 | 2 |
| 17 | 98 | 2 |

Typical Injections 0.2-10 µL

Compounds were named with the aid of the CambridgeSoft Chemistry Cartridge (v. 12.0.3.1212) software.

All reactions involving air- or moisture-sensitive reagents were performed under a nitrogen atmosphere using dried solvents and glassware.

Preparation of Intermediates

Preparation of Intermediate 1: (S)-methyl 1-(3-fluoro-2-methylphenyl)-3-oxocyclopentane-carboxylate

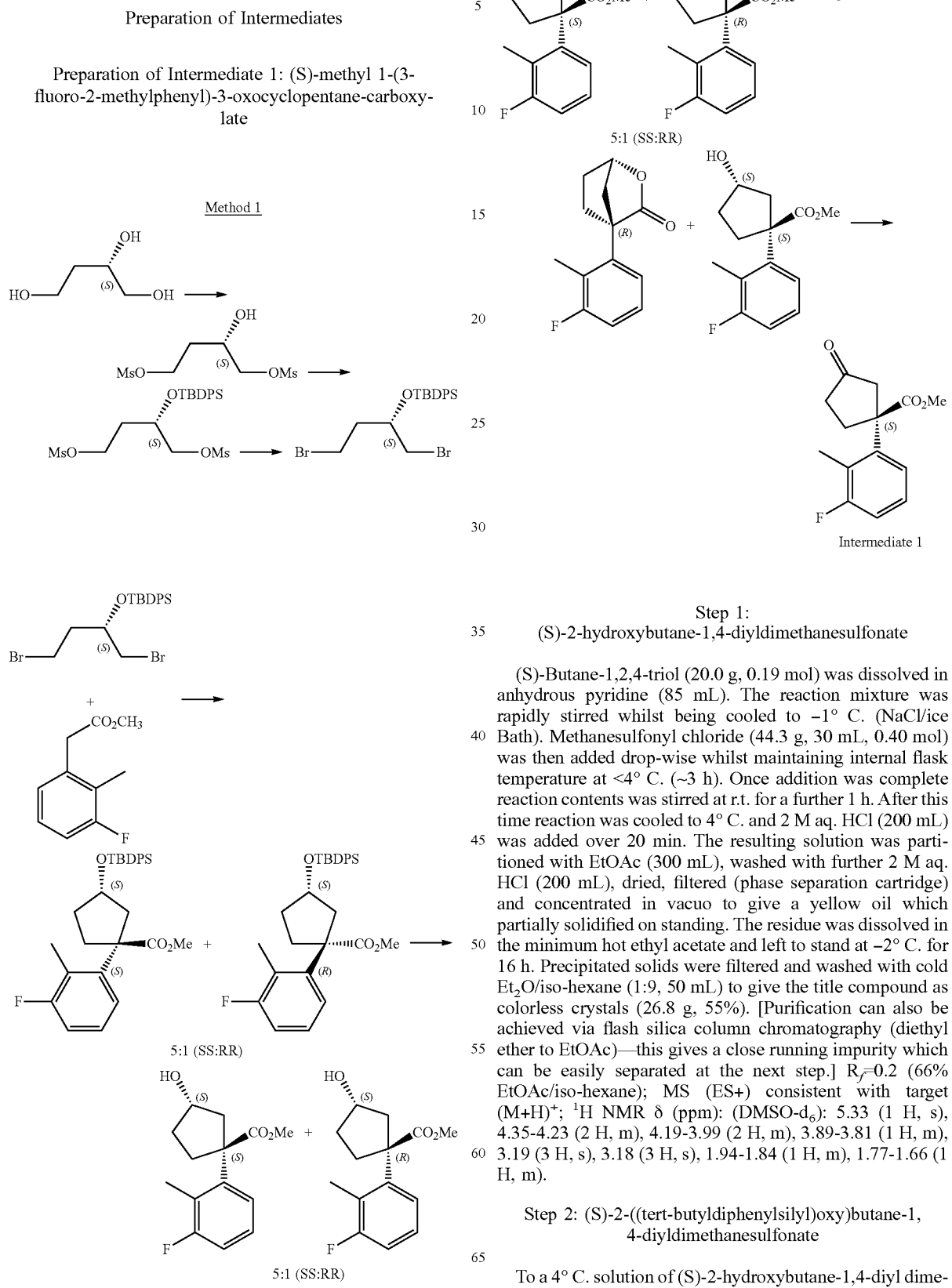

Step 1:
(S)-2-hydroxybutane-1,4-diyldimethanesulfonate (S)-Butane-1,2,4-triol (20.0 g, 0.19 mol) was dissolved in anhydrous pyridine (85 mL). The reaction mixture was rapidly stirred whilst being cooled to −1° C. (NaCl/ice Bath). Methanesulfonyl chloride (44.3 g, 30 mL, 0.40 mol) was then added drop-wise whilst maintaining internal flask temperature at <4° C. (~3 h). Once addition was complete reaction contents was stirred at r.t. for a further 1 h. After this time reaction was cooled to 4° C. and 2 M aq. HCl (200 mL) was added over 20 min. The resulting solution was partitioned with EtOAc (300 mL), washed with further 2 M aq. HCl (200 mL), dried, filtered (phase separation cartridge) and concentrated in vacuo to give a yellow oil which partially solidified on standing. The residue was dissolved in the minimum hot ethyl acetate and left to stand at −2° C. for 16 h. Precipitated solids were filtered and washed with cold $Et_2O$/iso-hexane (1:9, 50 mL) to give the title compound as colorless crystals (26.8 g, 55%). [Purification can also be achieved via flash silica column chromatography (diethyl ether to EtOAc)—this gives a close running impurity which can be easily separated at the next step.] $R_f$=0.2 (66% EtOAc/iso-hexane); MS (ES+) consistent with target (M+H)$^+$; $^1$H NMR δ (ppm): (DMSO-$d_6$): 5.33 (1 H, s), 4.35-4.23 (2 H, m), 4.19-3.99 (2 H, m), 3.89-3.81 (1 H, m), 3.19 (3 H, s), 3.18 (3 H, s), 1.94-1.84 (1 H, m), 1.77-1.66 (1 H, m).

Step 2: (S)-2-((tert-butyldiphenylsilyl)oxy)butane-1,4-diyldimethanesulfonate

To a 4° C. solution of (S)-2-hydroxybutane-1,4-diyl dimethanesulfonate (23.2 g, 0.09 mol) in anhydrous DMF (75 mL) was added tert-butylchlorodiphenylsilane (36.5 g, 34.5 mL, 0.11 mol) followed by imidazole (10.0 g, 0.15 mol). The reaction mixture was stirred at 4° C. for 1 h then at r.t. for a further 16 h. The reaction mixture was quenched using ice water (200 mL) with rapid stirring for 30 min. The corresponding solution was partitioned with EtOAc (300 mL), washed with water (2×200 mL), and then sat. NaCl solution (250 mL). The combined organic layers were dried, filtered (phase separation cartridge) and concentrated in vacuo to give a yellow oil. Purification by flash silica column chromatography (gradient elution, 0-50% EtOAc in iso-hexane) gave the title compound as a colorless glass (42.0 g, 93%). $R_f$=0.55 (66% EtOAc/iso-hexane); MS (ES+) consistent with target $(M+H)^+$; $^1$H NMR δ (ppm)(DMSO-$d_6$): 7.67-7.63 (4 H, m), 7.52-7.41 (6 H, m), 4.31-4.16 (2 H, m), 4.13-4.01 (3 H, m), 3.08 (3H, s), 3.02 (3 H, s), 1.92 (2 H, dd, J=12.2, 6.1 Hz), 1.02 (9 H, s).

Step 3: (S)-tert-butyl((1,4-dibromobutan-2-yl)oxy) diphenylsilane

To a solution of (S)-2-((tert-butyldiphenylsilyl)oxy)butane-1,4-diyl dimethanesulfonate (42.0 g, 0.08 mol) in anhydrous DMF (320 mL) was added lithium bromide (22.0 g, 0.25 mol). The reaction mixture was stirred at 105° C. for 1.5 h. The reaction mixture was cooled to r.t. and partitioned between EtOAc (500 mL) and water (300 mL). Organic layers were washed with further water (2×300 mL) and sat. NaCl solution (400 mL). The combined organic layers were dried, filtered (phase separation cartridge) and concentrated in vacuo to give a yellow oil. Purification by flash silica column chromatography (gradient elution, 0-10% EtOAc in iso-hexane) gave the title compound as a colorless oil which darkened upon standing (30.0 g, 80%). $R_f$=0.80 (60% EtOAc/iso-hexane); MS (ES+) consistent with target $(M+H)^+$; $^1$H NMR δ (ppm)(DMSO-$d_6$): 7.69-7.63 (4 H, m), 7.52-7.41 (6 H, m), 4.07-3.99 (1 H, m), 3.53-3.40 (4 H, m), 2.10 (2 H, dd, J=13.0, 6.5 Hz), 1.04 (9 H, s).

Step 4: (1S,3S)-methyl 1-(3-fluoro-2-methylphenyl)-3-hydroxycyclopentanecarboxylate To a solution of (S)-tert-butyl((1,4-dibromobutan-2-yl)oxy)diphenylsilane (6.43 g, 0.014 mol) and methyl 2-(3-fluoro-2-methylphenyl)acetate (2.0 g, 0.011 mol) in anhydrous DMF (80 mL) was added 18-crown-6 (0.2 g, 0.75 mmol). The reaction mixture was stirred at r.t. for 10 min then sodium hydride (60% dispersion in mineral oil 1.05 g, 0.03 mol) was added portion-wise over 1.5 h. Reaction mixture was stirred at r.t. for a further 16 h. The reaction mixture was cooled to 4° C. and quenched by drop-wise addition of 5% $NaH_2PO_4$ solution (15 mL). The solution was then partitioned between EtOAc (250 mL) and water (200 mL). The organic layer was washed with further water (2×150 mL), sat. NaCl solution (200 mL), then dried, filtered (phase separation cartridge) and concentrated in vacuo to give a yellow oil. The resultant oil was dissolved in anhydrous THF (80 mL) and TBAF (1 M in THF, 30 mL, 0.03 mol) was added. Reaction mixture was then stirred at r.t. for 3 h. After this time the reaction mixture was concentrated in vacuo under reduced pressure and purified by flash silica column chromatography (gradient elution, 0-33% EtOAc in iso-hexane) to give the title compound as a colorless oil (2.10 g, 78%, 5:1 mixture of isomers). $R_f$=0.1 (20% EtOAc/iso-hexane); MS (ES+) consistent with target $(M+H)^+$.

Step 5: lactonization to (1S,4R)-4-(3-fluoro-2-methylphenyl)-2-oxabicyclo[2.2.1]heptan-3-one To a solution of (1S,3S)-methyl 1-(3-fluoro-2-methylphenyl)-3-hydroxycyclopentanecarboxylate (5:1 (1S,3S):(1R:3S) mixture of isomers, 2.10 g, 0.0086 mol) in anhydrous acetonitrile (100 mL) was added DBU (1.44 g, 1.42 mL, 0.0095 mol). The reaction mixture was stirred at 80° C. for 20 h. The reaction mixture was cooled to r.t. and partitioned between DCM (125 mL) and 1 M HCl (100 mL). The organic layer was extracted, washed with water (100 mL), then dried, filtered (phase separation cartridge) and concentrated in vacuo to give a yellow oil. The residue was purified by flash silica column chromatography (gradient elution, 0-40% EtOAc in iso-hexane) to give the title compound (1S,4R)-4-(3-fluoro-2-methylphenyl)-2-oxabicyclo[2.2.1]heptan-3-one as a colorless oil (256 mg); $R_f$=0.3 (33% EtOAc/iso-hexane); MS (ES+) consistent with target $(M+H)^+$; $^1$H NMR δ (ppm)($CDCl_3$): 7.18-7.10 (1 H, m), 7.09-6.98 (2 H, m), 5.00 (1 H, d, J=2.1 Hz), 2.81 (1 H, dd, J=10.4, 2.4 Hz), 2.39-2.32 (1 H, m), 2.32 (3 H, d, J=2.8 Hz), 2.3-2.21 (1 H, m), 2.15-2.07 (2 H, m), 1.93 (1 H, d, J=10.3 Hz); $^{19}$F NMR: −114.43; and unreacted starting material (1S,3S)-methyl 1-(3-fluoro-2-methylphenyl)-3-hydroxycyclopentanecarboxylate as a colorless oil (1.63 g); $R_f$=0.15 (33% EtOAc/iso-hexane); MS (ES+) consistent with target $(M+H)^+$; $^1$H NMR δ (ppm)($CDCl_3$): 7.24 (1 H, d, J=8.03 Hz), 7.19-7.11 (1 H, m), 6.97-6.90 (1 H, m), 4.56-4.49 (1 H, m), 3.62 (3 H, s), 3.07 (1 H, dd, J=13.8, 6.6 Hz), 2.47-2.42 (2 H, m), 2.11 (3 H, d, J=2.8 Hz), 2.10-2.01 (1 H, m), 1.92 (1 H, ddd, J=13.9, 4.5, 1.1 Hz), 1.79-1.70 (1 H, m), 1.38 (1 H, d, J=4.2 Hz); $^{19}$F NMR: −114.83.

Step 6: (S)-methyl 1-(3-fluoro-2-methylphenyl)-3-oxocyclopentanecarboxylate (Intermediate 1)

To a solution of (1S,3S)-methyl 1-(3-fluoro-2-methylphenyl)-3-hydroxycyclopentanecarboxylate (1.60 g, 6.5 mmol) in anhydrous DCM (100 mL) was added Dess-Martin Periodinane (3.32 g, 7.8 mmol). The reaction mixture was stirred at r.t. for 4 h. Reaction mixture was quenched with a mixture of 10% $Na_2S_2O_3$ and sat. $NaHCO_3$ solution (1:1, 100 mL) and then rapidly stirred for 30 min. Organic layers were extracted with further DCM (2×50 mL), then dried, filtered (phase separation cartridge) and concentrated in vacuo to give a pale yellow oil. The residue was purified by flash silica column chromatography (gradient elution, 0-20% EtOAc in iso-hexane) to give the title compound as a colorless solid (1.42 g, 84%). $R_f$=0.25 (33% EtOAc/iso-hexane); $^1$H NMR δ (ppm)($CDCl_3$): 7.28-7.19 (1 H, m), 7.17-7.02 (2 H, m), 3.76 (3 H, s), 3.28 (1 H, d, J=17.9 Hz), 2.88-2.79 (1 H, m), 2.69-2.33 (4 H, m), 2.19 (3 H, d, J=2.7 Hz); SFC (Analytical) (CHIRALPAK IA 5/95 IPA/$CO_2$, 5.0 mL/min, 120 bar, 40° C.) RT 2.1 min (>99.5% ee); Chiral HPLC (Chiralpak IC 10/90 IPA/MeOH (50/50/0.1% formic acid)/heptane, 1.0 mL/min) RT 9.48 min.

Preparation of Intermediate 2: (R)-methyl 1-(3-fluoro-2-methylphenyl)-3-oxocyclopentane-carboxylate Method 2

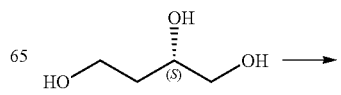

-continued

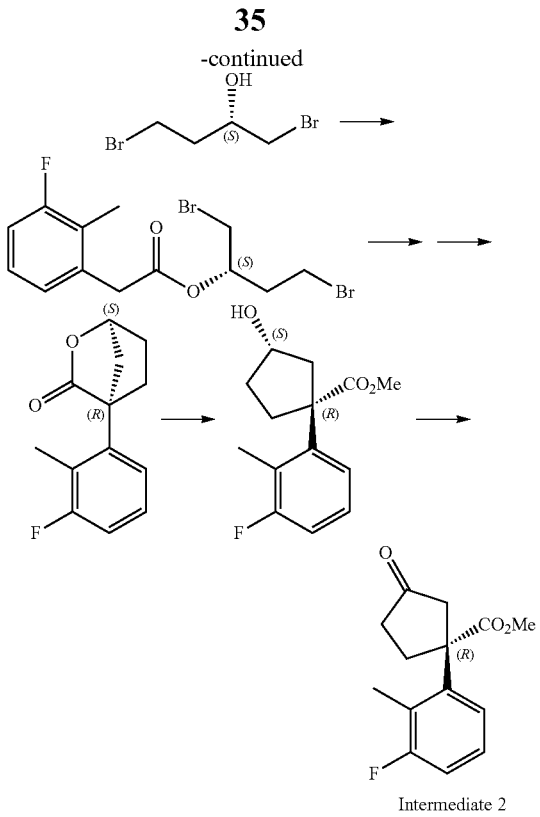

Intermediate 2

Step 1: (S)-1,4-dibromobutan-2-ol

To a stirred solution of (S)-butane-1,2,4-triol (2 g, 18.9 mmol) and triphenylphosphine (9.9 g, 37.7 mmol) in DCM (1 mL) at 0° C. was added N-bromosuccinimide (6.7 g, 37.7 mmol) portionwise. The mixture was allowed to warm to r.t. and stirred for 17 h. The reaction mixture was washed with water (2×100 mL) and sat. brine solution (100 mL) and the organics passed through a phase separator before concentrating in vacuo. The residue was dissolved in DCM (10 mL) and added to rapidly stirred Et$_2$O (200 mL). The resulting solid was removed by vacuum filtration. Additional solid precipitated in the filtrate during filtration, so this process was repeated several times to remove residual triphenylphosphine oxide. The filtrate was concentrated in vacuo and the resulting oil purified by flash silica column chromatography (gradient elution 5% EtOAc in i-hex to 10% EtOAc in i-hex) to give the title compound as a colourless oil (1.5 g, 35%). $^1$H NMR δ (ppm)(CDCl$_3$): 4.09-4.01 (1 H, m), 3.61-3.50 (3 H, m), 3.42 (1 H, dd, J=10.4, 6.7 Hz), 2.18 (1 H, dd, J=5.4, 0.8 Hz), 2.13-2.01 (2 H, m).

Step 2: (S)-1,4-dibromobutan-2-yl 2-(3-fluoro-2-methylphenyl)acetate

To a stirred solution of (S)-1,4-dibromobutan-2-ol (1.43 g, 6.16 mmol) in DCM (30 mL) was added 2-(3-fluoro-2-methylphenyl)acetic acid (941 mg, 5.60 mmol), dicyclohexylcarbodiimide (1.27 g, 6.16 mmol) and DMAP (20 mg, 0.16 mmol) and the mixture stirred at r.t. for 17 h. The reaction was filtered and a white solid was removed by filtration and washed with DCM (30×25 mL). The filtrate was collected and washed with 1 M HCl (30 mL), sat. brine solution (30 mL) and the organics passed through a phase separator and concentrated in vacuo. Purification by flash silica chromatography (gradient elution i-hex to 20% EtOAc in i-hex) gave the title compound as a white crystalline solid (2.06 g, 96%). $^1$H NMR δ (ppm)(CDCl$_3$): 7.15-7.07 (1 H, m), 7.02-6.93 (2 H, m), 5.20-5.12 (1 H, m), 3.70 (2 H, s), 3.58 (1 H, dd, J=11.1, 4.7 Hz), 3.45 (1 H, dd, J=11.1, 4.3 Hz), 3.34 (1 H, ddd, J=10.3, 6.6, 5.5 Hz), 3.25 (1 H, ddd, J=10.3, 8.4, 6.1 Hz), 2.35-2.26 (1 H, m), 2.24 (3 H, d, J=2.7 Hz), 2.26-2.12 (1 H, m).

Step 3: (1S,4R)-4-(3-fluoro-2-methylphenyl)-2-oxabicyclo[2.2.1]heptan-3-one

To a stirred solution of (S)-1,4-dibromobutan-2-yl 2-(3-fluoro-2-methylphenyl)acetate (2.05 g, 5.37 mmol) in 1,4-dioxane (50 mL) at r.t., was added LiHMDS (11.8 mL, 11.8 mmol, 1 M in THF) at a rate of 1 mL/min. After complete addition, the mixture was stirred for 1 h and quenched with 1 M HCl (20 mL) and then extracted into EtOAc (3×50 mL). The combined organics were washed with water (50 mL) and sat. brine solution (50 mL), separated, dried (MgSO$_4$), filtered and concentrated in vacuo. Purification by flash silica chromatography (gradient elution i-hex to 5% EtOAc in i-hex) gave the title compound as a white crystalline solid (890 mg, 75%). $^1$H NMR δ (ppm)(CDCl$_3$): 7.17-7.08 (1 H, m), 7.07-6.97 (2 H, m), 5.00 (1 H, d, J=2.10 Hz), 2.81 (1 H, dd, J=10.4, 2.4 Hz), 2.40-2.18 (2 H, m), 2.30 (3 H, d, 2.3 Hz), 2.13-2.07 (2 H, m), 1.93 (1 H, d, J=10.3 Hz).

Step 4: (1R,3S)-methyl-1-(3-fluoro-2-methylphenyl)-3-hydroxycyclopentanecarboxylate To a stirred solution of (1R,4S)-4-(3-fluoro-2-methylphenyl)-2-oxabicyclo[2.2.1]heptan-3-one (890 mg, 4.05 mmol) in MeOH (30 mL) was added 4 M HCl in dioxane (1 mL). The mixture was heated to 60° C. for 17 h and then concentrated in vacuo. Purification by flash silica chromatography (gradient elution i-hex to 30% EtOAc in i-hex) gave the title compound as a white crystalline solid (766 mg, 75% [95% based on recovered starting material]). $^1$H NMR δ (ppm)(CDCl$_3$): 7.18-7.06 (2 H, m), 6.98-6.89 (1 H, m), 4.42-4.37 (1 H, m), 3.66 (3 H, s), 2.74-2.69 (1 H, m), 2.66-2.58 (1 H, m), 2.55 (1 H, d, J=7.85 Hz), 2.29-2.13 (3 H, m), 2.13 (3 H, d, J=2.7 Hz), 1.83-1.72 (1 H, m).

Step 5: (R)-methyl-1-(3-fluoro-2-methylphenyl)-3-oxocyclopentanecarboxylate (Intermediate 2)

To a solution of (1S,3R)-methyl-1-(3-fluoro-2-methylphenyl)-3-hydroxycyclopentanecarboxylate (766 mg, 3.04 mmol) in anhydrous DCM (20 mL) was added Dess-Martin Periodinane (1.55 g, 3.64 mmol). The reaction mixture was stirred at r.t. for 4 h. The reaction mixture was quenched with a mixture of 10% Na$_2$S$_2$O$_3$ and sat. NaHCO$_3$ solution (1:1, 50 mL) and then rapidly stirred for 30 min. Organic layers were extracted with further DCM (2×50 mL), then dried, filtered (phase separation cartridge) and concentrated in vacuo to give a pale yellow oil. The residue was purified by flash silica column chromatography (gradient elution i-hex to 20% EtOAc in i-hex) to give the title compound as a colorless solid (656 mg, 86%). $^1$H NMR δ (ppm)(CDCl$_3$): 7.28-7.19 (1 H, m), 7.17-7.02 (2 H, m), 3.76 (3 H, s), 3.23 (1 H, d, J=17.9 Hz), 2.88-2.79 (1 H, m), 2.69-2.33 (4 H, m), 2.19 (3 H, d, J=2.7 Hz). SFC (Analytical) (CHIRALPAK IA 5/95 IPA/CO$_2$, 5.0 mL/min, 120 bar, 40° C.) RT 2.4 min; Chiral HPLC (Chiralpak IC 10/90 IPA/MeOH (50/50/0.1% formic acid)/heptane, 1.0 mL/min) RT 10.35 min (95.7% ee).

Step 6: Recrystallization of Intermediate 2

Intermediate 2 (1.8 g, Chiral HPLC: (Chiralpak IC 10/90 IPA/MeOH (50/50/0.1% formic acid)/heptane, 1.0 mL/min) 97.4% ee) was dissolved in minimum hot heptane and the solution allowed to cool. Crystals formed and the supernatant was decanted using a pipette. The process was repeated. The solid crystals were dried in vacuo to give the title compound (1.5 g). Chiral HPLC (Chiralpak IC 10/90 IPA/MeOH (50/50/0.1% formic acid)/heptane, 1.0 mL/min) >99.5% ee).

Preparation of Intermediate 3: (±)-methyl 1-(3-fluoro-2-methylphenyl)-3-oxocyclopentane carboxylate Intermediate 3

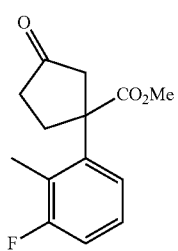

Prepared from (±)-butane-1,2,4-triol following the procedures described in Method 1 for the preparation of Intermediate 1 but omitting the DBU mediated lactonization step (step 5). LCMS (ES+) 251 (M+H)$^+$, RT 3.80 min (Analytical method 1); $^1$H NMR δ (ppm)(CDCl$_3$): 7.28-7.19 (1 H, m), 7.17-7.02 (2 H, m), 3.76 (3 H, s), 3.28 (1 H, d, J=17.9 Hz), 2.88-2.79 (1 H, m), 2.69-2.33 (4 H, m), 2.19 (3 H, d, J=2.7 Hz).

Preparation of Intermediate 4: methyl 3-bromo-1-(3-fluoro-2-methylphenyl)cyclopentane carboxylate Intermediate 4

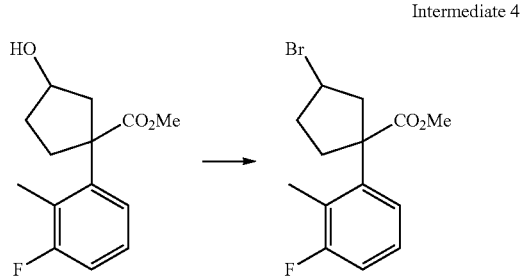 [SMILES: COC(=O)C1(c2cccc(F)c2C)CCC(O)C1 ; COC(=O)C1(c2cccc(F)c2C)CCC(Br)C1]

Bromine (0.225 mL, 4.4 mmol) was added dropwise to a stirred suspension of triphenylphosphine (1.15 g, 4.4 mmol) in MeCN (6.2 mL) under nitrogen at 0° C. Subsequently, a solution of methyl 1-(3-fluoro-2-methylphenyl)-3-hydroxycyclopentanecarboxylate (made following the procedure for the formation of Intermediate 1, steps 1-4, 1.01 g, 4 mmol) in MeCN (2 mL) was added dropwise and the reaction mixture was left to warm up to r.t. and was stirred for 18 h. The excess MeCN was removed in vacuo to give a pale yellow oil. Trituration in ether gave an off-white solid which was filtered and washed with ether and i-hex. The filtrate was evaporated in vacuo to give a pale yellow oil. Purification by flash silica column chromatography (elution 3% EtOAc in i-hex, R$_f$=0.25) gave the title compound as a colorless oil (0.08 g, 64%). MS (ES+) consistent with target (M+H)$^+$; $^1$H NMR δ (ppm)(CDCl$_3$) (1:8 mixture of diastereoisomers): 7.20-7.11 (1H, m), 7.04 (1H, d, J=7.6 Hz), 7.02-6.92 (1 H, m), 4.36-4.28 (1 H, m), 3.68 (3H, s), 3.01 (1 H, dd, J=14.4, 7.6 Hz), 2.80-2.70 (2 H, m), 2.45-2.32 (1 H, m), 2.29-2.15 (2 H, m), 2.10 (3 H, d, J=2.4 Hz).

Preparation of Intermediate 5: (±)-methyl 1-(3-fluoro-2-methylphenyl)-3-(((trifluoromethyl)sulfonyl)oxy)cyclopent-2-enecarboxylate Intermediate 5

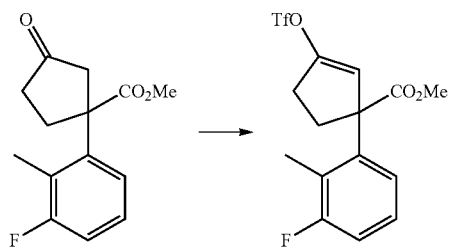

To a solution of Intermediate 3 (1.50 g, 6.00 mmol) in anhydrous THF (12 mL) was added drop-wise NaHMDS (1 M in THF, 6.00 mL, 6.00 mmol) at 0° C. The reaction mixture was stirred at 0° C. for 1 h. After this time N-phenylbistriflimide (2.40 g, 6.48 mmol) was added portionwise with 2 h additional stirring. The reaction mixture was quenched via addition of sat. NH$_4$Cl (5 mL) with rapid stirring for 10 min. The reaction mixture was partitioned between EtOAc (50 mL) and water (50 mL). The organic layer was separated, washed with brine (50 mL), then dried (MgSO$_4$), filtered using a phase separation cartridge and concentrated in vacuo to give a yellow oil. The residue was purified by flash silica column chromatography (gradient elution i-hex to 30% EtOAc in i-hex) to give the title compound as a colorless oil (1.73 g, 75%). MS (ES+) consistent with target (M+H)$^+$; $^1$H NMR δ (ppm)(CDCl$_3$): 7.14 (1 H, q, J=1.6 Hz), 6.97 (2 H, dd, J=1.6 Hz), 5.96 (1 H, s), 3.69 (3 H, s), 3.62-3.30 (1 H, m), 2.88-2.84 (1 H, m), 2.69-2.64 (1 H, m), 2.08 (3 H, d, J=2.4 Hz), 2.02-1.95 (1 H, m).

Comins' reagent (N,N-bis(trifluoromethylsulfonyl)-5-chloro-2-pyridylamine) may also be used in this method, in place of N-phenylbistriflimide.

Preparation of Intermediate 6: (S)-methyl 1-(3-fluoro-2-methylphenyl)-3-(((trifluoromethyl)sulfonyl)oxy)cyclopent-2-enecarboxylate

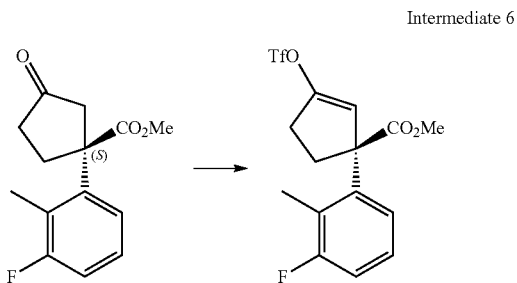

Intermediate 6

Prepared from Intermediate 1 following the procedure for the preparation of Intermediate 5. $^1$H NMR δ (ppm)(CDCl$_3$): 7.14 (1 H, q, J=1.6 Hz), 6.97 (2 H, dd, J=1.6 Hz), 5.96 (1 H, s), 3.69 (3 H, s), 3.62-3.30 (1 H, m), 2.88-2.84 (1 H, m), 2.69-2.64 (1 H, m), 2.08 (3 H, d, J=2.4 Hz), 2.02-1.95 (1 H, m).

Preparation of Intermediate 7: (S)-Methyl 1-phenyl-3-(((trifluoromethyl)sulfonyl)oxy)cyclopent-2-enecarboxylate

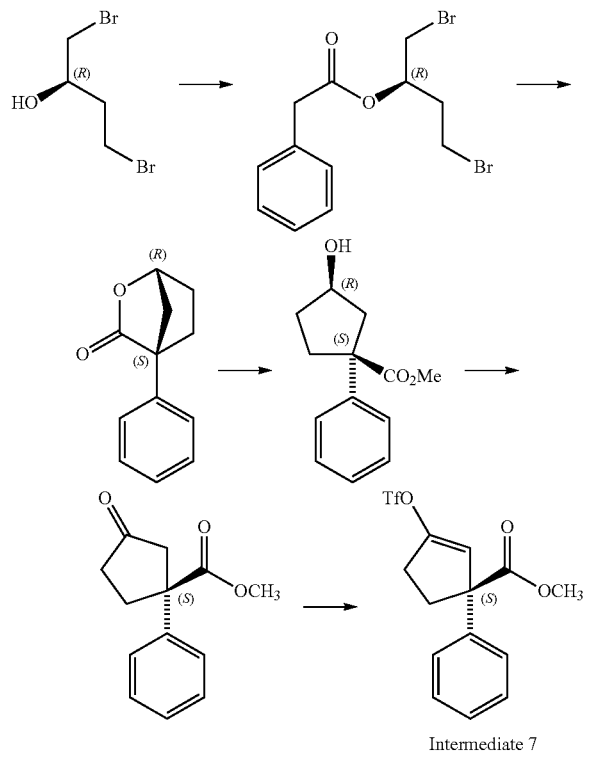

Intermediate 7

Step 1: (R)-1,4-Dibromobutan-2-yl 2-phenyl acetate

To a stirred solution of (R)-1,4-dibromobutan-2-ol (2.70 g, 11.6 mmol), prepared following step 1 of Method 2 using (R)-butane-1,2,4-triol in place of (S)-butane-1,2,4-triol, in DCM (50 mL) was added phenylacetic acid (1.44 g, 10.6 mmol), dicyclohexylcarbodiimide (2.18 g, 10.6 mmol) and DMAP (20 mg, catalytic) and the mixture stirred at r.t for 17 h. The white solid was filtered and washed with DCM (3×25 mL). The filtrate was collected and washed with 1 M HCl(aq) (30 mL), sat. brine solution (30 mL) and the organics passed through a phase separator and concentrated. Purification by flash silica chromatography (gradient elution iso-hexane to 20% EtOAc in iso-hexane) gave the title compound as a white crystalline solid (3.95 g, >99%).

Step 2: (1R,4S)-4-Phenyl-2-oxabicyclo[2.2.1]heptan-3-one

To a stirred solution of (R)-1,4-dibromobutan-2-yl 2-phenyl acetate (3.54 g, 1.1 mmol) in 1,4-dioxane (150 mL) at r.t. was added LiHMDS (24 mL, 1 M in THF, 24 mmol) at a rate of 1 mL/min. After complete addition, the mixture was stirred for 1 h and quenched with 1 M HCl(aq) (20 mL) and then extracted into EtOAc (3×50 mL). The combined organics were washed with water (50 mL) and sat. brine solution (50 mL), separated, dried (MgSO$_4$), filtered and concentrated. Purification by flash silica chromatography (gradient elution, 0-30% EtOAc in iso-hexane) gave the title compound as a white crystalline solid (1.01 g, 53%).

Step 3: (1S,3R)-Methyl 3-hydroxy-1-phenylcyclopentanecarboxylate

To a stirred solution of (1R,4S)-4-phenyl-2-oxabicyclo [2.2.1]heptan-3-one (1.01 g, 5.37 mmol) in MeOH (25 mL) was added 4 M HCl in dioxane (6 mL). The mixture was stirred at r.t for 17 h and then concentrated. Purification by flash silica chromatography (gradient elution, 0 -35% EtOAc in iso-hexane) gave the title compound as a white crystalline solid (699 mg, 59%).

Step 4: (S)-Methyl 3-oxo-1-phenylcyclopentanecarboxylate

To a solution of (1S,3R)-methyl 3-hydroxy-1-phenylcyclopentanecarboxylate (699 mg, 3.18 mmol) in dichloromethane (20 mL) was added Dess-Martin Periodinane (1.62 g, 3.81 mol). The reaction mixture was stirred at r.t. for 3 h. Reaction mixture was quenched with a mixture of 1% Na$_2$S$_2$O$_3$ and sat. aq. NaHCO$_3$ solution (1:1, 50 mL) and then rapidly stirred for 30 minutes. Organic layers were extracted with further CH$_2$Cl$_2$ (2×50 mL), then dried, filtered (phase separation cartridge) and concentrated to give a pale yellow oil. The residue was purified by flash silica column chromatography (gradient elution, 0 -20% EtOAc in iso-hexane) to give the title compound as a colorless solid (656 mg, 86%).

Step 5: (S)-Methyl 1-phenyl-3-(((trifluoromethyl) sulfonyl)oxy)cyclopent-2-enecarboxylate (Intermediate 7)

(S)-Methyl 3-oxo-1-phenylcyclopentanecarboxylate (630 mg, 2.89 mmol) and THF (25 mL) were combined under a nitrogen atmosphere and cooled with an ice bath. NaHMDS (1 M in THF) (5.2 mL, 5.2 mmol) was added dropwise followed after 20 minutes by N-(5-chloropyridin-2-yl)-1,1,1-trifluoro-N-((trifluoromethyl)sulfonyl)methanesulfonamide (1.59 g, 4.05 mmol). Reaction mixture was allowed to warm to room temperature and stirred for 3 hours. Reaction mixture was then diluted with CH$_2$Cl$_2$, washed with water, evaporated to dryness onto silica and purified by flash chromatography to give the title compound as a clear oil (590 mg, 58%).

Preparation of Intermediate 8: Methyl 1-(3-fluoro-2-methylphenyl)-4-oxocyclohexanecarboxylate

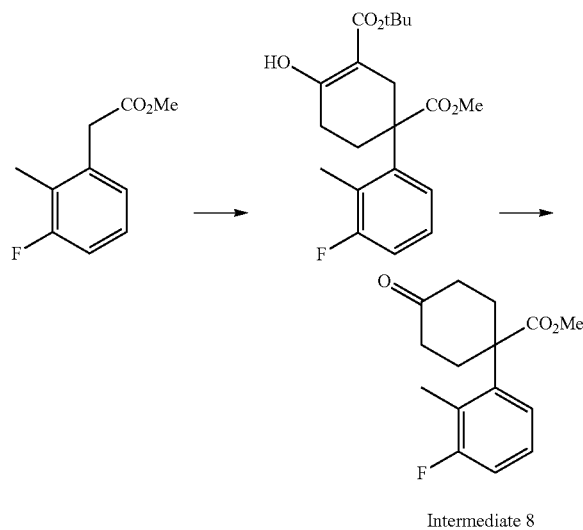

Intermediate 8

Step 1: 3-tert-Butyl 1-methyl 3'-fluoro-4-hydroxy-2'-methyl-1,2,5,6-tetrahydro-[1,1'-biphenyl]-1,3-dicarboxylate Methyl 2-(3-fluoro-2-methylphenyl)acetate (3.13 g, 17.2 mmol), DMF (30 mL) and tert-butyl acrylate (5.22 mL, 36.12 mmol) were combined at room temperature under a nitrogen atmosphere. Reaction mixture was cooled with an ice bath and NaH (6% in oil) (3.44 g, 86 mmol) was added portionwise. Reaction mixture was stirred at room temperature for 20 h and then carefully quenched with sat. aq. NH4Cl solution with ice bath cooling. The reaction mixture was extracted with EtOAc, then washed with water and brine and evaporated to dryness onto silica before purification by flash chromatography. The title compound was obtained as a white solid (2.14 g, 34%).

Step 2: Methyl 1-(3-fluoro-2-methylphenyl)-4-oxo-cyclohexanecarboxylate 3-tert-Butyl 1-methyl 3'-fluoro-4-hydroxy-2'-methyl-1,2,5,6-tetrahydro-[1,1'-biphenyl]-1,3-dicarboxylate (2.14 g, 5.88 mmol) and TFA (10 mL) were combined and stirred at room temperature for 20 h. The TFA was removed by evaporation in vacuo and the residue was azeotroped with toluene. Toluene (100 mL), MeOH (10 mL) and NaHCO3 (200 mg) were added and the mixture was heated to 105° C. for 20 h. The reaction mixture was then evaporated to dryness onto silica and purified by flash chromatography to give the title compound as a white solid (799 mg, 52%). MS (ES+) consistent with target (M+H)+.

Preparation of Intermediate 9: (S)-4-methoxybenzyl 1-(3-fluoro-2-methylphenyl)-3-(((trifluoromethyl)sulfonyl)oxy)cyclopent-2-enecarboxylate

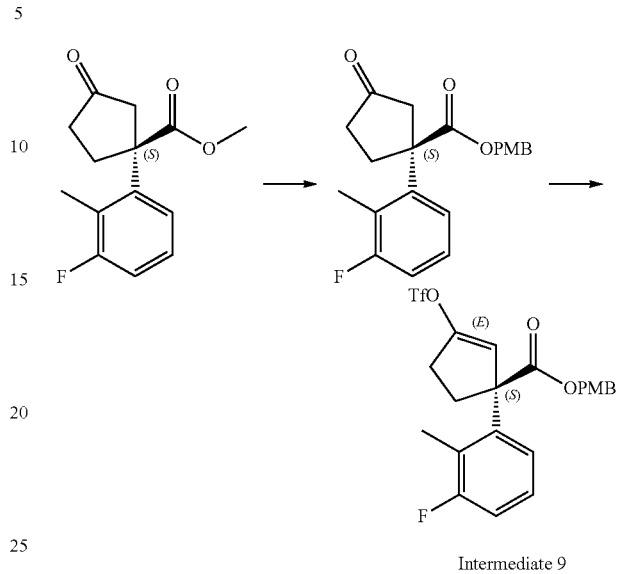

Intermediate 9

Step 1: (S)-4-methoxybenzyl 1-(3-fluoro-2-methylphenyl)-3-oxocyclopentanecarboxylate To a solution of Intermediate 1 (4.00 g, 15.6 mmol) in methanol (60 mL) was added lithium hydroxide hydrate (0.36 g, 85.0 mmol) and the reaction mixture heated to 65° C. under N2 for 2 h. After this time the reaction mixture was cooled to r.t. and residual methanol was removed under reduced pressure. The aqueous layer was diluted with additional water (45 mL) and extracted with dichloromethane (3×20 mL). Combined organics were discarded and the aqueous layer acidified to pH 5 using 1 N HCl, then extracted with EtOAc (3×50 mL). The combined organic layers were washed with brine (65 mL), then dried, filtered (phase separation cartridge) and concentrated to give the crude carboxylic acid.

To a solution of the crude acid (3.70 g, assumed quantitative yield, 15.6 mmol) in anhydrous acetonitrile (150 mL) was added cesium carbonate (9.76 g, 34.0 mmol), potassium iodide (0.40 g) and 4-methoxybenzychloride (3.20 g, 20.4 mmol) and the reaction mixture heated to 65° C. under N2 for 24 h. After this time the reaction mixture was cooled to r.t. and filtered through Celite, washing with EtOAc (3×50 mL). The filtrate was dried, filtered (phase separation cartridge) and concentrated. The crude reaction material was purified by silica chromatography (gradient elution, 0-33% EtOAc in iso-hexane) to give the title compound as a pale yellow oil (3.88 g, 64%).

$^1$H NMR δ (ppm)(CDCl3): 7.23-7.15 (1 H, m), 7.14 (2 H, d, J=8.3 Hz), 7.09-6.94 (2 H, m), 6.83 (2 H, d, J=8.2 Hz), 5.07 (2 H, d, J=2.2 Hz), 3.80 (3 H, s), 3.20 (1 H, d, J=17.9 Hz), 2.76-2.66 (1 H, m), 2.59-2.50 (1 H, m), 2.47 (1 H, d, J=17.8 Hz), 2.41-2.25 (2 H, m), 1.97 (3 H, d, J=2.8 Hz).

Step 2: (S)-4-methoxybenzyl 1-(3-fluoro-2-methylphenyl)-3-(((trifluoromethyl)sulfonyl)oxy)cyclopent-2 enecarboxylate (Intermediate 9)

To a solution of (S)-4-methoxybenzyl 1-(3-fluoro-2-methylphenyl)-3-oxocyclopentanecarboxylate (2.00 g, 5.61 mmol) in anhydrous THF (65 mL) was added drop-wise KHMDS (0.7 M in Toluene, 10 mL, 6.75 mmol) at −78° C. The reaction mixture was stirred at −78° C. for 1 h. After this time (N,N-bis(trifluoromethylsulfonyl)-5-chloro-2-pyridylamine) (3.80 g, 6.75 mmol) was added dropwise as solution in THF (10 mL) with 2 h additional stirring. The reaction mixture was quenched via addition of sat. aq. NH$_4$Cl (5 mL) with rapid stirring for 10 min. The reaction mixture was partitioned between EtOAc (50 mL) and water (50 mL). Organic layers were extracted, washed with brine (50 mL), then dried, filtered using a phase separation cartridge and concentrated to give a yellow oil. The crude reaction material was purified by flash silica chromatography (gradient elution, 0-20% EtOAc in iso-hexane) to give the title compound as a pale yellow oil (3.80 g, 75%).

$^1$H NMR δ (ppm)(CDCl$_3$): 7.18-7.10 (3 H, m), 7.01-6.91 (2 H, m), 6.85-6.80 (2 H, m), 5.90 (1 H, t, J=1.9 Hz), 5.12-5.01 (2 H, m), 3.80 (3H, s), 3.29 (1 H, ddd, J=13.2, 9.3, 4.2 Hz), 2.90-2.80 (1 H, m), 2.64 (1 H, dddd, J=16.5, 9.7, 4.2, 1.9 Hz), 2.01-1.93 (1 H, m), 1.93 (3 H, d, J=2.5 Hz).

Preparation of Intermediate 10: (S)-methyl 1-(3,4-difluoro-2-methylphenyl)-3-(((trifluoromethyl)sulfonyl)oxy)cyclopent-2-enecarboxylate

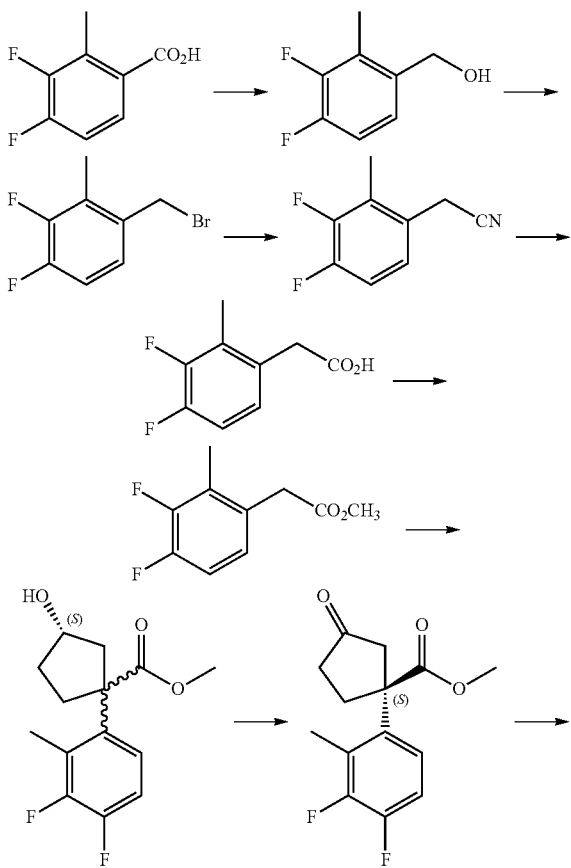

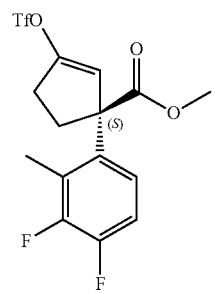

Intermediate 10

Step 1: (3,4-difluoro-2-methylphenyl)methanol

To a solution of 3,4-difluoro-2-methylbenzoic acid (9.50 g, 55.2 mmol) in anhydrous dichloromethane (200 mL) was added oxalyl chloride (8.57 g, 67.5 mmol, 6 mL) and DMF (0.1 mL) and the reaction mixture stirred at r.t. for 1 h and then refluxed for a further 1.5 h. After this time the reaction mixture was cooled to r.t. and concentrated under reduced pressure to give the crude acid chloride as a yellow oil. The crude mixture was dissolved in anhydrous THF (150 mL) and sodium borohydride (6.26 g, 166 mmol) added portion-wise at 0° C. The pale yellow suspension was stirred at 0° C. for 1 h then at r.t. for a further 20 h. After this time the reaction was carefully quenched with ice-water (25 mL), and volatile solvents removed under reduced pressure. The residue was partitioned between EtOAc (200 mL) and water (150 mL). The organic layers were extracted, washed with brine (150 mL) then dried, filtered (phase separation cartridge) and concentrated to give a colorless oil. The oil was triturated from iso-hexane/diethyl ether to give the title compound as a colorless solid (7.2 g, 82%).

Step 2: 1-(bromomethyl)-3,4-difluoro-2-methylbenzene

To a 4° C. solution of (3,4-difluoro-2-methylphenyl)methanol (7.0 g, 44.2 mmol) and carbon tetrabromide (17.6 g, 53.2 mmol) in anhydrous dichloromethane (100 mL) was added a dropwise solution of triphenylphosphine (14.0 g, 53.2 mmol) in DCM (25 mL). The reaction mixture was warmed to r.t. and stirred for 20 h. After this time the reaction mixture was concentrated under reduced pressure and the crude residue passed through a pad of silica gel (elution: iso-hexane/diethyl ether). Fractions containing the desired product were concentrated under reduced pressure to give a pale yellow oil. The crude reaction material was purified by flash silica chromatography (gradient elution iso-hexane to 20% EtOAc in iso-hexane) to give the title compound as a pale yellow oil (11.8 g) in an approximately 5:1 ratio with bromoform.

Step 3: 2-(3,4-difluoro-2-methylphenyl)acetonitrile

To a 4° C. solution of 1-(bromomethyl)-3,4-difluoro-2-methylbenzene (10.0 g, 45.2 mmol) and sodium cyanide (3.32 g, 67.8 mmol) in DMF (65 mL) was added water (8 mL). The reaction mixture was stirred at 4° C. for 3 hours. After this time the reaction mixture was partitioned between sat. aq. NaHCO$_3$/water (1:1, 300 mL) and diethyl ether (200 mL). The aqueous layer was extracted with diethyl ether (2×200 mL); the combined organics were washed with brine (150 mL) then dried, filtered (phase separation cartridge) and concentrated to give a brown oil. The crude reaction material was purified by flash silica chromatography (gradient elution, 0-33% EtOAc in iso-hexane) to give the title compound as a yellow oil (6.2 g, 83%).

Step 4: 2-(3,4-difluoro-2-methylphenyl)acetic acid

To a solution of 2-(3,4-difluoro-2-methylphenyl)acetonitrile (6.20 g, 37.1 mmol) in acetic acid (30 mL) was added c.$H_2SO_4$/water (1:1, 25 mL) and the reaction mixture was refluxed for 24 h. After this time the reaction mixture was cooled to r.t. and adjusted to pH 3 using solid $Na_2CO_3$. The aqueous reaction mixture was then extracted with dichloromethane (3×5 mL). The combined organics were washed with water (65 mL) and brine (65 mL), then dried, filtered (phase separation cartridge) and concentrated to give a pale yellow solid. The solid was triturated from iso-hexane/diethyl ether to give the title compound as a colorless solid (6.5 g, 94%).

Step 5: methyl 2-(3,4-difluoro-2-methylphenyl)acetate

To a solution of 2-(3,4-difluoro-2-methylphenyl)acetic acid (6.52 g, 35.0 mmol) in methanol (100 mL) was added c.$H_2SO_4$ (0.1 mL, cat.) and the reaction mixture was refluxed for 20 h. After this time the reaction mixture was cooled to r.t. and concentrated under reduced pressure. The crude residue was partitioned between EtOAc (75 mL) and sat. aq. $NaHCO_3$/water (1:1, 50 mL). The aqueous layer was extracted with EtOAc (2×50 mL); the combined organics washed with brine (50 mL), dried, filtered (phase separation cartridge) and concentrated to give a pale yellow oil. The crude reaction material was purified by flash silica chromatography (gradient elution, 0 -15% EtOAc in iso-hexane) to give the title compound as a colorless oil (7.12 g, 95%).

Step 6: (1S,3S)-methyl 1-(3,4-difluoro-2-methylphenyl)-3-hydroxycyclopentanecarboxylate To a solution of (S)-tert-butyl((1,4-dibromobutan-2-yl)oxy)diphenylsilane (4.70 g, 0.010 mol) and methyl 2-(3,4-difluoro-2-methylphenyl)acetate (2.0 g, 0.010 mol) in anhydrous DMF (90 mL) was added 18-crown-6 (0.1 g). The reaction mixture was stirred at r.t. for 10 min then sodium hydride (60% dispersion in mineral oil 0.96 g, 0.025 mol) was added portion-wise over 1.5 h. Reaction mixture was stirred at r.t. for a further 1.5 h. The reaction mixture was cooled to 4° C. and quenched by drop-wise addition of sat. aq. $NH_4Cl$ solution (10 mL) and residual DMF removed under reduced pressure. The residue was then partitioned between $Et_2O$ (240 mL) and water (100 mL). The organic layer was washed with further water (150 mL) and brine (200 mL), then dried, filtered (phase separation cartridge) and concentrated to give a yellow oil. This oil was dissolved in anhydrous THF (75 mL) and TBAF (1 M in THF, 0.02 mol, 20 mL) was added. Reaction mixture was then stirred at r.t. for 2 h. After this time the reaction mixture was concentrated under reduced pressure and purified by silica column chromatography (gradient elution, 0-40% EtOAc in iso-hexane) to give the title compound as a colorless oil (2.30 g, 83%, 8:1 mixture with (1R,3S)-methyl 1-(3,4-difluoro-2-methylphenyl)-3-hydroxycyclopentanecarboxylate). 625 mg of the title compound was separated from the mixture of isomers. $R_f$=0.1 (20% EtOAc/iso-hexane); MS (ES+) consistent with target (M+H)⁺.

Step 7: (S)-methyl 1-(3,4-difluoro-2-methylphenyl)-3-oxocyclopentanecarboxylate

To a solution of (1S,3S)-methyl 1-(3,4-difluoro-2-methylphenyl)-3-hydroxycyclopentanecarboxylate (0.6 g, 2.2 mmol) in anhydrous dichloromethane (30 mL) was added Dess-Martin Periodinane (1.20 g, 2.76 mmol). The reaction mixture was stirred at r.t. for 20 h. Reaction mixture was quenched with a mixture of 10% $Na_2S_2O_3$ and sat. aq. $NaHCO_3$ solution (1:1, 100 mL) and then rapidly stirred for 30 min. Organic layers were extracted with further $CH_2Cl_2$ (2×50 mL), then dried, filtered (phase separation cartridge) and concentrated to give a pale yellow oil. The residue was purified by silica column chromatography (gradient elution, 0-20% EtOAc in iso-hexane) to give the title compound as a colorless oil (0.58 g, 92%, >99.5% ee).

Step 8: (S)-methyl 1-(3,4-difluoro-2-methylphenyl)-3-(((trifluoromethyl)sulfonyl)oxy)cyclopent-2-enecarboxylate Prepared following the method used in step 2 in the synthesis of Intermediate 9 using (S)-methyl 1-(3,4-difluoro-2-methylphenyl)-3-oxocyclopentanecarboxylate in place of (S)-4-methoxybenzyl 1-(3-fluoro-2-methylphenyl)-3-oxocyclopentanecarboxylate.

Preparation of Examples

General Synthetic Methods

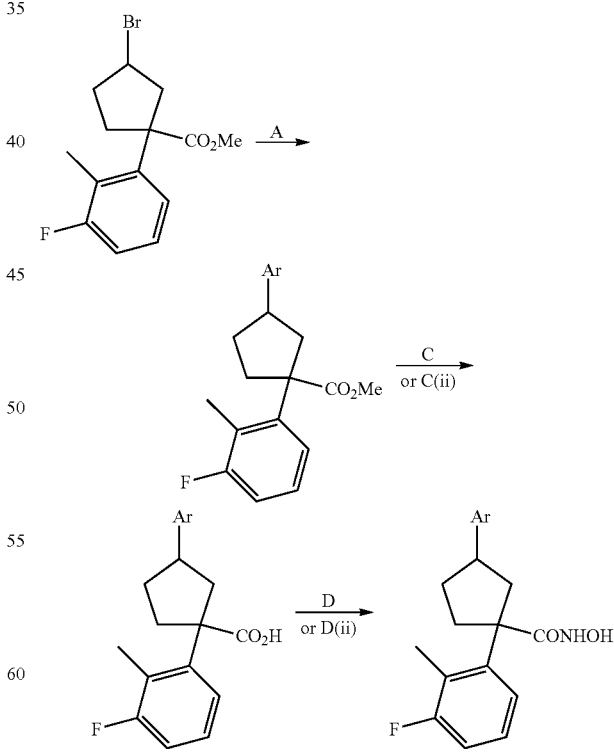

Method A (Suzuki-Miyaura Coupling)
To Intermediate 4 (394 mg, 1.25 mmol) in a sealed tube under nitrogen was added bathophenanthroline (41.6 mg, 0.125 mmol), aryl trifluoroborate potassium salt (1.275 mmol), NiBr$_2$.glyme (38.6 mg, 0.125 mmol) and s-BuOH (2.5 mL). To this was added LiHMDS (1 M in THF, 3.75 mL, 3.75 mmol). The reaction mixture was stirred at 60° C., under nitrogen, for 16 h. The mixture was diluted with EtOAc and passed through a short plug of silica, which was washed thoroughly with EtOAc. The filtrate was concentrated in vacuo.

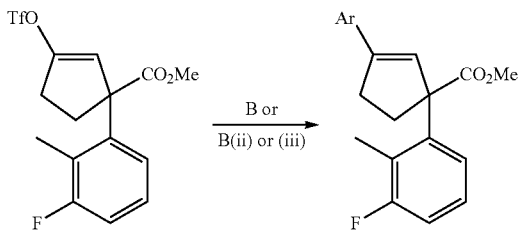

Method B (Suzuki Coupling)

To a solution of methyl 1-(3-fluoro-2-methylphenyl)-3-(((trifluoromethyl)sulfonyl)oxy)cyclopent-2-enecarboxylate (0.5 g, 1.31 mmol) in 1,2 dimethoxyethane (8 mL) was added boronic acid (1.31 mmol), potassium carbonate (0.362 g, 2.62 mmol) and water (4 mL). The reaction mixture was heated to 60° C. at which time a colorless solution formed. [1,1'-Bis(diphenylphosphino)ferrocene]dichloropalladium(II), complex with dichloromethane (0.06 g, 0.07 mmol) was added and the reaction mixture was heated to 80° C. under N$_2$ for 2 h. After this time the reaction mixture was cooled to r.t. and filtered through Celite, washing with EtOAc (3×10 mL). Combined organics were extracted with water (15 mL) then brine (20 mL). EtOAc layers were then dried, filtered (phase separation cartridge) and concentrated to give a brown residue.

Method B (ii) (Suzuki Coupling)

To a solution of methyl-1-(3-fluoro-2-methylphenyl)-3-(((trifluoromethyl)sulfonyl)oxy)cyclopent-2-enecarboxylate (0.2 g, 0.5 mmol) in 1,2 dimethoxyethane (8 mL) was added bis(pinacolato)diboron (0.15 g, 0.6 mmol), potassium acetate (00.6 g, 0.6 mmol), [1,1'-Bis(diphenylphosphino)ferrocene]dichloropalladium(II), complex with dichloromethane (0.03 g, 0.02 mmol) and water (2 mL). The reaction mixture was heated to 80° C. under N$_2$ for 2 h. After this time the reaction mixture was cooled to r.t. and aryl bromide (0.57 mmol), potassium carbonate (0.036 g, 1.31 mmol) and tetrakis(triphenylphosphine)palladium(0) (0.03 g, 0.026 mmol) were added and the reaction mixture heated to 110° C. under N$_2$ for 2 h. Reaction mixture was cooled to r.t. and filtered through Celite, washing with EtOAc (3×10 mL). Combined organics were extracted with water (15 mL) then brine (20 mL). EtOAc layers were then dried, filtered (phase separation cartridge) and concentrated.

Method B (iii) (Suzuki Coupling)

To a solution of methyl-1-(3-fluoro-2-methylphenyl)-3-(((trifluoromethyl)sulfonyl)oxy)cyclopent-2-enecarboxylate (0.3 g, 0.78 mmol) in 1,4 dioxane (8 mL) was added bis(pinacolato)diboron (0.298 g, 1.17 mmol), potassium acetate (0.154 g, 1.56 mmol), tris(dibenzylideneacetone)dipalladium(), (0.215 g, 0.24 mmol) and S-Phos (0.038 g, 0.094 mmol). The reaction mixture was heated to 80° C. under N$_2$ for 2 h. After this time the reaction mixture was cooled to r.t. and aryl bromide (0.86 mmol), cesium carbonate (0.51 g, 1.57 mmol) and palladium tetrakis(triphenylphosphine) (0.045 g, 0.039 mmol) were added and the reaction mixture heated to 110° C. under N$_2$ for 1 h. Reaction mixture was cooled to r.t. and filtered through Celite, washing with EtOAc (3×10 mL). Combined organics were extracted with water (15 mL) then brine (20 mL). EtOAc layers were then dried, filtered (phase separation cartridge) and concentrated.

Method B (iv) (Suzuki Coupling)

To a solution of aryl halide (0.400 g, 1.58 mmol) in dioxane (7 mL) was added bis(neopentyl glycolato)diboron (0.356 g, 1.58 mmol), potassium acetate (0.281 g, 2.87 mmol) and [1,1'-bis(diphenylphosphino)ferrocene]dichloropalladium(II), complex with dichloromethane (0.035 g, 0.04 mmol) and the reaction mixture heated to 100° C. under N$_2$ for 1 h. After this time the reaction mixture was cooled to r.t. and a solution of (S)-4-methoxybenzyl 1-(3-fluoro-2-methylphenyl)-3-(((trifluoromethyl)sulfonyl)oxy)cyclopent-2 enecarboxylate (0.70 g, 1.43 mmol) in anhydrous dioxane (1 mL) was added followed by a solution of cesium carbonate (0.70 g, 2.15 mmol) in water (1.2 mL). The reaction mixture was recapped and heated to 1° C. under N$_2$ for a further 2 h. Reaction mixture water was decanted, and the dioxane layers were then concentrated under reduced pressure.

Method C (Ester Hydrolysis)

To a solution of the ester in methanol (7 mL) was added 15% w/v sodium hydroxide solution (3 mL). The reaction mixture was capped and heated at 60° C. for 18 h. After this time the contents were cooled to r.t. and methanol was removed under reduced pressure. Aqueous residues were partitioned between EtOAc (40 mL) and 1 M aqueous HCl (20 mL). Organic layers were extracted, washed with brine (40 mL), dried, filtered (phase separation cartridge) and concentrated to give a colorless residue.

Method C (ii) (Ester Hydrolysis)

To a solution of the ester (0.0393 mmol) in MeOH (2 mL) was added 2 M KOH (0.075 mL, 1.5 mmol). The reaction mixture was heated at 120° C. for 2 h under microwave irradiation. The mixture was chilled (ice bath), neutralized to pH~7 with 2 M HCl (0.75 mL) and diluted with H$_2$O (5 mL). The mixture was extracted with EtOAc (2×20 mL) and the combined organic layers were dried (MgSO$_4$), filtered and concentrated in vacuo.

Method C (iii) (Ester Hydrolysis)

To a solution of ester (0.14 mmol) in THF/methanol/water (1:1:0.5, 2.5 mL) was added lithium hydroxide hydrate (0.03 g, 0.70 mmol). The reaction mixture was capped and heated at 65° C. for 18 h. After this time the contents were cooled to r.t. and methanol was removed under reduced pressure. Aqueous residues were partitioned between EtOAc (15 mL) and 1 M aqueous HCl (15 mL). Organic layers were extracted, washed with brine (20 mL), dried, filtered (phase separation cartridge) and concentrated.

Method D (Hydroxamic Acid Formation)

To a solution of carboxylic acid (0.08 g, 0.27 mmol) and triethylamine (0.08 g, 115 µL, 0.81 mmol) in anhydrous DMF (3 mL) was added tetramethylfluoroformamidinium hexafluorophosphate (0.09 g, 0.35 mmol) at 0° C. The reaction mixture was stirred at this temperature for 15 min, then O —(tetrahydro-2H-pyran-2-yl)hydroxylamine (0.05 g, 0.41 mmol) was added in a single portion. Reaction mixture was then stirred at r.t. for 24 h. After this time the reaction mixture was quenched by the addition of 1 M HCl solution (5 mL). The reaction was partitioned between EtOAc (30 mL) and 1 M HCl (15 mL). The organic layer was separated, washed with brine (40 mL), dried, filtered (phase separation cartridge) and concentrated to give the crude THP protected hydroxamic acid as a pale yellow oil. To this oil was added anhydrous methanol (3 mL) and 4 M HCl in dioxane (2 mL). The reaction mixture was stirred at r.t. for 30 min. After this time solvents were removed under reduced pressure to give crude hydroxamic acid which was purified by preparative HPLC.

Method D (ii) (Hydroxamic Acid Formation)

To a solution of the cyclopentanecarboxylic acid (0.284 mmol) in anhydrous DCM (4.2 mL) was added oxalyl chloride (0.106 mL, 1.25 mmol). The reaction was stirred at r.t. under nitrogen for 16 h. The excess reagent and DCM were removed under reduced pressure and the solid obtained was resuspended in anhydrous DCM (3 mL). To this was added 50% aqueous $NH_2OH$ (0.5 mL) and the reaction mixture was stirred at r.t. for 4 h. The mixture was chilled (ice bath), neutralized to pH~7 with 2 M HCl (0.8 mL) and diluted with $H_2O$ (2 mL). The mixture was extracted with EtOAc (3 mL) and the organic layer was dried ($MgSO_4$), filtered and concentrated in vacuo. Purification by preparative HPLC.

Method E (Cyclopentane Formation)

Substituted benzene acetic acid methyl ester (5.38 mmol), DMF (20 mL), 1,4-diiodobutane (0.71 mL, 5.38 mmol) and NaH (60% in oil, 440 mg, 11 mmol), were combined at r.t. under a nitrogen atmosphere and stirred for 22 h. Reaction mixture was then diluted with EtOAc (50 mL) and washed with water (4×20 mL) and brine (20 mL). The organic layer was dried ($MgSO_4$) and concentrated in vacuo.

Method F (Alkene Hydrogenation)

Alkene (0.74 mmol), 20% w/w Pd/C (60 mg) and ammonium formate (7.4 mmol) were suspended in MeOH (40 mL) or EtOH (40 mL) and stirred at reflux for 2 h. After cooling to r.t. the solids were removed by filtration through Celite, washing with EtOAc (3×20 mL). The filtrate was concentrated and the residue partitioned between water (40 mL) and DCM (20 mL). The organic layer was extracted with DCM (3×20 mL) and the combined organic extracts were dried (phase separation cartridge) and concentrated.

EXAMPLES

Where the absolute configuration of a single isomer is not known the configuration has been putatively assigned and is shown with an asterisk. For example (1S,3R*)-1-(3-fluoro-2-methyl-phenyl)-3-(5-fluoropyridin-3-yl)-N-hydroxycyclopentanecarboxamide is a single isomer for which the configuration at C1 is known absolutely but the configuration at C3 has been putatively assigned. Similarly, (1R*, 3R*)-1-(3-fluoro-2-methylphenyl)-N-hydroxy-3-phenylcyclopentanecarboxamide is a single isomer for which the configuration at both C1 and C3 has been putatively assigned.

Compounds are referred to as Diastereomer 1 (D1), Diastereomer 2 (D2) etc. where single isomers have been separated and tested but the absolute configuration of each isomer has not been determined.

Compounds are referred to as Diastereomer 1 racemic (D1, rac), Diastereomer 2 racemic (D2, rac) where diastereomers have been separated and tested as racemic mixtures and the relative configuration of each diastereomer has not been determined.

Example 1

1-(3-fluoro-2-methylphenyl)-N-hydroxy-3-(pyridin-3-yl)cyclopentanecarboxamide

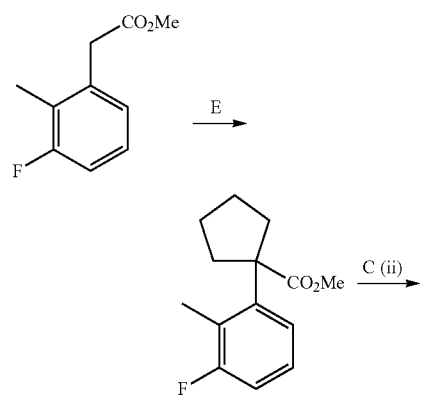

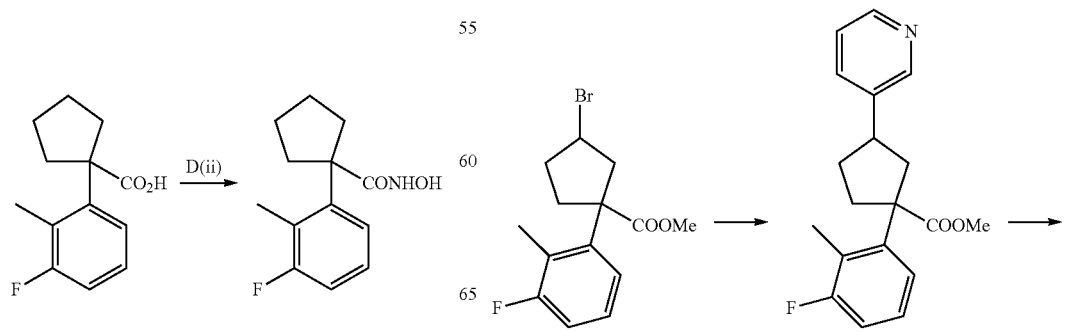

-continued

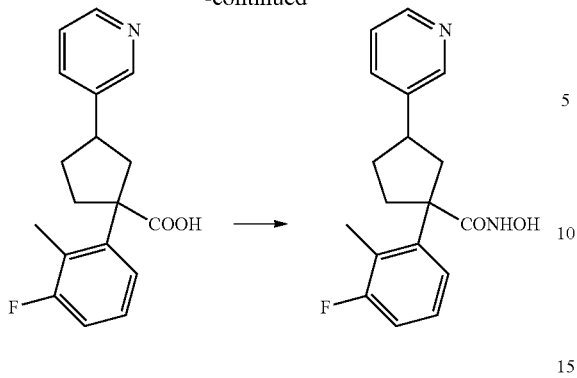

Step 1: methyl 1-(3-fluoro-2-methylphenyl)-3-(pyridin-3-yl)cyclopentanecarboxylate Following Method A, from Intermediate 4 (394 mg, 1.25 mmol), bathophenanthroline (41.6 mg, 0.125 mmol), potassium pyridine-3-trifluoroborate (236 mg, 1.275 mmol), NiBr$_2$.glyme (38.6 mg, 0.125 mmol) and s-BuOH (2.5 mL) were combined. To this was added LiHMDS (1 M in THF, 3.75 mL, 3.75 mmol). The brown product was purified by flash silica column chromatography (elution 50% EtOAc in i-hex, R$_f$=0.47) to give the title compound as a pale yellow oil (123 mg, 31%). MS (ES+) consistent with target (M+H)$^+$; $^1$H NMR δ (ppm)(CDCl$_3$) (1:1 mixture of diastereoisomers): 8.55-8.49 (1 H, m), 8.48-8.40 (1 H, m), 7.78-7.72 (0.5 H, m), 7.55-7.48 (0.5 H, m), 7.30-7.12 (3 H, m), 7.05-6.95 (1 H, m), 3.68 (1.5 H, s), 3.67 (1.5 H, s), 3.42-3.30 (0.5 H, m), 3.25-3.13 (0.5 H, m), 3.08 (0.5 H, dd, J=14.4, 7.6 Hz), 2.80-2.65 (2 H, m), 2.55-2.45 (0.5 H, m), 2.42-2.29 (2 H, m), 2.28-2.19 (0.5H, m), 2.18-2.05 (0.5H, m), 2.15 (1.5H, d, J=2.4 Hz), 2.10 (1.5H, d, J=2.4 Hz).

Step 2: 1-(3-fluoro-2-methylphenyl)-3-(pyridin-3-yl)cyclopentanecarboxylic acid

Following Method C (ii) from methyl 1-(3-fluoro-2-methylphenyl)-3-(3-pyridyl)cyclopentanecarboxylate (123 mg, 0.393 mmol) to give the title compound as an off-white solid (85 mg, 72%). MS (ES+) consistent with target (M+H)$^+$.

Step 3: 1-(3-fluoro-2-methylphenyl)-N-hydroxy-3-(pyridin-3-yl)cyclopentanecarboxamide Following Method D (ii) from 1-(3-fluoro-2-methylphenyl)-3-(3-pyridyl)cyclopentanecarboxylic acid (85 mg, 0.284 mmol). Purification by preparative HPLC gave the title compound as a racemic 2:1 mixture of diastereoisomers (6.8 mg, 8%). LCMS (ES+) 315 (M+H)$^+$, RT 2.22 min (Analytical method 1); $^1$H NMR δ (ppm)(DMSO-d$_6$): 10.01 (0.33 H, s), 9.92 (0.67H, s), 8.69 (0.33 H, s), 8.67 (0.67 H, s), 8.57-8.39 (2 H, m), 7.85-7.65 (1 H, m), 7.39-6.95 (4 H, m), 3.20-3.05 (1 H, m), 2.80-2.56 (2 H, m), 2.41-2.32 (1 H, m), 2.25-1.95 (5 H, m), 1.80-1.65 (1 H, m).

Example 2

(±)-(1S*,3R*)-1-(3-fluoro-2-methylphenyl)-N-hydroxy-3-(pyrimidin-5-yl)cyclopentanecarboxamide (D1, rac)

Example 3

(±)-(1S*,3S*)-1-(3-fluoro-2-methylphenyl)-N-hydroxy-3-(pyrimidin-5-yl)cyclopentanecarboxamide (D2, rac)

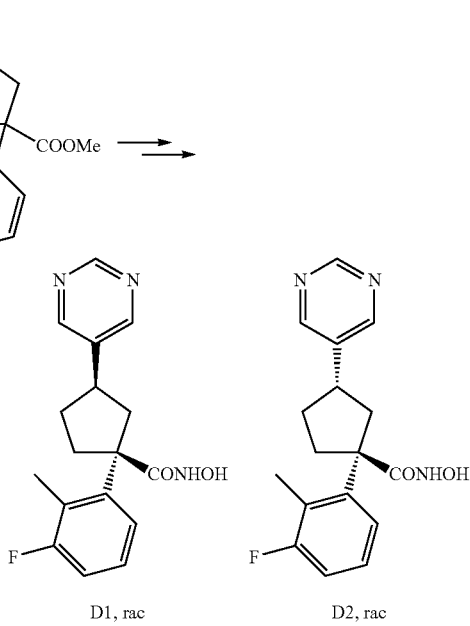

Relative Stereochemistry Putatively Assigned

Prepared following Method A, C (ii) and D (ii) from Intermediate 4 and potassium pyrimidine-5-trifluoroborate, analogous to the example described above.

Example 2 (Diastereomer 1 (D1, rac)): LCMS (ES+) 316 (M+H)$^+$, RT 2.82 min (Analytical method 1); $^1$H NMR δ (ppm)(DMSO-d$_6$): 10.02 (1 H, s), 9.03 (1 H, s), 8.72 (2 H, s), 8.69 (1 H, d, J=1.8 Hz), 7.31 (1 H, d, J=8.0 Hz), 7.25-7.16 (1 H, m), 7.06 (1 H, t, J=8.9 Hz), 3.30-3.18 (1 H, m), 2.99 (1 H, dd, J=12.5, 6.8 Hz), 2.80-2.70 (1 H, m), 2.30-2.20 (2 H, m), 2.14 (3 H, d, J=2.8 Hz), 2.12-2.07 (1 H, m), 1.80-1.72 (1 H, m).

Example 3 (Diastereomer 2 (D2, rac)): LCMS (ES+) 316 (M+H)', RT 2.94 min (Analytical method 1); $^1$H NMR δ (ppm)(DMSO-d$_6$): 9.95 (1 H, s), 9.05 (1 H, s), 8.82 (2 H, s), 8.69 (1 H, d, J=1.7 Hz), 7.32-7.19 (2 H, m), 7.08 (1 H, t, J=8.9 Hz), 3.19-3.08 (1 H, m), 2.68 (1 H, dd, J=13.2, 10.1 Hz), 2.63-2.55 (1 H, m), 2.42-2.32 (1 H, m), 2.28-2.11 (2 H, m), 2.09 (3 H, d, J=2.7 Hz), 1.83-1.71 (1 H, m).

Example 4

(1R*,3S*)-1-(3-fluoro-2-methylphenyl)-N-hydroxy-3-phenylcyclopentanecarboxamide (D1)

Example 5

(1S*,3R*)-1-(3-fluoro-2-methylphenyl)-N-hydroxy-3-phenylcyclopentanecarboxamide (D2)

Example 6

(1S*,3S*)-1-(3-fluoro-2-methylphenyl)-N-hydroxy-3-phenylcyclopentanecarboxamide (D3)

Example 7

(1R*,3R*)-1-(3-fluoro-2-methylphenyl)-N-hydroxy-3-phenylcyclopentanecarboxamide (D4)

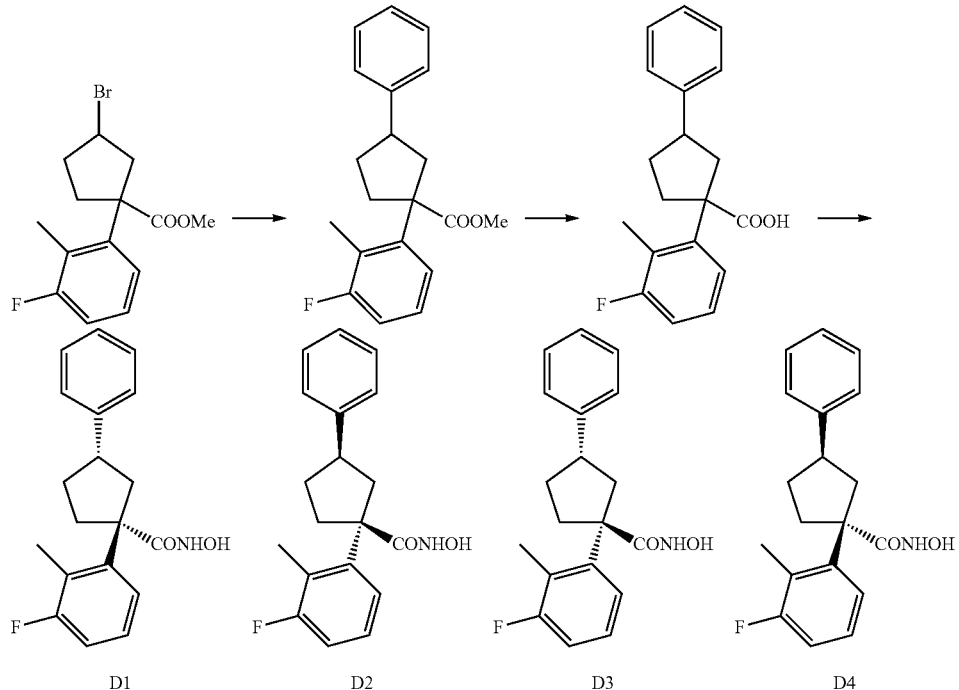

Relative and Absolute Stereochemistry Putatively Assigned

Step 1: methyl 1-(3-fluoro-2-methylphenyl)-3-phenylcyclopentanecarboxylate

Following Method A from Intermediate 4 (0.63 g, 2.00 mmol) and phenyl trifluoroborate potassium salt. The residue was purified by flash silica column chromatography (gradient elution iso-hexane to 50% EtOAc in i-hex) to give the title compound as a colorless oil (0.4 g, 64%). $^1$H NMR δ (ppm)(CDCl$_3$) (1:1 mixture of diastereoisomers): 7.33-7.07 (6 H, m), 6.95-6.91 (2 H, m), 3.68 (1.5 H, s), 3.67 (1.5 H, s), 3.42-3.28 (1 H, m), 3.22-3.13 (1H, m), 3.08 (0.5H, dd, J=14.4, 7.6 Hz), 2.8-2.65 (1 H, m), 2.55-2.45 (0.5 H, m), 2.32-2.18 (2 H, m), 2.15 (1.5 H, d, J=2.4 Hz), 2.10 (1.5 H, d, J=2.4 Hz), 1.91-1.80 (1H, m).

Step 2: 1-(3-fluoro-2-methylphenyl)-3-phenylcyclopentanecarboxylic acid

Following Method C (ii) from methyl 1-(3-fluoro-2-methylphenyl)-3-phenylcyclopentanecarboxylate (0.4 g, 0.52 mmol) without further purification gave the title compound as a pale yellow solid (0.3 g, 79%). MS (ES−) consistent with target (M−H)$^-$; $^1$H NMR δ (ppm)(CDCl$_3$) (1:1 mixture of diastereoisomers): 11.38 (1 H, br s), 7.30-7.10 (6 H, m), 6.95-6.88 (2 H, m), 3.38-3.31 (1 H, m), 3.20-3.05 (1.5 H, m), 2.80-2.65 (1.0 H, m), 2.62-2.55 (1.0 H, m), 2.50-2.41 (0.5 H, m), 2.39-2.21 (1 H, m), 2.15 (1.5 H, d, J=2.4 Hz), 2.10 (1.5 H, d, J=2.4 Hz), 1.92-1.81 (1H, m).

Step 3: 1-(3-fluoro-2-methylphenyl)-N-hydroxy-3-phenylcyclopentanecarboxamide Following Method D (ii) from 1-(3-fluoro-2-methylphenyl)-3-phenylcyclopentanecarboxylic acid (0.3 g, 0.1 mmol). Purification by preparative HPLC gave the title compound as a mixture of diastereoisomers (239 mg, 76%). LCMS (ES+) 314 (M+H)$^+$, Chiral preparative HPLC gave the 4 diastereomers.

Example 4 (Diastereomer 1 (D1)): LCMS (ES+) 331 (M+H)$^+$, RT 3.92 min (Analytical method 1); RT 6.97 min (Chiralpak IA 30/70 IPA/MeOH/FA (30/70/0.1%)/heptane, 1.0 mL/min); $^1$H NMR δ (ppm)(DMSO-d$_6$): 10.02 (1H, s), 8.74 (1H, s), 7.35-7.20 (7 H, m), 7.06 (1 H, t, J=8.4 Hz), 3.06-3.04 (1 H, m), 2.63-2.54 (2 H, m), 2.39-2.34 (1 H, m), 2.16-2.15 (2 H, m), 2.09 (3 H, s), 1.75-1.69 (1.0 H, m).

Example 5 (Diastereomer 2 (D2)): LCMS (ES+) 331 (M+H)$^+$; HPLC RT 11.04 min (Analytical method 3); RT 9.5 min (Chiralpak IA 20/80 IPA/MeOH/FA (20/80/0.1%)/heptane, 5.0 mL/min); $^1$H NMR δ (ppm)(DMSO-d$_6$): 10.02 (1H, s), 8.74 (1H, s), 7.35-7.20 (7 H, m), 7.06 (1 H, t, J=8.4 Hz), 3.06-3.04 (1 H, m), 2.63-2.54 (2 H, m), 2.39-2.34 (1 H, m), 2.16-2.15 (2 H, m), 2.09 (3 H, s), 1.75-1.69 (1.0 H, m).

Example 6 (Diastereomer 3 (D3)): LCMS (ES+) 331 (M+H)+; HPLC RT 11.01 (Analytical method 3); RT 12.7 min (Chiralpak IA 20/80 IPA/MeOH/FA (20/80/0.1%)/heptane, 5.0 mL/min); $^1$H NMR δ (ppm)(DMSO-$d_6$): 10.02 (1 H, s), 8.74 (1 H, s), 7.35-7.18 (7 H, m), 7.05 (1 H, t, J=8.4 Hz), 3.22-3.14 (1 H, m), 2.99-294 (1 H, m), 2.75-268 (1 H, m), 2.23-2.06 (2 H, m), 2.15 (3 H, s), 2.01-1.92 (1.0 H, m), 1.75-1.65 (1.0 H, m).

Example 7 (Diastereomer 4 (D4)): LCMS (ES+) 331 (M+H)+, RT 3.90 (Analytical method 1); RT 13.3 min (Chiralpak IA 30/70 IPA/MeOH/FA (30/70/0.1%)/heptane, 1.0 mL/min); $^1$H NMR δ (ppm)(DMSO-$d_6$): 10.02 (1 H, s), 8.74 (1 H, s), 7.35-7.18 (7 H, m), 7.05 (1 H, t, J=8.4 Hz), 3.22-3.14 (1 H, m), 2.99-294 (1 H, m), 2.75-268 (1 H, m), 2.23-2.06 (2 H, m), 2.15 (3 H, s), 2.01-1.92 (1.0 H, m), 1.75-1.65 (1.0 H, m).

Example 8

(±)-(1S*,3S*)1-(3-fluoro-2-methylphenyl)-N-hydroxy-3-(o-tolyl)cyclopentane carboxamide

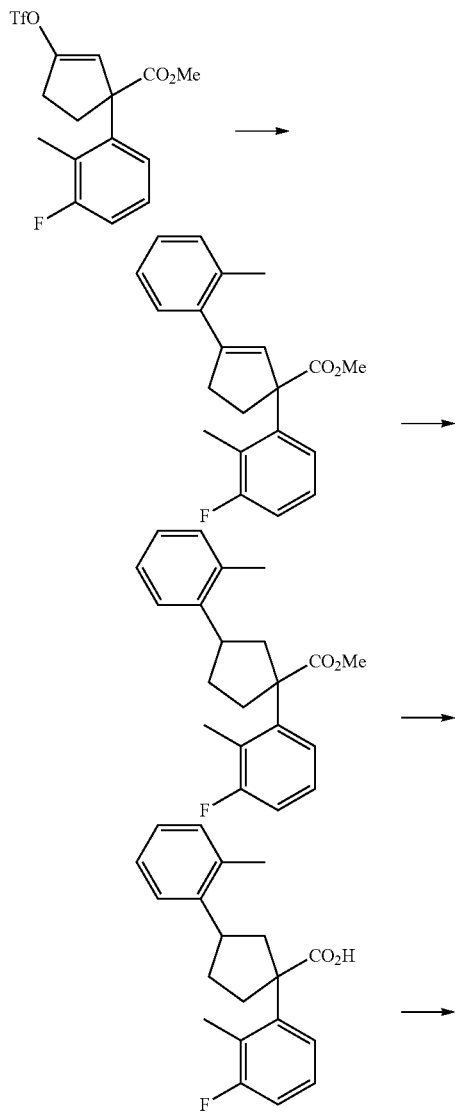

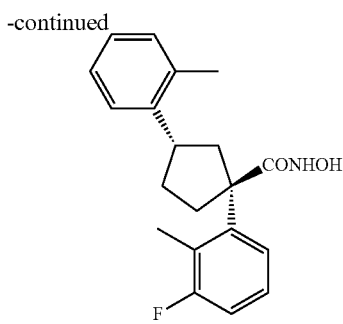

Relative Stereochemistry Putatively Assigned

Step 1: methyl 1-(3-fluoro-2-methylphenyl)-3-(o-tolyl)cyclopent-2-enecarboxylate Intermediate 5 (1 g, 2.62 mmol), o-tolylboronic acid (356 mg, 2.62 mmol), CsF (400 mg), DME (15 mL), MeOH (3 mL) and palladium tetrakis(triphenylphosphine) (20 mg) were combined in a sealed tube and heated with microwave irradiation to 120° C. for 1 h. The reaction mixture was then evaporated onto silica and purified by flash chromatography to give the title compound as a clear oil (922 mg).

Step 2: methyl 1-(3-fluoro-2-methylphenyl)-3-(o-tolyl)cyclopentanecarboxylate

Methyl 1-(3-fluoro-2-methylphenyl)-3-(o-tolyl)cyclopent-2-enecarboxylate (300 mg, 0.93 mmol), EtOAc (30 mL) and 10% Pd/C were combined and shaken under a hydrogen atmosphere at 15 psi for 6 h. Catalyst was filtered off and solvents removed by evaporation to give the title compound as a clear gum (263 mg).

Step 3: 1-(3-fluoro-2-methylphenyl)-3-(o-tolyl)cyclopentanecarboxylic acid

Methyl 1-(3-fluoro-2-methylphenyl)-3-(o-tolyl)cyclopentanecarboxylate (26 mg, 0.8 mmol), THF (3 mL), MeOH (3 mL) and 15% Aq. NaOH (1 mL) were combined in a sealed tube and heated with microwave irradiation to 120° C. for 1 h. Reaction mixture was then partitioned between EtOAc and 1 N HCl. The organic layer was dried ($MgSO_4$) and solvents removed by evaporation to give a clear gum (238 mg).

Step 4: 1-(3-fluoro-2-methylphenyl)-N-hydroxy-3-(o-tolyl)cyclopentanecarboxamide 1-(3-Fluoro-2-methylphenyl)-3-(o-tolyl)cyclopentanecarboxylic acid (238 mg, 0.76 mmol), DCM (20 mL) and oxalyl chloride (0.17 mL, 2 mmol) were combined and stirred at r.t. under a nitrogen atmosphere for 3 days. Reaction mixture was evaporated to dryness. To the residue was added DCM (1 mL) and 50% Aq hydroxylamine (1 mL) and the reaction stirred for 10 min at r.t. Reaction mixture was evaporated to dryness and purified by preparative HPLC to give the title compound as an off-white solid (99 mg). LCMS (ES+) 328 (M+H)+; RT 4.16 min (Analytical method 1); $^1$H NMR δ (ppm)(DMSO-$d_6$): 9.88 (1 H, s), 8.65 (1 H, s), 7.46 (1 H, d, J=8.0 Hz), 7.28-7.06 (6 H, m), 3.30-3.20 (1 H, m), 2.52-2.51

(1 H, m), 2.51-2.50 (1 H, m), 2.40-2.30 (1 H, m), 2.24 (3 H, s), 2.20-1.95 (2 H, m), 2.08 (3H, d, J=2.8 Hz), 1.52-1.51 (1H, m).

Example 9

(1S,3S*)-1-(3-fluoro-2-methyl-phenyl)-3-(5-fluoro-pyridin-3-yl)-N-hydroxycyclopentanecarboxamide (D1)

Example 10

(1S,3R*)-1-(3-fluoro-2-methyl-phenyl)-3-(5-fluoro-pyridin-3-yl)-N-hydroxycyclopentanecarboxamide (D2)

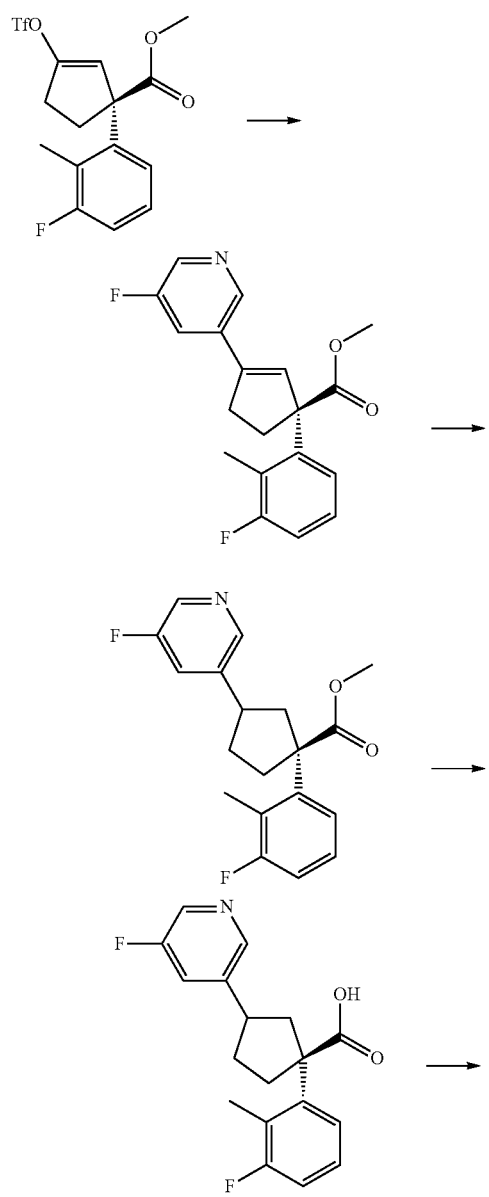

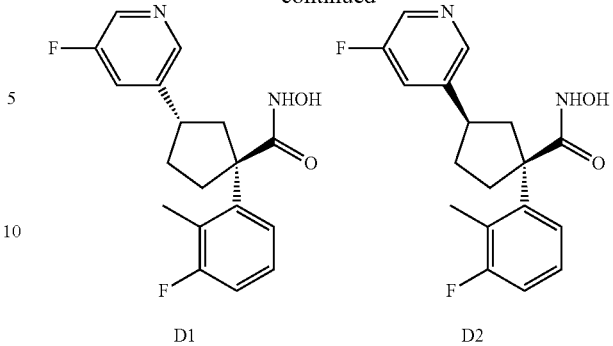

C3 Stereochemistry Putatively Assigned

Step 1: (S)-methyl 1-(3-fluoro-2-methylphenyl)-3-(5-fluoropyridin-3-yl)cyclopent-2-enecarboxylate Following Method B from Intermediate 6 (500 mg, 1.3 mmol) and 3-fluoropyridine-5-boronic acid utilizing $CsCO_3$, dioxane, water, palladium tetrakis(triphenylphosphine) at 100° C. The crude product was purified by flash column chromatography to give the title compound as a clear gum (350 mg, 81%). LCMS (ES+) consistent with target (M+H)+, $^1$H NMR δ (ppm)(CDCl$_3$): 8.60 (1 H, d, J=2.7 Hz), 8.41 (1 H, d, J=2.7 Hz), 7.53-7.48 (1 H, m), 7.17-7.08 (1 H, m), 7.04 (1 H, d, J=7.08 Hz), 6.96 (1H, t, J=7.8 Hz), 6.46 (1 H, s), 3.70 (3 H, s), 3.38 (1 H, ddd, J=13.2, 8.9, 4.5 Hz), 3.07-2.98 (1H, m), 2.83 (1H, dddd, J=16.1, 9.3, 4.5, 1.9 Hz), 2.14 (3H, d, J=2.6 Hz), 2.06 (1 H, ddd, J=13.2, 9.3, 6.0 Hz).

Step 2: (1S,3S*) and (1S,3R*)-methyl 1-(3-fluoro-2-methylphenyl)-3-(5-fluoropyridin-3-yl)-cyclopentanecarboxylate To a solution of (S)-methyl-1-(3-fluoro-2-methylphenyl)-3-(5-fluoropyridin-3-yl)cyclopent-2-enecarboxylate (0.125 g, 0.38 mmol) in methanol (20 mL) was added ammonium formate (0.125 g, 2.0 mmol), and palladium on charcoal (10%, 0.01 g). The reaction mixture was heated to 65° C. for 2 h. Reaction mixture was cooled to r.t. and filtered through Celite, washing with MeOH (3×10 mL). The solvent was removed in vacuo and the resulting solid was partitioned between water and DCM (3×20 mL). The combined organics were dried (MgSO$_4$), filtered (phase separation cartridge) and the solvent removed to yield the title compound as a pale yellow oil (0.12 g, 95%). LCMS (ES+) consistent with target (M+H)+; $^1$H NMR δ (ppm)(CDCl$_3$): 8.43-8.19 (2 H, m), 7.53-7.48 (1 H, m), 7.25-7.12 (2 H, m), 7.03-6.94 (1 H, m), 3.70 (3 H, s), 3.30-3.05 (1 H, m), 2.76 (1 H, dd, J=13.5, 10.3 Hz), 2.66 (1 H, ddd, J=13.2, 7.8, 3.4 Hz), 2.55-2.32 (2 H, m), 2.29-2.18 (1 H, m), 2.14 (3 H, d, J=2.6 Hz), 1.96-1.81 (1 H, m).

Step 3: (1S,3S*) and (1S,3R*)-1-(3-fluoro-2-methylphenyl)-3-(5-fluoropyridin-3-yl)cyclopentane carboxylic acid Following Method C from (S)methyl-1-(3-fluoro-2-methylphenyl)-3-(5-fluoropyridin-3-yl)cyclopentane carboxylate (120 mg, 0.36 mmol) and purified by preparative HPLC to give the title compound as a white solid (85 mg, 74%). LCMS (ES+) consistent with target (M+H)+; $^1$H NMR δ

(ppm)(CDCl$_3$): 11.0 (1 H, brs), 8.55 (1 H, s), 8.32 (1 H, s), 7.51 (1 H, t, J=9.7 Hz), 7.25-7.21 (2 H, m), 7.03-6.94 (1 H, m), 3.31-3.14 (1 H, m), 2.93-2.78 (1 H, m), 2.77-2.66 (1 H, m), 2.54-2.38 (2 H, m), 2.24-2.16 (1 H, m), 2.14 (3 H, d, J=2.6 Hz), 2.02-1.86 (1 H, m).

Step 4: (1S,3S*) 1-(3-fluoro-2-methyl-phenyl)-3-(5-fluoropyridin-3-yl)-N-hydroxycyclopentanecarboxamide and (1S,3R*) 1-(3-fluoro-2-methyl-phenyl)-3-(5-fluoropyridin-3-yl)-N-hydroxycyclopentanecarboxamide Following Method D from (S)-1-(3-fluoro-2-methylphenyl)-3-(5-fluoropyridin-3-yl)cyclopentanecarboxylic acid (170 mg, 0.54 mmol) and purified by preparative HPLC to give the racemic product as a cream solid (0.064 g, 35%). Preparative chiral purification provided the two diastereomers.

Example 9 (Diastereoisomer 1 (D1)): LCMS (ES+) 333 (M+H)$^+$; HPLC RT 9.49 min (Analytical method 3); RT 21.5 min (Chiralpak IC 10/90 IPA/MeOH (50/50/0.1% formic acid)/heptane, 5.0 mL/min, RT); $^1$H NMR δ (ppm)(DMSO-d$_6$): 10.02 (1 H, s), 8.73 (1 H, s), 8.52 (2 H, m), 7.86 (1 H, d, J=12.2 Hz), 7.35-7.26 (2 H, m), 7.12 (1 H, t, J=8.4 Hz), 3.28-3.04 (1 H, m), 2.75-2.54 (2 H, m), 2.41-2.32 (1 H, m), 2.31-2.15 (2 H, m), 2.12 (3 H, d, J=2.4 Hz), 1.83-1.79 (1.0 H, m).

Example 10 (Diastereoisomer 2 (D2)): LCMS (ES+) 333 (M+H)$^+$; RT 3.22 min (Analytical method 1); RT 23.5 min (Chiralpak IC 10/90 IPA/MeOH (50/50/0.1% formic acid)/heptane, 5.0 mL/min, RT); $^1$H NMR δ (ppm) (DMSO-d$_6$): 10.06 (1 H, s), 8.75 (1 H, s), 8.45 (1 H, d, J=2.8 Hz), 8.42 (1 H, s), 7.70 (1 H, d, J=12.2 Hz), 7.34 (1 H, d, J=8.4 Hz), 7.28 (1 H, q, J=8.4 Hz), 7.13 (1 H, t, J=8.4 Hz), 3.34-3.28 (1 H, m), 3.04-2.99 (1 H, m), 2.83-2.72 (1 H, m), 2.31-2.23 (1H, m), 2.19-2.07 (5 H, m), 1.83-1.73 (1.0 H, m).

Example 11

(1S,3S*)-1-(3-fluoro-2-methylphenyl)-3-(5-fluoropyridin-2-yl)-N-hydroxycyclopentane carboxamide (D1)

Example 12

(1S,3R*)-1-(3-fluoro-2-methylphenyl)-3-(5-fluoropyridin-2-yl)-N-hydroxycyclopentane carboxamide (D2)

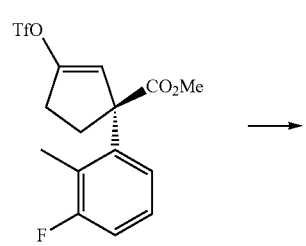

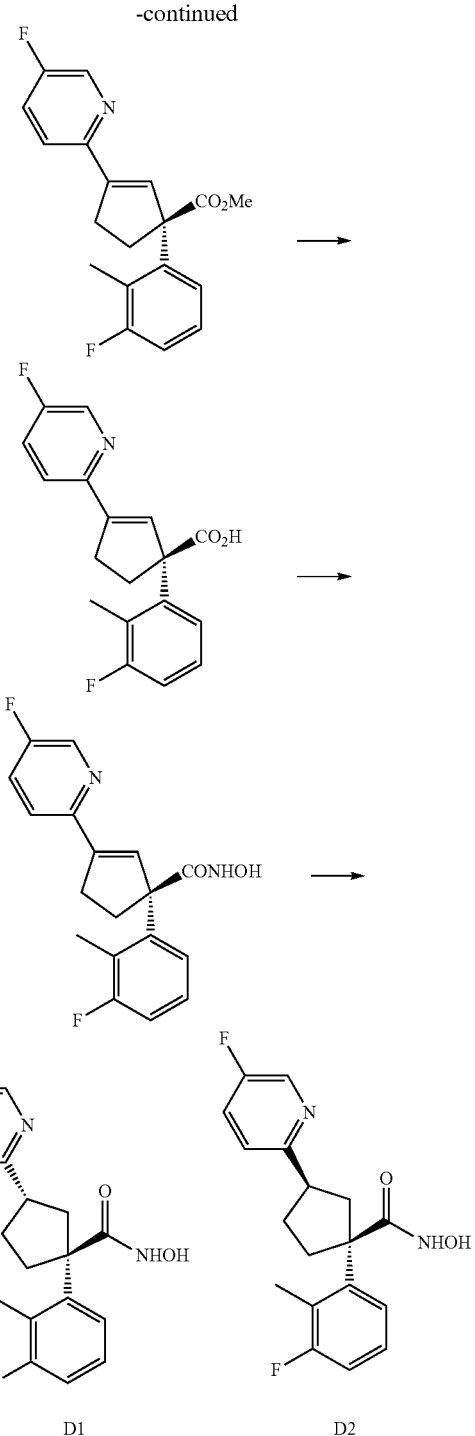

C3 Stereochemistry Putatively Assigned

Step 1: (S)-methyl 1-(3-fluoro-2-methylphenyl)-3-(5-fluoropyridin-2-yl)cyclopent-2-enecarboxylate Following Method B(iii) from Intermediate 6 (0.3 g, 0.78 mmol) in 1,4 dioxane (8 mL) was added bis(pinacolato)diboron (0.298 g, 1.17 mmol), potassium acetate (0.154 g, 1.56 mmol), tris(dibenzylideneacetone)dipalladium, (0.215 g, 0.24 mmol) and S-Phos (0.038 g, 0.094 mmol) The reaction mixture was heated at 80° C. under $N_2$ for 2 h. After this time the reaction mixture was cooled to r.t. and 2-bromo-5-fluoropyridine (0.152 g, 0.86 mmol), cesium carbonate (0.51 g, 1.57 mmol) and tetrakis(triphenylphosphine)palladium(0) (0.045 g, 0.039 mmol) were added and the reaction mixture heated at 110° C. under $N_2$ for 1 h. Reaction mixture was cooled to r.t. and filtered through Celite, washing with EtOAc (3×10 mL). Combined organics were extracted with water (15 mL) then brine (20 mL). EtOAc layers were then dried ($MgSO_4$), filtered (phase separation cartridge) and concentrated. The crude product was purified by flash column chromatography to give the title compound as a pale yellow gum (217 mg, 84%). LCMS (ES+) consistent with target (M+H)+; $^1$H NMR δ (ppm) ($CHCl_3$-d): 8.48 (1 H, d, J=2.8 Hz), 7.49-7.33 (2 H, m), 7.16-7.06 (2 H, m), 7.00-6.92 (1 H, m), 6.67 (1 H, s), 3.76-3.62 (3 H, m), 3.37 (1 H, ddd, J=13.0, 8.9, 4.5 Hz), 3.12-3.01 (1 H, m), 2.89 (1 H, dddd, J=16.0, 9.3, 4.5, 2.5 Hz), 2.13 (3 H, dd, J=8.9, 2.5 Hz), 2.11-1.99 (1 H, m).

Step 2: (S)-1-(3-fluoro-2-methylphenyl)-3-(5-fluoropyridin-2-yl)cyclopent-2-enecarboxylic acid Following Method C from (S)-methyl 1-(3-fluoro-2-methylphenyl)-3-(5-fluoropyridin-2-yl)cyclopent-2-enecarboxylate (217 mg) and used without further purification. The title compound was obtained as a pale yellow solid (187 mg, 72%). LCMS (ES+) consistent with target (M+H)+; $^1$H NMR δ (ppm)(DMSO-$d_6$): 12.71 (1 H, s), 8.56 (1 H, d, J=2.9 Hz), 7.85 (1 H, dd, J=8.8, 4.5 Hz), 7.74 (1 H, td, J=8.8, 2.9 Hz), 7.21-7.13 (1 H, m), 7.13-7.01 (2 H, m), 6.77 (1 H, s), 3.15 (1 H, ddd, J=13.0, 8.9, 4.6 Hz), 2.99-2.89 (1 H, m), 2.85-2.75 (1 H, m), 2.52 (1 H, under solvent peak), 2.13 (3 H, d, J=2.4 Hz).

Step 3: (S)-1-(3-fluoro-2-methylphenyl)-3-(5-fluoropyridin-2-yl)-N-hydroxycyclopent-2-enecarboxamide Following Method D from (S)-1-(3-fluoro-2-methylphenyl)-3-(5-fluoropyridin-2-yl)cyclopent-2-enecarboxylic acid (187 mg, 0.59 mmol) and purified by preparative HPLC to give the title compound as an off white solid (89 mg, 45%). LCMS (ES+) 331 (M+H)+. $^1$H NMR δ (ppm)(DMSO-$d_6$): 10.16 (1 H, s), 8.73 (1 H, s), 8.57 (1 H, d, J=2.88 Hz), 7.77-7.64 (2 H, m), 7.22-7.00 (3 H, m), 6.79 (1 H, s), 3.29-3.22 (1 H, m), 2.93-2.82 (1 H, m), 2.80-2.70 (1 H, m), 2.12 (3 H, d, J=2.4 Hz), 1.90-1.79 (1 H, m).

Step 4: (1S,3S*)-1-(3-fluoro-2-methylphenyl)-3-(5-fluoropyridin-2-yl)-N-hydroxycyclopentane carboxamide and (1S,3R*)-1-(3-fluoro-2-methylphenyl)-3-(5-fluoropyridin-2-yl)-N-hydroxy cyclopentanecarboxamide (S)-1-(3-Fluoro-2-methylphenyl)-3-(5-fluoropyridin-2-yl)-N-hydroxycyclopent-2-enecarboxamide (50 mg, 0.15 mmol) in ethanol (5 mL) was treated with ammonium formate (95 mg, 1.5 mmol) and 10% Pd/C (5 mg, 10% wt) and heated at 70° C. under $N_2$ for 1 h. The crude products were filtered and evaporated to yield a colorless gum (45 mg) which was purified by chiral preparative HPLC to give the title compounds as pale orange solids, Diastereomer 1 (6.3 mg) and Diastereomer 2 (10.4 mg).

Example 11 (Diastereomer 1 (D1)): LCMS (ES+) 333 (M+H)+; RT 9.82 min (Analytical method 3); RT 5.71 min (Chiralpak IC 20/80 IPA/MeOH (50/50/0.1% formic acid)/heptane, 5.0 mL/min, RT); $^1$H NMR δ (ppm)(DMSO-$d_6$): 10.04 (1 H, s), 8.71 (1 H, s), 8.51 (1 H, d, J=3.0 Hz), 7.66 (1 H, td, J=8.7, 3.0 Hz), 7.42 (1 H, dd, J=8.8, 4.5 Hz), 7.28-7.21 (2 H, m), 7.09 (1H, t, J=8.8 Hz), 3.44 (1 H, t, J=8.8 Hz), 3.01 (1 H, dd, J=12.5, 7.0 Hz), 2.75-2.69 (2 H, m), 2.21-2.13 (5 H, m), 1.91-1.84 (1 H, m).

Example 12 (Diastereomer 2 (D2)): LCMS (ES+) 333 (M+H)+; RT 9.79 min (Analytical method 3); RT 7.07 min (Chiralpak IC 2/8 IPA/MeOH (50/50/0.1% formic acid)/heptane, 5.0 mL/min, RT); $^1$H NMR δ (ppm)(DMSO-$d_6$): 10.04 (1 H, s), 8.69 (1 H, s), 8.54 (1 H, d, J=3.0 Hz), 7.70 (1 H, td, J=8.8, 3.0 Hz), 7.5 (1 H, dd, J=8.8, 4.5 Hz), 7.34-7.25 (2 H, m), 7.12 (1 H, t, J=8.8 Hz), 3.32 (1 H, d, J=11.1 Hz), 2.74-2.62 (2 H, m), 2.45 (1 H, dd, J=13.4, 7.7 Hz), 2.22-2.08 (5 H, m), 1.95-1.87 (1 H, m).

Example 13

(1r,4r)-4-(5-fluoropyridin-3-yl)-N-hydroxy-1-phenylcyclohexanecarboxamide (D1)

Example 14

(1s,4s)-4-(5-fluoropyridin-3-yl)-N-hydroxy-1-phenylcyclohexanecarboxamide (D2)

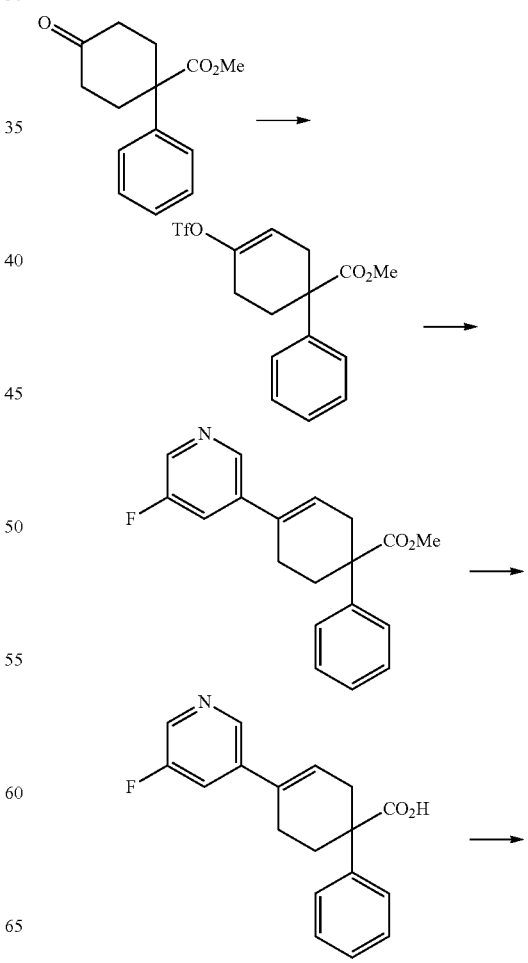

Step 1: methyl 4-(((trifluoromethyl)sulfonyl)oxy)-1,2,3,6-tetrahydro-[1,1'-biphenyl]-1-carboxylate Methyl 4-oxo-1-phenylcyclohexanecarboxylate (993 mg, 4.28 mmol), and THF (30 mL) were combined under nitrogen at r.t. Reaction mixture was cooled with an ice bath and NaHMDS (1 M in THF, 5.64 mL, 5.64 mmol) was added dropwise. After 30 min N-(5-chloro-2-pyridyl)bis(trifluoromethanesulfonimide) (1.68 g, 4.28 mmol) was added and the reaction mixture allowed to warm to r.t. with stirring over 4 h. Reaction mixture was diluted with $CH_2Cl_2$, washed with water and the organics evaporated to dryness on to silica and purified by flash chromatography to give the title compound as a clear oil (445 mg, 29%).

Step 2: methyl 4-(5-fluoropyridin-3-yl)-1,2,3,6-tetrahydro-[1,1'-biphenyl]-1-carboxylate Methyl 4-(((trifluoromethyl)sulfonyl)oxy)-1,2,3,6-tetrahydro-[1,1'-biphenyl]-1-carboxylate (445 mg, 1.22 mmol), 3-fluoropyridine-5-boronic acid (171 mg, 1.22 mmol), CsF (200 mg), DME (12 mL), MeOH (3 mL) and palladium tetrakis(triphenylphosphine) (20 mg) were combined in a sealed tube and microwave heated to 120° C. for 4 h. The reaction mixture was allowed to cool to r.t., evaporated to dryness onto silica and purified by flash chromatography to give the title compound as a white solid (216 mg, 57%). LCMS (ES+) consistent with target $(M+H)^+$.

Step 3: 4-(5-fluoropyridin-3-yl)-1,2,3,6-tetrahydro-[1,1'-biphenyl]-1-carboxylic acid Methyl 4-(5-fluoropyridin-3-yl)-1,2,3,6-tetrahydro-[1,1'-biphenyl]-1-carboxylate (215 mg, 0.69 mmol), MeOH (20 mL), 15% aq. NaOH soln. (2 mL) were combined in a sealed tube and heated to 65° C. for 24 h. Reaction mixture was evaporated to dryness then partitioned between EtOAc and $H_2O$/AcOH. Organic layer was dried ($MgSO_4$) and evaporated to dryness to give the title compound as a white solid (176 mg, 86%). LCMS (ES+) consistent with target $(M+H)^+$.

Step 4: 4-(5-fluoropyridin-3-yl)-N-hydroxy-1,2,3,6-tetrahydro-[1,1'-biphenyl]-1-carboxamide 4-(5-Fluoropyridin-3-yl)-1,2,3,6-tetrahydro-[1,1'-biphenyl]-1-carboxylic acid (176 mg, 0.57 mmol), DMF (3 mL), $Et_3N$ (0.24 mL, 1.7 mmol) and TFFH (225 mg, 0.855 mmol) were combined and stirred at r.t. under a nitrogen atmosphere. After 30 min $H_2NOTHP$ (94 mg, 0.8 mmol) was added and the reaction stirred for 18 h. MeOH (3 mL) and 2 N HCl in diethyl ether (2 mL) were then added and reaction stirred for 2 h. Volatile solvents were removed in vacuo and the remaining concentrated solution was purified by preparative HPLC to give the title compound as a white solid (136 mg, 76%). LCMS (ES+) consistent with target $(M+H)^+$; $^1H$ NMR δ (ppm)(DMSO-$d_6$): 1.46 (1H, s), 8.69 (1H, s), 8.52 (1H, m), 8.42 (1H, d, J=2.4 Hz), 7.73 (1H, dt, J=10.8 Hz, J=2 Hz), 7.46-7.22 (5H, m), 6.53 (1H, s), 2.99 (1H, m), 2.66 (1H, m), 2.48 (2H, m), 2.26-2.19 (2H, m).

Step 5: 4-(5-fluoropyridin-3-yl)-N-hydroxy-1-phenylcyclohexanecarboxamide 4-(5-Fluoropyridin-3-yl)-N-hydroxy-1,2,3,6-tetrahydro-[1,1'-biphenyl]-1-carboxamide (80 mg, 0.26 mmol), ethanol (20 mL), ammonium formate (100 mg) and Pd/C (10% Pd content, 5 mg) were combined in a round bottomed flask and heated at 65° C. for 1 h. Reaction mixture was then diluted with EtOAc, washed with water, dried ($MgSO_4$) and solvents removed in vacuo to give crude product which was purified by preparative HPLC to give the title compounds, Diastereomer 1 as a white solid (15 mg, 19%) where the aryl groups are syn relative to each other and Diastereomer 2 as a white solid (26 mg, 31%) where the aryl groups are anti relative to each other, as determined by nOe NMR experiments.

Example 13 (Diastereomer 1 (D1)): LCMS (ES+) 315 $(M+H)^+$; RT 8.98 min (Analytical method 3); $^1H$ NMR δ (ppm)(DMSO-$d_6$): 10.03 (1 H, s), 8.80 (1 H, s), 8.34 (1 H, d, J=2.8 Hz), 8.22 (1 H, m), 7.45 (2 H, m), 7.39 (3 H, m), 7.22 (1 H, m), 2.86-2.75 (3 H, m), 1.98-1.70 (4 H, m), 1.50-1.35 (2 H, m).

Example 14 (Diastereomer 2 (D2)): LCMS (ES+) 315 $(M+H)^+$; RT 3.28 min (Analytical method 1); $^1H$ NMR δ (ppm)(DMSO-$d_6$): 10.63 (1 H, s), 8.73 (1 H, s), 8.46 (1 H, d, J=2.8 Hz), 8.40 (1 H, m), 7.55 (1 H, m), 7.45 (2 H, m), 7.38 (2 H, m), 7.28 (1 H, m), 2.82-2.70 (3 H, m), 1.98-1.90 (2 H, m), 1.73-1.63 (4 H, m).

Example 15

1-(2,3-difluorophenyl)-N-hydroxycyclopentanecarboxamide

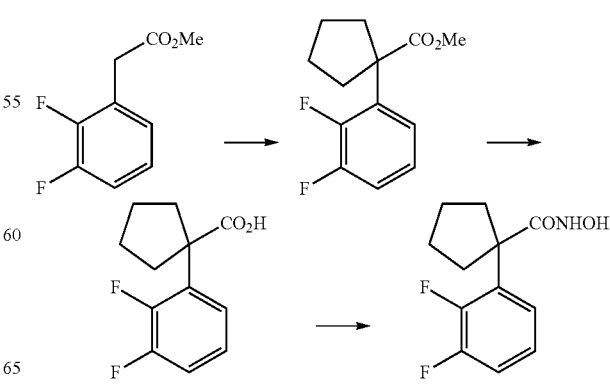

Step 1: methyl 1-(2,3-difluorophenyl)cyclopentanecarboxylate

Following Method E from methyl 2-(2,3-difluorophenyl) acetate (1 g, 5.38 mmol), DMF (20 mL), 1,4-diiodobutane (0.71 mL, 5.38 mmol) and NaH (60% in oil, 440 mg, 11 mmol) gave the title compound as a pale yellow oil (1.41 g). MS (ES+) consistent with (M+H)+.

Step 2: 1-(2,3-difluorophenyl)cyclopentanecarboxylic acid

Following Method C(ii) from methyl 1-(2,3-difluorophenyl)cyclopentanecarboxylate (1.41 g), MeOH (1 mL) and 15% aq. NaOH (3 mL) gave the title compound as a brown oil (1.2 g).

Step 3: 1-(2,3-difluorophenyl)-N-hydroxycyclopentanecarboxamide

Following Method D(ii) from 1-(2,3-difluorophenyl)cyclopentanecarboxylic acid (345 mg, 1.53 mmol), DCM (2 mL) and oxalyl chloride (0.25 mL, 3 mmol). Reaction mixture was evaporated to dryness and purified by preparative HPLC to give the title compound as a white solid (135 mg). LCMS (ES+) 242 (M+H)+; RT 3.23 min (Analytical method 1); $^1$H NMR δ (ppm)(DMSO-$d_6$): 10.21 (1 H, s), 8.67 (1 H, s), 7.32-7.29 (1 H, m), 7.20-7.15 (2 H, m), 2.52-2.45 (2 H, m), 1.88-1.83 (2 H, m), 1.66-1.61 (4 H, m).

Example 16

1-(2,3-dihydrobenzofuran-7-yl)-N-hydroxycyclopentanecarboxamide

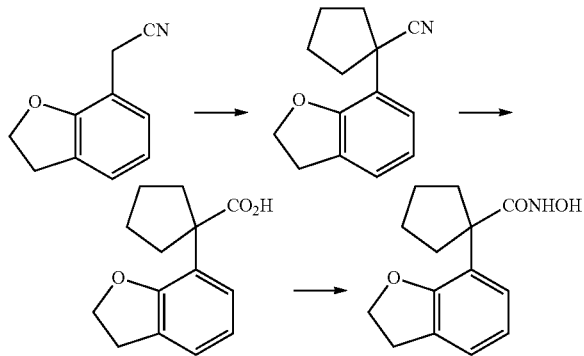

Step 1: 1-(2,3-dihydrobenzofuran-7-yl)cyclopentanecarbonitrile 2-(2,3-Dihydrobenzofuran-7-yl)acetonitrile (750 mg, 4.71 mmol), DMF (15 mL), 1,4-diiodobutane (0.62 mL, 4.71 mmol) and NaH (60% in oil, 400 mg, 10 mmol), were combined at r.t. under a nitrogen atmosphere and stirred for 18 h. Reaction mixture was then diluted with EtOAc, washed with water (3×), brine (1×), dried (MgSO$_4$) and solvents removed by evaporation to give the title compound as a yellow oil (1.16 g).

Step 2: 1-(2,3-dihydrobenzofuran-7-yl)cyclopentanecarboxylic acid 1-(2,3-Dihydrobenzofuran-7-yl)cyclopentanecarbonitrile (1.16 g), ethylene glycol (6 mL) and 15% aq. KOH solution (1 mL) were combined in a sealed tube and heated with microwave irradiation to 170° C. for 5 h. The reaction mixture was then partitioned between EtOAc and 1 N HCl. The organic layer was dried (MgSO$_4$) and solvents removed by evaporation to give a tan solid (226 mg). MS (ES−) consistent with target (M−H)−.

Step 3: 1-(2,3-dihydrobenzofuran-7-yl)-N-hydroxycyclopentanecarboxamide

Following Method D(ii) from 1-(2,3-dihydrobenzofuran-7-yl)cyclopentanecarboxylic acid to give the title compound as a cream solid (134 mg). LCMS (ES+) 248 (M+H)+; RT 3.24 min (Analytical method 1); $^1$H NMR δ (ppm)(DMSO-$d_6$): 9.91 (1 H, s), 8.54 (1 H, s), 7.10 (1 H, d, J=7.2 Hz), 7.08 (1H, d, J=7.2 Hz), 6.76 (1 H, t, J=7.2 Hz), 4.47 (2 H, t, J=8.8 Hz), 3.13 (2 H, t, J=8.8 Hz), 2.45-2.35 (2 H, m), 1.91-1.88 (2 H, m), 1.60-1.56 (4 H, m).

Example 17

1-(3-chloro-2-methylphenyl)-N-hydroxycyclopentanecarboxamide

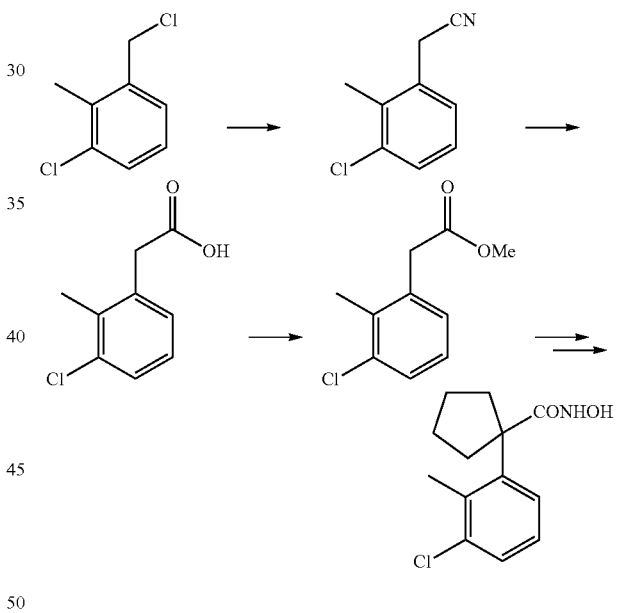

Step 1: 2-(3-chloro-2-methylphenyl)acetonitrile

2-Methyl-3-chlorobenzyl chloride (880 mg, 5 mmol), NaCN (294 mg, 6 mmol) and DMSO (20 mL) were combined and stirred at r.t. for 23 h. Reaction mixture was then diluted with EtOAc, washed with water (3×), dried (MgSO$_4$) and solvents removed by evaporation in vacuo to give an off-white solid (745 mg).

Step 2: 2-(3-chloro-2-methylphenyl)acetic acid 2-(3-Chloro-2-methylphenyl)acetonitrile (740 mg, 4.47 mmol), MeOH (10 mL) and 15% aq. KOH solution (2 mL) were combined in a sealed tube and heated with microwave irradiation to 120° C. for 12 h. Reaction mixture was then partitioned between EtOAc and 1 N HCl. Organic layer was dried (MgSO4) and solvent removed by evaporation to give an off-white solid (995 mg).

Step 3: methyl 2-(3-chloro-2-methylphenyl)acetate 2-(3-Chloro-2-methylphenyl)acetic acid (995 mg), MeOH (10 mL) and 2 N HCl in diethyl ether (6 mL) were combined and stirred at r.t. for 17 h. The reaction mixture was then evaporated onto silica and purified by flash chromatography to give a clear oil (635 mg). MS (ES+) consistent with target (M+H)+.

1-(3-Chloro-2-methylphenyl)-N-hydroxycyclopentanecarboxamide

Methyl 2-(3-chloro-2-methylphenyl)acetate was converted using Methods E, C(ii) and D(ii) analogous to the examples described above, to give the title compound as an off-white solid (50 mg). LCMS (ES+) 254/256 (M+H)+, RT 10.03 min (Analytical method 3); $^1$H NMR δ (ppm)(DMSO-d$_6$): 9.85 (1 H, s), 8.59 (1 H, s), 7.33-7.30 (2 H, m), 7.20-7.16 (1 H, m), 2.43-2.36 (2 H, m), 2.23 (3 H, s), 1.92-1.86 (2 H, m), 1.71-1.56 (4 H, m).

Example 18

1-(3-fluoro-2-methylphenyl)-N-hydroxycyclopentanecarboxamide

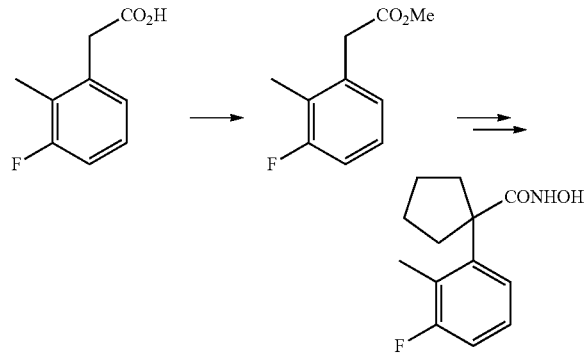

Step 1: methyl 2-(3-fluoro-2-methylphenyl)acetate 2-(3-Fluoro-2-methylphenyl)acetic acid (1 g, 5.95 mmol), MeOH (10 mL) and 2 N HCl in diethyl ether (6 mL) were combined and stirred at r.t. for 17 h. The reaction mixture was then evaporated to dryness to give a clear oil (1.07 g).
1-(3-Fluoro-2-methylphenyl)-N-hydroxycyclopentanecarboxamide Methyl 2-(3-fluoro-2-methylphenyl)acetate was converted using Methods E, C(ii) and D(ii) analogous to the examples described above, to give the title compound as an off white solid (4 mg). LCMS (ES+) 238 (M+H)+, RT 9.56 min (Analytical method 3); $^1$H NMR δ (ppm)(DMSO-d$_6$): 9.89 (1 H, s), 8.61 (1 H, s), 7.21-7.15 (2 H, m), 7.05-7.00 (1 H, m), 2.44-2.39 (2 H, m), 2.10 (3 H, d, J=2.8 Hz), 1.90-1.84 (2 H, m), 1.67-1.54 (4 H, m).

Example 19

1-(2-fluorophenyl)-N-hydroxycyclopentanecarboxamide

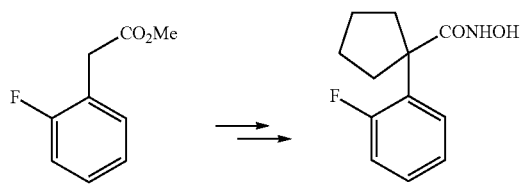

Methyl 2-(2-fluorophenyl)acetate was converted using Methods E, C(ii) and D(ii) analogous to the examples described above, to give the title compound as a white solid (147 mg). LCMS (ES+) 224 (M+H)+, RT 3.05 min (Analytical method 1); $^1$H NMR δ (ppm)(DMSO-d$_6$): 10.11 (1 H, s), 8.60 (1 H, s), 7.45-7.05 (4 H, m), 2.50-2.40 (2 H, m), 1.90-1.80 (2 H, m), 1.70-1.50 (4 H, m).

Example 20

1-(4-chlorophenyl)-N-hydroxycyclopentanecarboxamide

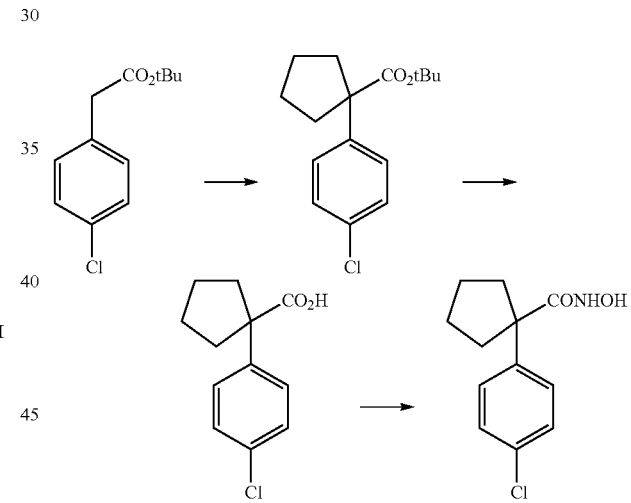

Step 1: tert-butyl 1-(4-chlorophenyl)cyclopentanecarboxylate

Following Method E from tert-Butyl 2-(4-chlorophenyl) acetate (1 g, 4.41 mmol) gave the title compound as a white solid (1.14 g).

Step 2: 1-(4-chlorophenyl)cyclopentanecarboxylic acid tert-Butyl 1-(4-chlorophenyl)cyclopentanecarboxylate (545 mg, 1.94 mmol) was combined with DCM (4 mL) and TFA (2 mL) and stirred at r.t. for 20 h. The reaction mixture was then evaporated onto silica and purified by flash chromatography to give the title compound as a white solid (153 mg).

Step 3: 1-(4-chlorophenyl)-N-hydroxycyclopentanecarboxamide

Following Method D(ii) from 1-(4-chlorophenyl)cyclopentanecarboxylic acid (150 mg) gave the title compound as an off-white solid (111 mg). LCMS (ES+) 240/242 (M+H)+, RT 8.70 min (Analytical method 2); $^1$H NMR δ (ppm) (DMSO-$d_6$): 10.45 (1 H, s), 8.65 (1 H, s), 7.36 (4 H, s), 2.55-2.45 (2 H, m), 1.85-1.70 (2 H, m), 1.65-1.55 (4 H, m).

Examples 21-37

The compounds in the Table below were prepared from commercially available starting materials using procedures analogous to those described above.

| Example # | Structure | Name | ES (M + H)+ |
|---|---|---|---|
| 21 | 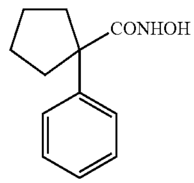 | N-Hydroxy-1-phenylcyclopentanecarboxamide | 206 |
| 22 | 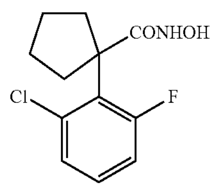 | 1-(2-Chloro-6-fluorophenyl)-N-hydroxycyclopentanecarboxamide | 258/260 |
| 23 | 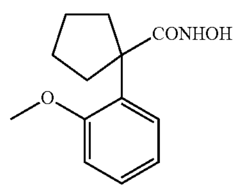 | N-Hydroxy-1-(2-methoxyphenyl)cyclopentanecarboxamide | 236 |
| 24 | 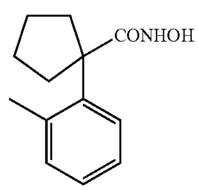 | N-Hydroxy-1-o-tolylcyclopentanecarboxamide | 220 |
| 25 | 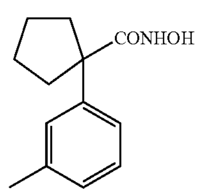 | N-Hydroxy-1-m-tolylcyclopentanecarboxamide | 220 |
| 26 | 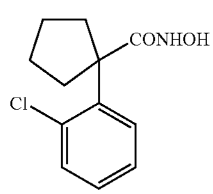 | 1-(2-Chlorophenyl)-N-hydroxycyclopentanecarboxamide | 240/242 |
| 27 | 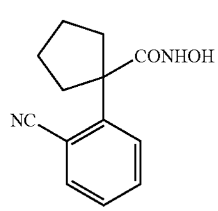 | 1-(2-Cyanophenyl)-N-hydroxycyclopentanecarboxamide | 231 |

-continued

| Example # | Structure | Name | ES (M + H)+ |
|---|---|---|---|
| 28 | 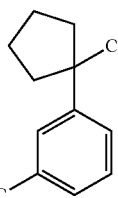 | 1-(3-Cyanophenyl)-N-hydroxycyclopentanecarboxamide | 231 |
| 29 | 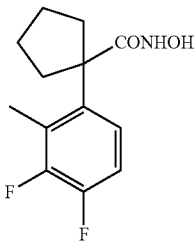 | 1-(3,4-Difluoro-2-methylphenyl)-N-hydroxycyclopentanecarboxamide | 256 |
| 30 | 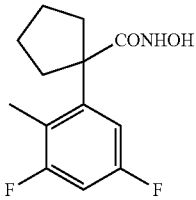 | 1-(3,5-Difluoro-2-methylphenyl)-N-hydroxycyclopentanecarboxamide | 256 |
| 31 | 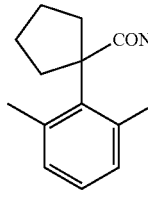 | 1-(2-Chloro-6-methylphenyl)-N-hydroxycyclopentanecarboxamide | 254/256 |
| 32 | 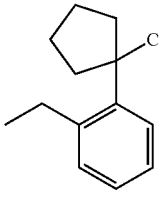 | 1-(2-Ethylphenyl)-N-hydroxycyclopentanecarboxamide | 234 |
| 33 | 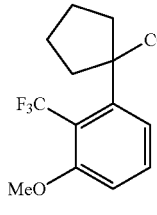 | N-Hydroxy-1-(3-methoxy-2-(trifluoromethyl)phenyl)cyclopentanecarboxamide | 304 |
| 34 | 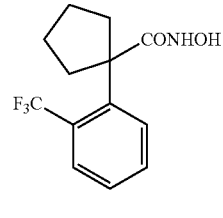 | N-Hydroxy-1-(2-(trifluoromethyl)phenyl)cyclopentanecarboxamide | 274 |

-continued

| Example # | Structure | Name | ES (M + H)+ |
|---|---|---|---|
| 35 | 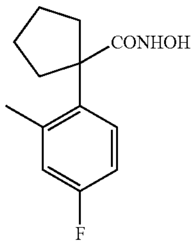 | 1-(4-Fluoro-2-methylphenyl)-N-hydroxycyclopentanecarboxamide | 238 |
| 36 | 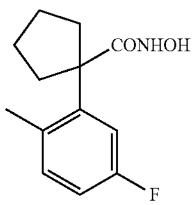 | 1-(5-Fluoro-2-methylphenyl)-N-hydroxycyclopentanecarboxamide | 238 |
| 37 | 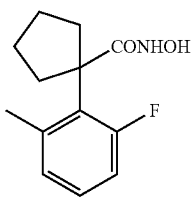 | 1-(2-Fluoro-6-methylphenyl)-N-hydroxycyclopentanecarboxamide | 238 |
| 38 | 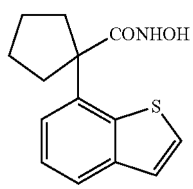 | 1-(Benzo[b]thiophen-7-yl)-N-hydroxycyclopentanecarboxamide | 262 |

Example 39

(1R,3S*)-1-(3-fluoro-2-methylphenyl)-3-(5-fluoropyridin-3-yl)-N-hydroxycyclopentanecarboxamide (D1)

Example 40

(1R,3R*)-1-(3-fluoro-2-methylphenyl)-3-(5-fluoropyridin-3-yl)-N-hydroxycyclopentanecarboxamide (D2)

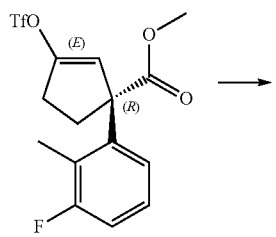

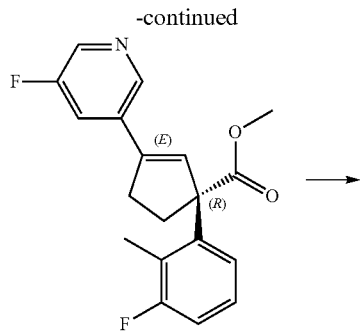

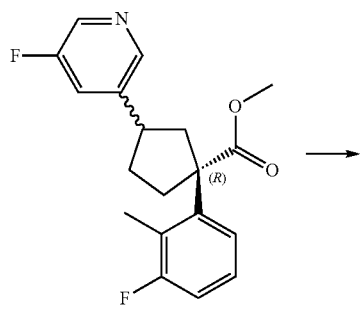

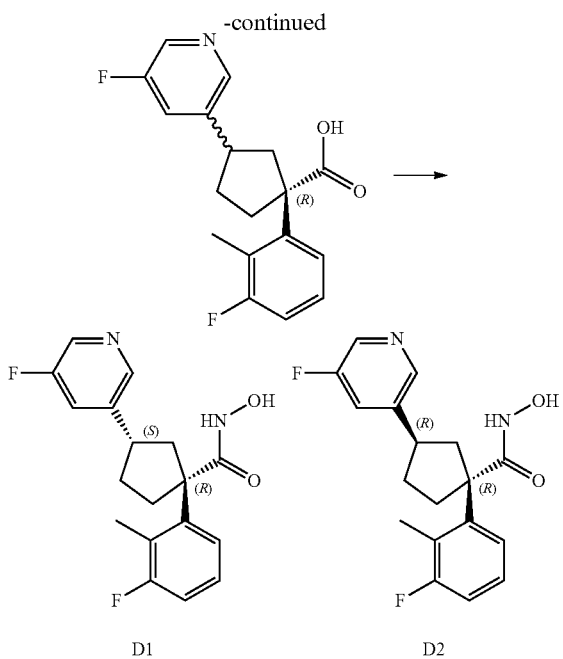

C3 Stereochemistry Putatively Assigned

Step 1: (R)-methyl 1-(3-fluoro-2-methylphenyl)-3-(5-fluoropyridin-3-yl)cyclopent-2-enecarboxylate Following Method B from Intermediate 6 (500 mg, 1.3 mmol) and 3-fluoropyridine-5-boronic acid utilizing Cs$_2$CO$_3$, dioxane, water and palladium tetrakis(triphenylphosphine) at 100° C. The crude product was purified by flash column chromatography to give the title compound as a clear gum (350 mg, 81%). LCMS (ES+) consistent with target (M+H)$^+$, $^1$H NMR δ (ppm)(CDCl$_3$): 8.60 (1 H, d, J=2.7 Hz), 8.41 (1 H, d, J=2.7 Hz), 7.53-7.48 (1 H, m), 7.17-7.08 (1 H, m), 7.04 (1 H, d, J=7.8 Hz), 6.96 (1H, t, J=7.8 Hz), 6.46 (1 H, s), 3.70 (3 H, s), 3.38 (1 H, ddd, J=13.2, 8.9, 4.5 Hz), 3.07-2.98 (1 H, m), 2.83 (1 H, dddd, J=16.1, 9.3, 4.5, 1.9 Hz), 2.14 (3 H, d, J=2.6 Hz), 2.06 (1 H, ddd, J=13.2, 9.3, 6.0 Hz).

Step 2: (1R,3S*) and (1R,3R*)-methyl 1-(3-fluoro-2-methylphenyl)-3-(5-fluoropyridin-3-yl)-cyclopentanecarboxylate To a solution of (R)-methyl-1-(3-fluoro-2-methylphenyl)-3-(5-fluoropyridin-3-yl)cyclopent-2-enecarboxylate (0.32 g, 0.98 mmol) in ethanol (20 mL) was added ammonium formate (0.125 g, 2.0 mmol), and palladium on charcoal (10 wt % Pd, 0.01 g). The reaction mixture was heated to 65° C. for 2 h. Reaction mixture was cooled to r.t. and filtered through Celite, washing with EtOH (3×10 mL). The solvent was removed in vacuo and the resulting solid was suspended in water (20 mL) and extracted with DCM (3×20 mL). The combined organics were dried (MgSO$_4$), filtered (phase separation cartridge) and the solvent removed to yield the title compound as a pale yellow oil (0.302 g, 96%). LCMS (ES+) consistent with target (M+H)$^+$; $^1$H NMR δ (ppm)(CDCl$_3$): 8.43-8.19 (2 H, m), 7.53-7.48 (1 H, m), 7.25-7.12 (2 H, m), 7.03-6.94 (1 H, m), 3.70 (3 H, s), 3.30-3.05 (1 H, m), 2.76 (1 H, dd, J=13.5, 10.3 Hz), 2.66 (1 H, ddd, J=13.2, 7.8, 3.4 Hz), 2.55-2.32 (2 H, m), 2.29-2.18 (1 H, m), 2.14 (3 H, d, J=2.6 Hz), 1.96-1.81 (1 H, m).

Step 3: (1R,3S*) and (1R,3R*)-1-(3-fluoro-2-methylphenyl)-3-(5-fluoropyridin-3-yl)cyclopentane carboxylic acid Following Method C from the mixture of isomers obtained in the previous step (302 mg, 0.36 mmol) to give the title compound as a white solid (255 mg, 88%). LCMS (ES+) consistent with target (M+H)$^+$; $^1$H NMR δ (ppm) (CDCl$_3$): 11.0 (1 H, brs), 8.55 (1 H, s), 8.32 (1 H, s), 7.51 (1 H, t, J=9.7 Hz), 7.25-7.21 (2 H, m), 7.03-6.94 (1 H, m), 3.31-3.14 (1 H, m), 2.93-2.78 (1 H, m), 2.77-2.66 (1 H, m), 2.54-2.38 (2 H, m), 2.24-2.16 (1 H, m), 2.14 (3 H, d, J=2.6 Hz), 2.02-1.86 (1 H, m).

Step 4: (1R,3S*) 1-(3-fluoro-2-methyl-phenyl)-3-(5-fluoropyridin-3-yl)-N-hydroxycyclopentanecarboxamide (D1) and (1R,3R*) 1-(3-fluoro-2-methyl-phenyl)-3-(5-fluoropyridin-3-yl)-N-hydroxycyclopentanecarboxamide (D2)

Following Method D from the mixture of isomers obtained in the previous step (255 mg, 0.80 mmol) and purified by preparative HPLC to give a mixture of diastereomers as a cream solid (0.085 g, 31%). Purification by preparative chiral HPLC provided diastereomer 1 (D1) as a beige solid (6.87 mg, 3%) and diastereomer 2 (D2) as a beige solid (17.7 mg, 7%).

Example 39 (Diastereomer 1 (D1)): LCMS (ES+) 333 (M+H)$^+$, RT 9.48 min (Analytical method 3); $^1$H NMR δ (ppm)(DMSO-d$_6$): 10.04 (1H, s), 8.72 (1H, s), 8.43 (1 H, d, J=2.6 Hz), 8.39 (1H, s), 7.69 (1H, dt, J=10.4, 2.2 Hz), 7.34 (1H, d, J=7.7 Hz), 7.28-7.21 (1H, m), 7.09 (1H, t, J=8.8 Hz), 3.33-3.29 (1H, m), 2.99 (1H, dd, J=12.8, 6.5 Hz), 2.82-2.74 (1H, m), 2.29-2.21 (1H, m), 2.17 (3H, d, J=2.6 Hz), 2.15-2.05 (2H, m), 1.81-1.71 (1H, m).

Example 40 (Diastereomer 2 (D2)): LCMS (ES+) 333 (M+H)$^+$, RT 9.49 min (Analytical method 3); $^1$H NMR δ (ppm)(DMSO-d$_6$): 9.99 (1H, s), 8.72 (1H, s), 8.47-8.44 (2H, m), 7.85 (1H, dt, J=10.3, 2.3 Hz), 7.34-7.26 (2H, m), 7.10 (1H, t, J=8.8 Hz), 3.27-3.17 (1H, m), 2.71 (1H, dd, J=13.0, 10.1 Hz), 2.41-2.34 (1H, m), 2.31-2.15 (2H, m), 2.12 (3H, d, J=2.8 Hz), 1.82-1.71 (1H, m). 1H obscured by DMSO peak.

Example 41

(1S,3R)-3-(5-fluoropyridin-3-yl)-N-hydroxy-1-phenylcyclopentanecarboxamide

Example 42

(1S,3S)-3-(5-fluoropyridin-3-yl)-N-hydroxy-1-phenylcyclopentanecarboxamide

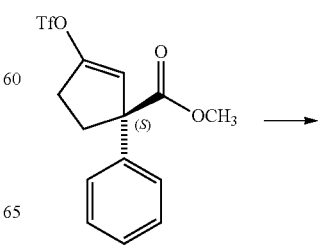

-continued

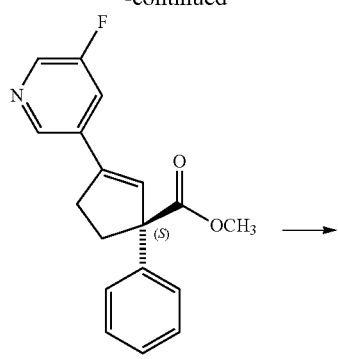

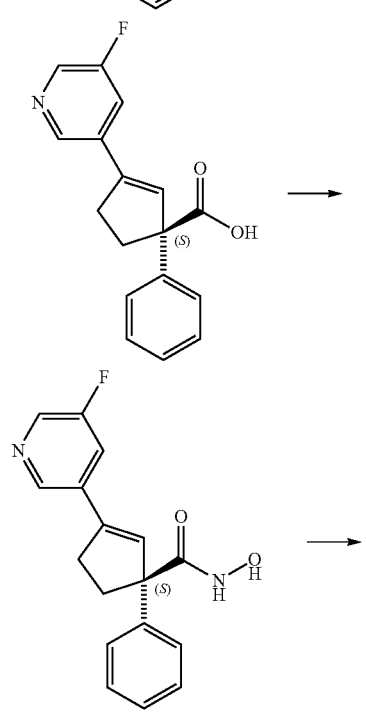

Step 1: (S)-methyl 3-(5-fluoropyridin-3-yl)-1-phenylcyclopent-2-enecarboxylate Following Method B from Intermediate 7 (4 mg, 1.14 mmol) and (5-fluoropyridin-3-yl)boronic acid (160 mg) utilizing $Cs_2CO_3$ (743 mg) in place of $K_2CO_3$. The crude product was purified by flash column chromatography (gradient elution, 0-50% EtOAc in iso-hexane) to give the title compound as a crystalline solid (300 mg).

Step 2: (S)-3-(5-fluoropyridin-3-yl)-1-phenylcyclopent-2-enecarboxylic acid

Following Method C from (S)-methyl 3-(5-fluoropyridin-3-yl)-1-phenylcyclopent-2-enecarboxylate (300 mg, 1.01 mmol), utilizing KOH in place of NaOH and heating for 2 h to give the title compound as a white solid (276 mg).

Step 3: (S)-3-(5-fluoropyridin-3-yl)-N-hydroxy-1-phenylcyclopent-2-enecarboxamide Following Method D from (S)-3-(5-fluoropyridin-3-yl)-1-phenylcyclopent-2-enecarboxylic acid (276 mg, 0.98 mmol). The title compound was obtained as a white solid (52 mg, 18%).

Step 4: (1S,3R)-3-(5-fluoropyridin-3-yl)-N-hydroxy-1-phenylcyclopentanecarboxamide (Example 41) and (1S,3S)-3-(5-fluoropyridin-3-yl)-N-hydroxy-1-phenylcyclopentanecarboxamide (Example 42)

A solution of (S)-3-(5-fluoropyridin-3-yl)-N-hydroxy-1-phenylcyclopent-2-enecarboxamide (70 mg, 0.23 mmol) in MeOH (6 mL) was passed through a H-cube apparatus (ThalesNano) in full $H_2$ mode equipped with a 10% Pd/C catalyst cartridge at r.t. Purification by preparative HPLC gave example 41 as a white solid (6.15 mg) and example 42 as a white solid (1.6 mg). The relative stereochemistry of example 41 was assigned by nOe NMR experiments.

Example 41: LCMS (ES+) 31 (M+H)$^+$, RT 3.07 min (Analytical method 1); $^1$H NMR δ (ppm)(DMSO-d$_6$): 10.49 (1H, s), 8.75 (1H, s), 8.45-8.38 (2H, m), 7.79-7.69 (1H, m), 7.45 (2H, d, J=7.1 Hz), 7.42-7.25 (3H, m), 3.29-3.21 (1H, m), 2.69-2.59 (3H, m), 2.27-2.12 (2H, m), 1.69-1.59 (1H, m).

Example 42: LCMS (ES+) 31 (M+H)$^+$, RT 9.18 min (Analytical method 3); $^1$H NMR δ (ppm)(DMSO-d$_6$): 8.44-8.40 (2H, m), 7.76-7.69 (1H, m), 7.44-7.39 (2H, m), 7.37-7.21 (3H, m), 2.97-2.86 (1H, m), 2.74-2.64 (1H, m), 2.32-2.19 (1H, m), 2.16-1.88 (2H, m), 1.82-1.73 (1H, m). NH and OH not observed. 1H obscured by water peak.

Example 43

(1S,3R)-3-(2-cyclopropyl-5-fluoropyridin-3-yl)-1-(3-fluoro-2-methylphenyl)-N-hydroxycyclopentanecarboxamide

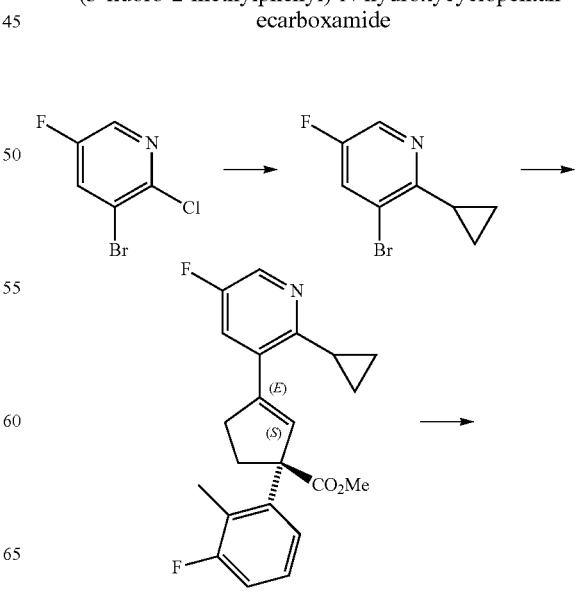

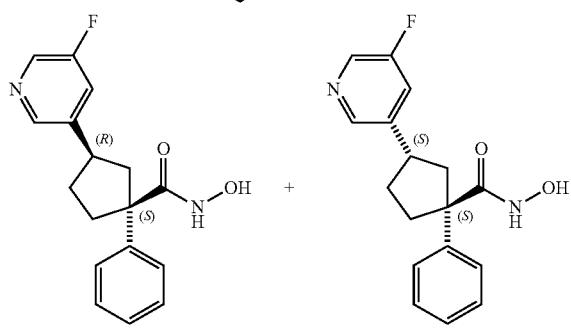

-continued

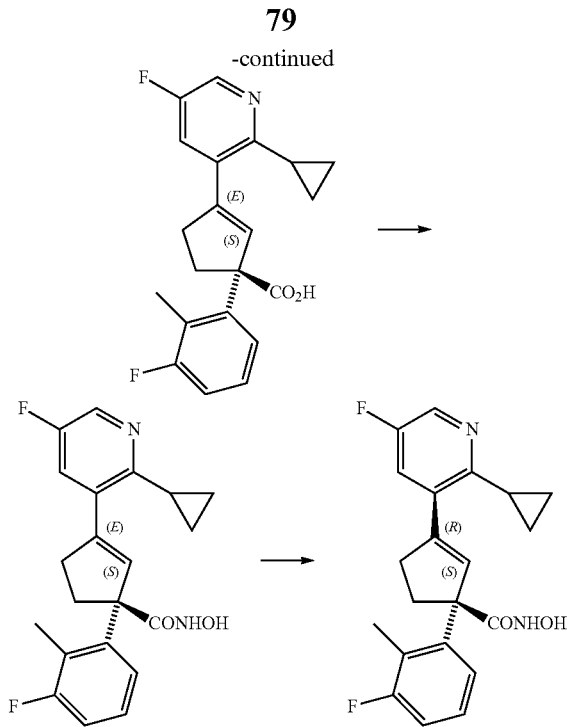

Step 1: 3-bromo-2-cyclopropyl-5-fluoropyridine

To a solution of 3-bromo-2-chloro-5-fluoropyridine (760 mg, 3.62 mmol) in THF (3 mL) was added a solution of cyclopropylzinc bromide in THF (0.5 M, 8 mL, 4 mmol) and Pd(PPh$_3$)$_4$ (125 mg) and the reaction mixture was stirred at 20° C. overnight. Additional cyclopropylzinc bromide (0.5 M, 4 mL, 2 mmol) and Pd(PPh$_3$)$_4$ (65 mg) was needed to consume all starting material. The reaction mixture was stirred at 20° C. for an additional 6 h, then it was partitioned between EtOAc (30 mL) and 1 M HCl (15 mL). The organic layer was separated, washed with brine (40 mL), dried, filtered (phase separation cartridge) and concentrated. Purification by flash column chromatography (SNAP column 25 g, iso-hexane-EtOAc: 0-25%) gave the title compound as a yellow oil (401 mg, 51%).

Step 2: (S)-methyl-3-(2-cyclopropyl-5-fluoropyridin-3-yl)-1-(3-fluoro-2-methylphenyl)cyclopent-2-enecarboxylate Following Method B (iii) from (S)-methyl-1-(3-fluoro-2-methylphenyl)-3-(((trifluoromethyl)sulfonyl)oxy)cyclopent-2-enecarboxylate (0.54 g, 1.4 mmol) and 3-bromo-2-cyclopropyl-5-fluoropyrimidine (0.40 g, 1.86 mmol). The crude product was purified by flash column chromatography to give the title compound as pale yellow oil (301 mg, 58%). MS (ES+) consistent with target (M+H)$^+$.

Step 3: (S)-3-(2-cyclopropyl-5-fluoropyridin-3-yl)-1-(3-fluoro-2-methylphenyl)cyclopent-2-enecarboxylic acid Following Method C from (S)-methyl-3-(2-cyclopropyl-5-fluoropyridin-3-yl)-1-(3-fluoro-2-methylphenyl)cyclopent-2-enecarboxylate (300 mg, 0.81 mmol). The crude product (25 mg) was used without further purification. MS (ES+) consistent with target (M+H)$^+$.

Step 4: (S)-3-(2-cyclopropyl-5-fluoropyridin-3-yl)-1-(3-fluoro-2-methylphenyl)-N-hydroxycyclopent-2-enecarboxamide Following Method D from (S)-3-(2-cyclopropyl-5-fluoropyridin-3-yl)-1-(3-fluoro-2-methylphenyl)cyclopent-2-enecarboxylic acid (250 mg, 0.70 mmol) and purified by preparative HPLC to give the title compound as a white solid (62 mg, 24%).

Step 5: (1S,3R)-3-(2-cyclopropyl-5-fluoropyridin-3-yl)-1-(3-fluoro-2-methylphenyl)-N-hydroxycyclopentanecarboxamide (S)-3-(2-Cyclopropyl-5-fluoropyridin-3-yl)-1-(3-fluoro-2-methylphenyl)-N-hydroxycyclopent-2-enecarboxamide (40 mg, 0.11 mmol) was dissolved in MeOH (11 mL) and passed through a H-cube apparatus (ThalesNano) in full H$_2$ mode equipped with a 1% Pd/C catalyst cartridge at r.t. Purification by preparative HPLC gave the title compound as a white solid (24.7 mg, 61%). The stereochemical configuration was assigned by nOe NMR experiments. LCMS (ES+) 373 (M+H)$^+$; $^1$H NMR δ (ppm)(DMSO-d$_6$): 10.20 (1 H, s), 8.72 (1 H, br s), 8.38 (1 H, d, J=1.5 Hz), 7.35-7.27 (3 H, m), 7.13-7.09 (1 H, m), 3.85 (1 H, m), 2.73-2.67 (2 H, m), 2.15 (3 H, s) 2.13-1.96 (4 H, m), 0.98-0.96 (2 H, m), 0.76-0.73 (2 H, m). (1H obscured by DMSO peak).

Example 44

(1S,3S*)-1-(3-fluoro-2-methylphenyl)-3-(5-fluoro-6-methoxypyridin-3-yl)-N-hydroxycyclopentanecarboxamide (D1)

Example 45

(1S,3R*)-1-(3-fluoro-2-methylphenyl)-3-(5-fluoro-6-methoxypyridin-3-yl)-N-hydroxycyclopentanecarboxamide (D2)

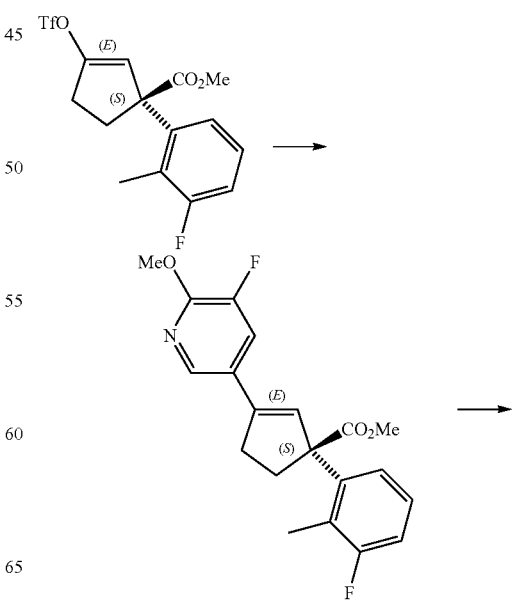

-continued

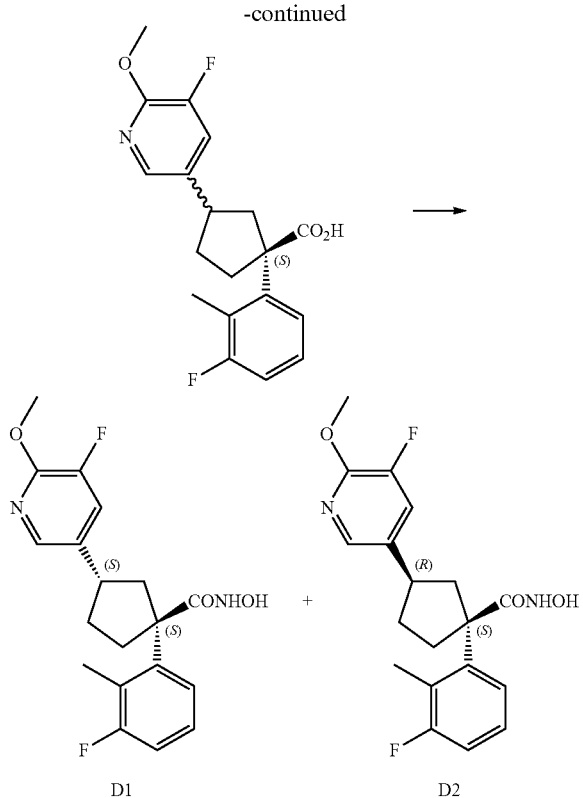

C3 Stereochemistry Putatively Assigned

Step 1: (S)-methyl 1-(3-fluoro-2-methylphenyl)-3-(5-fluoro-6-methoxypyridin-3-yl)cyclopent-2-enecarboxylate Following Method B from (S)-methyl 1-(3-fluoro-2-methylphenyl)-3-(((trifluoromethyl)sulfonyl)oxy)cyclopent-2-enecarboxylate (500 mg, 1.31 mmol) and 2-methoxy-3-fluoropyridine-5-boronic acid utilizing CsF, DME, MeOH and palladium tetrakis(triphenylphosphine) at 120° C. The crude product was purified by flash column chromatography to give the title compound as a clear gum (385 mg, 82%). MS (ES+) consistent with target (M+H)⁺.

Step 2: (S)-1-(3-fluoro-2-methylphenyl)-3-(5-fluoro-6-methoxypyridin-3-yl)cyclopentanecarboxylic acid (S)-Methyl-1-(3-fluoro-2-methylphenyl)-3-(5-fluoro-6-methoxypyridin-3-yl)cyclopent-2-enecarboxylate (165 mg, 0.46 mmol), MeOH (20 mL), ammonium formate (200 mg) and 10% palladium on carbon (20 mg) were combined and heated to 65° C. for 16 h. 15% aq. NaOH solution (3 mL) was then added and heating continued for 19 days. Reaction mixture was partitioned between EtOAc and acetic acid/water. The organic layer was dried (MgSO₄) and evaporated in vacuo to give the title compound as a tan solid (526 mg). LCMS (ES+) 348 (M+H)⁺.

Step 3: (1S,3S*)-1-(3-fluoro-2-methylphenyl)-3-(5-fluoro-6-methoxypyridin-3-yl)-N-hydroxycyclopentanecarboxamide (Example 45, D1) and (1S,3R*)-1-(3-fluoro-2-methylphenyl)-3-(5-fluoro-6-methoxypyridin-3-yl)-N-hydroxycyclopentanecarboxamide (Example 46, D2)

(S)-1-(3-fluoro-2-methylphenyl)-3-(5-fluoro-6-methoxypyridin-3-yl)cyclopentanecarboxylic acid (70 mg, 0.2 mmol), TFFH (75 mg, 0.28 mmol), DMF (2 mL) and Et₃N (0.14 mL, 1 mmol) were combined and stirred at room temperature under a nitrogen atmosphere. After 2 hours O-(tetrahydro-2H-pyran-2-yl)hydroxylamine (80 mg, 0.68 mmol) was added and the mixture stirred for 4 days. MeOH (2 mL) and 2 N HCl in diethyl ether (2 mL) were added and the mixture stirred for 4 h. Volatile solvents were removed in vacuo and the crude product was purified by preparative HPLC to give diastereomer 1 (D1) as a white solid (9.8 mg) and diastereomer 2 (D2) as a colorless glass (27.8 mg).

Example 44 (Diastereomer 1 (D1)): LCMS (ES+) 363 (M+H)⁺; $^1$H NMR δ (ppm)(DMSO-$d_6$): 9.91 (1 H, s), 8.67 (1 H, br s), 7.61 (1 H, dd, J=11.2, 2.0 Hz), 7.44 (1 H, s), 7.30-7.15 (2 H, m), 7.10-7.00 (1 H, m), 3.46 (3 H, s), 2.90-2.80 (1 H, m), 2.65-2.50 (2 H, m), 2.25-2.10 (2 H, m), 2.07 (3 H, d, J=2.8 Hz), 2.05-1.95 (1 H, m), 1.70-1.55 (1 H, m).

Example 45 (Diastereomer 2 (D2)): LCMS (ES+) 363 (M+H)⁺; $^1$H NMR δ (ppm)(DMSO-$d_6$): 9.93 (1 H, s), 8.67 (1 H, br s), 7.89 (1 H, d, J=1.6 Hz), 7.80 (1 H, dd, J=12.0, 1.6 Hz), 7.30-7.20 (2 H, m), 7.10-7.00 (1 H, m), 3.92 (3 H, s), 3.15-3.05 (1 H, m), 2.65-2.50 (2 H, m), 2.35-2.05 (3 H, m), 2.08 (3H, d, J=2.8 Hz), 1.75-1.60 (1 H, m).

Example 46

(1S,3R*)-3-(1-(Difluoromethyl)-1H-pyrazol-4-yl)-1-(3-fluoro-2-methylphenyl)-N-hydroxy cyclopentane carboxamide

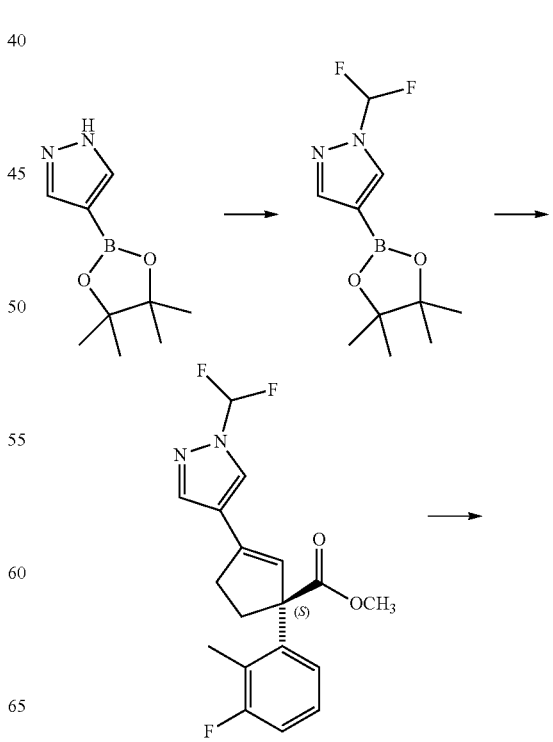

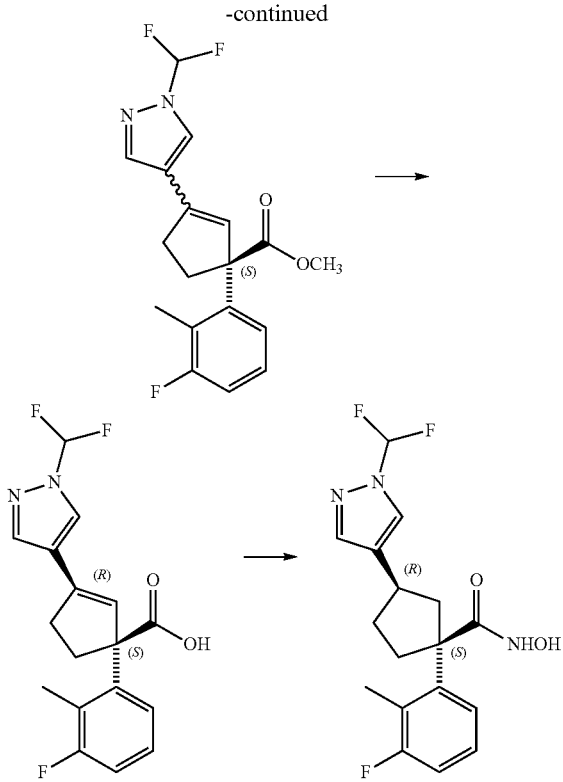

C3 Stereochemistry Putatively Assigned

Step 1: 1-(difluoromethyl)-4-(4,4,5,5-tetramethyl-1,3,2-dioxaborolan-2-yl)-1H-pyrazole A 100 mL round bottom flask was charged with 4-pyrazoleboronic acid pinacol ester (1.0 g, 5.15 mmol), 18-crown-6 (0.27 g, 1.03 mmol) and anhydrous acetonitrile (25 mL). The reagents were stirred until a colorless solution formed then sodium chlorodifluoroacetate (0.94 g, 6.18 mmol) was added and the reaction mixture heated to reflux for 18 h. After this time the reaction mixture was cooled to r.t. and the precipitated solid removed by filtration through Celite, washing with EtOAc (3×20 mL). Combined organics were filtered through a hydrophobic frit and condensed to give a pale yellow oil. The crude product was purified by flash silica column chromatography (gradient elution, 0-33% EtOAc in iso-hexane) to give the title compound as a colorless solid (1.06 g, 84%). MS (ES+) consistent with target (M+H)+.

Step 2: (S)-methyl 3-(1-(difluoromethyl)-1H-pyrazol-4-yl)-1-(3-fluoro-2-methylphenyl)cyclopent-2-enecarboxylate Following Method B from (S)-methyl 1-(3-fluoro-2-methylphenyl)-3-(((trifluoromethyl)sulfonyl)oxy)cyclopent-2-enecarboxylate (0.15 g, 0.40 mmol) and 1-(difluoromethyl)-4-(4,4,5,5-tetramethyl-1,3,2-dioxaborolan-2-yl)-1H-pyrazole (0.10 g, 0.41 mmol). The crude product was purified by flash silica column chromatography (gradient elution, 0-33% EtOAc in iso-hexane) to give the title compound as a colorless oil (0.12 g, 77%). MS (ES+) consistent with target (M+H)+.

Step 3: (S)-methyl 3-(1-(difluoromethyl)-1H-pyrazol-4-yl)-1-(3-fluoro-2-methylphenyl)cyclopentane carboxylate To a stirred solution of (S)-methyl 3-(1-(difluoromethyl)-1H-pyrazol-4-yl)-1-(3-fluoro-2-methylphenyl)cyclopent-2-enecarboxylate (0.28 g, 0.80 mmol) in $CH_3OH$ (20 mL) was added ammonium formate (0.2 g, 3.2 mmol), 20% w/w Pd/C (0.07 g, catalytic) and the mixture was stirred at reflux for 1 h. The black suspension was filtered through Celite and washed with EtOAc (3×10 mL). The filtrate was collected and washed with water (20 mL), brine (20 mL) and the organics passed through a phase separator and concentrated. This gave the title compound as a white solid (0.27 g, 97%, 8:1 mixture of diasteromers). The mixture of isomers was purified by SFC to give the major isomer as a colorless oil (0.16 g, d.r.>50:1). $^1H$ NMR δ (ppm)($CDCl_3$): 7.70 (1 H, s), 7.60(1 H, s), 7.22-7.12 (3 H, m), 7.02-6.92 (1 H, m), 3.65 (3 H, s), 3.19-3.06 (1 H, m), 2.70-2.56 (2 H, m), 2.48 (1 H, dd, J=13.38, 8.04 Hz), 2.34-2.15 (2 H, m), 2.10 (3 H, d, J=2.80 Hz), 1.89-1.75 (1 H, m).

Step 4: (1S,3R*)-3-(1-(difluoromethyl)-1H-pyrazol-4-yl)-1-(3-fluoro-2-methylphenyl)cyclopentanecarboxylic acid To a stirred solution of (S)-methyl 3-(1-(difluoromethyl)-1H-pyrazol-4-yl)-1-(3-fluoro-2-methylphenyl)cyclopentane carboxylate (0.9 g, 0.23 mmol) in methanol (4 mL), THF (4 mL) and water (0.4 mL) at r.t., was added $LiOH \cdot H_2O$ (0.20 g, 4.68 mmol) and the mixture was stirred at 65° C. for 72 h. The colourless suspension was concentrated under reduced pressure and partitioned between $CH_2Cl_2$ (15 mL) and sat. $NaHCO_3$ solution (15 mL). The aqueous layers were acidified to pH=3 and extracted with EtOAc (3×15 mL). Combined organic layers were washed with sat. NaCl solution (20 mL), and the organics passed through a phase separator and concentrated. This gave the title compound as a white solid (0.08 g, 88%). $^1H$ NMR δ (ppm)($CDCl_3$): 7.68 (1 H, s), 7.60 (1 H, s), 7.23-7.12 (3 H, m), 7.03-6.95 (1 H, m), 3.18-3.09 (1 H, m), 2.74-2.66 (1 H, m), 2.64 (1 H, dd, J=13.43, 10.16 Hz), 2.52 (1 H, dd, J=13.43, 8.15 Hz), 2.35 (1 H, ddd, J=13.20, 9.51, 7.16 Hz), 2.28-2.20 (1 H, m), 2.18 (3 H, d, J=2.76 Hz), 1.90-1.80 (1 H, m).

Step 5: (1S,3R*)-3-(1-(difluoromethyl)-1H-pyrazol-4-yl)-1-(3-fluoro-2-methylphenyl)-N-hydroxy cyclopentane carboxamide (1S,3R)-3-(1-(Difluoromethyl)-1H-pyrazol-4-yl)-1-(3-fluoro-2-methylphenyl)cyclopentanecarboxylic acid (0.9 g, 0.25 mmol), TFFH (0.8 mg, 0.30 mmol), DMF (3 mL) and $Et_3N$ (0.11 mL, 0.75 mmol) were combined and stirred at room temperature under a nitrogen atmosphere. After 1 h O-(tetrahydro-2H-pyran-2-yl)hydroxylamine (0.06 g, 0.50 mmol) was added and the mixture stirred for 24 h. The yellow solution was taken up in EtOAc (10 mL), washed with water (2×10 mL) and brine (10 mL). The organic layer was passed through a phase separator and concentrated. To the crude residue was added MeOH (2 mL) and 4 M HCl in dioxane (0.5 mL) and the mixture stirred for 2 h. Volatile solvents were removed under reduced pressure and the remaining crude product was purified by preparative HLPC to give the title compound as a white solid. LCMS (ES+) 354 (M+H)+; RT 3.54 min (Analytical method 1); $^1H$ NMR δ (ppm)(DMSO-$d_6$): 9.85 (1 H, s), 8.62 (1 H, s), 8.05 (1 H, s), 7.72 (1 H, s), 7.71 (1 H, t, J=59.6 Hz), 7.25-7.16 (2 H, m), 7.07-7.01 (1 H, m), 3.02-2.94 (1 H, m), 2.42 (1 H, dd, J=13.1, 10.0 Hz), 2.37-2.28 (1 H, m), 2.12-2.05 (2 H, m), 2.06 (4 H, d, J=2.9 Hz), 1.66-1.59 (1 H, m).

Example 47

(1S,3R*)-1-(3-fluoro-2-methylphenyl)-N-hydroxy-3-(1-(2-morpholinoethyl)-1H-pyrazol-4-yl)cyclopentanecarboxamide

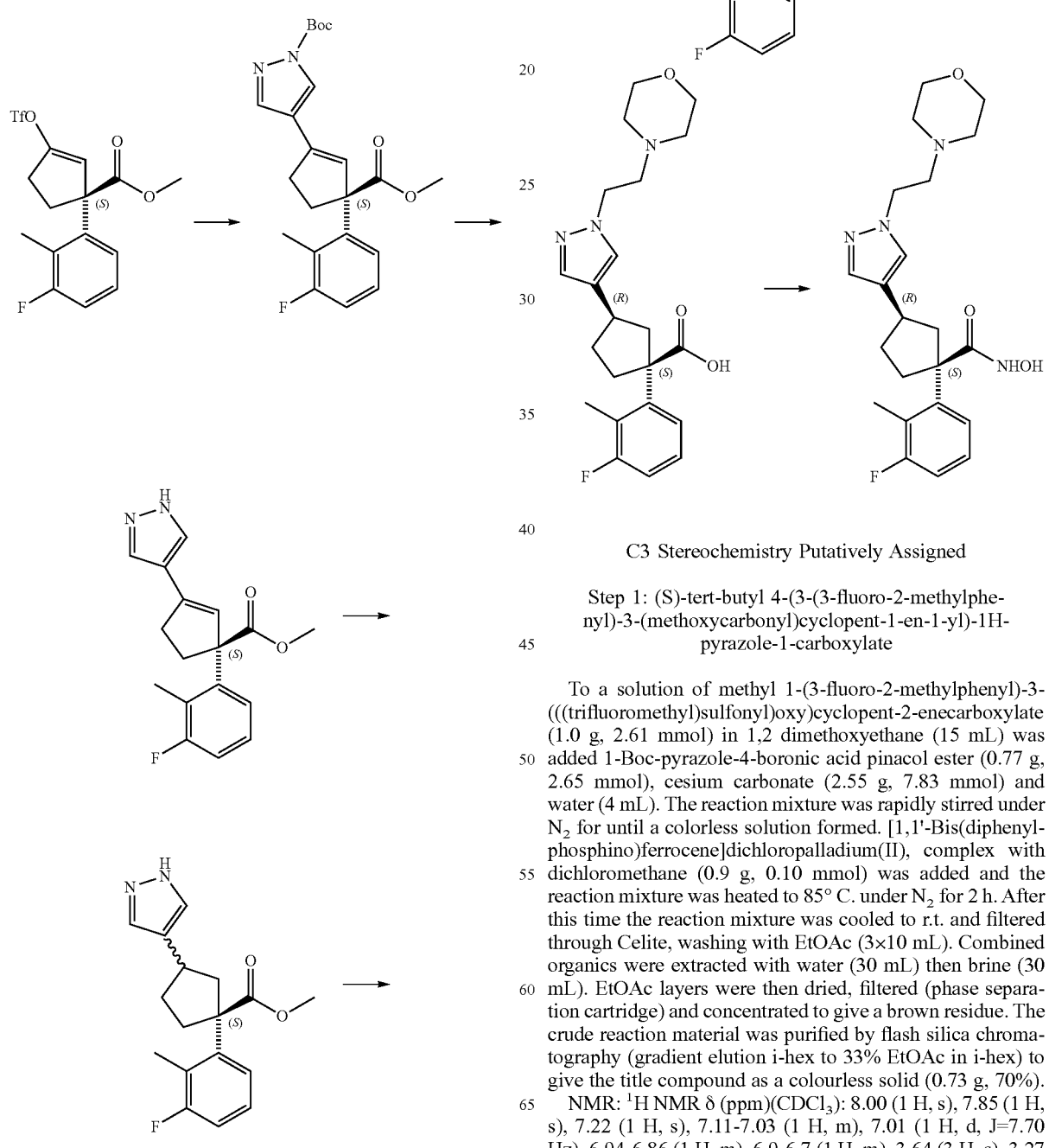

C3 Stereochemistry Putatively Assigned

Step 1: (S)-tert-butyl 4-(3-(3-fluoro-2-methylphenyl)-3-(methoxycarbonyl)cyclopent-1-en-1-yl)-1H-pyrazole-1-carboxylate To a solution of methyl 1-(3-fluoro-2-methylphenyl)-3-(((trifluoromethyl)sulfonyl)oxy)cyclopent-2-enecarboxylate (1.0 g, 2.61 mmol) in 1,2 dimethoxyethane (15 mL) was added 1-Boc-pyrazole-4-boronic acid pinacol ester (0.77 g, 2.65 mmol), cesium carbonate (2.55 g, 7.83 mmol) and water (4 mL). The reaction mixture was rapidly stirred under $N_2$ for until a colorless solution formed. [1,1'-Bis(diphenylphosphino)ferrocene]dichloropalladium(II), complex with dichloromethane (0.9 g, 0.10 mmol) was added and the reaction mixture was heated to 85° C. under $N_2$ for 2 h. After this time the reaction mixture was cooled to r.t. and filtered through Celite, washing with EtOAc (3×10 mL). Combined organics were extracted with water (30 mL) then brine (30 mL). EtOAc layers were then dried, filtered (phase separation cartridge) and concentrated to give a brown residue. The crude reaction material was purified by flash silica chromatography (gradient elution i-hex to 33% EtOAc in i-hex) to give the title compound as a colourless solid (0.73 g, 70%).

NMR: $^1$H NMR δ (ppm)(CDCl$_3$): 8.00 (1 H, s), 7.85 (1 H, s), 7.22 (1 H, s), 7.11-7.03 (1 H, m), 7.01 (1 H, d, J=7.70 Hz), 6.94-6.86 (1 H, m), 6.9-6.7 (1 H, m), 3.64 (3 H, s), 3.27

(1 H, ddd, J=13.29, 8.79, 4.31 Hz), 2.90-2.79 (1 H, m), 2.70-2.61 (1 H, m), 2.08 (3 H, d, J=2.51 Hz), 1.93 (1 H, ddd, J=13.11, 9.35, 6.06 Hz), 1.62 (9 H, s).

Step 2: (S)-methyl 1-(3-fluoro-2-methylphenyl)-3-(1H-pyrazol-4-yl)cyclopent-2-enecarboxylate To a solution of (S)-tert-butyl 4-(3-(3-fluoro-2-methylphenyl)-3-(methoxycarbonyl)cyclopent-1-en-1-yl)-1H-pyrazole-1-carboxylate (0.73 g, 1.82 mmol) in dichloromethane (20 mL) was added trifluoroacetic acid (1.5 mL). The reaction mixture was stirred at r.t. for 16 h. After this time the reaction mixture was extracted (3×10 mL CH$_2$Cl$_2$) with sat. NaHCO$_3$ (15 mL). Dichloromethane layers were then dried, filtered (phase separation cartridge) and concentrated to give a colourless solid which was used without further purification (0.54 g, 98%).

NMR: $^1$H NMR δ (ppm)(CDCl$_3$): 7.67 (2 H, s), 7.22 (1 H, s), 7.10-7.03 (2 H, m), 6.93-6.86 (1 H, m), 6.14 (1 H, br s), 6.00-5.98 (1 H, m), 3.64 (3 H, s), 3.27 (1 H, ddd, J=13.25, 8.78, 4.29 Hz), 2.92-2.81 (1 H, m), 2.71-2.62 (1 H, m), 2.09 (3 H, d, J=2.52 Hz), 1.91 (1 H, ddd, J=13.06, 9.34, 6.09 Hz).

Step 3: (S)-methyl 1-(3-fluoro-2-methylphenyl)-3-(1H-pyrazol-4-yl)cyclopentanecarboxylate To a solution of ((S)-methyl 1-(3-fluoro-2-methylphenyl)-3-(1H-pyrazol-4-yl)cyclopent-2-enecarboxylate (0.58 g, 1.93 mmol) in methanol (20 mL) was added ammonium formate (1.24 g, 19.3 mmol) and 20% palladium on carbon (0.15 g). The reaction mixture was refluxed for 1 h. After this time the reaction mixture was cooled to r.t. and filtered through Celite, washing with EtOAc (3×15 mL). Combined organics were extracted with water (30 mL) then brine (30 mL). EtOAc layers were then dried, filtered (phase separation cartridge) and concentrated to give the title compound as a colorless oil (0.57 g, 98%, 6:1 mixture of isomers).

NMR (Major Isomer): $^1$H NMR δ (ppm)(CDCl$_3$): 7.53 (1 H, s), 7.23-7.14 (2 H, m), 7.04-6.94 (1 H, m), 6.73 (1 H, s), 3.68 (3 H, s), 3.23-3.10 (1 H, m), 2.78-2.50 (3 H, m), 2.32-2.18 (2 H, m), 2.13 (3 H, d, J=2.74 Hz), 1.91-1.75 (1 H, m).

Step 4: (S)-methyl 1-(3-fluoro-2-methylphenyl)-3-(1-(2-morpholinoethyl)-1H-pyrazol-4-yl)cyclopentanecarboxylate To a solution of (S)-methyl 1-(3-fluoro-2-methylphenyl)-3-(1H-pyrazol-4-yl)cyclopentanecarboxylate (0.27 g, 0.89 mmol) in acetonitrile (15 mL) was added cesium carbonate (0.87 g, 2.68 mmol) and potassium iodide (0.02 g). 4-(2-Chloroethyl) morpholine hydrochloride (0.22 g, 1.07 mmol) was added and the reaction mixture was heated to 65° C. under N$_2$ for 18 h. After this time the reaction mixture was cooled to r.t. and filtered through Celite, washing with acetonitrile (3×15 mL) and the combined organics concentrated under reduced pressure. The crude residue was partitioned between EtOAc (30 mL) and water (30 mL). The organic layers were extracted washed with brine (30 mL), then dried, filtered (phase separation cartridge) and concentrated. The crude reaction material was purified by flash silica chromatography (gradient elution, 0-4% CH$_3$OH in CH$_2$Cl$_2$) to give the title compound as a colorless oil (0.36 g, 96%).

Step 5: (1S,3R)-1-(3-fluoro-2-methylphenyl)-3-(1-(2-morpholinoethyl)-1H-pyrazol-4-yl)cyclopentanecarboxylic acid Following Method C from (S)-methyl 1-(3-fluoro-2-methylphenyl)-3-(1-(2-morpholinoethyl)-1H-pyrazol-4-yl)cyclopentanecarboxylate (300 mg, 0.72 mmol). Purification by preparative HPLC gave the title compound as a colorless oil (21 mg). NMR (Major Isomer): $^1$H NMR δ (ppm) (DMSO-d$_6$): 12.50 (1H, br s), 7.65 (1 H, s), 7.37 (1 H, s), 7.32-7.26 (2 H, m), 7.14-7.08 (1 H, m), 4.20 (2 H, t, J=6.79 Hz), 3.60 (4 H, t, J=4.49 Hz), 3.04 (1 H, s), 2.72 (2 H, t, J=6.71 Hz), 2.60 (2 H, d, J=10.78 Hz), 2.49-2.38 (5 H, m), 2.21-2.16 (1 H, m), 2.15 (3 H, d, J=2.77 Hz), 1.80-1.61 (1 H, m).

Step 6: (1S,3R)-1-(3-fluoro-2-methylphenyl)-N-hydroxy-3-(1-(2-morpholinoethyl)-1H-pyrazol-4-yl)cyclopentanecarboxamide Following Method D from (1S,3R)-methyl 1-(3-fluoro-2-methylphenyl)-3-(1-(2-morpholinoethyl)-1H-pyrazol-4-yl)cyclopentanecarboxylate (160 mg, 0.40 mmol) and purified by preparative HPLC to give the title compound as a colorless solid (54.2 mg, 33%). LCMS (ES+) 417 (M+H)$^+$. $^1$H NMR δ (ppm)(CD$_3$OD): 7.70 (1 H, s), 7.57 (1 H, s), 7.39-7.26 (2 H, m), 7.08 (1 H, t, J=8.8 Hz), 4.49 (2 H, t, J=6.2 Hz), 3.89 (4 H, t, J=4.6 Hz), 3.34 (2 H, t, J=6.2 Hz), 3.24-3.13 (1 H, m), 3.05 (4 H, br s), 2.79-2.69 (1 H, m), 2.63 (1H, dd, J=13.2, 10.3 Hz), 2.52 (1 H, dd, J=13.2, 7.6 Hz), 2.34-2.23 (2 H, m), 2.24 (3 H, d, J=2.9 Hz), 1.96-1.83 (1 H, m). Two exchangeable protons not observed.

Example 48

(1 S,3R*)-1-(3-Fluoro-2-methylphenyl)-3-(5-fluoro-6-(2-(pyrrolidin-1-yl)ethoxy)pyridin-3-yl)-N-hydroxycyclopentanecarboxamide

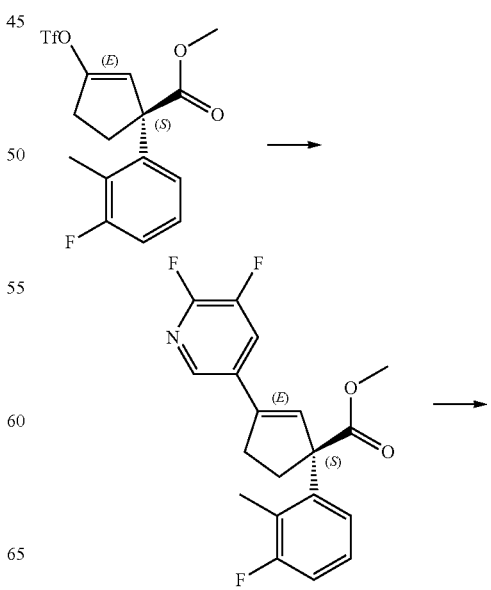

89
-continued

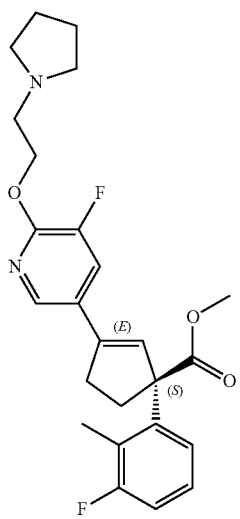

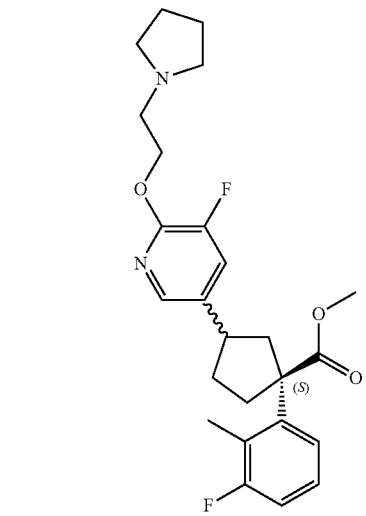

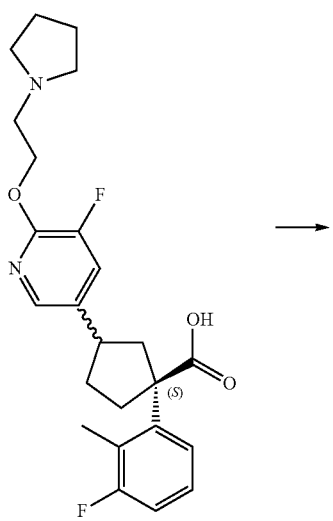

90
-continued

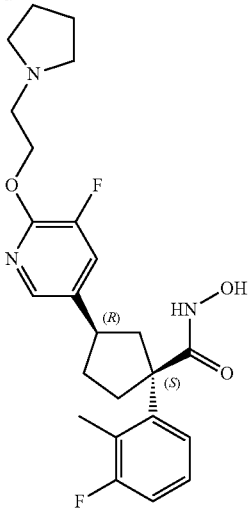

C3 Stereochemistry Putatively Assigned

Step 1: (S)-methyl 3-(5,6-difluoropyridin-3-yl)-1-(3-fluoro-2-methylphenyl)cyclopent-2-enecarboxylate Following Method B (ii) from (S)-methyl 1-(3-fluoro-2-methylphenyl)-3-(((trifluoromethyl)sulfonyl)oxy)cyclopent-2-enecarboxylate (0.36 g, 1.0 mmol) and 5-bromo-2,3-difluoropyridine (0.19 g, 0.1 mmol). The crude product was purified by flash silica column chromatography (gradient elution, 0-25% EtOAc in iso-hexane) to give the title compound as a pale yellow oil (0.23 g, 66%). MS (ES+) consistent with target (M+H)$^+$; $^1$H NMR δ (ppm)(CDCl$_3$): 8.09 (1H, d, J=1.1 Hz), 7.73-7.68 (1 H, m), 7.14-7.10 (1 H, m), 7.03-6.95 (2 H, m), 6.36 (1 H, t, J=1.8 Hz), 3.74 (3 H, s), 3.40 (1 H, ddd, J=13.2, 8.7, 4.3 Hz), 3.15-3.04 (1 H, m), 2.83-2.81 (1 H, m), 2.14 (3 H, d, J=2.5 Hz), 2.10-2.00 (1 H, m).

Step 2: (S)-methyl 1-(3-fluoro-2-methylphenyl)-3-(5-fluoro-6-(2-(pyrrolidin-1-yl)ethoxy)pyridin-3-yl) cyclo pent-2-enecarboxylate To a solution of 2-hydroxyethylpyrrolidine (0.08 g 0.7 mmol) in DMF (10.0 mL) was added NaH (0.03 g, 0.75 mmol) and the reaction mixture stirred at r.t. for 20 min. (S)-Methyl 3-(5,6-difluoropyridin-3-yl)-1-(3-fluoro-2-methylphenyl)cyclopent-2-enecarboxylate (0.23 g, 0.67 mmol) was added and stirring continued for 16 h. The reaction was quenched with water, extracted with ethyl acetate (3×30 mL), concentrated onto silica and purified by silica column chromatography (gradient elution, 0-100% EtOAc in iso-hexane) to yield the title compound as a yellow oil (0.160 g, 55%). LCMS (ES+) consistent with target (M+H)$^+$, $^1$H NMR δ (ppm)(CDCl$_3$): 8.09 (1 H, s) 7.53 (1 H, d, J=12.8 Hz), 7.14-7.10 (1 H, m), 7.04 (1 H, d, J=6.8 Hz), 6.96 (1 H, t, J=6.8 Hz), 6.21 (1 H, t, J=1.8 Hz), 4.56 (2 H, t, J=6.0 Hz), 3.69 (3 H, s), 3.40-3.32 (1 H, m), 3.08-2.96 (3 H, m), 2.83-2.81 (1 H, m), 2.66-2.61 (4 H, m), 2.14 (3 H, d, J=2.5 Hz), 2.10-2.00 (1 H, m), 1.84-1.78 (4 H, m).

Step 3: (S)-methyl 1-(3-fluoro-2-methylphenyl)-3-(5-fluoro-6-(2-(pyrrolidin-1-yl)ethoxy)pyridin-3-yl) cyclo pentanecarboxylate To a solution of (S)-methyl 1-(3-fluoro-2-methylphenyl)-3-(5-fluoro-6-(2-(pyrrolidin-1-yl)ethoxy)pyridin-3-yl)cyclopent-2-enecarboxylate (0.16 g, 0.36 mmol) in ethanol (20 mL) was added ammonium formate (0.125 g, 2.0 mmol), and palladium on charcoal (10% w/w, 0.01 g). The reaction mixture was heated to 65° C. for 2 h. Reaction mixture was cooled to r.t. and filtered through Celite, washing with EtOH (3×10 mL). The solvent was removed in vacuo and the resulting solid was partitioned between water and DCM (3×20 mL). The combined organics were dried (MgSO$_4$), filtered (phase separation cartridge) and the solvent removed to yield the title compound as a pale yellow oil (0.155 g, 95.5%) which was used in the next step without further purification. LCMS (ES+) consistent with target (M+H)$^+$.

Step 4: (S)-1-(3-fluoro-2-methylphenyl)-3-(5-fluoro-6-(2-(pyrrolidin-1-yl)ethoxy)pyridin-3-yl)cyclopentane carboxylic acid Following Method C from (S)-methyl-1-(3-fluoro-2-methylphenyl)-3-(5-fluoro-6-(2-(pyrrolidin-1-yl)ethoxy)pyridin-3-yl)cyclopentanecarboxylate (0.155 mg, 0.35 mmol) to give the title compound as a cream solid (100 mg, 66%), which was used in the next step without further purification. LCMS (ES+) consistent with target (M+H)$^+$.

Step 5: (1S,3R)-1-(3-fluoro-2-methylphenyl)-3-(5-fluoro-6-(2-(pyrrolidin-1-yl)ethoxy)pyridin-3-yl)-N-hydroxy cyclopentanecarboxamide Following Method D from (S)-1-(3-fluoro-2-methylphenyl)-3-(5-fluoro-6-(2-(pyrrolidin-1-yl)ethoxy)pyridin-3-yl)cyclopentanecarboxylic acid (100 mg, 0.23 mmol) and purified by preparative HPLC to give the title compound as a white solid (24 mg, 23%). LCMS (ES+) 446 (M+H)$^+$, RT 8.75 min (Analytical method 3); $^1$H NMR δ (ppm)(DMSO-d$_6$): 9.93 (1 H, s), 8.68 (1 H, s), 7.90 (1 H, s), 7.71 (1 H, d, J=12.8 Hz), 7.28-7.02 (3 H, m), 4.46 (2 H, t, J=6.0 Hz), 3.12-3.08 (1 H, m), 2.92-2.86 (3 H, m), 2.75-2.65 (1 H, m), 2.64-2.51 (5 H, m), 2.39-2.29 (1 H, m), 2.28-2.15 (1 H, m) 2.14 (3 H, d, J=2.5 Hz), 2.10-2.00 (1 H, m), 1.78-1.70 (4 H, m).

Example 49

(1S,3R*)-1-(3-Fluoro-2-methylphenyl)-N-hydroxy-3-(1-methyl-1H-pyrazol-5-yl)cyclopentane carboxamide (D1)

Example 50

(1S,3S*)-1-(3-Fluoro-2-methylphenyl)-N-hydroxy-3-(1-methyl-1H-pyrazol-5-yl)cyclopentanecarboxamide (D2)

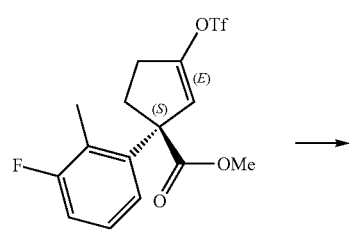

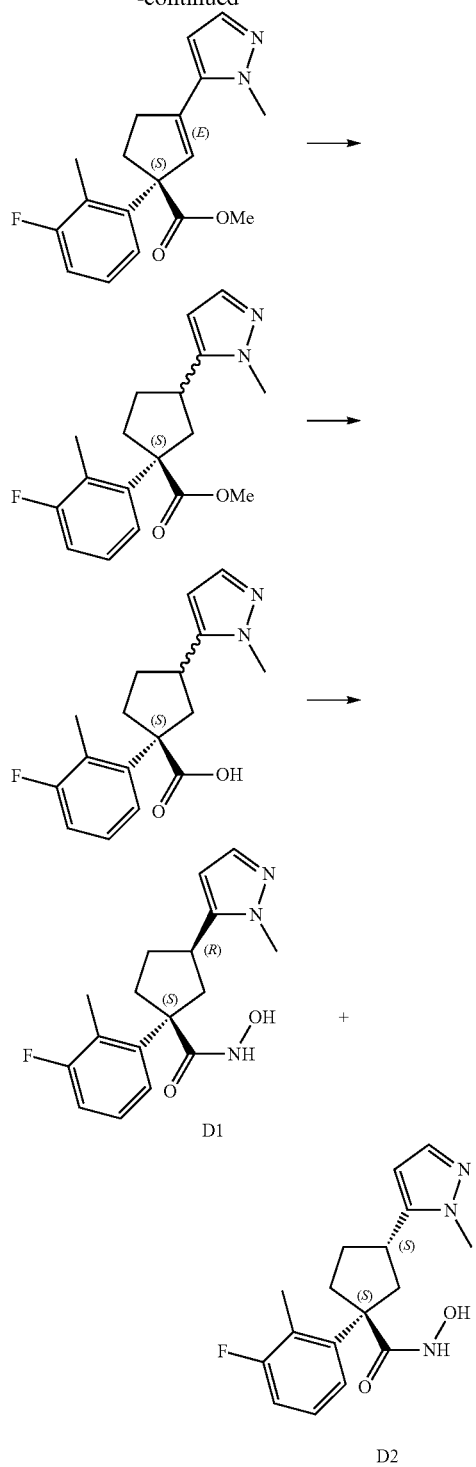

C3 Stereochemistry Putatively Assigned

Step 1: (S)-methyl 1-(3-fluoro-2-methylphenyl)-3-(1-methyl-1H-pyrazol-5-yl)cyclopent-2-enecarboxylate Following Method B from (S)-methyl 1-(3-fluoro-2-methylphenyl)-3-(((trifluoromethyl)sulfonyl)oxy)cyclopent-2-enecarboxylate (300 mg, 0.79 mmol) and (1-methyl- 1H-pyrazol-5-yl)boronic acid utilizing CsF, DME, MeOH and palladium tetrakis(triphenylphosphine) at 120° C. The crude product was purified by flash column chromatography to give the title compound as a clear oil (221 mg). MS (ES+) consistent with target (M+H)+.

Step 2: (S)-methyl 1-(3-fluoro-2-methylphenyl)-3-(1-methyl-1H-pyrazol-5-yl)cyclopentanecarboxylate A solution of (S)-methyl 1-(3-fluoro-2-methylphenyl)-3-(1-methyl-1H-pyrazol-5-yl)cyclopent-2-enecarboxylate (326 mg, 1.04 mmol) in EtOH (10 mL) in a pressure tube was purged with nitrogen and treated with 20% w/w Pd/C (163 mg, 0.31 mmol) and ammonium formate (653 mg, 10.4 mmol). The tube was sealed and heated to 80° C. for 1.5 h. The solids were removed by filtration through Celite and the filtrate concentrated. The residue was diluted with water and extracted with EtOAc (3×). The combined organic extracts were dried (phase separation cartridge) and concentrated to give a mixture of isomers of the title compound as a colorless gum (283 mg).

Step 3: (S)-1-(3-fluoro-2-methylphenyl)-3-(1-methyl-1H-pyrazol-5-yl)cyclopent-2-enecarboxylic acid Following Method C from (S)-methyl 1-(3-fluoro-2-methylphenyl)-3-(1-methyl-1H-pyrazol-5-yl)cyclopent-2-enecarboxylate (220 mg) and the impure crude material used without further purification (313 mg). MS (ES+) consistent with target (M+H)+.

Step 4: (1S,3R*)-1-(3-fluoro-2-methylphenyl)-N-hydroxy-3-(1-methyl-1H-pyrazol-5-yl)cyclopentane carboxamide (Example 49, D1) and (1S,3S*)-1-(3-fluoro-2-methylphenyl)-N-hydroxy-3-(1-methyl-1H-pyrazol-5-yl)cyclopentane carboxamide (Example 50, D2)

Following Method D using the diastereomeric mixture of (S)-methyl 1-(3-fluoro-2-methylphenyl)-3-(1-methyl-1H-pyrazol-5-yl)cyclopentanecarboxylate from the previous step (0.205 g, 0.68 mmol). Purification by preparative HPLC gave Example 49 (D1) as a white solid (22 mg) and Example 50 (D2) as a white solid (5.5 mg).

Example 49 (diastereomer 1 (D1)): LCMS (ES+) 318 (M+H)+, RT 8.92 min (Analytical method 3); $^1$H NMR δ (ppm) (400 MHz, CDCl$_3$); 7.76 (2H, s), 7.39 (1H, d, J=1.9 Hz), 7.26-7.19 (2H, m), 7.09-7.03 (1H, m), 6.23 (1H, d, J=1.6 Hz), 3.78 (3H, s), 3.19-3.09 (1H, m), 2.77-2.66 (2H, m), 2.49 (1H, dd, J=13.4, 7.6 Hz), 2.33-2.20 (2H, m), 2.14 (3H, d, J=2.9 Hz), 2.05-1.88 (1H, m).

Example 50 (diastereomer 2 (D2)): LCMS (ES+) 318 (M+H)+, RT 9.09 min (Analytical method 3); $^1$H NMR δ (ppm) (400 MHz, CDCl$_3$); 7.72 (1H, s), 7.34 (1H, d, J=1.6 Hz), 7.24-7.21 (2H, m), 7.8-7.2 (2H, m), 5.91 (1H, d, J=1.5 Hz), 3.84 (3H, s), 3.58-3.49 (1H, m), 3.00 (1H, dd, J=12.9, 7.3 Hz), 2.73-2.66 (1H, m), 2.39-2.27 (2H, m), 2.14 (3H, d, J=2.4 Hz), 1.83-1.74 (1H, m). OH not observed.

Example 51

(1S,3R*)-3-(1-(2-(diethylamino)ethyl)-1H-pyrazol-4-yl)-1-(3-fluoro-2-methylphenyl)-N-hydroxycyclopentanecarboxamide

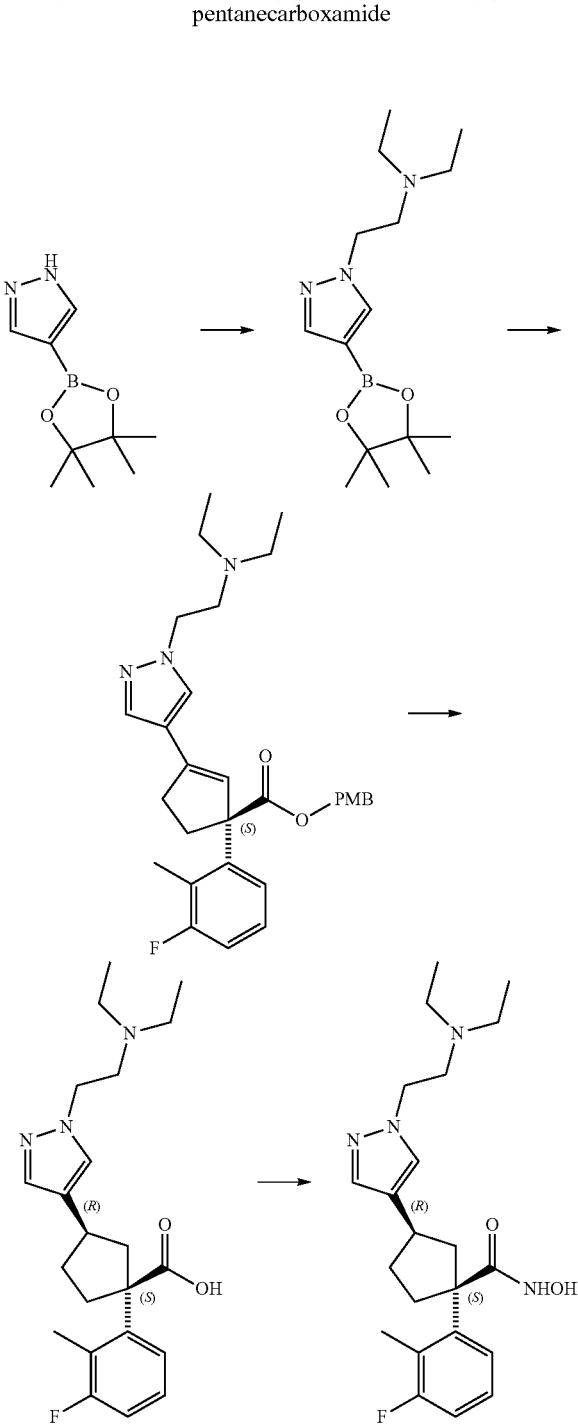

C3 Stereochemistry Putatively Assigned

Step 1: N,N-diethyl-2-(4-(4,4,5,5-tetramethyl-1,3,2-dioxaborolan-2-yl)-1H-pyrazol-1-yl)ethanamine To a solution of 4-(4,4,5,5-tetramethyl-1,3,2-dioxaborolan-2-yl)-1H-pyrazole (1.00 g, 5.15 mmol) in acetonitrile (15 mL) was added cesium carbonate (6.00 g, 15.5 mmol), potassium iodide (0.30 g) and 2-chloro-N,N-diethylethanamine hydrochloride (1.30 g, 7.73 mmol) and the reaction mixture heated to 50° C. under N₂ for 1.5 h. After this time the reaction mixture was cooled to r.t. and filtered through Celite, washing with EtOAc (3×20 mL). Combined organics were concentrated under reduced pressure to give the title compound as a pale yellow oil which was used without further purification (1.32 g, 87%).

¹H NMR δ (ppm)(CDCl₃): 7.77 (1 H, s), 7.72 (1 H, s), 4.18 (2 H, t, J=7.05 Hz), 2.86 (2 H, t, J=7.05 Hz), 2.53 (4 H, q, J=7.06 Hz), 1.32-1.30 (12 H, m), 1.00 (6 H, t, J=3.71 Hz). Contaminated with ~20% 2-chloro-N,N-diethylethanamine.

Step 2: (S)-4-methoxybenzyl 3-(1-(2-(diethylamino) ethyl)-1H-pyrazol-4-yl)-1-(3-fluoro-2-methylphenyl) cyclopent-2-enecarboxylate To a solution of (S)-4-methoxybenzyl 1-(3-fluoro-2-methylphenyl)-3-(((trifluoromethyl)sulfonyl)oxy)cyclopent-2-enecarboxylate (0.488 g, 1.0 mmol) in 1,2 dimethoxyethane (6 mL) was added N,N-diethyl-2-(4-(4,4,5,5-tetramethyl-1,3,2-dioxaborolan-2-yl)-1H-pyrazol-1-yl) ethanamine (0.293 g, 1.00 mmol), cesium carbonate (0.8 g, 2.0 mmol) and water (2 mL). The reaction mixture was heated to 60° C. after which time a colorless solution formed. [1,1'-bis(diphenylphosphino)ferrocene]dichloropalladium(II), complex with dichloromethane (0.4 g, 0.4 mmol) was added and the reaction mixture was heated to 85° C. under N₂ for 1 h. After this time the reaction mixture was cooled to r.t. and filtered through Celite, washing with EtOAc (3×10 mL). Combined organics were extracted with water (15 mL) then brine (20 mL). EtOAc layers were then dried, filtered (phase separation cartridge) and concentrated to give a brown residue. The crude reaction material was purified by SCX cartridge (gradient elution CH₂Cl₂ to CH₃OH to 1.5N NH₃ in CH₃OH) to give the title compound as a pale yellow oil (0.26 g, 78%).

¹H NMR δ (ppm)(CDCl₃): 7.63 (1 H, s), 7.50 (1 H, s), 7.18-7.11 (2 H, m), 7.12-7.06 (2 H, m), 6.97-6.89 (1 H, m), 6.84-6.79 (2 H, m), 5.96 (1 H, t, J=1.79 Hz), 5.07 (2 H, s), 4.39-4.31 (2 H, m), 3.79 (3 H, s), 3.26 (1 H, ddd, J=13.28, 8.82, 4.34 Hz), 3.26-3.11 (2 H, m), 2.91-2.79 (6 H, m), 2.70-2.61 (1 H, m), 1.98 (3 H, d, J=2.53 Hz), 1.97-1.88 (1 H, m), 1.11 (6 H, t, J=7.18 Hz).

Step 3: (1S,3R*)-3-(1-(2-(diethylamino)ethyl)-1H-pyrazol-4-yl)-1-(3-fluoro-2-methylphenyl)cyclopentanecarboxylic acid To a solution of (S)-4-methoxybenzyl 3-(1-(2-(diethylamino)ethyl)-1H-pyrazol-4-yl)-1-(3-fluoro-2-methylphenyl)cyclopent-2-enecarboxylate (0.25 g, 0.51 mmol) in methanol (15 mL) was added ammonium formate (0.33 g, 5.20 mmol) and 2% palladium on carbon (0.06 g). The reaction mixture was refluxed for 2 h. After this time the reaction mixture was cooled to r.t. and filtered through Celite, washing with CH₃OH (3×15 mL). Combined organics were concentrated under reduced pressure and the residue resuspended in EtOAc (30 mL). The organic layer was extracted with water (25 mL) then brine (20 mL). EtOAc layers were then dried, filtered (phase separation cartridge) and concentrated. The crude reaction material was purified by SCX cartridge (gradient elution CH₂Cl₂ to CH₃OH to 1.5 M NH₃ in CH₃OH) to give a 3:1 diastereomeric mixture of the title compound as a pale yellow oil (0.08 g, 65%). Purification by preparative chiral HPLC gave a single diastereomer, putatively assigned (3R) stereochemistry.

Step 4: (1S,3R*)-3-(1-(2-(diethylamino)ethyl)-1H-pyrazol-4-yl)-1-(3-fluoro-2-methylphenyl)-N-hydroxycyclopentanecarboxamide Following Method D from (1S,3R*)-3-(1-(2-(diethylamino)ethyl)-1H-pyrazol-4-yl)-1-(3-fluoro-2-methylphenyl)cyclopentanecarboxylic acid (47 mg, 0.12 mmol) and purified by preparative HPLC to give the title compound as a colorless solid (18.0 mg, 18%). LCMS (ES+) 403 (M+H)⁺, RT 8.30 min (Analytical method 3); ¹H NMR δ (ppm)(400 MHz, CD₃OD): 7.62 (1H, s), 7.48 (1H, s), 7.33-7.23 (2H, m), 7.03 (1H, t, J=8.7 Hz), 4.30-4.25 (2H, m), 3.18-3.03 (3H, m), 2.75-2.67 (6H, m), 2.57-2.49 (2H, m), 2.27-2.15 (3H, m), 2.18 (3H, d, J=3.3 Hz), 1.90-1.78 (1H, m), 1.14-1.07 (6H, m).

Example 52

N—((R)-1-(dipropylamino)propan-2-yl)-4-((1R*, 3S)-3-(3-fluoro-2-methylphenyl)-3-(hydroxycarbamoyl)cyclopentyl)benzamide (D1)

Example 53

N—((R)-1-(dipropylamino)propan-2-yl)-4-((1S*, 3S)-3-(3-fluoro-2-methylphenyl)-3-(hydroxycarbamoyl)cyclopentyl)benzamide (D2)

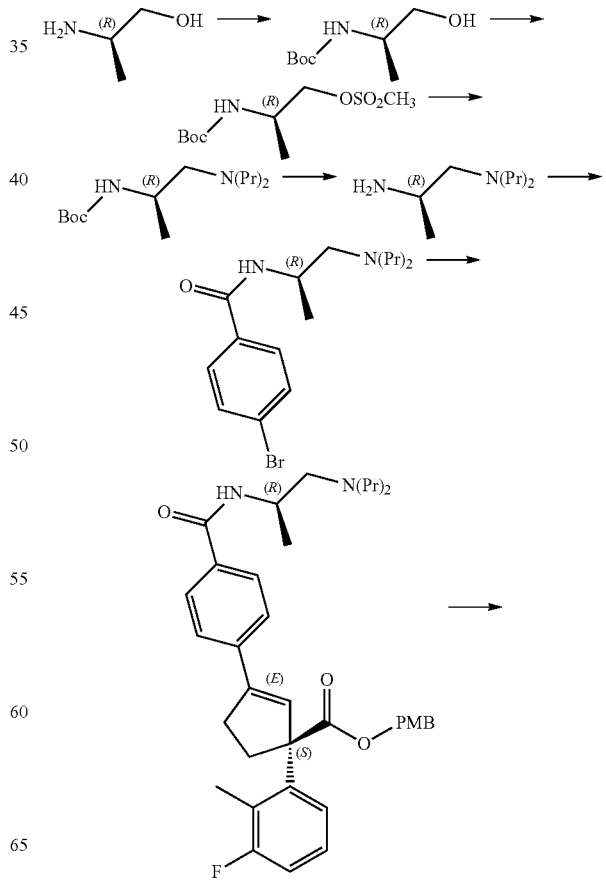

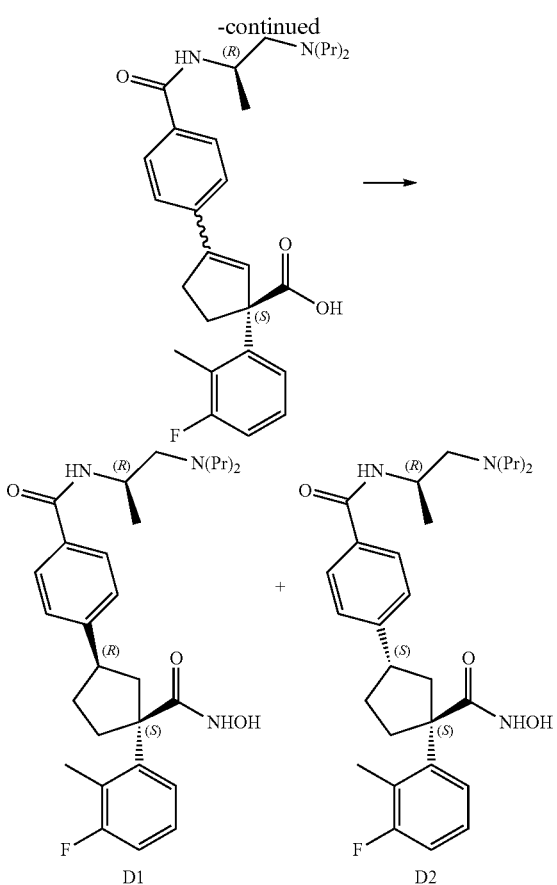

Step 1:
(R)-tert-butyl(1-hydroxypropan-2-yl)carbamate

To a solution of D-alaninol (5.0 g, 66.58 mmol) in anhydrous THF (50 mL) at 0° C. was added dropwise Boc₂O (15.26 g, 70.0 mmol) as a solution in anhydrous THF (20 mL) over 30 minutes. The reaction mixture was stirred at 0° C. for a further 1 h and then warmed to r.t. over a further 16 h. After this time the organics were concentrated under reduced pressure and the residue triturated with iso-hexane to give a solid which was filtered and air dried to give the title compound as a colorless solid (10.4 g, 89%).
¹H NMR δ (ppm)(CDCl₃): 4.64 (1 H, s), 3.77 (1 H, s), 3.64 (1 H, d, J=11.0 Hz), 3.51 (1 H, t, J=7.8 Hz), 2.62 (1 H, br s), 1.70 (2 H, s), 1.45 (9 H, s), 1.15 (3 H, d, J=6.8 Hz).

Step 2: (R)-2-((tert-butoxycarbonyl)amino)propyl methanesulfonate

To a solution of (R)-tert-butyl(1-hydroxypropan-2-yl)carbamate (3.0 g, 17.2 mmol) in anhydrous dichloromethane (65 mL) at 0° C. was added triethylamine (2.59 g, 25.68 mmol), followed by mesyl chloride (2.16 g, 18.92 mmol) as a solution in anhydrous dichloromethane (30 mL), added dropwise over 1 h. The reaction mixture was stirred at 0° C. for a further 1 h and then warmed to r.t. for a further 2 h. After this time the organics layers were washed with water (65 mL), sat. aq. NaHCO₃ solution (60 mL) and brine (6 mL). Dichloromethane layers were then dried, filtered (phase separation cartridge) and concentrated. The residue was triturated with iso-hexane to give a solid which was filtered and air dried to give the title compound as a colorless solid (4.10 g, 94%).

¹H NMR δ (ppm)(CDCl₃): 4.55 (1 H, s), 4.15 (1 H, s), 4.08 (1 H, ddd, J=10.0, 4.3, 1.6 Hz), 3.90 (1 H, s), 2.96 (3 H, d, J=1.3 Hz), 1.66-1.47 (1 H, m), 1.38 (9 H, s), 1.17 (3 H, dd, J=6.9, 1.7 Hz).

Step 3: (R)-tert-butyl(1-(dipropylamino)propan-2-yl)carbamate

To a solution of (R)-2-((tert-butoxycarbonyl)amino)propyl methanesulfonate (3.2 g, 12.6 mmol) in anhydrous DMF (30 mL) was added cesium carbonate (12.4 g, 37.9 mmol) and dipropylamine (2.60 g, 25.27 mmol) and the reaction mixture was heated at 65° C. for 18 h. After this time the reaction mixture was cooled to r.t. and filtered through Celite, washing with CH₃OH (3×30 mL). The combined organic layers were then dried, filtered (phase separation cartridge) and concentrated to minimum volume. The crude reaction material was purified by SCX cartridge (gradient elution CH₂Cl₂ to CH₃OH to 1.5 M NH₃ in CH₃OH) to give the title compound as a colorless solid after drying under high vacuum (1.80 g, 55%).
¹H NMR δ (ppm)(CDCl₃): 4.81 (1 H, s), 3.62-3.52 (1 H, m), 2.46-2.24 (7H, m), 1.48-1.37 (13 H, m), 1.14 (3 H, d, J=6.4 Hz), 0.91-0.83 (6 H, m).

Step 4: (R)—N¹,N¹-dipropylpropane-1,2-diamine

To a solution of (R)-tert-butyl(1-(dipropylamino)propan-2-yl)carbamate (1.8 g, 6.97 mmol) in anhydrous dichloromethane (15 mL) at 0° C. was added trifluoroacetic acid (3 mL) and the reaction mixture was stirred at 0° C. for 1 h and then at r.t. for a further 1 h. After this time the reaction mixture was concentrated to minimum volume. The crude reaction material was purified by SCX cartridge (gradient elution CH₂Cl₂ to CH₃OH to 1.5N NH₃ in CH₃OH) to give the title compound as a pale brown oil (0.61 g, 55%).
¹H NMR δ (ppm)(CHCl₃-d): 3.00-2.89 (1 H, m), 2.47-2.20 (6 H, m), 2.18-2.05 (1 H, m), 0.99 (3 H, d, J=6.32 Hz), 0.87 (6 H, t, J=7.34 Hz).

Step 5: (R)-4-bromo-N-(1-(dipropylamino)propan-2-yl)benzamide

To a solution of (R)—N¹,N¹-dipropylpropane-1,2-diamine (0.25 g, 1.58 mmol) in anhydrous DMF (5 mL) was added 4-bromobenzoic acid (0.32 g, 1.58 mmol), HATU (0.90 g, 2.37 mmol) and DIPEA (0.62 g, 4.74 mmol). The reaction mixture was then stirred at r.t. under N₂ for 4 h. After this time the reaction mixture was diluted with EtOAc (20 mL), washed with water (20 mL), sat. aq. NaHCO₃ (2×15 mL) and brine (20 mL). The organic layer was dried, filtered and concentrated under reduced pressure to give an orange residue. The crude reaction material was purified by flash silica chromatography (gradient elution, 0-100% EtOAc in iso-hexane) to give the title compound as a colorless oil (0.28 g, 52%), which was used without further purification.

Step 6: (S)-4-methoxybenzyl 3-(4-(((R)-1-(dipropylamino)propan-2-yl)carbamoyl)phenyl)-1-(3-fluoro-2-methylphenyl)cyclopent-2-enecarboxylate To a solution of (R)-4-bromo-N-(1-(dipropylamino)propan-2-yl)benzamide (0.28 g, 0.82 mmol) in anhydrous dioxane (5 mL) was added bis(neopentyl glycolato)diboron (0.20g, 0.90 mmol), potassium acetate (0.16 g, 1.64 mmol) and [1,1'-bis(diphenylphosphino)ferrocene]dichloropalladium(II), complex with dichloromethane (0.04 g, 0.04 mmol) were added and the reaction mixture heated to 85° C. under N$_2$ for 16 h. After this time the reaction mixture was cooled to r.t. and a solution of (S)-4-methoxybenzyl 1-(3-fluoro-2-methylphenyl)-3-(((trifluoromethyl)sulfonyl)oxy) cyclopent-2 enecarboxylate (0.4 g, 0.82 mmol) in anhydrous dioxane (1 mL) was added followed by a solution of cesium carbonate (0.40 g, 1.25 mmol) in water (1 mL). The reaction mixture was recapped and heated to 85° C. under N$_2$ for a further 24 h. Reaction mixture water was decanted, and the dioxane layers were then concentrated under reduced pressure. The crude reaction material was purified by flash silica chromatography (KP-NH cartridge, gradient elution, 0-25% EtOAc in iso-hexane) to give the title compound as a colorless oil (0.30 g, 60%).

$^1$H NMR δ (ppm)(CDCl$_3$): 7.77 (2 H, d, J=8.18 Hz), 7.54 (2 H, d, J=8.19 Hz), 7.17-7.11 (2 H, m), 7.11-7.03 (2 H, m), 6.96-6.90 (1 H, m), 6.84-6.77 (2 H, m), 6.37 (1 H, s), 5.07 (2 H, s), 4.04-3.95 (1 H, m), 3.78 (3 H, s), 3.32 (1 H, ddd, J=13.22, 8.77, 4.35 Hz), 3.5-2.95 (1 H, m), 2.87-2.78 (1 H, m), 2.52-2.32 (6 H, m), 2.06-1.97 (4 H, m), 1.53-1.38 (4 H, m), 1.32 (3 H, d, J=6.27 Hz), 0.86 (6 H, t, J=7.34 Hz).

Step 7: (S)-3-(4-(((R)-1-(dipropylamino)propan-2-yl)carbamoyl)phenyl)-1-(3-fluoro-2-methylphenyl) cyclopentanecarboxylic acid To a solution of (S)-4-methoxybenzyl 3-(4-(((R)-1-(dipropylamino)propan-2-yl)carbamoyl)phenyl)-1-(3-fluoro-2-methylphenyl)cyclopent-2-enecarboxylate (0.30 g, 0.50 mmol) in methanol (15 mL) was added ammonium formate (0.47 g, 4.70 mmol) and 20% palladium on carbon (0.06 g). The reaction mixture was refluxed for 2 h. After this time the reaction mixture was cooled to r.t. and filtered through Celite, washing with CH$_3$OH (3×15 mL). Combined organics were concentrated under reduced pressure and the residue resuspended in EtOAc (30 mL). The organic layer was extracted with water (25 mL) then brine (20 mL). EtOAc layers were then dried, filtered (phase separation cartridge) and concentrated. The crude reaction material was purified by SCX cartridge (gradient elution CH$_2$Cl$_2$ to CH$_3$OH to 1.5 M NH$_3$ in CH$_3$OH) to give the title compound as a colorless semi-solid (0.15 g, 70%, d.r.=1:1).

Step 8: N—((R)-1-(dipropylamino)propan-2-yl)-4-((1R*,3S)-3-(3-fluoro-2-methylphenyl)-3-(hydroxycarbamoyl)cyclopentyl)benzamide (Example 52, diastereomer 1 (D1)) and N—((R)-1-(dipropylamino)propan-2-yl)-4-((1S*,3S)-3-(3-fluoro-2-methylphenyl)-3-(hydroxycarbamoyl)cyclopentyl) benzamide (Example 53, diastereomer 2 (D2))

Following Method D from (S)-3-(4-(((R)-1-(dipropylamino)propan-2-yl)carbamoyl)phenyl)-1-(3-fluoro-2-methylphenyl)cyclopentanecarboxylic acid (150 mg, 0.31 mmol) and purified by preparative HPLC to give example 52 (D1) as a colorless solid (21.0 mg, 21%) and example 53 (D2) as a colorless solid.

Example 52 (D1): LCMS (ES+) 498 (M+H)$^+$, RT 2.69 (Analytical method 1); $^1$H NMR δ (ppm)(CD$_3$OD): 7.81 (2 H, d, J=8.1 Hz), 7.50 (2H, d, J=8.3 Hz), 7.38 (1H, d, J=7.7 Hz), 7.31-7.25 (1H, m), 7.6 (1H, t, J=8.9 Hz), 3.51 (1H, dd, J=1.7, 3.2 Hz), 3.29-3.16 (2H, m), 2.77-2.68 (6H, m), 2.51 (1H, dd, J=13.6, 7.3 Hz), 2.37-2.29 (1H, m), 2.27-2.21 (1H, m), 2.19 (3H, d, J=2.9 Hz), 2.03-1.94 (1H, m), 1.62 (6H, br s), 1.32 (3H, d, J=6.5 Hz), 0.97 (6H, t, J=7.2 Hz). Two exchangeable protons not observed.

Example 53 (D2): LCMS (ES+) 498 (M+H)$^+$, RT 2.63 min (Analytical method 1); $^1$H NMR δ (ppm)(CD$_3$OD): 7.78 (2H, d, J=8.3 Hz), 7.37-7.33 (3H, m), 7.28-7.21 (1H, m), 7.03 (1H, t, J=8.9 Hz), 3.52-3.42 (2H, m), 3.12-3.06 (1H, m), 2.77-2.68 (4H, m), 2.39-2.29 (2H, m), 2.20 (3H, d, J=2.6 Hz), 2.12-2.04 (1H, m), 1.96-1.84 (1H, m), 1.63-1.62 (4H, m), 1.32 (3H, d, J=6.7 Hz), 0.97 (6H, t, J=7.3 Hz). Two exchangeable protons not observed. Four protons obscured by methanol peak.

Example 54

(1S,3R*)-3-(1-(difluoromethyl)-1H-indazol-6-yl)-1-(3-fluoro-2-methylphenyl)-N-hydroxycyclopentanecarboxamide Example 55

(1S,3S*)-3-(1-(difluoromethyl)-1H-indazol-6-yl)-1-(3-fluoro-2-methylphenyl)-N-hydroxycyclopentanecarboxamide

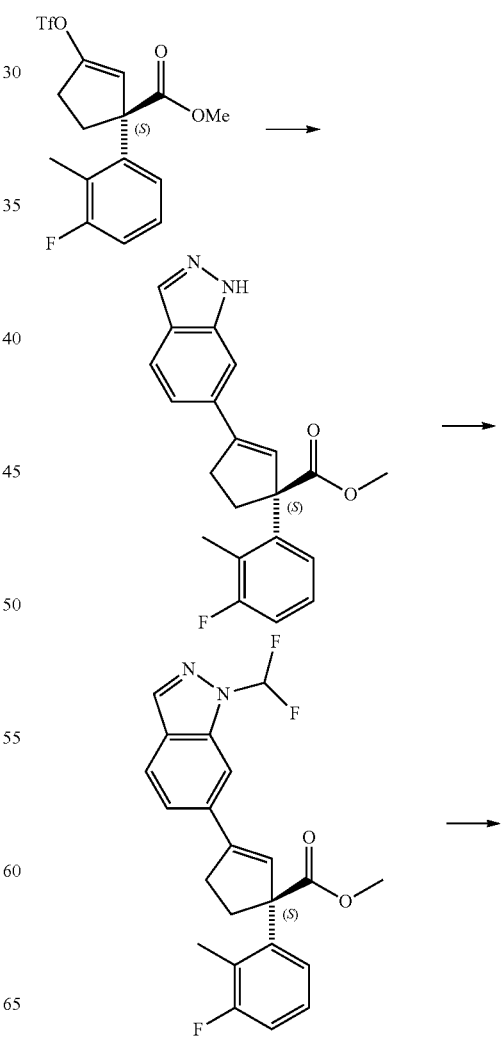

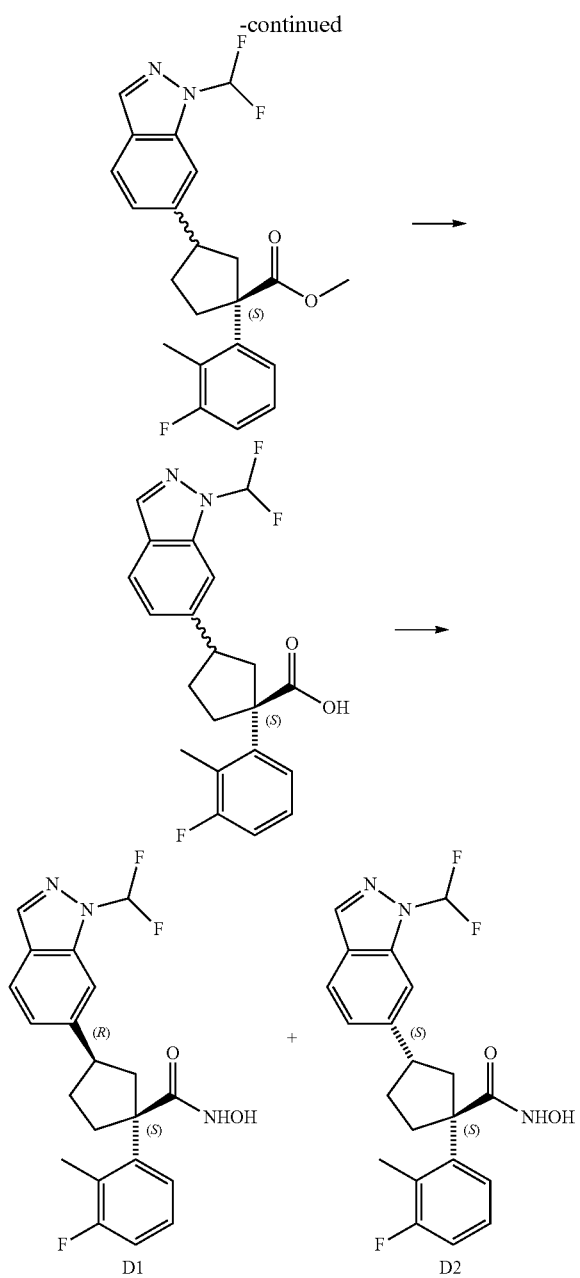

Step 1: (S)-methyl 1-(3-fluoro-2-methylphenyl)-3-(1H-indazol-6-yl)cyclopent-2-enecarboxylate Following Method B from (S)-methyl 1-(3-fluoro-2-methylphenyl)-3-(((trifluoromethyl)sulfonyl)oxy)cyclopent-2-enecarboxylate (0.3 g, 0.79 mmol) and 6-(4,4,5,5-tetramethyl-1,3,2-dioxaborolan-2-yl)-1H-indazole (0.26 g, 0.16 mmol). The crude product was purified by silica column chromatography (gradient elution, 0-25% EtOAc in iso-hexane) to give the title compound as a colorless solid (0.15 g, 56%).

Step 2: (S)-methyl 3-(1-(difluoromethyl)-1H-indazol-6-yl)-1-(3-fluoro-2-methylphenyl)cyclopent-2-enecarboxylate A 25 mL round bottom flask was charged with (S)-methyl 1-(3-fluoro-2-methylphenyl)-3-(1H-indazol-6-yl)cyclopent-2-enecarboxylate (0.14 g, 0.48 mmol), 18-crown-6 (0.02 g, 0.09 mmol) and anhydrous acetonitrile (10 mL). The reagents were stirred until a colorless solution formed then sodium chlorodifluoroacetate (0.08 g, 0.48 mmol) was added and the reaction mixture refluxed for 18 h. After this time a further portion of 18-crown-6 (0.2 g, 0.9 mmol) and sodium chlorodifluoroacetate (0.08 g, 0.48 mmol) were added and the reaction mixture was refluxed for a further 20 h. After this time the reaction was cooled to r.t. and precipitated solid filtered through Celite, washing with EtOAc (3×20 mL). The combined organics were then dried and filtered (phase separator) to give a yellow residue. The crude product was purified by silica column chromatography (gradient elution, 0-20% EtOAc in iso-hexane) to give the title compound as a colorless oil (0.07 g, 28%).

Step 3: (S)-methyl 3-(1-(difluoromethyl)-1H-indazol-6-yl)-1-(3-fluoro-2-methylphenyl)cyclopentanecarboxylate A suspension of (S)-methyl 3-(1-(difluoromethyl)-1H-indazol-6-yl)-1-(3-fluoro-2-methylphenyl)cyclopent-2-enecarboxylate (210 mg, 0.52 mmol), ammonium formate (340 mg, 5.20 mmol) and 20% w/w Pd/C (65 mg) in MeOH (10 mL) was stirred at reflux for 10 h. After cooling to r.t. the mixture was filtered through Celite, washing with MeOH (3×15 mL). The filtrate was concentrated and the residue partitioned between water (40 mL) and DCM (20 mL). The organic layer was extracted with DCM (3×20 mL) and the combined organic extracts were dried (phase separation cartridge) and concentrated to give a colorless oil. Purification by preparative SFC isolated the two diastereomers of the title compound as colorless oils (48 mg and 128 mg), which were reacted separately in the following step.

Step 4: (S)-3-(1-(difluoromethyl)-1H-indazol-6-yl)-1-(3-fluoro-2-methylphenyl)cyclopentanecarboxylic acid Following Method C(iii) from each diastereomer of (S)-methyl 3-(1-(difluoromethyl)-1H-indazol-6-yl)-1-(3-fluoro-2-methylphenyl)cyclopentanecarboxylate isolated in the previous step (48 mg and 128 mg), using 25 equivalents of LiOH and heating for 72 h. The title compounds were obtained as colorless solids (28 mg and 48 mg respectively) which were reacted separately in the following step.

Step 5: (1S,3R*)-3-(1-(difluoromethyl)-1H-indazol-6-yl)-1-(3-fluoro-2-methylphenyl)-N-hydroxycyclopentanecarboxamide (D1) and (1S,3S*)-3-(1-(difluoromethyl)-1H-indazol-6-yl)-1-(3-fluoro-2-methylphenyl)-N-hydroxycyclopentanecarboxamide (D2)

Following Method D from each diastereomer of (S)-3-(1-(difluoromethyl)-1H-indazol-6-yl)-1-(3-fluoro-2-methylphenyl)cyclopentanecarboxylic acid isolated in the previous step (28 mg and 48 mg). Example 54 (D1, 14.7 mg) and example 55 (D2, 1.4 mg) were obtained as colorless solids.

Example 54 (diastereomer 1 (D1)): LCMS (ES+) 44 (M+H)$^+$, RT 3.75 min (Analytical method 1); $^1$H NMR δ (ppm)(DMSO-d$_6$): 9.95 (1H, s), 8.83 (1H, s), 8.70 (1H, s), 8.14 (1H, t, J=59.2 Hz), 7.78 (1H, d, J=8.8 Hz), 7.59 (1H, s), 7.37-7.26 (3H, m), 7.11 (1H, t, J=8.6 Hz), 3.28-3.17 (1H, m), 2.75-2.62 (2H, m), 2.43 (1H, dd, J=12.8, 8.1 Hz), 2.28-2.15 (2H, m), 2.13 (3H, d, J=2.8 Hz), 1.89-1.78 (1H, m).

Example 55 (diastereomer 2 (D2)): LCMS (ES+) 3.65 min (Analytical method 1); $^1$H NMR δ (ppm)(DMSO-$d_6$): 1.5 (1H, s), 8.82 (1H, s), 8.72 (1H, br s), 8.13 (1H, t, J=58.7 Hz), 7.74 (1H, d, J=9.1 Hz), 7.52 (1H, s), 7.35 (1H, d, J=7.6 Hz), 7.29-7.21 (1H, m), 7.12-7.06 (2H, m), 3.06 (1H, dd, J=12.4, 7.1 Hz), 2.82-2.70 (1H, m), 2.29-2.03 (3H, m), 2.18 (3H, d, J=2.5 Hz), 1.87-1.76 (1H, m). 1H obscured by water peak.

Example 56

(1S,3R*)-1-(3-fluoro-2-methylphenyl)-N-hydroxy-3-(1-methyl-1H-indazol-6-yl)cyclopentanecarboxamide

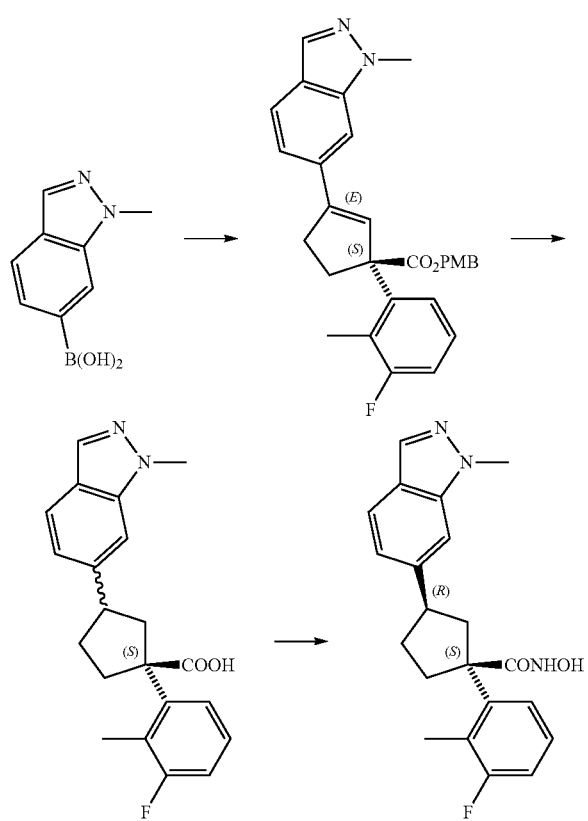

C3 Stereochemistry Putatively Assigned

Step 1: (S)-methyl 1-(3-fluoro-2-methylphenyl)-3-(1-methyl-1H-indazol-6-yl)cyclopent-2-enecarboxylate Following Method B from (1-methyl-1H-indazol-6-yl)boronic acid (152 mg, 0.86 mmol) and Intermediate 9 (350 mg, 0.72 mmol). Purification by flash chromatography (gradient elution, 0-50% EtOAc in iso-hexane) gave the title compound as a pale yellow foam (338 mg, 96%).

Step 2: (S)-1-(3-fluoro-2-methylphenyl)-3-(1-methyl-1H-indazol-6-yl)cyclopentanecarboxylic acid Following Method F from (S)-methyl 1-(3-fluoro-2-methylphenyl)-3-(1-methyl-1H-indazol-6-yl)cyclopent-2-enecarboxylate (338 mg). Purification by silica column chromatography (gradient elution, 0-100% EtOAc in DCM) gave the title compound as a colorless solid (180 mg) in a 4:1 d.r. The diastereomers were separated by chiral preparative HPLC and the major diastereomer used in the following step.

Step 3: (1S,3R*)-1-(3-fluoro-2-methylphenyl)-N-hydroxy-3-(1-methyl-1H-indazol-6-yl)cyclopentanecarboxamide Following Method D from (S)-1-(3-fluoro-2-methylphenyl)-3-(1-methyl-1H-indazol-6-yl)cyclopentanecarboxylic acid. The title compound was obtained as a colorless solid. LCMS (ES+) 368 (M+H)$^+$, RT 3.63 min (Analytical method 1); $^1$H NMR δ (ppm)(DMSO-$d_6$): 9.94 (1H, s), 8.70 (1H, s), 7.99 (1H, s), 7.71 (1H, d, J=8.4 Hz), 7.55 (1H, s), 7.37-7.26 (2H, m), 7.20 (1H, d, J=8.4 Hz), 7.11 (1H, t, J=8.8 Hz), 4.05 (3H, s), 3.29-3.20 (1H, m), 2.73-2.63 (2H, m), 2.47 (1H, dd, J=12.9, 7.6 Hz), 2.25-2.16 (2H, m), 2.14 (3H, d, J=2.5 Hz), 1.93-1.82 (1H, m).

Example 57

(1S,3R*)-1-(3-fluoro-2-methylphenyl)-N-hydroxy-3-(imidazo[1,2-a]pyridin-7-yl)cyclopentanecarboxamide (D1)

Example 58

(1S,3S*)-1-(3-fluoro-2-methylphenyl)-N-hydroxy-3-(imidazo[1,2-a]pyridin-7-yl)cyclopentanecarboxamide (D2)

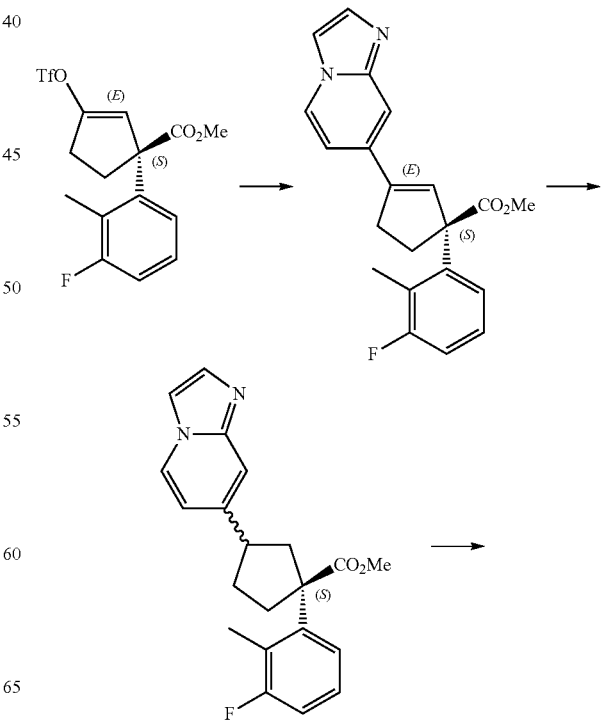

-continued

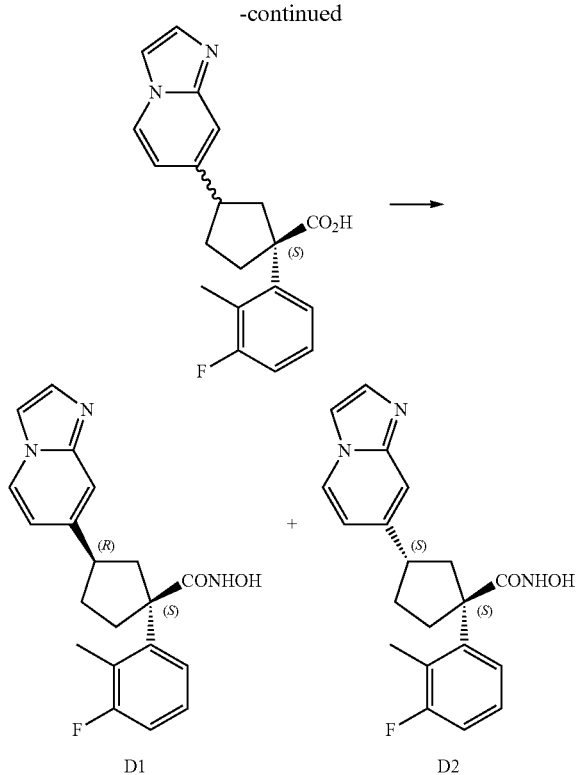

C3 Stereochemistry Putatively Assigned

Following Methods B, F, C and D from Intermediate 6 and imidazo[1,2-a]pyridin-7-ylboronic acid. The title compounds were obtained as white solids.

Example 57 (diastereomer 1 (D1)): LCMS (ES+) 354 (M+H)+, RT 7.16 min (Analytical method 3); $^1$H NMR δ (ppm)(DMSO-d$_6$): 9.96 (1H, s), 8.71 (1H, s), 8.53 (1H, d, J=7.0 Hz), 7.91 (1H, s), 7.56 (1H, s), 7.47 (1H, s), 7.36-7.25 (2H, m), 7.11 (1H, t, J=8.8 Hz), 7.03 (1H, d, J=7.2 Hz), 3.24-3.14 (1H, m), 2.76-2.60 (2H, m), 2.42-2.34 (1H, m), 2.29-2.14 (2H, m), 2.13 (3H, d, J=2.6 Hz), 1.85-1.74 (1H, m).

Example 58 (diastereomer 2 (D2)): LCMS (ES+) 354 (M+H)+, RT 8.05 min (Analytical method 3); $^1$H NMR δ (ppm)(DMSO-d$_6$): 10.05 (1H, s), 8.71 (1H, s), 8.49 (1H, d, J=7.0 Hz), 7.90 (1H, s), 7.55 (1H, s), 7.39 (1H, s), 7.35 (1H, d, J=7.8 Hz), 7.28-7.21 (1H, m), 7.09 (1H, t, J=8.8 Hz), 6.84 (1H, dd, J=7.0, 1.6 Hz), 3.04 (1H, dd, J=6.9, 12.3 Hz), 2.80-2.70 (1H, m), 2.17 (3H, d, J=2.6 Hz), 2.28-2.02 (3H, m), 1.83-1.73 (1H, m). 1 proton obscured by water peak.

Example 59

(1S,3R*)-3-(2-cyclopropyl-1-oxoisoindolin-5-yl)-1-(3-fluoro-2-methylphenyl)-N-hydroxycyclopentanecarboxamide

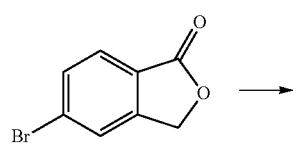

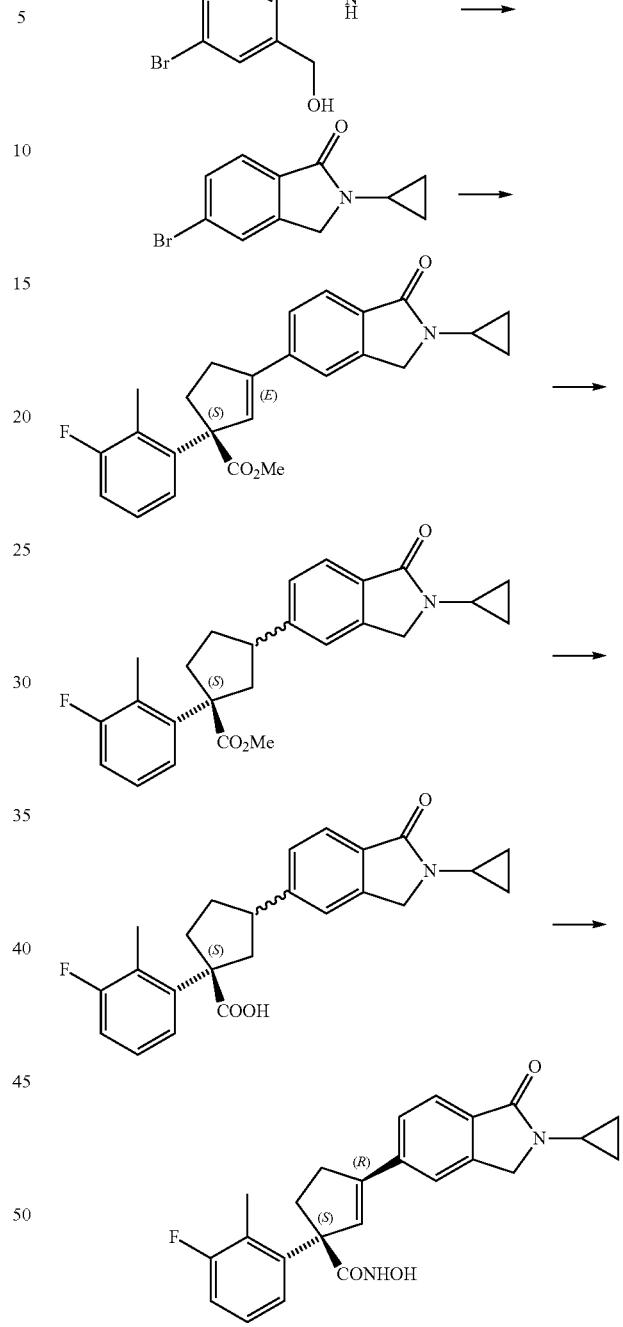

C3 Stereochemistry Putatively Assigned

Step 1:
4-bromo-N-cyclopropyl-2-(hydroxymethyl)benzamide

A solution of cyclopropylamine (0.98 mL, d=0.824, 14.1 mmol) in dry CH$_2$Cl$_2$ (35 mL) was treated with AlMe$_3$ (2 M in hexanes, 7.0 mL, 14 mmol) and the mixture stirred for 15 min. 5-Bromoisobenzofuran-1(3H)-one (2.00 g, 9.39 mmol) was added in two portions 60 s apart and the reaction mixture was then stirred at 40° C. for 16 h. After cooling to rt, the reaction vessel was placed in a cold water bath and 1 M HCl (100 mL) was added cautiously. The resulting slurry was extracted with CH$_2$Cl$_2$ (4×75 mL), dried (Na$_2$SO$_4$) and concentrated to yield the title compound as a white powder.

Step 2: 5-bromo-2-cyclopropylisoindolin-1-one

A stirred solution of 4-bromo-N-cyclopropyl-2-(hydroxymethyl)benzamide (925 mg, 3.42 mmol) in N,N'-dimethylimidazol-2-one (11 mL) held at 0° C. under N$_2$ was treated with i-PrMgCl (2 M in THF, 3.8 mL, 7.6 mmol) over 60 s. The reaction was stirred at r.t. for 30 min before cooling to 0° C. and being treated with bis(dimethylamino)phosphoryl chloride (0.64 mL, d=1.18, 4.43 mmol) over 60 s. The reaction was allowed to warm to r.t. over 1 h and stirred for a further 63 h before being quenched at 0° C. with 3 M HCl (10 mL). The mixture was extracted with EtOAc (3×50 mL) and the combined organics were washed with water (2×20 mL), dried (Na$_2$SO$_4$) and concentrated. Purification by flash silica chromatography (gradient elution, 0-100% EtOAc in iso-hexane) gave the title compound as a white powder (269 mg, 33% over two steps).

Step 3: (S)-methyl 3-(2-cyclopropyl-1-oxoisoindolin-5-yl)-1-(3-fluoro-2-methylphenyl)cyclopent-2-enecarboxylate A suspension of Intermediate 6 (386 mg, 1.01 mmol), bis(pinacolato)diboron (281 mg, 1.11 mmol), PdCl$_2$(dppf) (38.0 mg, 0.05 mmol) and KOAc (112 mg, 1.14 mmol) in DME (8 mL) was purged with N$_2$ and stirred at 75° C. for 2 h. After cooling to rt, Pd(PPh$_3$)$_4$ (46 mg, 0.04 mmol), Cs$_2$CO$_3$ (389 mg, 1.19 mmol) and a solution of 5-bromo-2-cyclopropylisoindolin-1-one (269 mg, 1.07 mmol) in 2:1 DME:MeOH (3 mL) were added. The mixture was purged again with N$_2$ and stirred at 110° C. for 30 min. After cooling to r.t., the reaction was partitioned between water (20 mL) and EtOAc (40 mL) and the organics were washed with water (2×20 mL), brine (20 mL), dried (Na$_2$SO$_4$) and concentrated. Purification by flash silica chromatography (gradient elution, 0-100% EtOAc in iso-hexane) gave the title compound as an orange liquid (293 mg, 72%).

Step 4: (S)-methyl 3-(2-cyclopropyl-1-oxoisoindolin-5-yl)-1-(3-fluoro-2-methylphenyl)cyclopentanecarboxylate A suspension of (S)-methyl 3-(2-cyclopropyl-1-oxoisoindolin-5-yl)-1-(3-fluoro-2-methylphenyl)cyclopent-2-enecarboxylate (293 mg, 0.72 mmol), ammonium formate (432 mg, 6.85 mmol) and 10% Pd/C (30 mg) in EtOH (10 mL) was stirred at reflux under N$_2$ for 1.5 h. Solids were removed by filtration through Celite, washing with MeOH (5×5 mL). The filtrate was concentrated, then partitioned between water (20 mL) and CH$_2$Cl$_2$ (20 mL). The organic layer was concentrated to yield a 3:1 mixture of diastereomers of the title compound as a colorless liquid (261 mg, 89%).

Step 5: (S)-3-(2-cyclopropyl-1-oxoisoindolin-5-yl)-1-(3-fluoro-2-methylphenyl)cyclopentanecarboxylic acid (S)-Methyl 3-(2-cyclopropyl-1-oxoisoindolin-5-yl)-1-(3-fluoro-2-methylphenyl)cyclopentanecarboxylate (3:1 diastereomeric mixture, 261 mg, 0.64 mmol) and KOH (14.6 M in H$_2$O, 0.5 mL, 7.32 mmol) in MeOH (2 mL) were stirred at 75° C. in a sealed tube for 19 h. The mixture was partitioned between water (20 mL) and CH$_2$Cl$_2$ (20 mL); the aqueous layer was acidified to pH 1 using 3 M HCl and extracted with CH$_2$Cl$_2$ (2×20 mL) and EtOAc (2×20 mL), dried (phase separator) and concentrated to yield a 3:1 diastereomeric mixture of the title compound as a white foam (108 mg, 43%).

Step 6: (1S,3R*)-3-(2-cyclopropyl-1-oxoisoindolin-5-yl)-1-(3-fluoro-2-methylphenyl)-N-hydroxycyclopentanecarboxamide A stirred solution of (S)-3-(2-cyclopropyl-1-oxoisoindolin-5-yl)-1-(3-fluoro-2-methylphenyl)cyclopentanecarboxylic acid (3:1 mixture of diastereomers, 108 mg, 0.27 mmol) in dry DMF (1 mL) at 0° C. under N$_2$ was treated with Et$_3$N (0.11 mL, 0.79 mmol) and TFFH (93 mg, 0.35 mmol). After stirring at r.t. for 40 min, the mixture was cooled to 0° C. and O-THP hydroxylamine (60.2 mg, 0.51 mmol) was added. The mixture was then stirred at r.t. for 17 h before cautious addition of HCl (4 M in dioxane, 1 mL, 4 mmol) and MeOH (2 mL). After a further 3 h at r.t. the mixture was concentrated. Purification by preparative HPLC yielded the title compound (1.4 mg, 1%) as a white solid. LCMS (ES+) 49 (M+H)$^+$; $^1$H NMR δ (ppm)(DMSO-d$_6$): 9.91 (1H, s), 8.67 (1H, s), 7.57 (1H, d, J=8.0 Hz), 7.53 (1H, s), 7.45 (1H, d, J=8.0 Hz), 7.37-7.22 (2H, m), 7.07 (1H, t, J=8.6 Hz), 4.37 (2H, s), 3.20-3.16 (1H, m), 2.95-2.89 (1H, m), 2.67-2.60 (2H, m), 2.43-2.34 (1H, m), 2.23-2.8 (2H, m), 2.9 (3H, d, J=1.6 Hz), 1.84-1.73 (1H, m), 0.87-0.73 (4H, m).

Example 60

(1S,3R*)-1-(3-fluoro-2-methylphenyl)-N-hydroxy-3-(1-methyl-1H-indazol-7-yl)cyclopentanecarboxamide

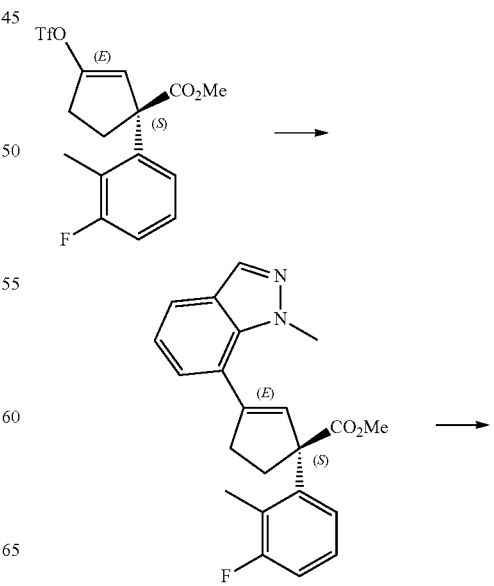

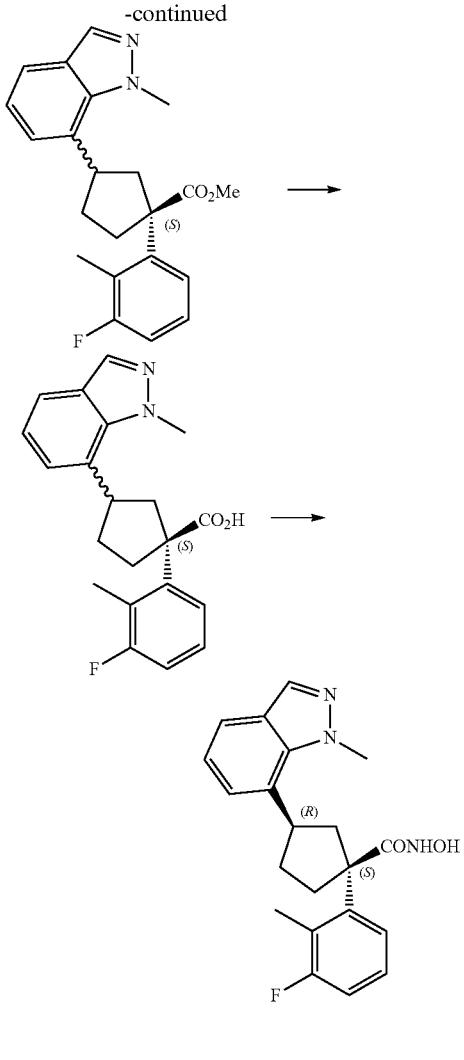

C3 Stereochemistry Putatively Assigned

Following Methods B, F, C and D from Intermediate 6 and (1-methyl-1H-indazol-7-yl)boronic acid. The title compound was the major diastereomer obtained. LCMS (ES+) 367 (M+H)$^+$, RT 10.22 min (Analytical method 3); $^1$H NMR δ (ppm)(DMSO-d$_6$): 9.96 (1 H, s), 8.69 (1 H, d, J=1.6 Hz), 7.98 (1 H, d, J=0.3 Hz), 7.64-7.53 (2 H, m), 7.35 (1 H, d, J=7.9 Hz), 7.32-7.22 (1 H, m), 7.18-7.03 (2 H, m), 4.09 (3 H, s), 3.96-3.84 (1 H, m), 2.87 (1 H, dd, J=13.1, 10.0 Hz), 2.65-2.54 (1 H, m), 2.43-2.25 (2 H, m), 2.24-2.13 (1 H, m), 2.11 (3 H, d, J=2.7 Hz), 1.90-1.77 (1 H, m).

Example 61

(1S,3R*)-3-(7-fluoro-1H-indazol-6-yl)-1-(3-fluoro-2-methylphenyl)-N-hydroxycyclopentanecarboxamide

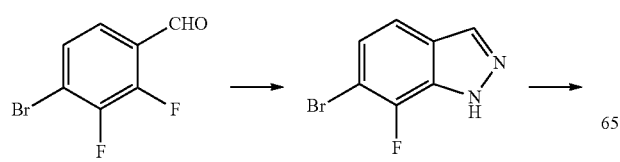

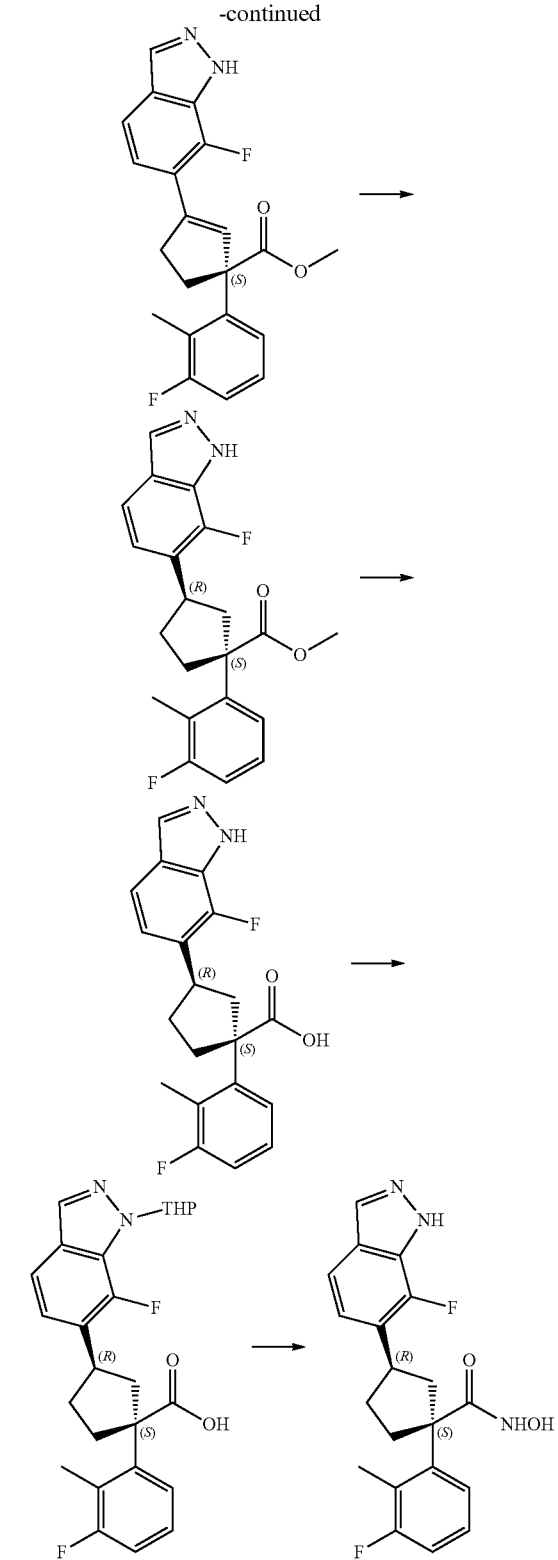

C3 Stereochemistry Putatively Assigned

Step 1: 6-bromo-7-fluoro-1H-indazole

4-Bromo-2,3 difluorobenzaldehyde (1.0 g, 4.52 mmol), potassium carbonate (0.75 g, 5.50 mmol), methoxyamine HCl (0.42 g, 5.0 mmol) and 1,2 dimethoxyethane (12 mL) were charged to an oven-dried 25 mL screw capped tube. The reaction mixture was then heated at 40° C. for 3 h—TLC shows complete consumption of the aldehyde. After this time the suspension was cooled to r.t. and filtered through a pad of Celite washing with EtOAc (3×5 mL). Combined organic layers were concentrated to ~5 mL volume to give the crude methoxyamine intermediate. This material was transferred to a new screw capped vial and diluted with 1,2 dimethoxyethane (10 mL), hydrazine monohydrate (3 mL) was then added and the reaction mixture was heated to 90° C. overnight. After this time the reaction mixture was cooled to r.t. and the solvent volume was removed to ~5 mL volume, water (20 mL) was added and the solid residues filtered and air dried to yield the title compound as a colorless solid (0.79 g, 81%). $^1$H NMR δ (ppm)(DMSO-d$_6$): 13.82 (1 H, s), 8.22 (1 H, s), 7.58 (1 H, d, J=8.55 Hz), 7.31 (1 H, dd, J=8.55, 5.67 Hz).

Steps 2-3: (1S,3R*)-methyl 3-(7-fluoro-1H-indazol-6-yl)-1-(3-fluoro-2-methylphenyl)cyclopentanecarboxylate Following Methods B(iii) and F from Intermediate 6 (0.7 g, 1.83 mmol) and 6-bromo-7-fluoro-1H-indazole (0.395 g, 1.84 mmol). Purification by preparative HPLC yielded one diastereomer in sufficient purity for further reaction, putatively assigned (1S,3R) stereochemistry. $^1$H NMR δ (ppm) (CDCl$_3$): 10.08 (1 H, s), 8.08 (1 H, d, J=3.57 Hz), 7.56-7.51 (1 H, m), 7.33 (2 H, dd, J=8.49, 5.91 Hz), 7.28-7.20 (2 H, m), 7.04-6.98 (1 H, m), 3.71 (3 H, s), 2.80-2.73 (2 H, m), 2.58 (1 H, dd, J=13.47, 8.10 Hz), 2.40 (1 H, ddd, J=13.10, 9.55, 7.06 Hz), 2.29-2.19 (1 H, m), 2.13 (3 H, d, J=2.79 Hz), 2.09-1.98 (1 H, m).

Step 4: (1S,3R*)-3-(7-fluoro-1H-indazol-6-yl)-1-(3-fluoro-2-methylphenyl)cyclopentanecarboxylic acid Following Method C from (1S,3R*)-methyl 3-(7-fluoro-1H-indazol-6-yl)-1-(3-fluoro-2-methylphenyl)cyclopentanecarboxylate (120 mg, 0.32 mmol). The title compound was obtained as a colorless solid (100 mg, 92%).

Step 5: (1S,3R*)-3-(7-fluoro-1-(tetrahydro-2H-pyran-2-yl)-1H-indazol-6-yl)-1-(3-fluoro-2-methylphenyl)cyclopentanecarboxylic acid To a solution of (1S,3R*)-3-(7-fluoro-1H-indazol-6-yl)-1-(3-fluoro-2-methylphenyl)cyclopentanecarboxylic acid (80.0 mg, 0.22 mmol) in dichloromethane (1 mL) was added dihydropyran (50.0 mg, 0.60 mmol) and pTSA.H$_2$O (10 mg). The reaction mixture was stirred at r.t. for 16 h. After this time the crude reaction mixture was washed with sat. aq. NaHCO$_3$ solution (1 mL) and the organic layers were dried, filtered (phase separation cartridge) and concentrated. The crude reaction material was used without further purification.

Step 6: (1S,3R*)-3-(7-fluoro-1H-indazol-6-yl)-1-(3-fluoro-2-methylphenyl)-N-hydroxycyclopentane carboxamide Following Method D from (1S,3R*)-3-(7-fluoro-1-(tetrahydro-2H-pyran-2-yl)-1H-indazol-6-yl)-1-(3-fluoro-2-methylphenyl)cyclopentanecarboxylic acid (60 mg, 0.14 mmol) and purified by preparative HPLC to give the title compound as a colorless solid (11.2 mg, 14%). LCMS (ES+) 372 (M+H)$^+$, 9.79 min (Analytical method 3); $^1$H NMR δ (ppm)(DMSO-d$_6$): 13.47 (1 H, s), 9.93 (1 H, s), 8.68 (1 H, s), 8.11 (1 H, s), 7.56 (1 H, d, J=8.4 Hz), 7.33-7.24 (3 H, m), 7.09 (1 H, s), 3.50-3.43 (1 H, m), 2.70-2.65 (2 H, m), 2.42-2.34 (1 H, m), 2.25-2.18 (1 H, m), 2.15-2.11 (1 H, m), 2.09 (3 H, d, J=2.8 Hz), 1.86-1.80 (1 H, m).

Example 62

(1S,3R*)-3-(2-cyclopropylbenzo[d]oxazol-5-yl)-1-(3-fluoro-2-methylphenyl)-N-hydroxycyclopentanecarboxamide

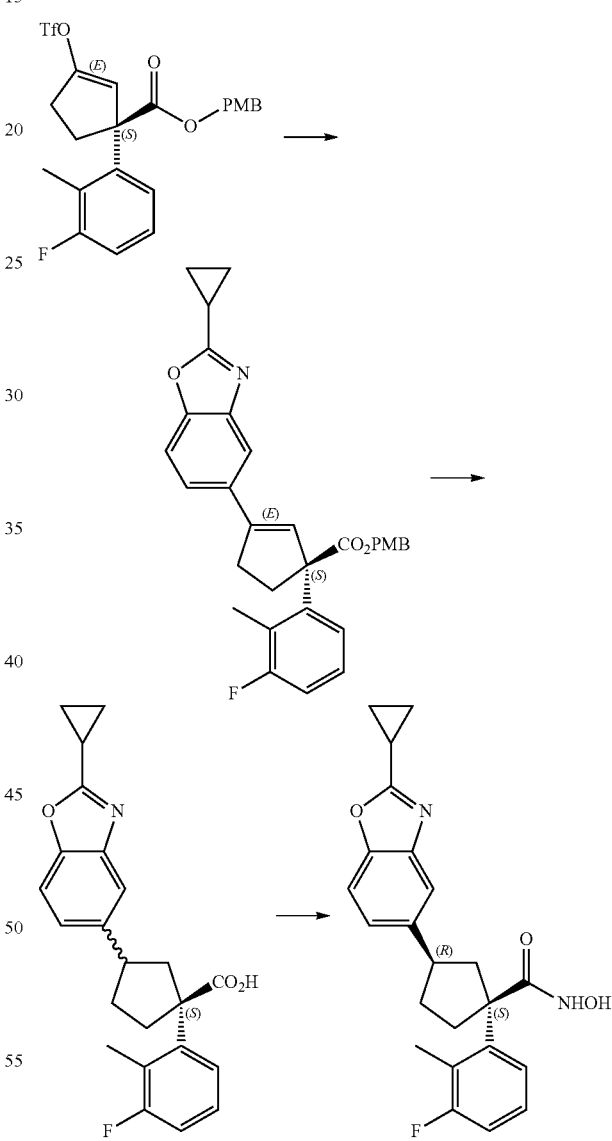

C3 Stereochemistry Putatively Assigned

Following Methods B(iii), F and D from Intermediate 9 and 5-bromo-2-cyclopropyl-1,3-benzoxazole. The title compound was obtained as an off-white solid. LCMS (ES+) 395 (M+H)$^+$, RT 10.93 (Analytical method 3); $^1$H NMR δ (ppm)(DMSO-d$_6$): 9.93 (1H, d, J=1.8 Hz), 8.69 (1H, d, J=1.8 Hz), 7.61 (1H, d, J=1.3 Hz), 7.55 (1H, d, J=8.3 Hz), 7.35-7.24 (3H, m), 7.13-7.7 (1H, m), 3.26-3.16 (1H, m), 2.72-2.63 (2H, m), 2.45-2.36 (1H, m), 2.33-2.14 (3H, m), 2.12 (3H, d, J=2.9 Hz), 1.83-1.72 (1H, m), 1.24-1.13 (4H, m).

Example 63

(1S,3R*)-1-(3-fluoro-2-methylphenyl)-N-hydroxy-3-(1-methyl-1H-indazol-5-yl)cyclopentanecarboxamide (D1)

Example 64

(1S,3S*)-1-(3-fluoro-2-methylphenyl)-N-hydroxy-3-(1-methyl-1H-indazol-5-yl)cyclopentanecarboxamide (D2)

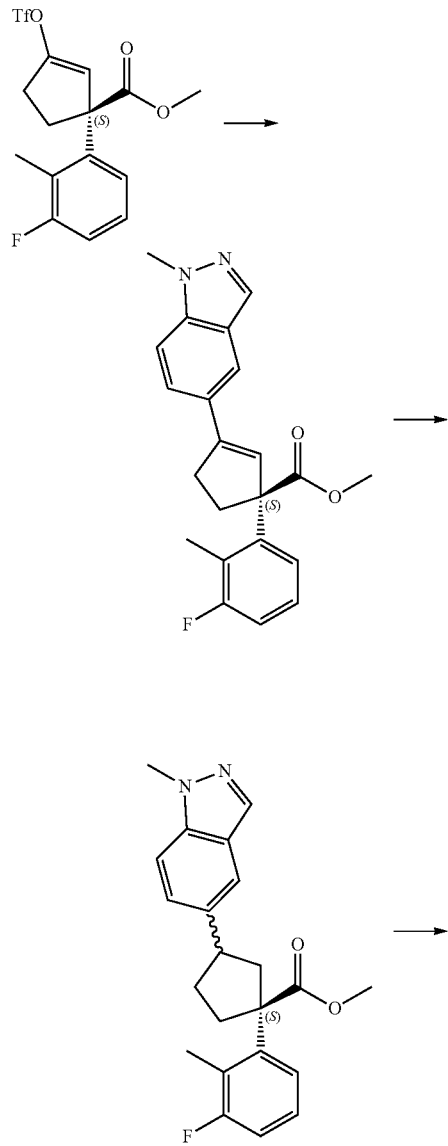

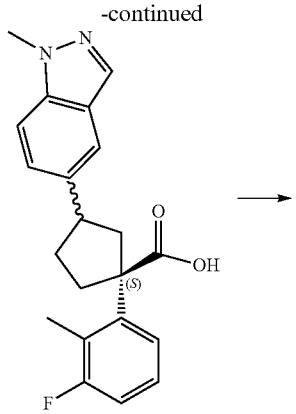

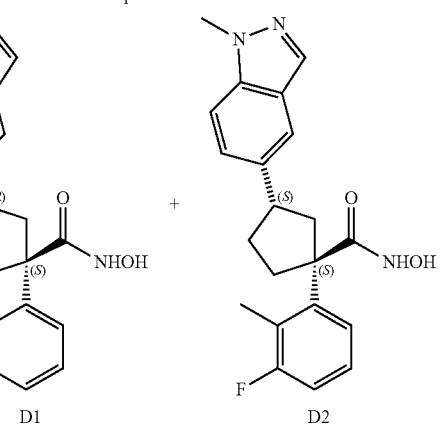

D1 + D2

C3 Stereochemistry Putatively Assigned

Following Methods B, F, C and D from Intermediate 6 (0.28 g, 0.72 mmol) and (1-methyl-1H-indazol-5-yl)boronic acid (0.15 g, 0.80 mmol). The 3:1 diastereomeric mixture resulting from step 3 was separated by preparative HPLC.

Example 63 (diastereomer 1 (D1)) was obtained as a colorless solid (24.2 mg). LCMS (ES+) 368 (M+H)+, RT 10.3 min (Analytical method 3); $^1$H NMR δ (ppm)(DMSO-d$_6$): 9.91 (1 H, d, J=1.8 Hz), 8.67 (1 H, d, J=1.7 Hz), 7.97 (1 H, d, J=0.9 Hz), 7.66 (1 H, s), 7.59 (1 H, d, J=8.7 Hz), 7.45 (1 H, dd, J=8.7, 1.6 Hz), 7.33 (1 H, d, J=7.9 Hz), 7.31-7.23 (1 H, m), 7.09 (1 H, t, J=8.9 Hz), 4.04 (3 H, s), 3.20 (1 H, t, J=9.1 Hz), 2.72-2.60 (2 H, m), 2.43 (1 H, dd, J=13.3, 7.8 Hz), 2.23-2.12 (2 H, m), 2.11 (3 H, d, J=2.8 Hz), 1.83-1.74 (1 H, m).

Example 64 (diastereomer 2 (D2)) was obtained as a colorless solid (11.2 mg). LCMS (ES+) 368 (M+H)+, RT 10.1 min (Analytical method 3); $^1$H NMR δ (ppm)(DMSO-d$_6$): 10.03 (1 H, s), 8.70 (1 H, s), 7.95 (1 H, s), 7.60-7.54 (2 H, m), 7.35-7.25 (3 H, m), 7.23 (1 H, d, J=8.1 Hz), 7.07 (1 H, t, J=8.9 Hz), 4.03 (3 H, s), 3.13-2.92 (1 H, m), 2.78-2.74 (1 H, m), 2.27-2.16 (2 H, m), 2.16 (3 H, d, J=2.7 Hz), 2.04 (1 H, t, J=12.0 Hz), 1.89-1.61 (1 H, m).

Example 65

(1S,3R*)-3-(2-(difluoromethyl)-2H-indazol-6-yl)-1-(3-fluoro-2-methylphenyl)-N-hydroxycyclopentanecarboxamide (D1)

Example 66

(1S,3S*)-3-(2-(difluoromethyl)-2H-indazol-6-yl)-1-(3-fluoro-2-methylphenyl)-N-hydroxycyclopentanecarboxamide (D2)

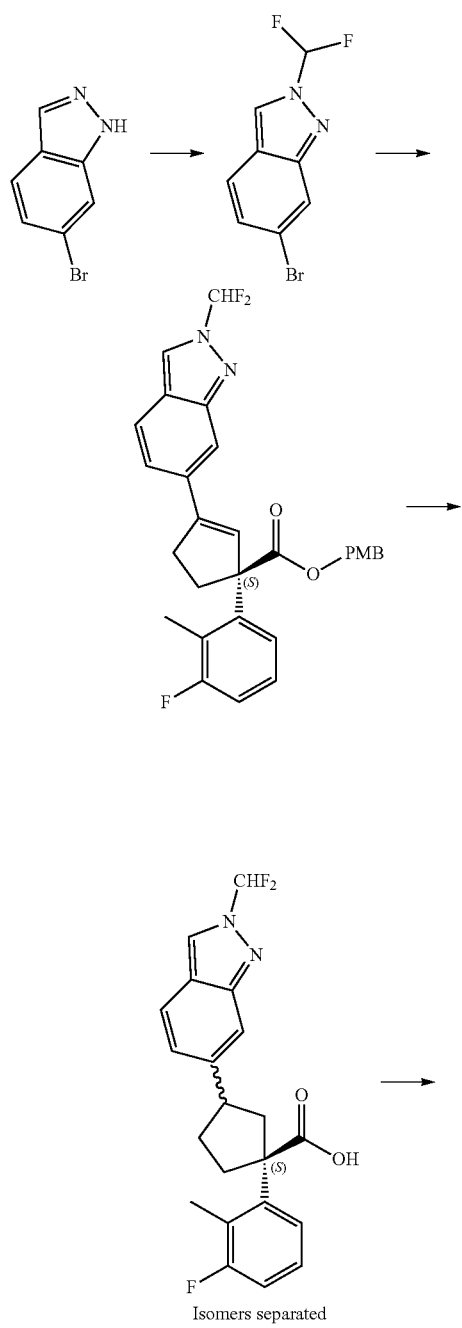

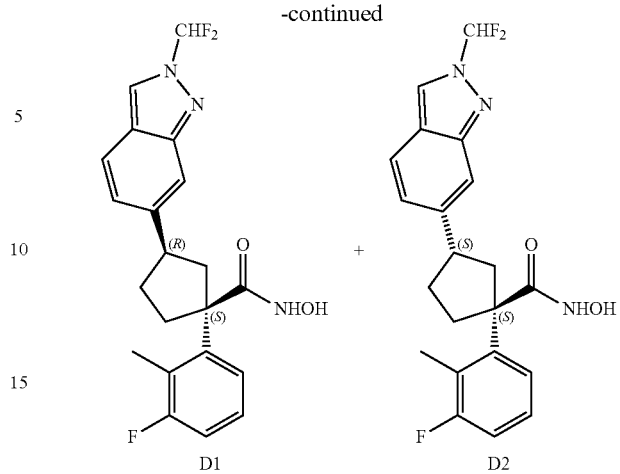

C3 Stereochemistry Putatively Assigned

Step 1: 6-bromo-2-(difluoromethyl)-2H-indazole

A suspension of NaH (6 wt % in oil, 320 mg, 8.16 mmol) in dry DMF (20 mL) under $N_2$ was treated with a solution of 6-bromo-1H-indazole (1.32 g, 6.80 mmol) in dry DMF (4 mL), added dropwise over 5 min. The mixture was stirred for 30 min before chlorodifluoromethane was bubbled through the solution for 5 min. The mixture was then heated at 80° C. in a sealed tube for 16 h. After cooling to r.t. the mixture was diluted with EtOAc (60 mL) and washed with sat. aq. $NH_4Cl$ (50 mL), water (50 mL) and brine (50 mL), dried (phase separation cartridge) and concentrated. The residue was purified by silica column chromatography (gradient elution, 0-15% EtOAc in iso-hexane) to give the title compound as an orange solid (554 mg, 33%).

Steps 2-4: (1S,3R*)-3-(2-(difluoromethyl)-2H-indazol-6-yl)-1-(3-fluoro-2-methylphenyl)-N-hydroxycyclopentanecarboxamide (D1) and (1S,3S*)-3-(2-(difluoromethyl)-2H-indazol-6-yl)-1-(3-fluoro-2-methylphenyl)-N-hydroxycyclopentanecarboxamide (D2)

Following Methods B(iii), F and D from Intermediate 9 (391 mg) and 6-bromo-2-(difluoromethyl)-2H-indazole (197 mg). The 1:1 diastereomeric mixture resulting from step 3 was separated by preparative HPLC.

Example 65 (diastereomer 1 (D1)) was obtained as a colorless solid (53 mg). LCMS (ES+) 404 (M+H)+, RT 3.84 min (Analytical method 1); $^1$H NMR δ (ppm)(DMSO-$d_6$): 10.06 (1 H, s), 8.72 (1 H, s), 8.36 (1 H, s), 8.19 (1 H, t, J=58.2 Hz), 7.82 (1 H, d, J=8.3 Hz), 7.72 (1 H, s), 7.34 (1 H, d, J=7.9 Hz), 7.29-7.20 (2 H, m), 7.09 (1 H, t, J=8.9 Hz), 3.42-3.35 (1 H, m), 3.06 (1 H, dd, J=12.4, 6.7 Hz), 2.81-2.74 (1 H, m), 2.31-2.23 (1 H, m), 2.21-2.13 (4 H, m), 2.13-2.04 (1 H, m), 1.87-1.79 (1 H, m).

Example 66 (diastereomer 2 (D2)) was obtained as a colorless solid (19 mg). LCMS (ES+) 404 (M+H)+, RT 3.89 min (Analytical method 1); $^1$H NMR δ (ppm)(DMSO-$d_6$): 9.79 (1 H, s), 8.56 (1 H, s), 8.23 (1 H, s), 8.05 (1 H, t, J=58.3 Hz), 7.71 (1 H, d, J=8.4 Hz), 7.65 (1 H, s), 7.29 (1 H, d, J=8.4 Hz), 7.20 (1 H, d, J=7.9 Hz), 7.18-7.10 (1 H, m), 6.96

(1 H, t, J=8.9 Hz), 3.14 (1 H, t, J=9.4 Hz), 2.33 (1 H, dd, J=13.5, 7.7 Hz), 2.13-2.02 (2 H, m), 1.98 (3 H, d, J=2.7 Hz), 1.70 (1 H, t, J=9.4 Hz).

Example 67

(1S,3R*)-3-(3-fluoro-1-methyl-1H-indazol-6-yl)-1-(3-fluoro-2-methylphenyl)-N-hydroxycyclopentanecarboxamide (D1)

Example 68

(1S,3S*)-3-(3-fluoro-1-methyl-1H-indazol-6-yl)-1-(3-fluoro-2-methylphenyl)-N-hydroxycyclopentanecarboxamide (D2)

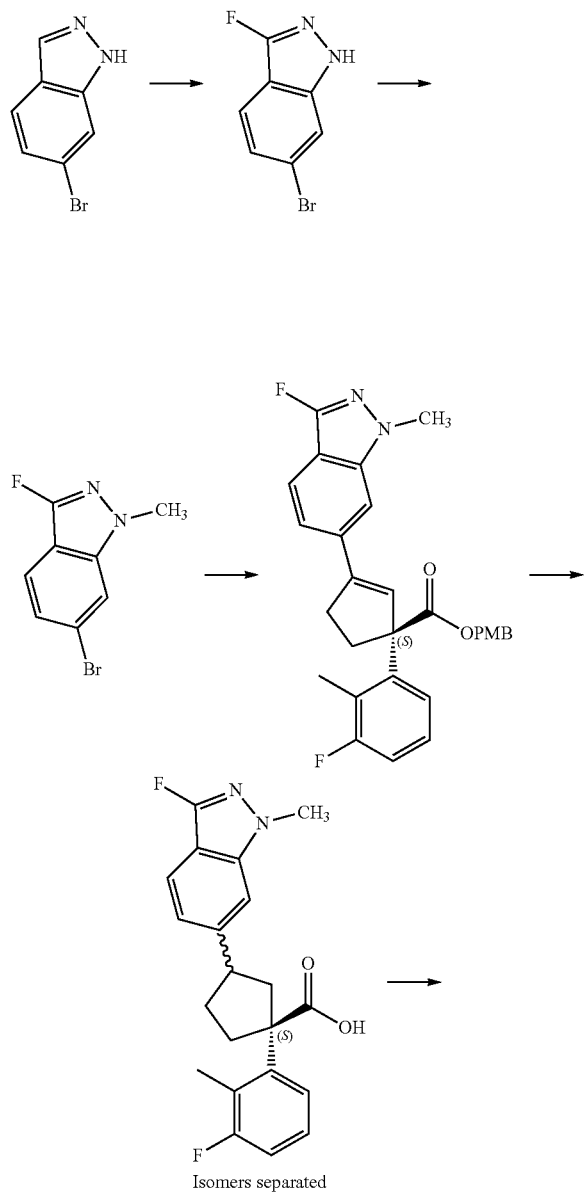

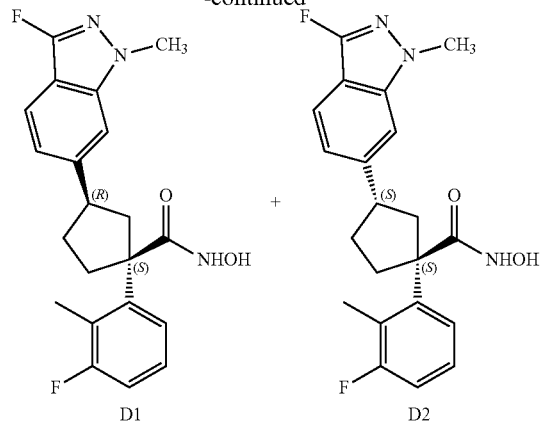

C3 Stereochemistry Putatively Assigned

Step 1: 6-bromo-3-fluoro-1H-indazole

To a solution of 6-bromo-1H-indazole (2.19 g, 10.7 mmol) in acetonitrile (30 mL) was added Selectfluor® (7.50 g, 21.4 mmol) and acetic acid (1.5 mL) and the reaction mixture heated to 95° C. under $N_2$ for 2 h. After this time the reaction mixture was cooled to r.t. and filtered through Celite, washing with $CH_2Cl_2$ (3×40 mL). Combined organics were concentrated under reduced pressure and the residue resuspended in $CH_2Cl_2$ (1 mL). The organic layer was extracted with water (2×75 mL) then brine (50 mL). EtOAc layers were then dried, filtered (phase separation cartridge) and concentrated. The crude reaction material was purified by flash silica chromatography (gradient elution, 0-33% EtOAc in iso-hexane) to give the title compound as a yellow solid (0.42 g, 18%).

$^1$H NMR δ (ppm)(CDCl$_3$): 9.36 (1 H, s), 7.92 (1 H, s), 7.61-7.57 (1 H, m), 7.36 (1 H, dd, J=8.96, 2.37 Hz).

Step 2: 6-bromo-3-fluoro-1-methyl-1H-indazole

To a solution of 6-bromo-3-fluoro-1H-indazole (0.30 g, 1.40 mmol) in acetonitrile (10 mL) was added cesium carbonate (0.91 g, 2.80 mmol) and iodomethane (0.24 g, 1.70 mmol, 110 μL) and the reaction mixture heated to 65° C. under $N_2$ for 2.5 h. After this time the reaction mixture was cooled to r.t. and filtered through Celite, washing with EtOAc (3×20 mL). Combined organics were concentrated under reduced pressure. The crude reaction material was purified by flash silica chromatography (gradient elution, 0-20% EtOAc in iso-hexane) to give the title compound as colorless needles (0.12 g, 38%).

$^1$H NMR δ (ppm)(CDCl$_3$): 7.62-7.54 (2 H, m), 7.32-7.29 (1 H, m), 3.96 (3 H, d, J=1.11 Hz).

Steps 3-5: (1S,3R*)-3-(3-fluoro-1-methyl-1H-indazol-6-yl)-1-(3-fluoro-2-methylphenyl)-N-hydroxycyclopentanecarboxamide (D1) and (1S,3S*)-3-(3-fluoro-1-methyl-1H-indazol-6-yl)-1-(3-fluoro-2-methylphenyl)-N-hydroxycyclopentanecarboxamide (D2)

Following Methods B(iii), F and D from Intermediate 9 (244 mg, 0.50 mmol) and 6-bromo-3-fluoro-1-methyl-1H-indazole (115 mg, 0.50 mmol). Example 67 (D1) was obtained as a colorless solid. LCMS (ES+) 386 (M+H)$^+$, RT 11.0 min (Analytical method 3); $^1$H NMR δ (ppm)(DMSO-$d_6$): 9.96 (1H, s), 8.71 (1H, s), 7.66 (1H, d, J=8.5 Hz), 7.56 (1H, s), 7.36-7.26 (3H, m), 7.11 (1H, t, J=8.9 Hz), 3.92 (3H, d, J=1.1 Hz), 3.27-3.22 (1H, m), 2.72-2.64 (2H, m), 2.45 (1H, dd, J=13.2, 7.7 Hz), 2.27-2.15 (2H, m), 2.13 (3H, d, J=2.6 Hz), 1.92-1.81 (1H, m).

Example 68 (D2) was obtained as a colorless solid. LCMS (ES+) 386 (M+H)$^+$, RT 10.9 min (Analytical method 3); $^1$H NMR δ (ppm)(DMSO-$d_6$): 10.09 (1 H, s), 8.79 (1 H, s), 7.66-7.60 (1 H, m), 7.54 (1 H, s), 7.38 (1 H, d, J=7.99 Hz), 7.33-7.22 (1 H, m), 7.15-7.06 (2H, m), 3.93 (3 H, d, J=1.06 Hz), 3.4 (1 H, dd, J=12.47, 6.69 Hz), 2.87-2.76 (1 H, m), 2.34-2.21 (2 H, m), 2.20 (3 H, d, J=2.74 Hz), 2.19-2.09 (2 H, m), 1.88-1.79 (1 H, m).

Example 69

(1S,3R*)-1-(3-fluoro-2-methylphenyl)-N-hydroxy-3-(1-methyl-1H-benzo[d]imidazol-5-yl)cyclopentanecarboxamide

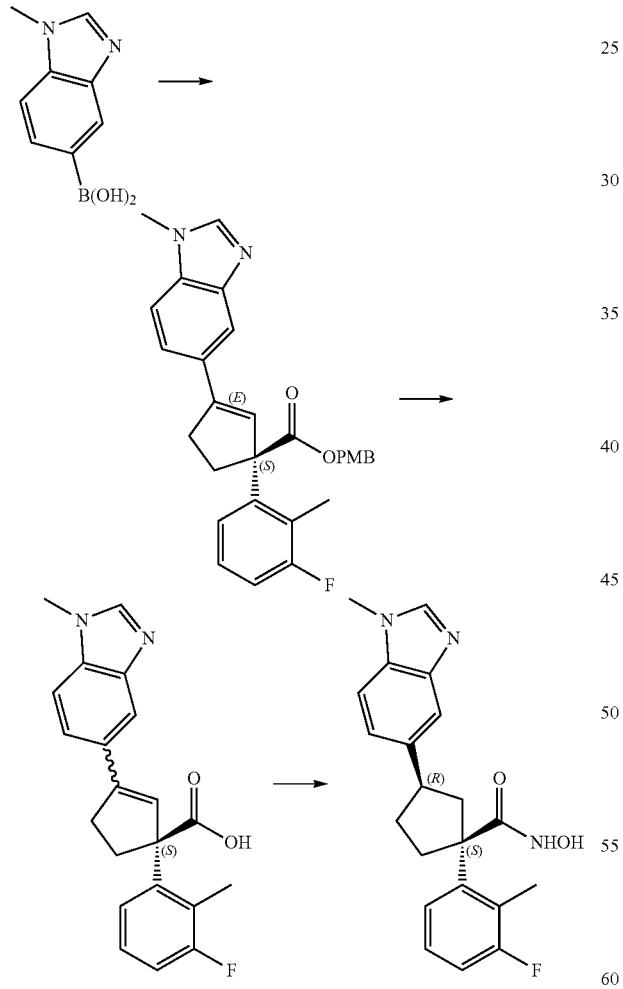

C3 Stereochemistry Putatively Assigned

Following Methods B, F and D from (1-methyl-1H-benzo[d]imidazol-5-yl)boronic acid and Intermediate 9. The title compound was the major diasteromer formed and was obtained as a white solid. LCMS (ES+) 368 (M+H)$^+$, RT 8.49 min (Analytical method 3); $^1$H NMR δ (ppm)(DMSO-$d_6$): 9.94 (1H, s), 8.69 (1H, s), 8.64 (1H, s), 7.71 (1H, s), 7.66 (1H, d, J=8.4 Hz), 7.44 (1H, d, J=8.4 Hz), 7.35 (1H, d, J=7.4 Hz), 7.32-7.25 (1H, m), 7.11 (1H, t, J=8.9 Hz), 3.94 (3H, s), 3.30-3.25 (1H, m), 2.74-2.65 (2H, m), 2.48-2.36 (1H, m), 2.26-2.15 (2H, m), 2.14-2.11 (3H, m), 1.85-1.76 (1H, m).

Example 70

(1S,3R*)-1-(3-Fluoro-2-methylphenyl)-N-hydroxy-3-(1-methyl-1H-benzo[d]imidazol-6-yl)cyclopentanecarboxamide (D1)

Example 71

(1S,3S*)-1-(3-Fluoro-2-methylphenyl)-N-hydroxy-3-(1-methyl-1H-benzo[d]imidazol-6-yl)cyclopentanecarboxamide (D2)

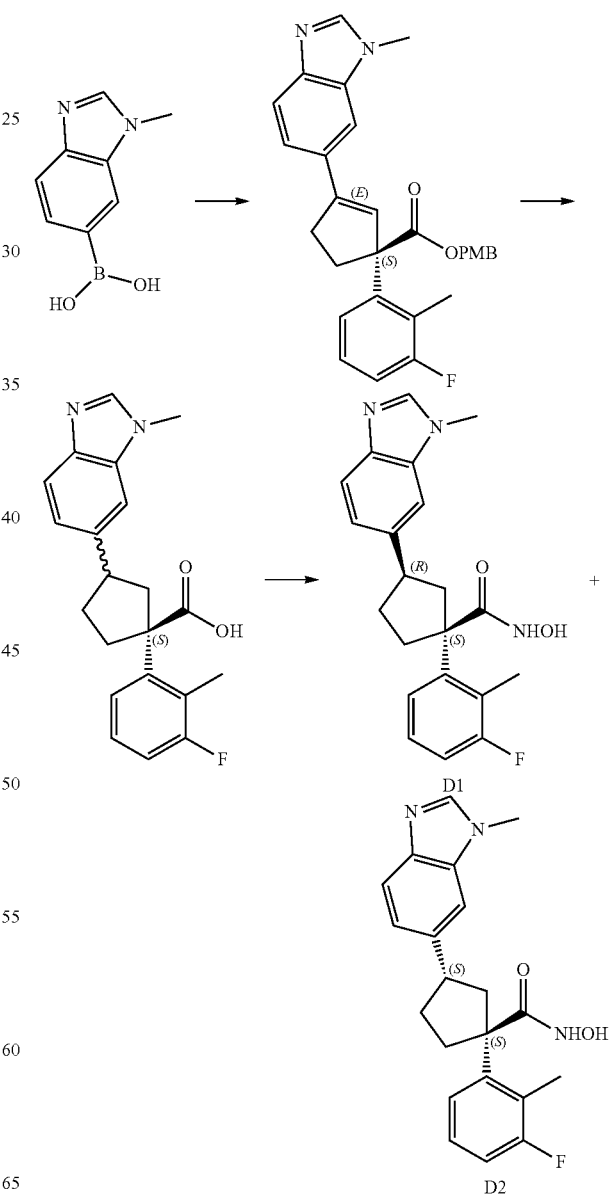

121

C3 Stereochemistry Putatively Assigned

Following Methods B, F and D from Intermediate 9 (0.57 g, 1.2 mmol) and (1-methyl-1H-benzo[d]imidazol-6-yl)boronic acid (227 mg, 1.3 mmol). The diastereomers were separated after the final synthetic step.

Example 70 (D1) was obtained as an off-white solid (8.6 mg). LCMS (ES+) 368 (M+H)+, RT 8.42 min (Analytical method 3); $^1$H NMR δ (ppm)(DMSO-d$_6$): 9.73 (1H, s), 8.49 (1H, s), 7.94 (1H, s), 7.40 (1H, d, J=8.3 Hz), 7.32 (1H, s), 7.16-7.03 (3H, m), 6.94-6.88 (1H, m), 3.66 (3H, s), 3.09-3.01 (1H, m), 2.99-2.49 (1H, m), 2.28 (1H, dd, J=13.4, 7.6 Hz), 2.2-1.95 (2H, m), 1.95-1.91 (4H, m), 1.70-1.61 (1H, m).

Example 71 (D2) was obtained as an off-white solid (8.7 mg). LCMS (ES+) 368 (M+H)+, RT 2.40 min (Analytical method 1); $^1$H NMR δ (ppm)(DMSO-d$_6$): 10.06 (1H, s), 8.75 (1H, s), 8.14 (1H, s), 7.58 (1H, d, J=8.3 Hz), 7.46 (1H, s), 7.37 (1H, d, J=7.8 Hz), 7.31-7.23 (1H, m), 7.13 (2H, dd, J=8.5, 1.6 Hz), 3.85 (3H, s), 3.22 (1H, s), 3.04 (1H, dd, J=12.3, 6.7 Hz), 2.87-2.78 (1H, m), 2.31-2.22 (1H, m), 2.20 (3H, d, J=2.5 Hz), 2.17-2.12 (2H, m), 1.90-1.79 (1H, m).

Example 72

(1S,3R*)-1-(3-fluoro-2-methylphenyl)-N-hydroxy-3-(1-methyl-1H-benzo[d]imidazol-6-yl)cyclopentanecarboxamide (D1)

Example 73

(1S,3S*)-1-(3-fluoro-2-methylphenyl)-N-hydroxy-3-(1-methyl-1H-benzo[d]imidazol-6-yl)cyclopentanecarboxamide (D2)

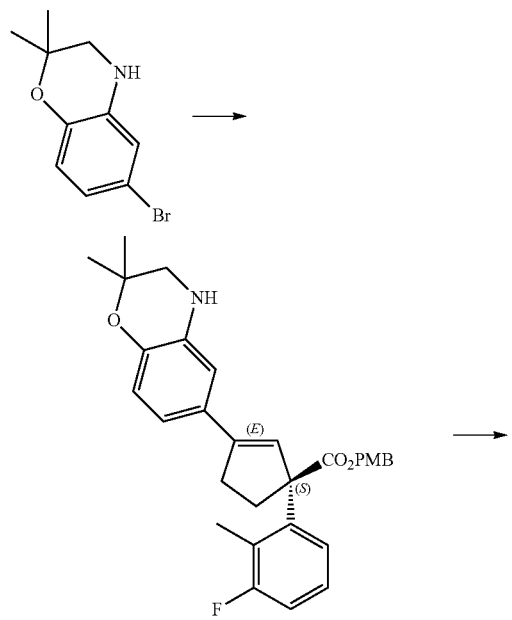

122

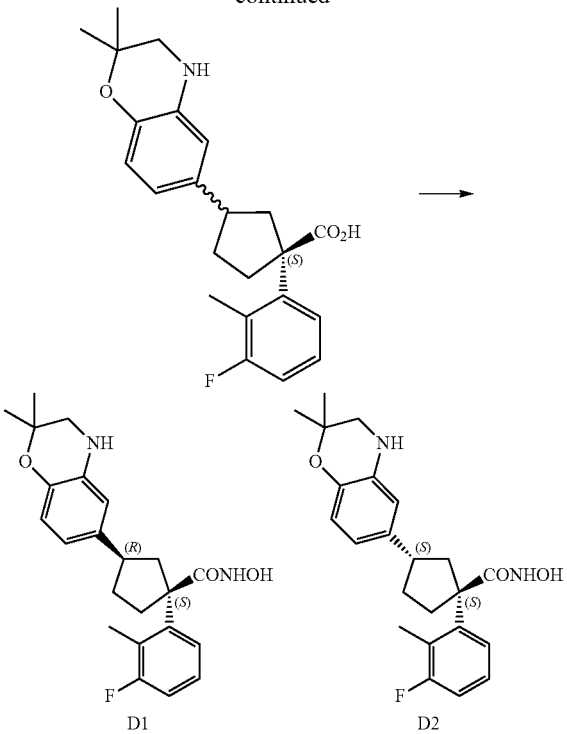

C3 Stereochemistry Putatively Assigned

Step 1: (S)-4-methoxybenzyl 3-(2,2-dimethyl-3,4-dihydro-2H-benzo[b][1,4]oxazin-6-yl)-1-(3-fluoro-2-methylphenyl)cyclopent-2-enecarboxylate Following Method B(iii) from Intermediate 9 (0.50 g, 1.0 mmol) and 6-bromo-2,2-dimethyl-3,4-dihydro-2H-benzo[b][1,4]oxazine (0.36 mg, 1.5 mmol). Purification by flash silica chromatography (gradient elution, 0-40% EtOAc in iso-hexane) gave the title compound as a yellow oil (0.37 g, 74%). LCMS (ES+) consistent with target (M+H)+.

Step 2: (1 S)-3-(2,2-Dimethyl-3,4-dihydro-2H-benzo[b][1,4]oxazin-6-yl)-1-(3-fluoro-2-methylphenyl)cyclopentanecarboxylic acid A solution of (S)-4-Methoxybenzyl 3-(2,2-dimethyl-3,4-dihydro-2H-benzo[b][1,4]oxazin-6-yl)-1-(3-fluoro-2-methylphenyl)cyclopent-2-enecarboxylate (0.37 g, 0.74 mmol) in methanol (20 mL) was passed through the H-cube (20% Pd(OH)$_2$/C cartridge at 50° C. and 60 bar pressure) on a continuous flow for 2 h. After removing the solvent the title compound was obtained as a yellow oil (0.4 g, 100%). LCMS (ES+) consistent with target (M+H)+.

Step 3: Following Method D from (1S)-3-(2,2-dimethyl-3,4-dihydro-2H-benzo[b][1,4]oxazin-6-yl)-1-(3-fluoro-2-methylphenyl)cyclopentanecarboxylic acid (99 mg, 0.26 mmol) and purified by preparative HPLC Example 72 (D1) was obtained as a white solid (5.3 mg). LCMS (ES+) 399 (M+H)+, RT 10.8 min (Analytical method 3); $^1$H NMR δ (ppm)(DMSO-d$_6$): 9.99 (1H, s), 8.69 (1H, s), 7.31-7.22 (2H, m), 7.07 (1H, t, J=9.0 Hz), 6.52 (1H, d, J=8.1

Hz), 6.46 (1H, d, J=2.0 Hz), 6.35 (1H, dd, J=1.9, 8.2 Hz), 5.75 (1H, s), 2.97 (2H, s), 2.36 (2H, dd, J=1.6, 3.7 Hz), 2.15 (3H, d, J=2.8 Hz), 2.13-2.05 (3H, m), 1.87 (1H, t, J=11.7 Hz), 1.70-1.63 (1H, m), 1.24 (6H, s).

Example 73 (D2) was obtained as a white solid (29.6 mg). LCMS (ES+) 399 (M+H)$^+$, RT 3.92 min (Analytical method 1); $^1$H NMR δ (ppm)(DMSO-d$_6$): 9.86 (1H, s), 7.29-7.24 (2H, m), 7.11-7.05 (H, m), 6.58-6.56 (1H, m), 6.54 (1H, s), 6.46 (1H, dd, J=8.1, 2.0 Hz), 2.99 (2H, s), 2.93-2.84 (1H, m), 2.68-2.61 (1H, m), 2.50-2.32 (3H, m), 2.10 (3H, d, J=2.8 Hz), 2.09-1.99 (2H, m), 1.73-1.63 (1H, m), 1.25 (6H, s). One exchangeable proton not observed.

Example 74

(1S,3R*)-1-(3-Fluoro-2-methylphenyl)-N-hydroxy-3-(2-(trifluoromethyl)-1H-benzo[d]imidazol-6-yl)cyclopentanecarboxamide

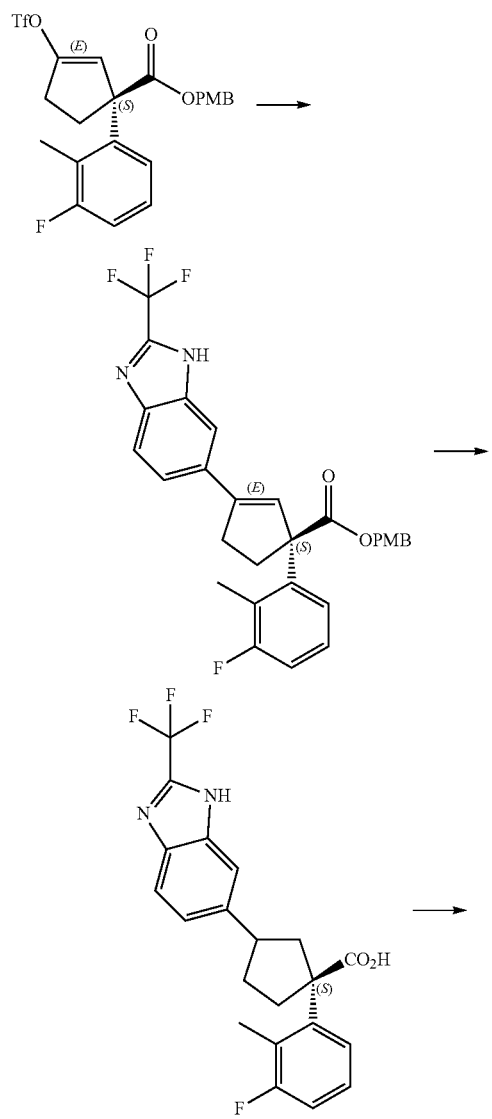

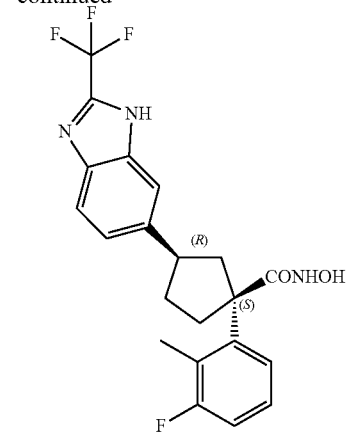

Step 1: (S)-4-Methoxybenzyl 1-(3-fluoro-2-methylphenyl)-3-(2-(trifluoromethyl)-1H-benzo[d]imidazol-6-yl)cyclopent-2-enecarboxylate Following Method B (iii) from (S)-4-methoxybenzyl 1-(3-fluoro-2-methylphenyl)-3-(2-(trifluoromethyl)-1H-benzo[d]imidazol-6-yl)cyclopent-2-enecarboxylate (600 mg, 1.23 mmol) and 6-bromo-2-(trifluoromethyl)-1H-benzo[d]imidazole (489 mg, 1.84 mmol). Purification by flash column chromatography (gradient elution i-hex to EtOAc) gave the title compound as an orange oil (230 mg, 36%).

Step 2: (1 S)-1-(3-Fluoro-2-methylphenyl)-3-(2-(trifluoromethyl)-1H-benzo[d]imidazol-6-yl)cyclopentanecarboxylic acid Prepared in a similar manner to Example 73 from (S)-4-methoxybenzyl 1-(3-fluoro-2-methylphenyl)-3-(2-(trifluoromethyl)-1H-benzo[d]imidazol-6-yl)cyclopent-2-enecarboxylate (230 mg, 0.44 mmol). The title compound was isolated as a colorless oil (198 mg, 85%).

Step 3: (1 S,3R*)-1-(3-Fluoro-2-methylphenyl)-N-hydroxy-3-(2-(trifluoromethyl)-1H-benzo[d]imidazol-6-yl)cyclopentanecarboxamide Following Method D from (1S)-1-(3-fluoro-2-methylphenyl)-3-(2-(trifluoromethyl)-1H-benzo[d]imidazol-6-yl)cyclopentanecarboxylic acid (198 mg, 0.44 mmol). Purification by preparative HPLC gave the title compound as a white solid (71 mg). LCMS (ES+) 422 (M+H)$^+$, RT 3.64 min (Analytical method 1); $^1$H NMR δ (ppm)(DMSO-d$_6$): 13.86-13.84 (1H, m), 9.95 (1H, d, J=1.3 Hz), 8.72 (1H, s), 7.79-7.77 (1H, m), 7.64-7.60 (1H, m), 7.52-7.23 (3H, m), 7.15-7.09 (1H, m), 3.35-3.20 (2H, m), 2.73-2.68 (3H, m), 2.30-2.11 (4H, m), 1.87-1.78 (1H, m).

Example 75

(1S,3S*)-3-(Benzo[d]thiazol-2-yl)-1-(3-fluoro-2-methylphenyl)-N-hydroxycyclopentanecarboxamide (D1)

Example 76

(1S,3R*)-3-(Benzo[d]thiazol-2-yl)-1-(3-fluoro-2-methylphenyl)-N-hydroxycyclopentanecarboxamide (D2)

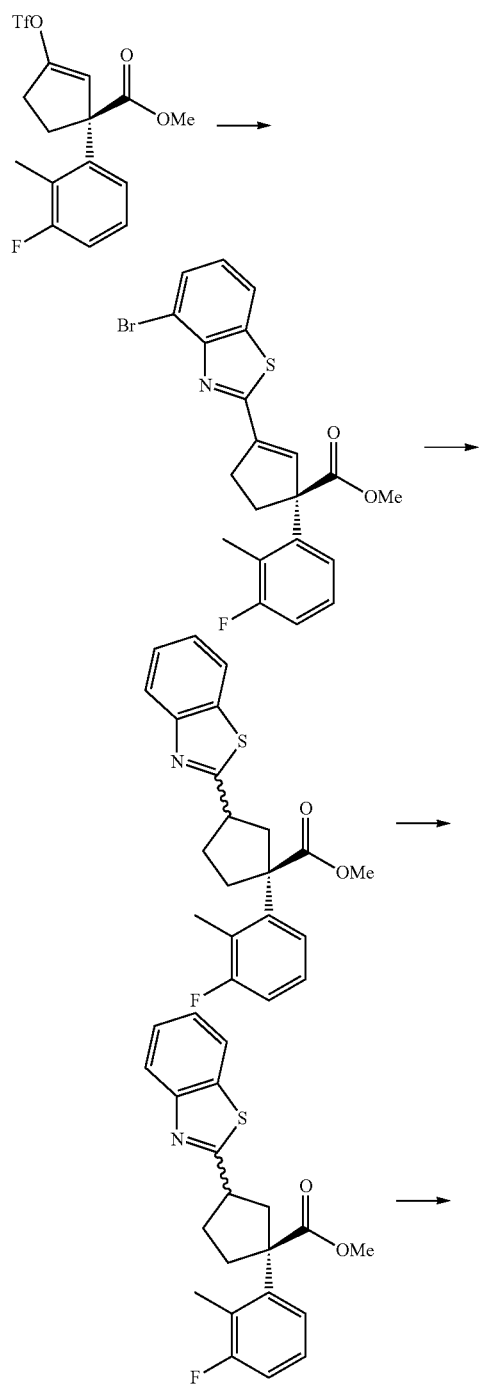

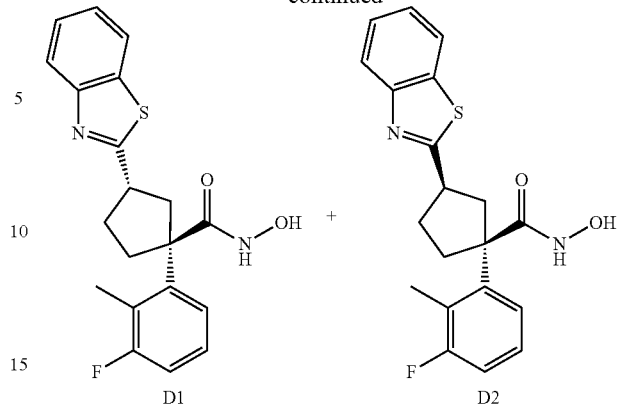

C3 Stereochemistry Putatively Assigned

Step 1: (S)-Methyl 3-(4-bromobenzo[d]thiazol-2-yl)-1-(3-fluoro-2-methylphenyl)cyclopent-2-enecarboxylate Following Method B (ii) from Intermediate 6 (0.50 g, 1.31 mmol) and 5-bromo-2-chlorobenzo[d]thiazole (0.32 g, 1.31 mmol). Purification by flash silica chromatography (gradient elution i-hex to 50% EtOAc in i-hex) gave the title compound as a pale yellow gum (0.45 g, 74%).

Step 2: (S)-Methyl 3-(benzo[d]thiazol-2-yl)-1-(3-fluoro-2-methylphenyl)cyclopentanecarboxylate To a solution of (S)-methyl 3-(4-bromobenzo[d]thiazol-2-yl)-1-(3-fluoro-2-methylphenyl)cyclopent-2-enecarboxylate (0.43 g, 0.096 mmol) in ethanol (20 mL) was added 20% Pd/C (43 mg) and the mixture was treated with hydrogen at atmospheric pressure for 2 h. The reaction was filtered to remove the Pd/C and evaporated in vacuo to yield title compound as a pale yellow gum (0.36 g, 3:2 mixture of diastereoisomers).

Step 3: (S)-3-(Benzo[d]thiazol-2-yl)-1-(3-fluoro-2-methylphenyl)cyclopentanecarboxylic acid Following Method C from (S)-methyl 3-(benzo[c]thiazol-2-yl)-1-(3-fluoro-2-methylphenyl)cyclopentanecarboxylate (361 mg, 0.096 mmol) gave the title compound as a pale yellow gum (330 mg, 90% over 2 steps).

Step 4: (1S,3S*)-3-(Benzo[d]thiazol-2-yl)-1-(3-fluoro-2-methylphenyl)-N-hydroxycyclopentanecarboxamide and (1S,3S*)-3-(benzo[d]thiazol-2-yl)-1-(3-fluoro-2-methylphenyl)-N-hydroxycyclopentanecarboxamide Following Method D from (S)-3-(benzo[d]thiazol-2-yl)-1-(3-fluoro-2-methylphenyl)cyclopentanecarboxylic acid (170 mg, 0.43 mmol). Purification by preparative HPLC gave the title compounds as off white solids. LCMS (ES+) consistent with target (M+H)+. The enantiomers were separated by Chiralpak IA 30/70 EtOH (0.1% FA)/heptane, 1.0 ml/min, r.t. (1S,3S*)-3-(Benzo[d]thiazol-2-yl)-1-(3-fluoro-2-methylphenyl)-N-hydroxycyclopentanecarboxamide (D1) (15 mg). LCMS (ES+) 371 (M+H)+, RT 3.86 min (Analytical method 1); $^1$H NMR δ (ppm)(DMSO-$d_6$): 10.08 (1 H, s), 8.73 (1 H, s), 8.04 (1 H, d, J=7.9 Hz), 7.92 (1 H, d, J=8.1 Hz), 7.50-7.45 (1 H, m), 7.42-7.37 (1 H, m), 7.28 (1 H, d, J=7.9 Hz), 7.25-7.17 (1 H, m), 7.06 (1 H, t, J=8.9 Hz), 3.76 (1 H, t, J=8.9 Hz), 3.22 (1 H, dd, J=12.7, 7.6 Hz), 2.72-2.61 (1 H, m), 2.37-2.14 (6 H, m), 2.11-2.1 (1 H, m). (1S,3R*)-3-(benzo[d]thiazol-2-yl)-1-(3-fluoro-2-methylphenyl)-N-hydroxycyclopentanecarboxamide (D2) (15 mg). LCMS (ES+) 371 (M+H)+, RT 3.84 min (Analytical method 1); ¹H NMR δ (ppm)(DMSO-d₆): 9.98 (1 H, s), 8.70 (1 H, s), 8.09-8.05 (1 H, m), 7.95 (1 H, d, J=8.1 Hz), 7.52-7.47 (1 H, m), 7.41 (1 H, td, J=7.6, 1.2 Hz), 7.32-7.22 (2 H, m), 7.10 (1 H, t, J=8.7 Hz), 3.64 (1 H, t, J=8.7 Hz), 2.88 (1 H, dd, J=13.3, 10.0 Hz), 2.63-2.56 (1 H, m), 2.34-2.18 (3 H, m), 2.13 (3 H, dd, J=13.3, 2.8 Hz), 2.08-1.97 (1 H, m).

Example 77

(1S,3S*)-3-(2-cyclopropylbenzo[d]thiazol-6-yl)-1-(3-fluoro-2-methylphenyl)-N-hydroxycyclopentanecarboxamide (D1)

Example 78

(1S,3R*)-3-(2-cyclopropylbenzo[d]thiazol-6-yl)-1-(3-fluoro-2-methylphenyl)-N-hydroxycyclopentanecarboxamide (D2)

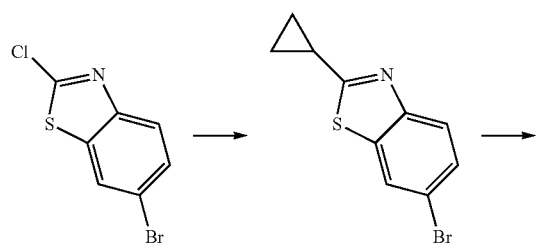

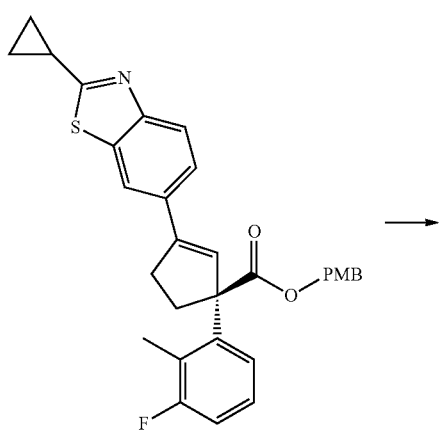

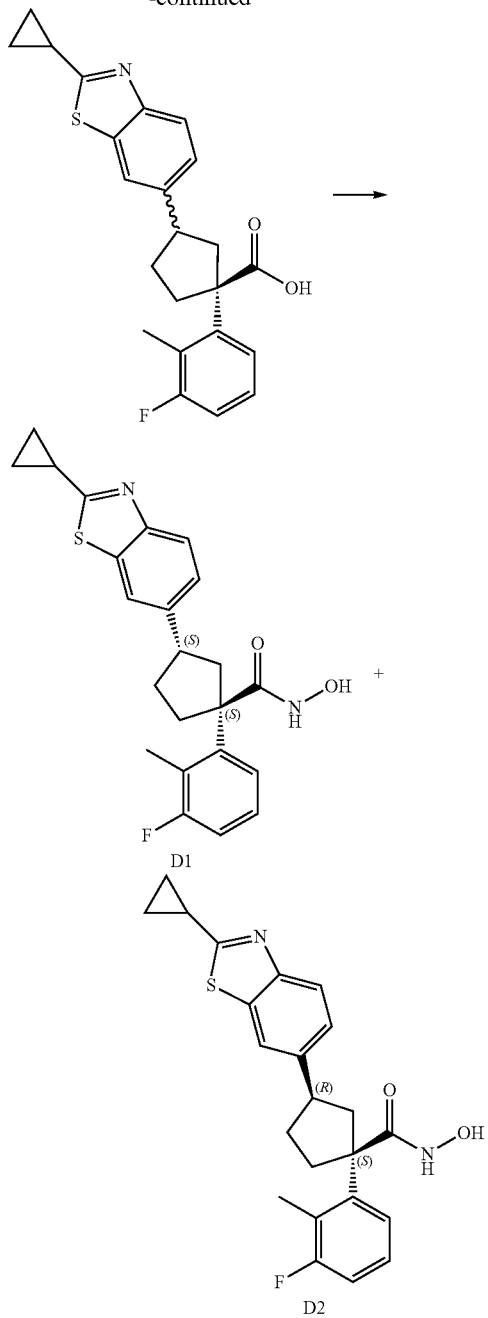

C3 Stereochemistry Putatively Assigned

Step 1: 6-bromo-2-cyclopropylbenzo[d]thiazole

To a solution of 6-bromo-2-chlorobenzo[d]thiazole (0.50 g, 2.02 mmol) and Pd(PPh₃)₄ (70 mg, 0.06 mmol) in THF (5 mL) was added dropwise cyclopropyl zinc bromide (0.5 M in THF, 4.0 mL, 2.02 mmol), over 15 min. The reaction mixture heated to 60° C. under N2 for 18 h. The reaction mixture was cooled to 0° C. and quenched with saturated sodium hydrogen carbonate solution (10 mL). The corresponding solution was partitioned with ethyl acetate (50 mL), washed with saturated sodium hydrogen carbonate solution (30 mL), dried over MgSO4 and concentrated to give an orange solid. The crude reaction material was purified by flash silica chromatography (gradient elution i-hex to 50% EtOAc in i-hex) to give the title compound as a pale orange solid (0.40 g, 78%). LCMS (ES+) consistent with target (M+H)+. 1H NMR δ (ppm)(CHCl3-d): 7.92 (1 H, dd, J=5.48, 1.97 Hz), 7.76-7.67 (1 H, m), 7.54-7.43 (1 H, m), 2.41-2.33 (1 H, m), 1.29-1.18 (4 H, m).

Step 2: (S)-4-Methoxybenzyl 3-(2-cyclopropyl-benzo[d]thiazol-6-yl)-1-(3-fluoro-2-methylphenyl)cyclopent-2-enecarboxylate Following Method B (iv) from 6-bromo-2-cyclopropyl-benzo[d]thiazole (0.2590 g, 1.0 mmol) and Intermediate 9 (0.50 g, 1.02 mmol). Purification by flash silica chromatography (gradient elution i-hex to 40% EtOAc in i-hex) gave the title compound as a pale yellow oil (0.303 g, 59%).

Step 4: (S)-3-(2-Cyclopropylbenzo[d]thiazol-6-yl)-1-(3-fluoro-2-methylphenyl)cyclopentanecarboxylic acid Following Method F from (S)-4-methoxybenzyl 3-(2-cyclopropylbenzo[d]thiazol-6-yl)-1-(3-fluoro-2-methylphenyl)cyclopent-2-enecarboxylate (303 mg, 0.59 mmol) gave the title compound as a pale yellow gum (171 mg, 73%).

Step 5: (1S,3S*)-3-(2-Cyclopropylbenzo[d]thiazol-6-yl)-1-(3-fluoro-2-methylphenyl)-N-hydroxycyclopentanecarboxamide and (1S,3R*)-3-(2-cyclopropylbenzo[c]thiazol-6-yl)-1-(3-fluoro-2-methylphenyl)-N-hydroxycyclopentanecarboxamide Following Method D from (S)-3-(2-cyclopropylbenzo[d]thiazol-6-yl)-1-(3-fluoro-2-methylphenyl)cyclopentanecarboxylic acid (170 mg, 0.43 mmol) and purified by preparative HPLC to give the title compounds as white solids. LCMS (ES+) consistent with target (M+H)+. (1S,3S*)-3-(2-Cyclopropylbenzo[d]thiazol-6-yl)-1-(3-fluoro-2-methylphenyl)-N-hydroxycyclopentanecarboxamide (D1) (6 mg). LCMS (ES+) 411 (M+H)+, RT 4.07 min (Analytical method 1); 1H NMR δ (ppm)(DMSO-d6): 9.99 (1 H, s), 8.67 (1 H, s), 7.86 (1 H, d, J=1.7 Hz), 7.71 (1 H, d, J=8.3 Hz), 7.28 (2 H, dd, J=7.8, 1.7 Hz), 7.23-7.15 (1 H, m), 7.03 (1 H, t, J=8.9 Hz), 3.02-2.91 (1 H, m), 2.75-2.67 (1 H, m), 2.23-2.05 (5 H, m), 2.00 (2 H, t, J=12.0 Hz), 1.72 (1 H, t, J=9.9 Hz), 1.21-1.14 (2 H, m), 1.09-1.04 (2 H, m), 1 H obscured by water. (1S,3R*)-3-(2-Cyclopropylbenzo[d]thiazol-6-yl)-1-(3-fluoro-2-methylphenyl)-N-hydroxycyclopentanecarboxamide (D2) (18 mg). LCMS (ES+) 411 (M+H)+, RT 4.12 min (Analytical method 1); 1H NMR δ (ppm)(DMSO-d6): 9.91 (1 H, s), 8.67 (1 H, s), 7.95 (1 H, d, J=1.7 Hz), 7.77 (1 H, d, J=8.4 Hz), 7.45 (1 H, dd, J=8.45, 1.7 Hz), 7.33-7.21 (2 H, m), 7.07 (1 H, t, J=8.4 Hz), 3.23-3.14 (1 H, m), 2.63 (2 H, m), 2.45-2.35 (2 H, m), 2.22-2.07 (5 H, m), 1.83-1.73 (1 H, m), 1.25-1.17 (2 H, m), 1.14-1.08 (2 H, m).

Example 79

(1S,3S*)-3-(2-Cyclopropylbenzo[d]thiazol-5-yl)-1-(3-fluoro-2-methylphenyl)-N-hydroxycyclopentanecarboxamide (D1)

Example 80

(1 S,3R*)-3-(2-Cyclopropylbenzo[c]thiazol-5-yl)-1-(3-fluoro-2-methylphenyl)-N-hydroxycyclopentanecarboxamide (D2)

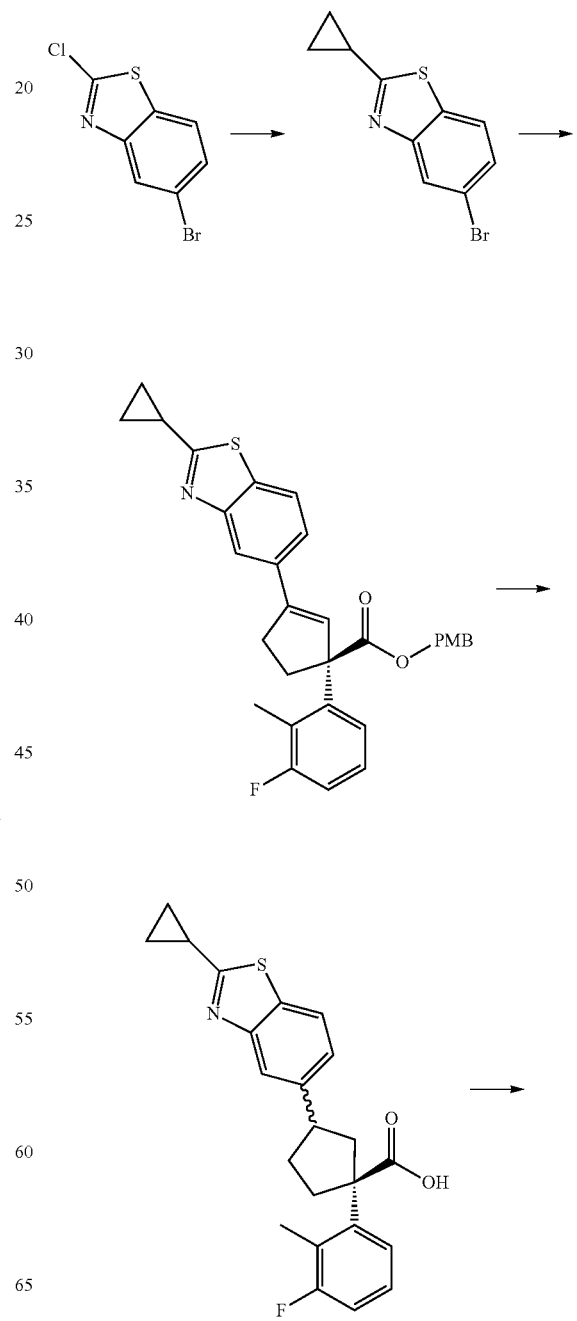

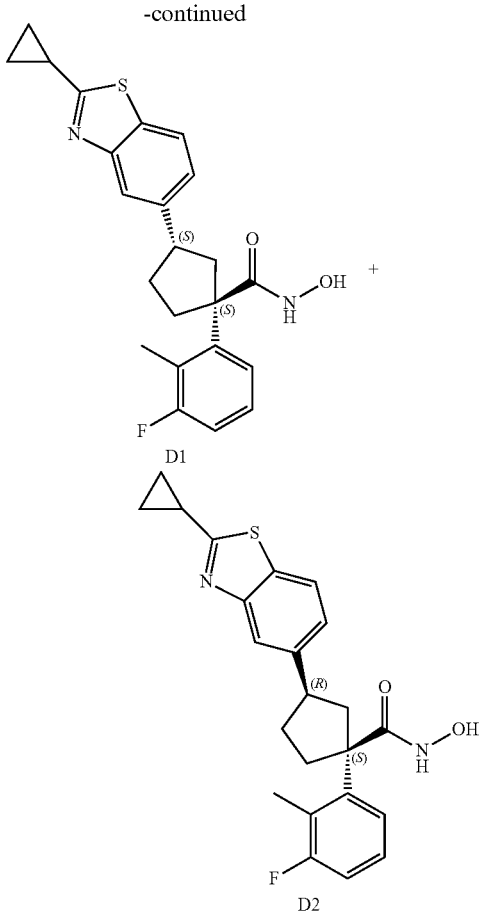

D1

D2

C3 Stereochemistry Putatively Assigned

Step 1: 5-Bromo-2-cyclopropylbenzo[d]thiazole

To a solution of 5-bromo-2-chlorobenzo[d]thiazole (0.50 g, 2.02 mmol) and Pd(PPh$_3$)$_4$ (70 mg, 0.06 mmol) in THF (5 mL) was added dropwise cyclopropyl zinc bromide (0.5 M in THF, 4.0 mL, 2.02 mmol), over 15 min. The reaction mixture heated to 60° C. under N$_2$ for 18 h. The reaction mixture was cooled to 0° C. and quenched with saturated sodium hydrogen carbonate solution (10 mL). The corresponding solution was partitioned with ethyl acetate (50 mL), washed with saturated sodium hydrogen carbonate solution (30 mL), dried over MgSO$_4$ and concentrated to give an orange solid. The crude reaction material was purified by flash silica chromatography (gradient elution i-hex to 50% EtOAc in i-hex) to give the title compound as a pale yellow solid (0.45 g, 88%). LCMS (ES+) consistent with target (M+H)$^+$.

Step 2: (S)-4-Methoxybenzyl 3-(2-cyclopropyl-benzo[d]thiazol-5-yl)-1-(3-fluoro-2-methylphenyl)cyclopent-2-enecarboxylate Following Method B (iv) from 5-bromo-2-cyclopropyl-benzo[d]thiazole (0.400 g, 1.58 mmol) and Intermediate 9 (0.70 g, 1.43 mmol). Purification by flash silica chromatography (gradient elution i-hex to 40% EtOAc in i-hex) gave the title compound as a pale yellow oil (0.49 g, 66%).

Step 3: (S)-3-(2-Cyclopropylbenzo[d]thiazol-5-yl)-1-(3-fluoro-2-methylphenyl)cyclopentanecarboxylic acid Following Method F from (S)-4-methoxybenzyl 3-(2-cyclopropylbenzo[d]thiazol-5-yl)-1-(3-fluoro-2-methylphenyl)cyclopent-2-enecarboxylate (490 mg, 0.95 mmol) gave the title compound as a pale yellow gum (340 mg, 90%).

Step 4: (1S,3S*)-3-(2-Cyclopropylbenzo[d]thiazol-5-yl)-1-(3-fluoro-2-methylphenyl)-N-hydroxycyclopentanecarboxamide (D1) and (1 S,3R*)-3-(2-cyclopropylbenzo[c]thiazol-5-yl)-1-(3-fluoro-2-methylphenyl)-N-hydroxycyclopentanecarboxamide (D2)

Following Method D from (S)-3-(2-cyclopropylbenzo[d]thiazol-5-yl)-1-(3-fluoro-2-methylphenyl)cyclopentanecarboxylic acid (340 mg, 0.86 mmol) and purified by preparative HPLC to give the title compounds as off white solids. LCMS (ES+) consistent with target (M+H)$^+$. (1S,3S*)-3-(2-cyclopropylbenzo[d]thiazol-5-yl)-1-(3-fluoro-2-methylphenyl)-N-hydroxycyclopentanecarboxamide (D1) (44 mg). LCMS (ES+) 411 (M+H)$^+$, RT 4.12 min (Analytical method 1); $^1$H NMR δ (ppm)(DMSO-d$_6$): 10.01 (1 H, s), 8.69 (1 H, s), 7.88 (1 H, d, J=8.2 Hz), 7.68 (1 H, d, J=1.6 Hz), 7.34-7.15 (3 H, m), 7.05 (1 H, t, J=8.9 Hz), 3.30-3.24 (1 H, m), 3.03 (1 H, dd, J=12.5, 6.8 Hz), 2.77-2.64 (1 H, m), 2.50-2.43 (1 H, m), 2.27-2.07 (5 H, m), 2.08-1.95 (1 H, m), 1.83-1.69 (1 H, m), 1.25-1.07 (4 H, m). (1S,3R*)-3-(2-cyclopropylbenzo[d]thiazol-5-yl)-1-(3-fluoro-2-methylphenyl)-N-hydroxycyclopentanecarboxamide (D2) (84 mg). LCMS (ES+) 411 (M+H)$^+$, RT 4.10 min (Analytical method 1); $^1$H NMR δ (ppm)(DMSO-d$_6$): 9.93 (1 H, s), 8.67 (1 H, s), 7.90 (1 H, d, J=8.2 Hz), 7.84 (1 H, d, J=1.6 Hz), 7.37 (1 H, dd, J=8.2, 1.7 Hz), 7.34-7.20 (2 H, m), 7.07 (1 H, t, J=8.8 Hz), 3.27-3.14 (1 H, m), 2.69-2.61 (2 H, m), 2.50-2.35 (2 H, m), 2.24-2.07 (5 H, m), 1.83-1.72 (1 H, m), 1.25-1.09 (4 H, m).

Example 81

(1S,3R)-3-(5-Fluoro-1-methyl-1H-indazol-6-yl)-1-(3-fluoro-2-methylphenyl)-N-hydroxycyclopentanecarboxamide

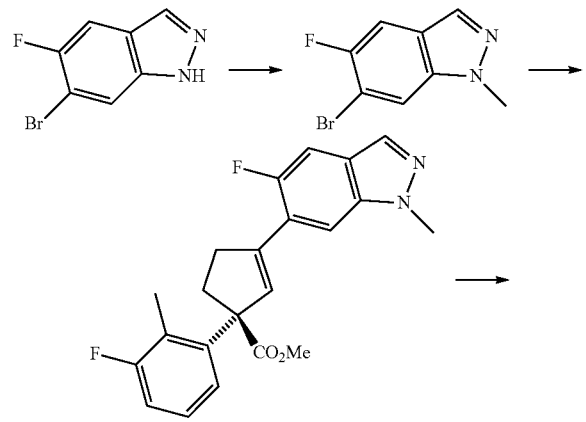

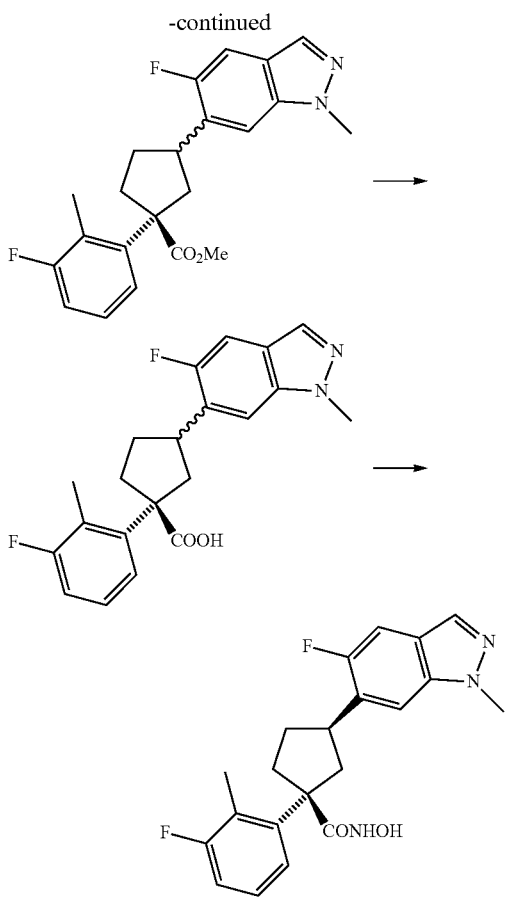

C3 Stereochemistry Putatively Assigned

Step 1: 6-Bromo-5-fluoro-1-methyl-1H-indazole

A stirred solution of 6-bromo-5-fluoro-1H-indazole (1.00 g, 4.65 mmol) in dry MeCN (10 mL) was treated at r.t. with Cs$_2$CO$_3$ (3.06 g, 9.39 mmol) and MeI (0.35 mL, 5.62 mmol). The reaction was heated to 70° C. for 3 h. After cooling to r.t., the mixture was filtered, washing with EtOAc (50 mL), and concentrated. Purification by silica column chromatography gave the title compound (562 mg, 2.45 mmol, 53%) as a cream powder.

Step 2: (S)-Methyl 3-(5-fluoro-1-methyl-1H-indazol-6-yl)-1-(3-fluoro-2-methylphenyl)cyclopent-2-enecarboxylate Following Method B(ii) using 6-bromo-5-fluoro-1-methyl-1H-indazole (304 mg, 1.33 mmol), bis(neopentylglycolato)diboron (403 mg, 1.78 mmol) and Intermediate 6 (452 mg, 1.18 mmol). Purification by silica column chromatography gave the title compound (410 mg, 1.07 mmol, 81%) as a colorless oil.

Step 3: Methyl 3-(5-fluoro-1-methyl-1H-indazol-6-yl)-1-(3-fluoro-2-methylphenyl)cyclopentanecarboxylate Following Method F from (S)-methyl 3-(5-fluoro-1-methyl-1H-indazol-6-yl)-1-(3-fluoro-2-methylphenyl)cyclopent-2-enecarboxylate (410 mg, 1.07 mmol). The mixture was filtered and concentrated to yield a diastereomeric mixture of the title compound (417 mg) as a white powder which was used without further purification.

Step 4: 3-(5-fluoro-1-methyl-1H-indazol-6-yl)-1-(3-fluoro-2-methylphenyl)cyclopentanecarboxylic acid Following Method C(ii) from methyl 3-(5-fluoro-1-methyl-1H-indazol-6-yl)-1-(3-fluoro-2-methylphenyl)cyclopentanecarboxylate (412 mg). The title compound was obtained as a diastereomeric mixture (305 mg, 0.82 mmol, 77% over two steps) as a white powder.

Step 5: (1S,3R)-3-(5-Fluoro-1-methyl-1H-indazol-6-yl)-1-(3-fluoro-2-methylphenyl)-N-hydroxycyclopentanecarboxamide Following Method D(ii) from the diastereomeric mixture of 3-(5-fluoro-1-methyl-1H-indazol-6-yl)-1-(3-fluoro-2-methylphenyl)cyclopentane carboxylic acid (221 mg, 0.60 mmol). Purification by preparative HPLC gave the title compound (149 mg, 0.39 mmol, 65%) as a white solid. LCMS (ES+) 386 (M+H)$^+$, RT 3.79 min. (Analytical method 1); $^1$H NMR δ (ppm)(4 MHz, DMSO-d$_6$): 9.91 (1H, s), 8.67 (1H, s), 7.97 (1H, s), 7.70 (1H, d, J=6 Hz), 7.49 (1H, d, J=10.8 Hz), 7.30-7.26 (2H, m), 7.08 (1H, app t, J=8 Hz), 4.06 (3H, s), 3.35-3.30 (1H, m), 2.72-2.65 (1H, m), 2.57-2.50 (2H, m), 2.19-2.15 (2H, m), 2.11 (3H, d, J=2.8 Hz), 1.95-1.84 (1H, m).

Example 82

(1S,3S*)-3-(7-Fluoro-1-methyl-1H-indazol-6-yl)-1-(3-fluoro-2-methylphenyl)-N-hydroxycyclopentanecarboxamide (D1)

Example 83

(1S,3R*)-3-(7-Fluoro-1-methyl-1H-indazol-6-yl)-1-(3-fluoro-2-methylphenyl)-N-hydroxycyclopentanecarboxamide (D2)

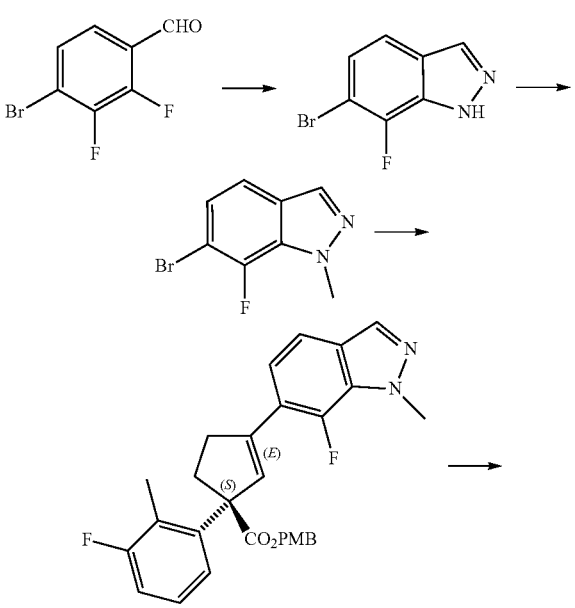

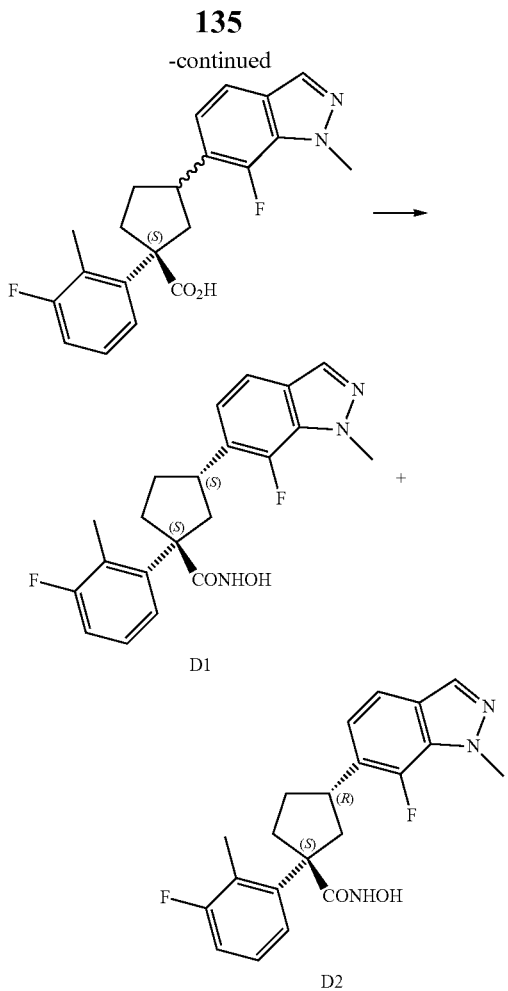

D1

D2

C3 Stereochemistry Putatively Assigned

Step 1: 6-Bromo-7-fluoro-1H-indazole

4-Bromo-2,3-difluorobenzaldehyde (1.0 g, 4.52 mmol), methoxyamine hydrochloride (418 mg, 5.00 mmol) and potassium carbonate (749 mg, 5.50 mmol) in DME (12 mL) were stirred at 4° C. for 3.5 h. The resulting suspension was cooled to r.t. and filtered through a celite pad, washing with EtOAc (3×1 mL). The combined organics were concentrated to ~5 mL and to this was added hydrazine monohydrate (3 mL). The reaction mixture was stirred at 9° C. overnight. The mixture was cooled to r.t. and poured onto H$_2$O (2 mL). The solvents were partially removed under reduced pressure and the resulting solid was filtered, washed with H$_2$O (2×10 mL) and i-hex (3×15 mL) and dried to constant weight to give the title compound as a colorless solid (791 mg, 81%).

Step 2: 6-Bromo-7-fluoro-1-methyl-1H-indazole

To a stirred solution of 6-bromo-7-fluoro-1H-indazole (1.00 g, 4.65 mmol) and potassium carbonate (1.28 g, 9.30 mmol) in MeCN (10 mL) was added iodomethane (434 µl, 6.98 mmol). The reaction mixture was heated to 60° C. for 2.5 h, then allowed to cool to r.t. and filtered through celite, washing with EtOAc (3×20 mL). The combined organics were combined and concentrated. Purification by flash column chromatography (gradient elution i-hex to 33% EtOAc in i-hex) gave the title compound as a colorless solid (610 mg, 57%).

Step 3: (S)-4-Methoxybenzyl 3-(7-fluoro-1-methyl-1H-indazol-6-yl)-1-(3-fluoro-2-methylphenyl)cyclopent-2-enecarboxylate Following Method B (iv) from 6-bromo-7-fluoro-1-methyl-1H-indazole (188 mg, 0.82 mmol) and Intermediate 9 (400 mg, 0.82 mmol). Purification by flash column chromatography gave the title compound as a colorless oil (280 mg, 70%).

Step 4: (S)-3-(7-Fluoro-1-methyl-1H-indazol-6-yl)-1-(3-fluoro-2-methylphenyl)cyclopentanecarboxylic acid Following Method F from (S)-4-methoxybenzyl 3-(7-fluoro-1-methyl-1H-indazol-6-yl)-1-(3-fluoro-2-methylphenyl)cyclopent-2-enecarboxylate (150 mg, 0.25 mmol). The crude product was purified by SCX cartridge to give the title compound as a colorless semi-solid (150 mg, 98%, 1:1 mixture of diastereoisomers).

Step 5: (1S,3S*)-3-(7-Fluoro-1-methyl-1H-indazol-6-yl)-1-(3-fluoro-2-methylphenyl)-N-hydroxycyclopentanecarboxamide and (1S,3R*)-3-(7-fluoro-1-methyl-1H-indazol-6-yl)-1-(3-fluoro-2-methylphenyl)-N-hydroxycyclopentanecarboxamide Following Method D from (S)-3-(7-fluoro-1-methyl-1H-indazol-6-yl)-1-(3-fluoro-2-methylphenyl)cyclopentanecarboxylic acid (150 mg, 0.31 mmol). Purification by preparative HPLC gave the title compounds as colorless solids. LCMS (ES+) consistent with target (M+H)$^+$. (1S,3S*)-3-(7-Fluoro-1-methyl-1H-indazol-6-yl)-1-(3-fluoro-2-methylphenyl)-N-hydroxycyclopentanecarboxamide (60 mg). LCMS (ES+) 386 (M+H)$^+$, RT 3.82 min (Analytical method 1); $^1$H NMR δ (ppm)(400 MHz, MeOD): Hydroxamic acid protons not observed, 7.94 (1H, d, J=2.4 Hz), 7.44 (1H, d, J=8.4 Hz), 7.36 (1H, d, J=7.8 Hz), 7.31-7.22 (1H, m), 7.06-6.95 (2H, m), 4.21 (3H, s), 3.94-3.81 (1H, m), 3.15-3.04 (1H, m), 2.79-2.71 (1H, m), 2.42-2.27 (3H, m), 2.20 (3H, d, J=2.8 Hz), 2.04-1.93 (1H, m); (1S,3R*)-3-(7-Fluoro-1-methyl-1H-indazol-6-yl)-1-(3-fluoro-2-methylphenyl)-N-hydroxycyclopentanecarboxamide (22 mg). LCMS (ES+) 386 (M+H)$^+$, RT 3.84 min (Analytical method 1); $^1$H NMR δ (ppm)(4 MHz, MeOD): Hydroxamic acid protons not observed, 7.96 (1H, d, J=2.3 Hz), 7.52 (1H, d, J=8.3 Hz), 7.38 (1H, d, J=7.8 Hz), 7.35-7.26 (2H, m), 7.05 (1H, dd, J=8.8, 8.8 Hz), 4.22 (3H, s), 3.70-3.58 (1H, m), 2.84-2.69 (2H, m), 2.52 (1H, dd, J=7.3, 13.1 Hz), 2.37-2.28 (1H, m), 2.19 (4H, d, J=2.5 Hz), 2.11-2.01 (1H, m).

Example 84

(1S,3S*)-1-(3-Fluoro-2-methylphenyl)-N-hydroxy-3-(quinolin-6-yl)cyclopentanecarboxamide (D1)

Example 85

(1S,3R*)-1-(3-Fluoro-2-methylphenyl)-N-hydroxy-3-(quinolin-6-yl)cyclopentanecarboxamide (D2)

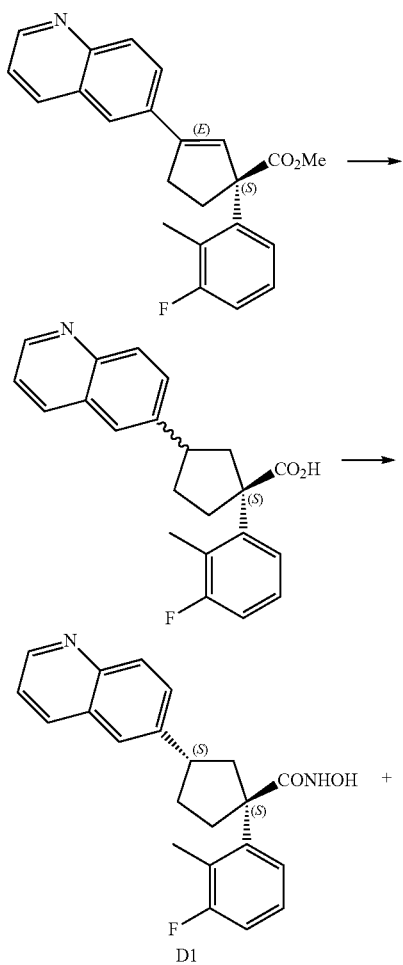

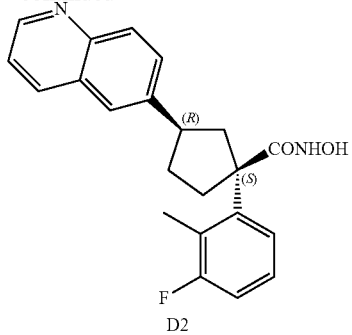

D2

C3 Stereochemistry Putatively Assigned

Step 1: (S)-Methyl 1-(3-fluoro-2-methylphenyl)-3-(quinolin-6-yl)cyclopent-2-enecarboxylate Intermediate 6 (550 mg, 1.44 mmol), quinolin-6-ylboronic acid (260 mg, 1.5 mmol), CsF (200 mg), DME (15 ml), MeOH (3 ml) and palladiumtetrakistriphenylphosphine (2 mg) were combined in a sealed tube and heated in a microwave to 120° C. for 2 h. The reaction mixture was then evaporated to dryness onto silica and purified by flash chromatography to give the title compound as a clear gum (459 mg). LCMS (ES+) consistent with target (M+H)$^+$.

Step 2: (1S)-1-(3-Fluoro-2-methylphenyl)-3-(quinolin-6-yl)cyclopentanecarboxylic acid Following Method F and Method C from (S)-methyl 1-(3-fluoro-2-methylphenyl)-3-(quinolin-6-yl)cyclopent-2-enecarboxylate (450 mg, 1.24 mmol). Purification by preparative HPLC gave the title compound as a tan foam (191 mg, 44%). LCMS (ES+) consistent with target (M+H)$^+$.

Step 3: (1S,3S)-1-(3-Fluoro-2-methylphenyl)-N-hydroxy-3-(quinolin-6-yl)cyclopentanecarboxamide and (1S,3R)-1-(3-fluoro-2-methylphenyl)-N-hydroxy-3-(quinolin-6-yl)cyclopentanecarboxamide Following Method D from (1S)-1-(3-fluoro-2-methylphenyl)-3-(quinolin-6-yl)cyclopentanecarboxylic acid (191 mg, 0.547 mmol). Purification by preparative HPLC gave the title compounds. (1S,3S)-1-(3-Fluoro-2-methylphenyl)-N-hydroxy-3-(quinolin-6-yl)cyclopentanecarboxamide as a white solid (D1) (4 mg). LCMS (ES+) 365 (M+H)$^+$, RT 2.56 min (Analytical method 1); $^1$H NMR δ (ppm)(DMSO-d$_6$): 10.05 (1 H, s), 8.90-8.80 (1 H, m), 8.72 (1 H, s), 8.35-8.20 (1 H, m), 8.00-7.85 (1 H, m), 7.82 (1 H, s), 7.70-7.60 (1 H, m), 7.50-7.40 (1 H, m), 7.35-6.95 (3 H, m), 3.10-3.00 (1 H, m), 3.00-2.80 (1 H, m), 2.80-2.70 (1 H, m), 2.40-2.00 (6 H, m), 1.90-1.70 (1 H, m). (1S,3R)-1-(3-Fluoro-2-methylphenyl)-N-hydroxy-3-(quinolin-6-yl)cyclopentanecarboxamide (D2) as a clear glass (16 mg). LCMS (ES+) 365 (M+H)$^+$, RT 2.62 min (Analytical method 1); $^1$H NMR δ (ppm)(DMSO-d$_6$): 9.93 (1 H, br s), 8.84 (1H, dd, J=4 Hz and 1.6 Hz), 8.71 (1H, br s), 8.30 (1H, dd, J=8.8 Hz and 1.2 Hz), 7.98 (1 H, d, J=8.4 Hz), 7.90-7.75 (2 H, m), 7.51 (1 H, dd, J=8.4 Hz and 4.4 Hz), 7.40-7.20 (2 H, m), 7.15-7.5 (1 H, m), 3.4-3.25 (1 H, m), 2.80-2.60 (2 H, m), 2.60-2.40 (1 H, m), 2.30-2.10 (2 H, m), 2.13 (3 H, d, J=2.8 Hz), 1.95-1.75 (1 H, m).

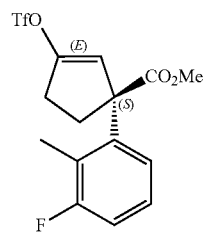

Example 86

(1S,3R*)-1-(3,4-difluoro-2-methylphenyl)-N-hydroxy-3-(1-methyl-1H-indazol-6-yl)cyclopentanecarboxamide

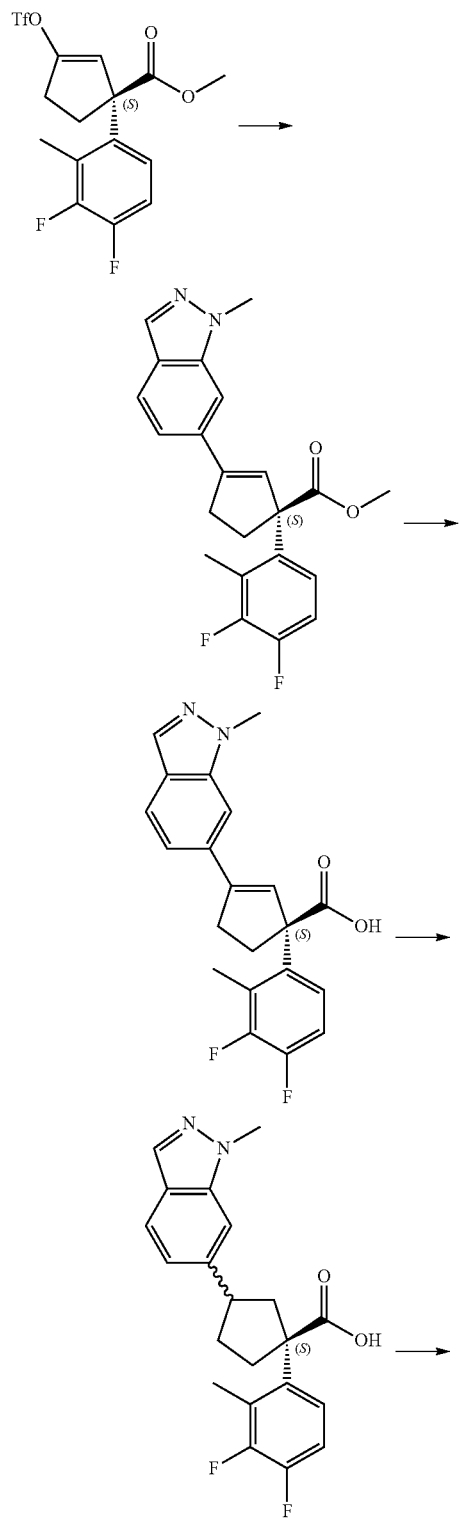

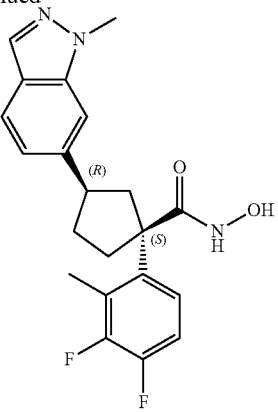

C3 Stereochemistry Putatively Assigned

Step 1: (S)-methyl 1-(3,4-difluoro-2-methylphenyl)-3-(1-methyl-1H-indazol-6-yl)cyclopent-2-enecarboxylate Following Method B (ii) from Intermediate 10 (0.62 g, 1.55 mmol) and (1-methyl-1H-indazol-6-yl) boronic acid (0.34 g, 1.90 mmol). Purification by flash silica column chromatography (gradient elution i-hex to 35% EtOAc in i-hex) gave the title compound as a colorless oil (0.58 g, 97%). $^1$H NMR δ (ppm)(CHCl$_3$-d): 7.96 (1 H, d, J=0.95 Hz), 7.70 (1 H, dd, J=8.45, 0.80 Hz), 7.47-7.39 (2 H, m), 7.06 (1 H, ddd, J=8.79, 4.98, 1.76 Hz), 7.01-6.89 (1 H, m), 6.36 (1 H, t, J=1.80 Hz), 4.10 (3 H, s), 3.71 (3 H, s), 3.37 (1 H, ddd, J=13.01, 8.92, 4.62 Hz), 3.16-3.07 (1 H, m), 2.92 (1 H, dddd, J=15.91, 9.24, 4.61, 1.88 Hz), 2.23-2.16 (3 H, m), 2.06-1.97 (1 H, m).

Step 2: (S)-1-(3,4-difluoro-2-methylphenyl)-3-(1-methyl-1H-indazol-6-yl)cyclopent-2-enecarboxylic acid Following Method C (iii) from (S)-methyl 1-(3,4-difluoro-2-methylphenyl)-3-(1-methyl-1H-indazol-6-yl)cyclopent-2-enecarboxylate (0.57 g, 1.55 mmol). Crude reaction material was azeotroped from CHCl$_3$ to give the title compound as a colorless foam (0.55 g, 95%). $^1$H NMR δ (ppm)(CHCl$_3$-d): 7.97 (1 H, d, J=0.92 Hz), 7.75-7.66 (1 H, m), 7.46-7.39 (2 H, m), 7.08 (1 H, ddd, J=8.81, 4.89, 1.65 Hz), 6.95 (1 H, q, J=8.71 Hz), 6.42 (1 H, s), 4.09 (2 H, s), 3.33 (1 H, ddd, J=13.16, 8.72, 4.35 Hz), 3.17-3.6 (1 H, m), 2.98-2.89 (1 H, m), 2.28 (3 H, d, J=2.72 Hz), 2.09-1.99 (1 H, m).

Step 3: (S)-1-(3,4-difluoro-2-methylphenyl)-3-(1-methyl-1H-indazol-6-yl)cyclopentanecarboxylic acid Following Method F from (S)-1-(3,4-difluoro-2-methylphenyl)-3-(1-methyl-1H-indazol-6-yl)cyclopent-2-enecarboxylic acid (430 mg, 1.22 mmol). Azeotroping from CHCl$_3$ gave the title compound as a colorless foam as a 2:1 mixture of diastereoisomers (360 mg, 83%).

Step 4: (1S,3R*)-1-(3,4-Difluoro-2-methylphenyl)-N-hydroxy-3-(1-methyl-1H-indazol-6-yl)cyclopent-2-enecarboxamide Following Method D from (S)-1-(3,4-difluoro-2-methylphenyl)-3-(1-methyl-1H-indazol-6-yl)cyclopentanecarboxylic acid (300 mg, 0.81 mmol). Purification by preparative HPLC gave the title compound as a colorless solid (65 mg, 64%). LCMS (ES+) 386 (M+H)+, RT 3.76 min (Analytical method 1); $^1$H NMR δ (ppm)(DMSO-d$_6$): 9.93 (1H, s), 8.69 (1H, s), 7.96 (1H, s), 7.68 (1H, d, J=8.4 Hz), 7.52 (1H, s), 7.33-7.23 (2H, m), 7.17 (1H, d, J=8.5 Hz), 4.02 (3H, s), 3.26-3.15 (1H, m), 2.68-2.59 (2H, m), 2.45-2.33 (1H, m), 2.18-2.13 (5H, m), 1.92-1.80 (1H, m).

Example 87

(1 S,3R*)-1-(3-fluoro-2-methylphenyl)-N-hydroxy-3-(pyrrolidin-1-yl)cyclopentanecarboxamide (D1)

Example 88

(1 S,3S*)-1-(3-fluoro-2-methylphenyl)-N-hydroxy-3-(pyrrolidin-1-yl)cyclopentanecarboxamide (D2)

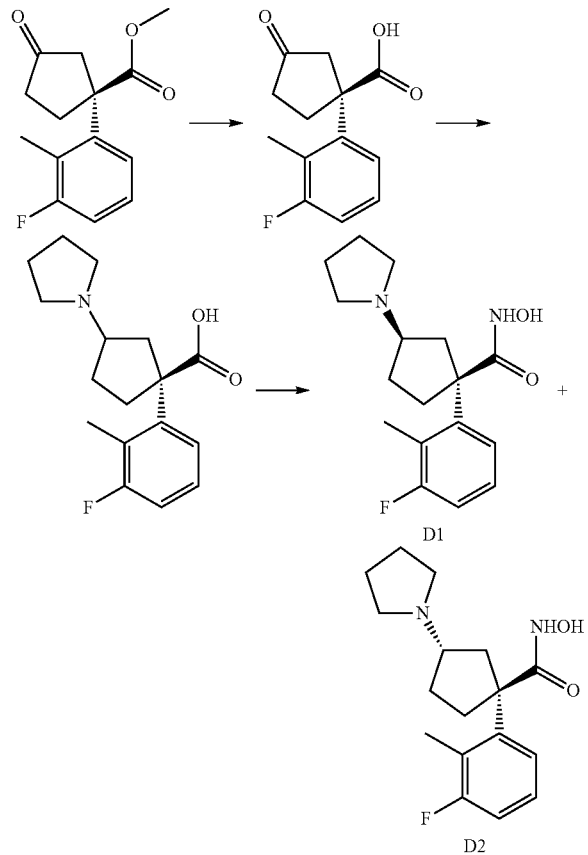

C3 Stereochemistry Putatively Assigned

Step 1: (1S)-1-(3-fluoro-2-methylphenyl)-3-oxocyclopentanecarboxylic acid

To a solution of Intermediate 1 (0.5 g, 2 mmol) in methanol (10 mL) was added 15% NaOH solution (5.3 mL) were combined in a sealed tube and heated to 70° C. for 24 h. The reaction mixture was then in vacuo partitioned between EtOAc and H$_2$O/adjusted to pH 7 with 1M HCl. Organic layer was dried (MgSO$_4$) and evaporated in vacuo to give the title compound as a pale orange gum (501 mg). This was used crude in the next step.

Step 2: (1S)-1-(3-Fluoro-2-methylphenyl)-3-(pyrrolidin-1-yl)cyclopentanecarboxylic acid To a solution of (1S)-1-(3-fluoro-2-methylphenyl)-3-oxo-cyclopentanecarboxylic acid (25 mg, 1.6 mmol) in DCM (5 mL) and acetic acid (0.125 mL) was added pyrrolidine (0.266 mL, 3.18 mmol) and stirred for 45 min. PS-Me$_3$N (CNBH$_3$) (4 mg, 1.6 mmol) was added and stirred slowly for 17 h. The resin was filtered off and the filtrate evaporated in vacuo. The crude product was applied to an SCX (5 g) cartridge and eluted with ~1.5 m NH$_3$ in MeOH. The filtrate was evaporated in vacuo to give a brown gum (0.34 g). Used in the next step without further purification.

Step 3: (1S,3R)-1-(3-Fluoro-2-methylphenyl)-N-hydroxy-3-(pyrrolidin-1-yl)cyclopentanecarboxamide and (1S,3S)-1-(3-fluoro-2-methylphenyl)-N-hydroxy-3-(pyrrolidin-1-yl)cyclopentanecarboxamide Following Method D from (1S)-1-(3-fluoro-2-methylphenyl)-3-(pyrrolidin-1-yl)cyclopentanecarboxylic acid (0.34 g, 1.16 mmol). Purification by preparative HPLC gave the title compounds as pale orange solids (58 mg 17% and 68 mg, 20%). LCMS (ES+) consistent with target (M+H)+. (1S,3R)-1-(3-Fluoro-2-methylphenyl)-N-hydroxy-3-(pyrrolidin-1-yl)cyclopentanecarboxamide (D1). LCMS (ES+) 37 (M+H)+, RT 1.96 min (Analytical method 1); $^1$H NMR δ (ppm)(DMSO-d$_6$): 9.94 (1 H, s), 8.22 (1 H, s), 7.27-7.09 (2 H, m), 7.08-6.98 (1 H, m), 2.96-2.76 (3 H, m), 2.68 (2 H, s), 2.49-2.37 (2 H, m), 2.17 (3 H, dd, J=5.3, 2.6 Hz), 2.12-2.04 (1 H, m), 2.01-1.87 (1 H, m), 1.82-1.61 (6 H, m). (1S,3S)-1-(3-Fluoro-2-methylphenyl)-N-hydroxy-3-(pyrrolidin-1-yl)cyclopentanecarboxamide (D2). LCMS (ES+) 307 (M+H)+, RT 2.13 min (Analytical method 1); $^1$H NMR δ (ppm)(DMSO-d$_6$): 8.25 (1 H, s), 7.26-6.98 (3 H, m), 2.84 (2 H, s), 2.67 (2 H, s), 2.55-2.43 (1 H, m), 2.42-2.26 (1 H, m), 2.28-2.17 (1 H, m), 2.14-1.95 (4 H, m), 1.93-1.82 (1 H, m), 1.94-1.48 (6H, m).

Example 89

(1S,3R*)-1-(3-fluoro-2-methylphenyl)-N-hydroxy-3-morpholinocyclopentanecarboxamide (D1)

Example 9

(1S,3S*)-1-(3-fluoro-2-methylphenyl)-N-hydroxy-3-morpholinocyclopentanecarboxamide (D2)

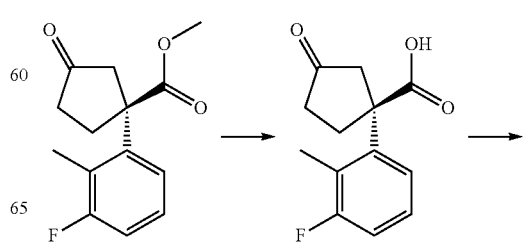

143

-continued

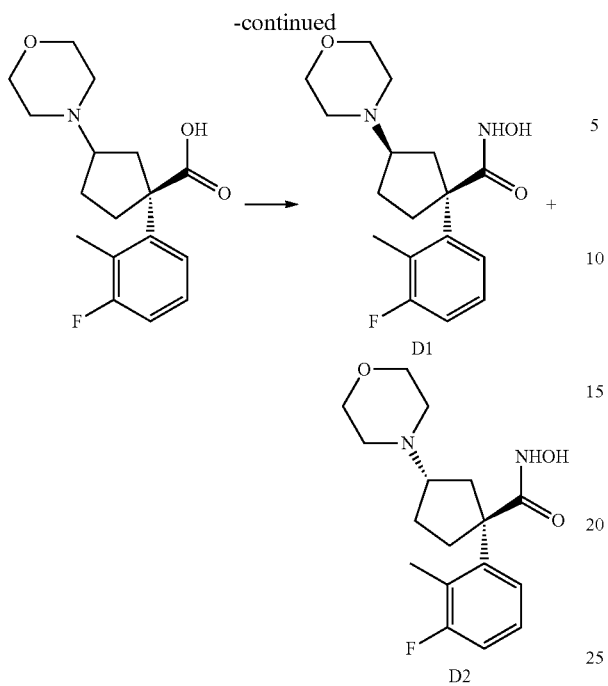

C3 Stereochemistry Putatively Assigned

Prepared in a similar manner to Examples 87 and 88 from morpholine. Purification by preparative HPLC gave the title compounds. LCMS (ES +) consistent with target (M+H)+.

144

(1S,3R)-1-(3-Fluoro-2-methylphenyl)-N-hydroxy-3-morpholinocyclopentanecarboxamide (D1). LCMS (ES+) 323 (M+H)+, RT 1.95 min (Analytical method 1); $^1$H NMR δ (ppm)(DMSO-d$_6$): 9.93-9.89 (1H, m), 8.28 (1H, s), 7.24-7.15 (2H, m), 7.3 (1H, t, J=8.8 Hz), 3.58-3.48 (4H, m), 2.84 (1H, dd, J=7.0, 12.4 Hz), 2.47-2.34 (4H, m), 2.17 (1H, dd, J=2.6, 13.9 Hz), 2.09 (3H, d, J=2.6 Hz), 2.04-1.85 (3H, m), 1.64 (1H, dd, J=9.6, 12.4 Hz), 1.49 (1H, ddd, J=8.5, 12.2, 17.0 Hz); (1S,3S)-1-(3-fluoro-2-methylphenyl)-N-hydroxy-3-morpholinocyclopentanecarboxamide (D2). LCMS (ES+) 323 (M+H)+, RT 2.04 min (Analytical method 1); $^1$H NMR δ (ppm)(DMSO-d$_6$): 9.94-9.94 (1H, m), 8.71 (1H, s), 7.22-7.14 (3H, m), 7.04 (2H, dd, J=8.9, 8.9 Hz), 3.57 (4H, dd, J=4.5, 4.5 Hz), 2.46-2.04 (8H, m), 2.04-1.94 (2H, m), 1.85-1.75 (2H, m), 1.55 (2H, ddd, J=8.4, 12.3, 16.8 Hz).

Example 91

(1S,3R)-1-(3-Fluoro-2-methylphenyl)-N-hydroxy-3-((1-methyl-1H-indazol-6-yl)oxy)cyclopentanecarboxamide Example 92

(1S,3S)-1-(3-Fluoro-2-methylphenyl)-N-hydroxy-3-((1-methyl-1H-indazol-6-yl)oxy)cyclopentanecarboxamide

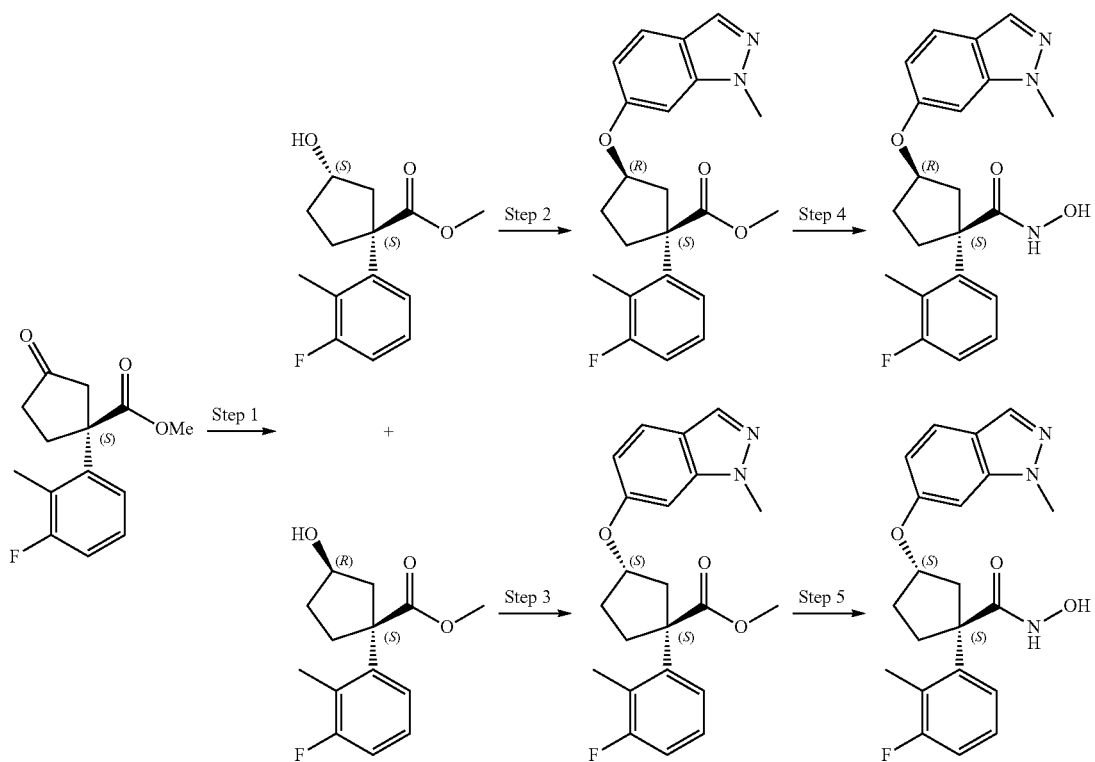

Step 1: (1S,3S)-Methyl 1-(3-fluoro-2-methylphenyl)-3-((5-fluoropyridin-3-yl)oxy)cyclopentanecarboxylate and (1S,3R)-methyl 1-(3-fluoro-2-methylphenyl)-3-((5-fluoropyridin-3-yl)oxy)cyclopentanecarboxylate Sodium borohydride (0.38 g, 1.25 mmol) was added portionwise over 15 min to a solution of Intermediate 1 (2.0 g, 1.0 mmol) in methanol at 0° C. The reaction was stirred for 1 h at 0° C. before quenching with brine (10 mL). The reaction was poured into water (120 mL) and extracted with EtOAc. Combined organics were washed with brine, dried (MgSO$_4$) and evaporated in vacuo to yield a colorless oil (2.06 g). Purification by flash silica chromatography (gradient elution i-hex to 55% EtOAc in i-hex) to yield partial separation of the two isomers of the title compounds as colorless gums. (1S,3S)-Methyl 1-(3-fluoro-2-methylphenyl)-3-((5-fluoropyridin-3-yl)oxy)cyclopentanecarboxylate (18 mg, 9%), $^1$H NMR δ (ppm)(CHCl$_3$-d): 7.19-7.10 (1 H, m), 6.95 (1 H, t, J=8.8 Hz), 4.54 (1 H, t, J=5.3 Hz), 3.62 (2 H, s), 3.08 (1 H, dd, J=13.8, 6.5 Hz), 2.49-2.40 (2 H, m), 2.13-2.08 (3 H, m), 1.91 (1 H, ddd, J=13.8, 4.5, 1.1 Hz), 1.80-1.70 (1 H, m), 1.38 (1 H, dd, J=14.9, 4.0 Hz), (OH not seen) and (1S,3R)-methyl 1-(3-fluoro-2-methylphenyl)-3-((5-fluoropyridin-3-yl)oxy)cyclopentanecarboxylate (670 mg, 33%), $^1$H NMR δ (ppm)(CHCl$_3$-d): 7.19-7.05 (2 H, m), 7.00-6.90 (1 H, m), 4.45-4.36 (1 H, m), 3.67 (2 H, s), 2.75-2.70 (1 H, m), 2.65-2.56 (2 H, m), 2.27-2.09 (6 H, m), 1.84-1.71 (1 H, m), (OH not seen).

Step 2: (1S,3R)Methyl 1-(3-fluoro-2-methylphenyl)-3-((1-methyl-1H-indazol-6-yl)oxy)cyclopentanecarboxylate Di-isopropylazodicarboxylate (0.12 mL, 0.59 mmol) was added dropwise over 15 min at 0° C. to a solution of (1S,3S)-methyl 1-(3-fluoro-2-methylphenyl)-3-hydroxycyclopentanecarboxylate (100 mg, 0.39 mmol), 6-hydroxy-1-methyl-1H-indazole (88.1 mg, 0.59 mmol) and triphenylphosphine (156 mg, 0.59 mmol) in THF (2 mL). The reaction was warmed to r.t. and stirred for 2 h. The solution was poured into EtOAc (35 mL), washed with 1 N NaOH, dried (MgSO$_4$) and evaporated in vacuo to yield a bright yellow gum (450 mg). Purification by flash silica chromatography (gradient elution i-hex to 60% EtOAc in i-hex) gave the title compound as a pale yellow gum (296 mg).

Step 3: (1S,3S)-Methyl 1-(3-fluoro-2-methylphenyl)-3-((1-methyl-1H-indazol-6-yl)oxy)cyclopentanecarboxylate Procedure as for Step 2 gave the title compound as a pale yellow gum (640 mg).

Step 4: (1S,3R)-1-(3-Fluoro-2-methylphenyl)-N-hydroxy-3-((1-methyl-1H-indazol-6-yl)oxy)cyclopentanecarboxamide Following Method C and D from (1S,3R)-methyl 1-(3-fluoro-2-methylphenyl)-3-phenoxycyclopentanecarboxylate (295 mg, 0.39 mmol) Preparative HPLC gave the title compound as a white solid (34 mg). LCMS (ES+) 384 (M+H)$^+$, RT 3.48 min (Analytical method 1); $^1$H NMR δ (ppm)(DMSO-d$_6$): 9.88 (1 H, s), 8.59 (1 H, s), 7.81 (1 H, d, J=0.8 Hz), 7.52 (1 H, d, J=8.8 Hz), 7.22-7.12 (2 H, m), 7.08-6.94 (2 H, m), 6.67 (1 H, dd, J=8.8, 2.0 Hz), 4.97-4.84 (1 H, m), 3.96-3.82 (3 H, m), 2.66-2.45 (3 H, m), 2.08-1.93 (5 H, m), 1.83-1.73 (1 H, m).

Step 5: (1S,3S)-1-(3-fluoro-2-methylphenyl)-N-hydroxy-3-((1-methyl-1H-indazol-6-yl)oxy)cyclopentanecarboxamide Following Method C and D from (1S,3R)-methyl 1-(3-fluoro-2-methylphenyl)-3-((5-fluoropyridin-3-yl)oxy). Purification by preparative HPLC gave the title compound as a white solid (138 mg, 76%). LCMS (ES+) 384 (M+H)$^+$, RT 3.52 min (Analytical method 1); $^1$H NMR δ (ppm)(DMSO-d$_6$): 9.92 (1 H, s), 8.63 (1 H, s), 7.80 (1 H, d, J=0.8 Hz), 7.48 (1 H, d, J=8.8 Hz), 7.25-7.08 (2 H, m), 7.04-6.90 (2 H, m), 6.55 (1 H, dd, J=8.8, 2.0 Hz), 5.00-4.95 (1 H, m), 3.91 (3 H, s), 3.34-3.25 (1 H, m), 2.36-2.26 (2 H, m), 2.11-1.98 (4 H, m), 1.81-1.72 (2 H, m).

Example 93

(1S,3R)-1-(3-fluoro-2-methylphenyl)-3-((5-fluoropyridin-3-yl)oxy)-N-hydroxycyclopentanecarboxamide Example 94

(1S,3S)-1-(3-fluoro-2-methylphenyl)-3-((5-fluoropyridin-3-yl)oxy)-N-hydroxycyclopentanecarboxamide

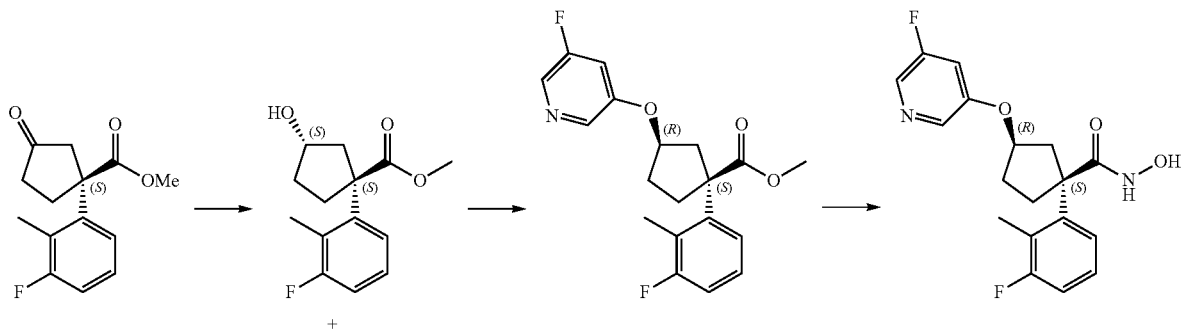

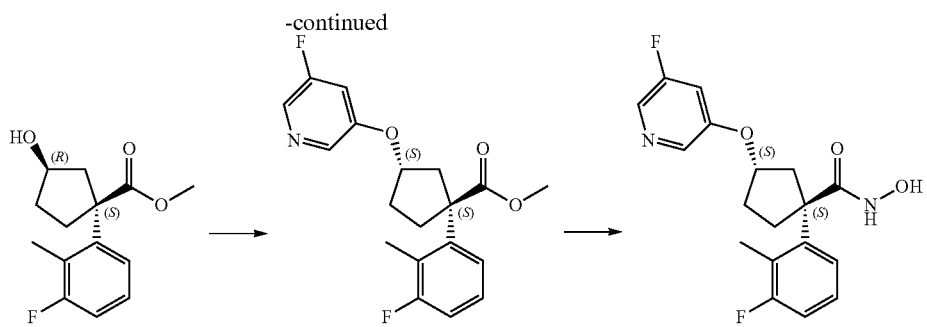

Prepared in a similar manner to Examples 91 and 92 from 3-fluoro-5-hydroxy pyridine (188 mg, 1.67 mmol). Purification by preparative HPLC gave the title compounds. LCMS (ES+) 349 (M+H)+, RT 3.29 min (Analytical method 1); (1S,3R)-1-(3-fluoro-2-methylphenyl)-3-((5-fluoropyridin-3-yl)oxy)-N-hydroxycyclopentanecarboxamide as a white solid (36 mg). $^1$H NMR δ (ppm)(DMSO-$d_6$): 9.97 (1 H, s), 8.67 (1 H, s), 8.18-8.13 (2 H, m), 7.42 (1 H, dt, J=11.2, 2.4 Hz), 7.28-7.13 (2 H, m), 7.13-7.03 (1 H, m), 4.98 (1 H, t, J=5.1 Hz), 2.74-2.66 (1 H, m), 2.60-2.51 (2 H, m), 2.20-2.00 (5 H, m), 1.88-1.79 (1 H, m) and (1S,3S)-1-(3-fluoro-2-methylphenyl)-3-((5-fluoropyridin-3-yl)oxy)-N-hydroxycyclopentanecarboxamide as a white solid (52 mg). LCMS (ES+) 349 (M+H)+, RT 3.38 min (Analytical method 1); $^1$H NMR δ (ppm)(DMSO-$d_6$): 9.97 (1H, s), 8.67 (1H, s), 8.17 (2H, d, J=2.3 Hz), 7.45-7.40 (1H, m), 7.25-7.19 (2H, m), 7.11-7.04 (1H, m), 4.99-4.96 (1H, m), 2.75-2.67 (1H, m), 2.6-2.52 (1H, m, obscured by DMSO), 2.12-2.08 (6H, m), 1.89-1.80 (1H, m).

Example 95

(1S,3R)-1-(3-fluoro-2-methylphenyl)-N-hydroxy-3-phenoxycyclopentanecarboxamide

Example 96

(1S,3S)-1-(3-fluoro-2-methylphenyl)-N-hydroxy-3-phenoxycyclopentanecarboxamide

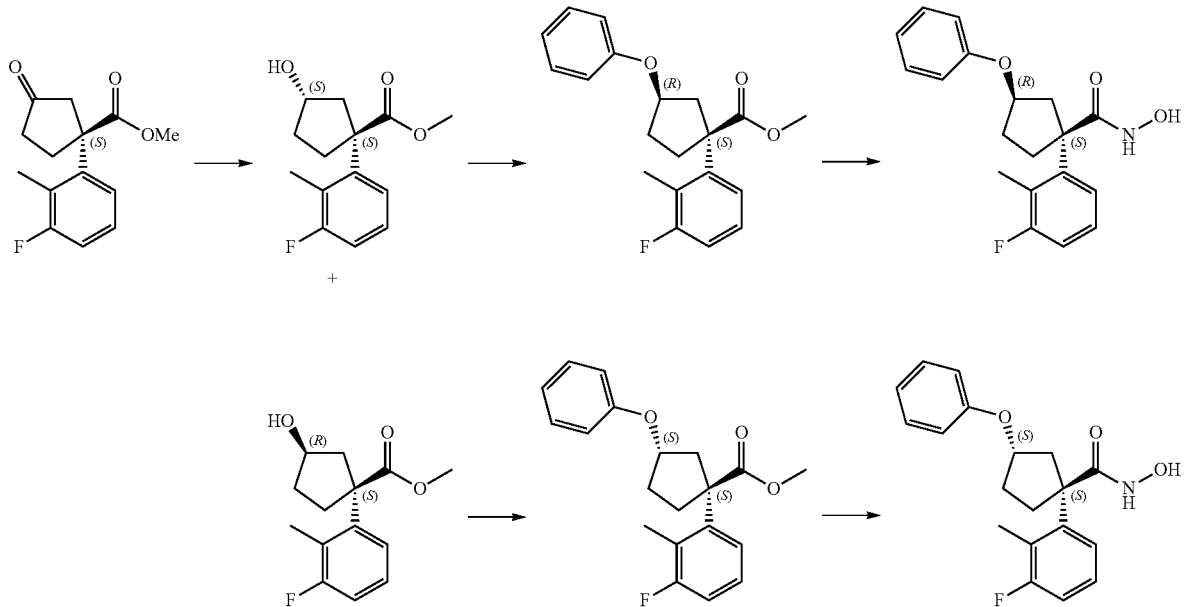

Prepared in a similar manner to Example 91 and 92 from phenol (136 mg, 1.45 mmol). Purification by preparative HPLC gave the title compounds. LCMS (ES+) consistent with target (M+H)+. (1S,3R)-1-(3-fluoro-2-methylphenyl)-N-hydroxy-3-phenoxycyclopentanecarboxamide as a white solid (99 mg). LCMS (ES+) 33 (M+H)+, RT 3.82 min (Analytical method 1); $^1$H NMR δ (ppm)(DMSO-$d_6$): 9.94 (1 H, s), 8.66 (1 H, s), 7.31-7.17 (4 H, m), 7.10-7.02 (1 H, m), 6.91 (3 H, t, J=7.8 Hz), 4.84 (1 H, s), 2.69-2.61 (1 H, m), 2.58-2.51 (2 H, m), 2.15-1.93 (5 H, m), 1.84-1.75 (1 H, m). (1S,3S)-1-(3-fluoro-2-methylphenyl)-N-hydroxy-3-phenoxycyclopentanecarboxamide as a pale yellow glass (170 mg). LCMS (ES+) 330 (M+H)+, RT 3.93 min (Analytical method 1); $^1$H NMR δ (ppm)(DMSO-$d_6$): 9.98 (1 H, s), 8.68 (1 H, s), 7.30-7.15 (4 H, m), 7.5 (1 H, t, J=8.9 Hz), 6.93-6.80 (3 H, m), 4.91 (1 H, tt, J=6.6, 3.4 Hz), 3.28 (1 H, dd, J=14.0, 6.8 Hz), 2.43-2.26 (2 H, m), 2.12-1.99 (4 H, m), 1.85-1.75 (2 H, m).

Example 97

(1S,3S)-1-(3-fluoro-2-methylphenyl)-3-((4-fluorobenzyl)oxy)-N-hydroxycyclopentanecarboxamide

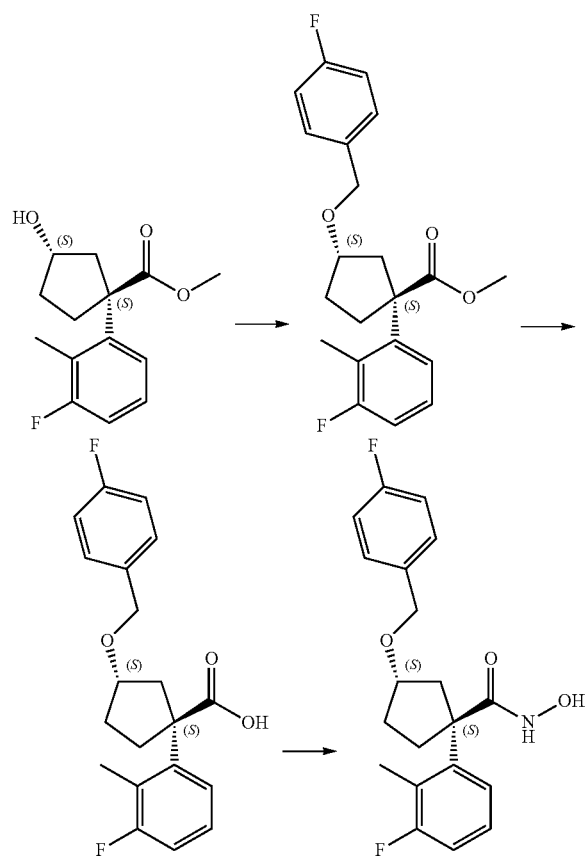

Step 1: (1S,3S)-methyl 1-(3-fluoro-2-methylphenyl)-3-((4-fluorobenzyl)oxy)cyclopentanecarboxylate Sodium hydride (9.5 mg, 0.24 mmol) was added portionwise over 2 min to a solution of (1S,3S)-methyl 1-(3-fluoro-2-methylphenyl)-3-hydroxycyclopentanecarboxylate (50 mg, 0.20 mmol) in DMF (1 mL) at 0° C. The reaction was stirred for 20 min at 0° C. then 4-fluorobenzyl bromide (27 μL, 0.22 mmol) was added and warmed to r.t. for 1 h. The reaction was poured into water (10 mL) and extracted with diethyl ether. Combined organics were washed with brine, dried (MgSO$_4$) and evaporated in vacuo to yield a colorless oil (89 mg). This purified by flash silica chromatography (gradient elution i-hex to 60% EtOAc in i-hex) to yield the title compound as a colorless gum (46 mg, 64%).

Step 2: (1S,3S)-1-(3-fluoro-2-methylphenyl)-3-((4-fluorobenzyl)oxy)cyclopentanecarboxylic acid Following Method C from (1S,3S)-methyl 1-(3-fluoro-2-methylphenyl)-3-((4-fluorobenzyl)oxy)cyclopentanecarboxylate (46 mg, 0.13 mmol) gave the title compound as a white foam (43.1 mg, 97%).

Step 3: (1S,3S)-1-(3-fluoro-2-methylphenyl)-3-((4-fluorobenzyl)oxy)-N-hydroxycyclopentanecarboxamide Following Method D from (1S,3S)-1-(3-fluoro-2-methylphenyl)-3-((4-fluorobenzyl)oxy)cyclopentanecarboxylic acid (43 mg, 0.12 mmol). Purification by preparative HPLC to give the title compound as a white solid (25 mg, 55%). LCMS (ES+) 362 (M+H)+, RT 3.81 min (Analytical method 1); $^1$H NMR δ (ppm)(DMSO-$d_6$): 9.91 (1 H, s), 8.63 (1 H, s), 7.32-7.24 (3 H, m), 7.22-7.08 (3 H, m), 7.04 (1 H, t, J=8.9 Hz), 4.44-4.33 (2 H, m), 4.10 (1 H, p, J=5.3 Hz), 3.04 (1 H, dd, J=13.6, 6.8 Hz), 2.33 (1 H, dt, J=12.5, 6.0 Hz), 2.26-2.08 (4 H, m), 1.92-1.79 (1 H, m), 1.78-1.69 (2 H, m).

Example 98

1-phenyl-N-hydroxycyclohexylcarboxamide

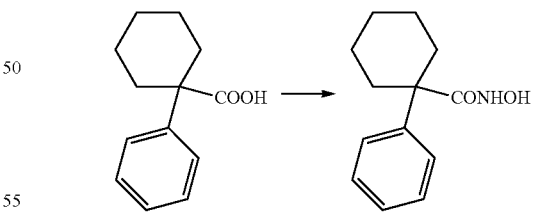

Following Method D(ii) from 1-phenyl-1-cyclohexylcarboxylic acid (0.204 g, 0.1 mmol). Purification by recrystallization from EtOAc gave the title compound as a white solid (180 mg, 82%). LCMS (ES+) 22 (M+H)+, RT 9.47 min (Analytical method 3); $^1$H NMR δ (ppm)(DMSO-$d_6$): 10.4 (1 H, s), 8.62 (1 H, s), 7.38-7.29 (4 H, m), 7.20 (1 H, t, J=7.2 Hz), 2.36 (2 H, d, J=13.4 Hz), 1.67-1.42 (7 H, m), 1.28-1.23 (1 H, m).

Example 99

(1r,4r)-1-(3-fluoro-2-methylphenyl)-4-(5-fluoropyridin-3-yl)-N-hydroxycyclohexanecarboxamide (D1)

Example 1

(1s,4s)-1-(3-fluoro-2-methylphenyl)-4-(5-fluoropyridin-3-yl)-N-hydroxycyclohexanecarboxamide (D2)

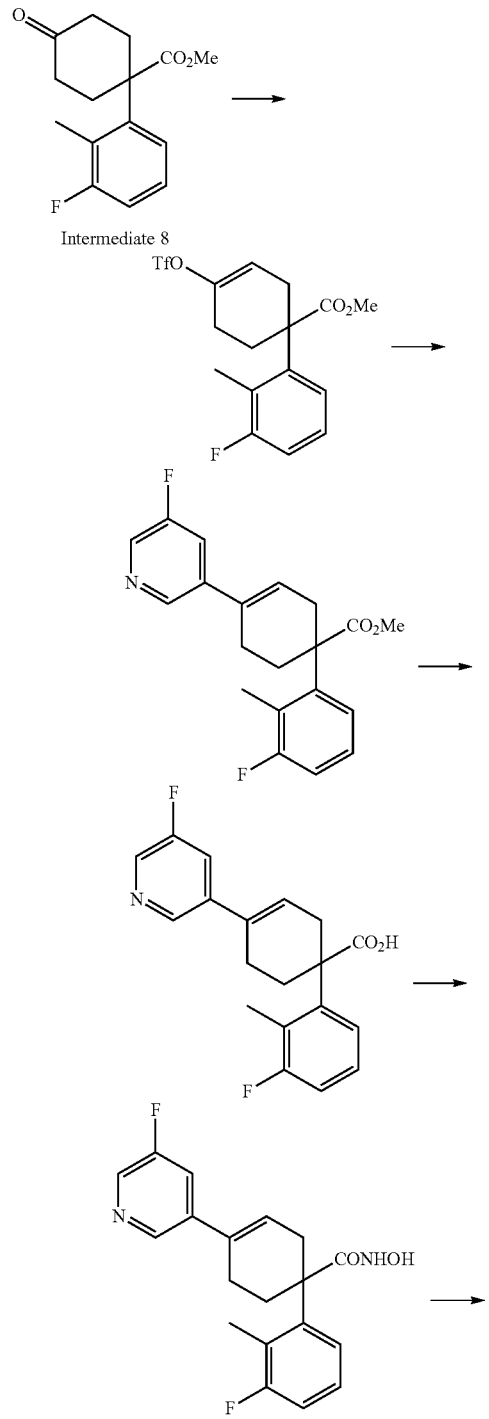

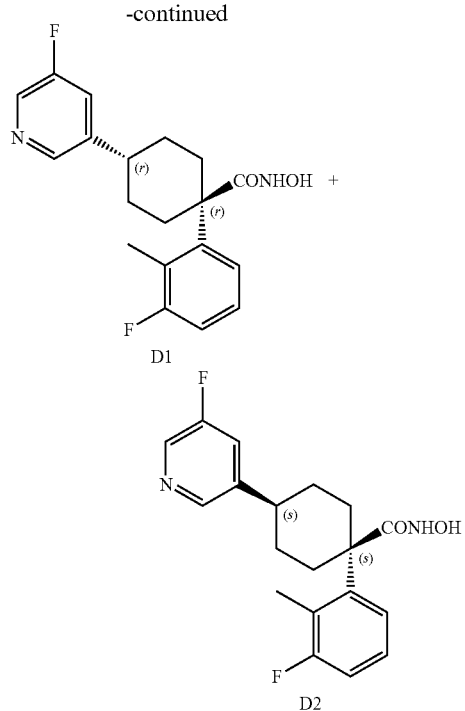

Step 1: methyl 3'-fluoro-2'-methyl-4-(((trifluoromethyl)sulfonyl)oxy)-1,2,3,6-tetrahydro-[1,1'-biphenyl]-1-carboxylate Intermediate 8 (79 mg, 2.99 mmol) and THF (20 mL) were combined under a nitrogen atmosphere and cooled with an ice bath. NaHMDS (1 M in THF, 4.5 mL, 4.5 mmol) was added dropwise followed after 20 minutes by N-(5-chloropyridin-2-yl)-1,1,1-trifluoro-N-((trifluoromethyl)sulfonyl)methanesulfonamide (1.38 g, 3.5 mmol). Reaction mixture was allowed to warm to room temperature and stirred for 3 h. Reaction mixture was then diluted with DCM, washed with water, evaporated to dryness onto silica and purified by flash chromatography to give the title compound as a colorless oil (730 mg, 62%).

Step 2: methyl 3'-fluoro-4-(5-fluoropyridin-3-yl)-2'-methyl-1,2,3,6-tetrahydro-[1,1'-biphenyl]-1-carboxylate Methyl 3'-fluoro-2'-methyl-4-(((trifluoromethyl)sulfonyl)oxy)-1,2,3,6-tetrahydro-[1,1'-biphenyl]-1-carboxylate (326 mg, 0.82 mmol), 5-fluoropyridine-3-boronic acid (116 mg, 0.82 mmol), CsF (12 mg), DME (12 mL), MeOH (2 mL) and palladium tetrakis(triphenylphosphine) (1 mg) were combined in a sealed tube and heated by microwave to 12° C. for 2 h. The reaction mixture was then evaporated to dryness onto silica and purified by flash chromatography to give the title compound as a crystalline solid (234 mg, 83%). MS (ES+) consistent with target (M+H)$^+$.

Step 3: 3'-fluoro-4-(5-fluoropyridin-3-yl)-2'-methyl-1,2,3,6-tetrahydro-[1,1'-biphenyl]-1-carboxylic acid Following Method C from methyl 3'-fluoro-4-(5-fluoropyridin-3-yl)-2'-methyl-1,2,3,6-tetrahydro-[1,1'-biphenyl]-1-carboxylate (23 mg, 0.67 mmol). The reaction mixture was then evaporated in vacuo then partitioned between EtOAc and H₂O/AcOH. Organic layer was dried (MgSO₄) and evaporated in vacuo to give the title compound as a cream solid (181 mg, 82%). MS (ES+) consistent with target (M+H)⁺.

Step 4: 3'-fluoro-4-(5-fluoropyridin-3-yl)-N-hydroxy-2'-methyl-1,2,3,6-tetrahydro-[1,1'-biphenyl]-1-carboxamide 3'-Fluoro-4-(5-fluoropyridin-3-yl)-2'-methyl-1,2,3,6-tetrahydro-[1,1'-biphenyl]-1-carboxylic acid (180 mg, 0.547 mmol), TFFH (188 mg, 0.71 mmol), DMF (3 mL) and Et₃N (0.35 mL, 2.5 mmol) were combined and stirred at room temperature under a nitrogen atmosphere. After 1 h O-(tetrahydro-2H-pyran-2-yl)hydroxylamine (117 mg, 1 mmol) was added and the mixture stirred for 4 days. MeOH (2 mL) and 2 N HCl in diethyl ether (2 mL) were both added and the mixture stirred for 17 h. Volatile solvents were removed in vacuo and the crude material was purified by preparative HPLC to give the title compound as a white solid (92 mg, 49%). LCMS (ES+) consistent with target (M+H)⁺

Step 5: (1r,4r)-1-(3-fluoro-2-methylphenyl)-4-(5-fluoropyridin-3-yl)-N-hydroxycyclohexanecarboxamide and (1s,4s)-1-(3-fluoro-2-methylphenyl)-4-(5-fluoropyridin-3-yl)-N-hydroxycyclohexanecarboxamide 3-Fluoro-4-(5-fluoropyridin-3-yl)-N-hydroxy-2'-methyl-1,2,3,6-tetrahydro-[1,1'-biphenyl]-1-carboxamide (50 mg, 0.145 mmol), EtOH (10 mL) and Pd/C (10% Pd content) (5 mg) were combined and stirred under a hydrogen atmosphere for 21 h. The catalyst was filtered off and solvents removed in vacuo. Purification by preparative HPLC gave (1r,4r)-1-(3-fluoro-2-methylphenyl)-4-(5-fluoropyridin-3-yl)-N-hydroxycyclohexanecarboxamide (D1) as a white solid (12 mg). LCMS (ES+) 347 (M+H)⁺, RT 3.47 min (Analytical method 1); ¹H NMR δ (ppm)(DMSO-d₆): 9.88 (1 H, s), 8.63 (1 H, s), 8.38 (1 H, d, J=2.8 Hz), 8.29 (1 H, t, J=1.6 Hz), 7.46 (1 H, dt, J=2 Hz and 10 Hz), 7.34 (1 H, d, J=8 Hz), 7.26 (1 H, dd, J=8 Hz and 14.4 Hz), 7.08 (1 H, t, J=8.8 Hz), 2.82-2.72 (1 H, m), 2.65-2.50 (1 H, m), 2.45-2.35 (2 H, m), 2.12 (3 H, d, J=3.2 Hz), 2.15-2.05 (1 H, m), 1.85-1.75 (2 H, m), 1.55-1.40 (2 H, m); and (1s,4s)-1-(3-fluoro-2-methylphenyl)-4-(5-fluoropyridin-3-yl)-N-hydroxycyclohexanecarboxamide (D2) as a white solid (28 mg). LCMS (ES+) 347 (M+H)⁺, RT 3.22 min (Analytical method 1); ¹H NMR δ (ppm)(DMSO-d₆): 10.15 (1 H, s), 8.65 (1 H, s), 8.42 (1 H, d, J=2.8 Hz), 8.36 (1 H, t, J=2 Hz), 7.49 (1 H, dt, J=2.4 Hz and 10.4 Hz), 7.30-7.20 (2 H, m), 7.10-7.00 (1 H, m), 2.80-2.70 (1 h, m), 2.60-2.50 (2 H, m), 2.25 (3 H, d, J=3.2 Hz), 2.10-1.90 (2 H, m), 1.85-1.75 (2 H, m), 1.75-1.65 (2 H, m).

Example 101

(1r,4r)-1-(3-fluoro-2-methylphenyl)-N-hydroxy-4-phenoxycyclohexanecarboxamide

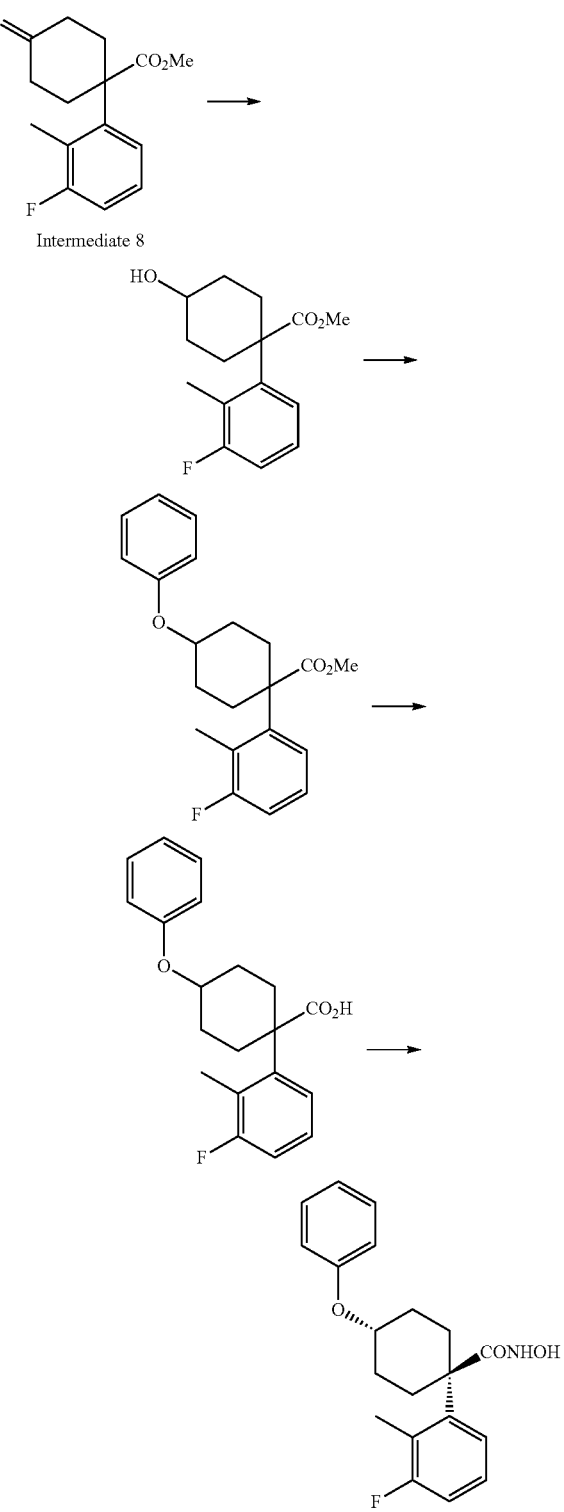

Intermediate 8

Step 1: methyl 1-(3-fluoro-2-methylphenyl)-4-hydroxycyclohexanecarboxylate

Intermediate 8 (8 mg, 3.3 mmol) and MeOH (100 ml) were combined. NaBH$_4$ (152 mg, 4 mmol) was added portionwise—care effervescence. Reaction mixture was stirred for 18 hours. Reaction mixture was evaporated to dryness and partitioned between EtOAc and 1N HCl. Organic layer was dried (MgSO$_4$) and evaporated to dryness to give the title compound as a clear gum (795 mg, 99%). LCMS (ES+) consistent with target (M−OH)$^+$.

Step 2: methyl 1-(3-fluoro-2-methylphenyl)-4-phenoxycyclohexanecarboxylate

Methyl 1-(3-fluoro-2-methylphenyl)-4-hydroxycyclohexanecarboxylate (490 mg, 1.8 mmol), phenol (346 mg, 3.68 mmol), triphenyl phosphine (725 mg, 2.76 mmol) and THF (10 ml) were combined under a nitrogen atmosphere. Reaction mixture was ice bath cooled and DEAD (0.43 ml, 2.76 mmol) was added dropwise. Reaction mixture was stirred for 17 hours as it warmed to room temperature. Reaction mixture was diluted with EtOAc, washed with 10% NaOH soln. (2×), water (1×), dried (MgSO$_4$), evaporated onto silica and purified by flash chromatography to give the title compound as a clear gum (244 mg). Used crude in next step.

Step 3: 1-(3-fluoro-2-methylphenyl)-4-phenoxycyclohexanecarboxylic acid

Methyl 1-(3-fluoro-2-methylphenyl)-4-phenoxycyclohexanecarboxylate (240 mg), MeOH (10 ml) and 15% aq. NaOH soln. (2 ml) were combined in a sealed tube and hot block heated to 65° C. for 9 days. Reaction was cooled and evaporated to dryness. Residue was partitioned between 1N HCl and EtOAc. Organics were dried (MgSO$_4$) and evaporated to dryness to give the title compound as a clear gum (212 mg). LCMS (ES−) consistent with target (M−H)$^−$.

Step 4: (1r,4r)-1-(3-fluoro-2-methylphenyl)-N-hydroxy-4-phenoxycyclohexanecarboxamide 1-(3-Fluoro-2-methylphenyl)-4-phenoxycyclohexanecarboxylic acid (212 mg, 0.65 mmol), TFFH (211 mg, 0.8 mmol), DMF (2 ml) and triethylamine (0.42 ml) were combined and stirred for 3 hours. O-(Tetrahydro-2H-pyran-2-yl)hydroxylamine (117 mg, 1 mmol) was then added and stirring continued for 4 days. Volatile solvents were removed in vacuo. MeOH (3 ml) and 2N HCl in diethyl ether (2 ml) were added and reaction mixture was stirred for 4 hours. Volatile solvents were removed in vacuo and remaining crude material was purified by Prep HPLC to give the title compound as a white solid (59 mg). LCMS (ES+) 344 (M+H)$^+$, RT 3.98 min (Analytical method 1); $^1$H NMR δ (ppm)(DMSO-d$_6$): 10.02 (1 H, s), 8.64 (1 H, s), 7.30-7.20 (4 H, m), 7.12-7.02 (1 H, m), 6.95-6.85 (3 H, m), 4.60-4.50 (1 H, m), 2.20 (3 H, d, J=2.4 Hz), 2.20-1.95 (6 H, m), 1.70-1.60 (2 H, m).

Example 102

(1s,4s)-1-(3-fluoro-2-methylphenyl)-4-((4-fluorobenzyl)oxy)-N-hydroxycyclohexanecarboxamide

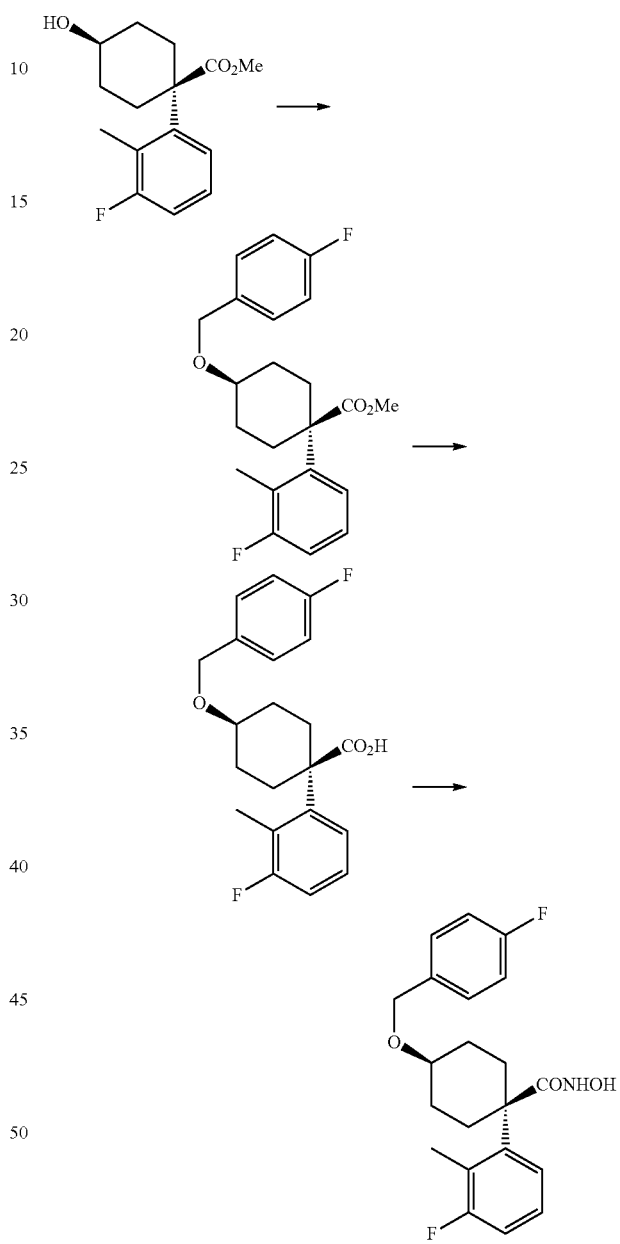

Step 1: (1s,4s)-methyl 1-(3-fluoro-2-methylphenyl)-4-((4-fluorobenzyl)oxy)cyclohexanecarboxylate (1s,4s)-Methyl 1-(3-fluoro-2-methylphenyl)-4-hydroxycyclohexanecarboxylate (793 mg, 2.98 mmol), DMF (15 ml) and 4-fluorobenzyl bromide (0.37 ml, 2.98 mmol) were combined under nitrogen at room temperature. NaH (60% disperse in oil) (120 mg, 3 mmol) was added and the reaction mixture was stirred for 19 hours. Reaction mixture was then diluted with EtOAc, washed with water (4×), dried (MgSO4), evaporated to dryness onto silica and purified by flash chromatography to give the title compound as a white solid (149 mg).

Step 2: (1s,4s)-1-(3-fluoro-2-methylphenyl)-4-((4-fluorobenzyl)oxy)cyclohexanecarboxylic acid (1 s,4s)-Methyl 1-(3-fluoro-2-methylphenyl)-4-((4-fluorobenzyl)oxy)cyclohexanecarboxylate (149 mg, 0.4 mmol), MeOH (15 ml) and 15% Aq. NaOH soln. (2 ml) were combined in a sealed tube and hot block heated to 70° C. for 10 days. Reaction mixture was evaporated to dryness, diluted with EtOAc, washed with 1N HCl and evaporated to dryness once more to give a clear glass (133 mg) which was purified by prep HPLC to give the title compound as a white solid (53 mg). LCMS (ES−) consistent with target (M−H)⁻.

Step 3: (1s,4s)-1-(3-fluoro-2-methylphenyl)-4-((4-fluorobenzyl)oxy)-N-hydroxycyclohexanecarboxamide (1s,4s)-1-(3-fluoro-2-methylphenyl)-4-((4-fluorobenzyl)oxy)cyclohexanecarboxylic acid (53 mg, 0.147 mmol), TFFH (53 mg, 0.2 mmol), DMF (1 ml) and Et₃N (0.2 ml) were combined and stirred at room temperature for 1 h. O-(Tetrahydro-2H-pyran-2-yl)hydroxylamine (117 mg, 1 mmol) was then added and stirring continued for 1 day. Volatile solvents were removed in vacuo. MeOH (5 ml) and 2N HCl in diethyl ether (2 ml) were added and reaction mixture was stirred for 2 hours. Volatile solvents were removed in vacuo and remaining crude material was purified by Prep HPLC to give the title compound as an off white solid (18 mg, 33%). LCMS (ES+) 376 (M+H)⁺, RT 3.97 min (Analytical method 1); ¹H NMR δ (ppm) (DMSO-d₆): 10.08 (1 H, s), 8.62 (1 H, s), 7.40-7.35 (2 H, m), 7.25-7.10 (4 H, m), 7.10-7.00 (1 H, m), 4.48 (2 H, s), 2.45-2.35 (3 H, m), 2.20 (3 H, d, J=2.4 Hz), 1.9-1.55 (6 H, m).

Example 103

(1s,4s)-1-(3-fluoro-2-methylphenyl)-N-hydroxy-4-(1-methyl-1H-indazol-6-yl)cyclohexanecarboxamide Example 104

(1r,4r)-1-(3-fluoro-2-methylphenyl)-N-hydroxy-4-(1-methyl-1H-indazol-6-yl)cyclohexanecarboxamide

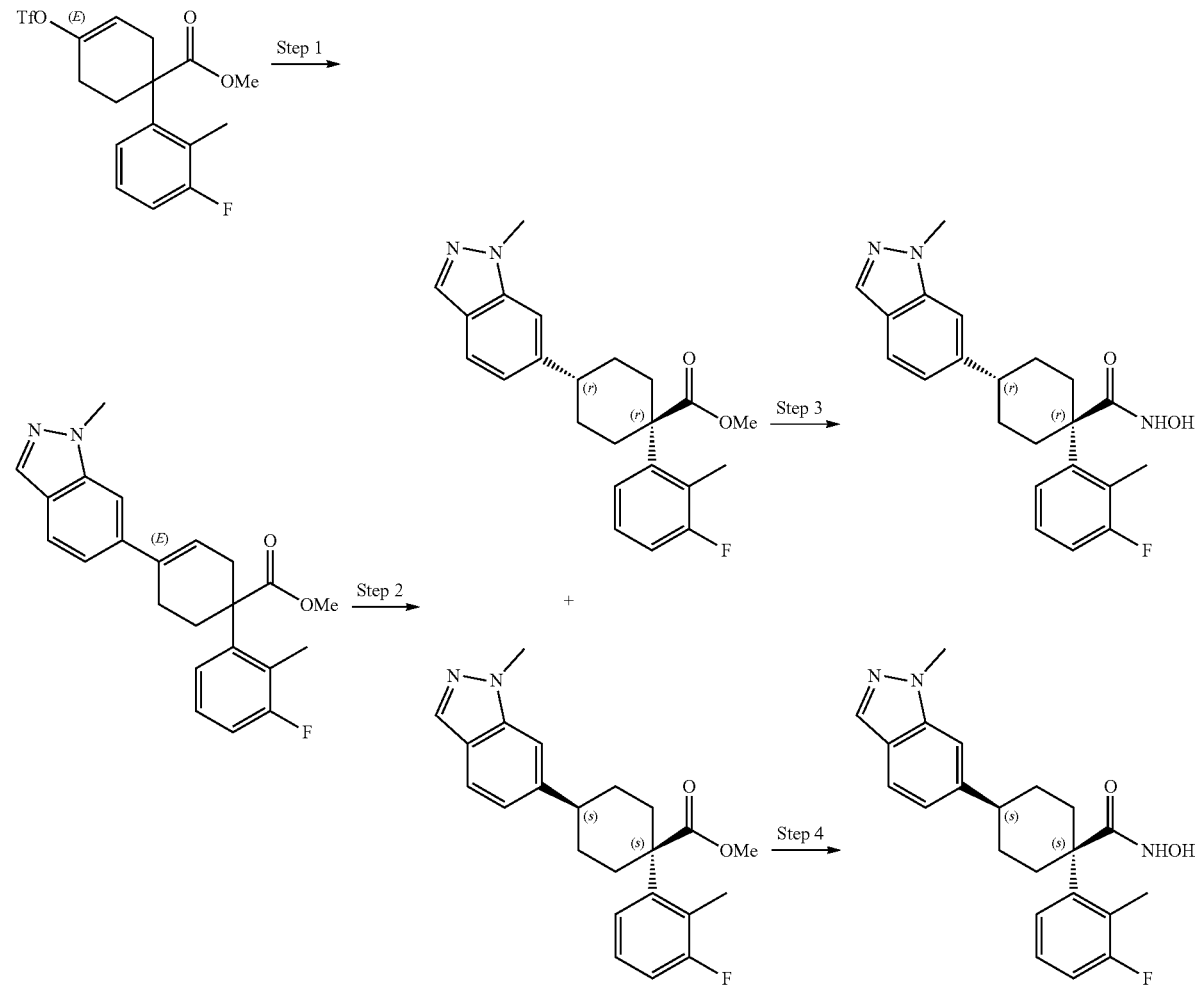

Step 1: methyl 3'-fluoro-2'-methyl-4-(1-methyl-1H-indazol-6-yl)-1,2,3,6-tetrahydro-[1,1'-biphenyl]-1-carboxylate To a solution of methyl 3'-fluoro-2'-methyl-4-(((trifluoromethyl)sulfonyl)oxy)-1,2,3,6-tetrahydro-[1,1'-biphenyl]-1-carboxylate (6 mg, 1.51 mmol) in dry DME (8 mL) in a reaction tube was added 1-methyl-1H-indazol-6-yl boronic acid (27 mg, 1.51 mmol) and $Cs_2CO_3$ (1.48 g, 4.55 mmol). The resulting mixture was degassed with nitrogen bubbling for 5 min. $Pd(dppf)Cl_2.CHCl_3$ (49 mg, 0.61 mmol) was added, the tube sealed and the reaction heated at 85° C. for 24 h. The reaction was evaporated to dryness and partitioned between water (25 mL) and EtOAc (2×25 mL). The organic layers were combined and condensed. The crude product was purified using a Biotage 25 g SNAP column eluting with 0-20% EtOAc in hexane to give the title compound as a colourless oil (500 mg, 88%).

Step 2: (1 s,4s)-methyl 1-(3-fluoro-2-methylphenyl)-4-(1-methyl-1H-indazol-6-yl)cyclohexanecarboxylate and (1 r,4r)-methyl 1-(3-fluoro-2-methylphenyl)-4-(1-methyl-1H-indazol-6-yl)cyclohexanecarboxylate To ammonium formate (8 mg, 13.3 mmol) in a round bottom flask was added methyl 3'-fluoro-2'-methyl-4-(1-methyl-1H-indazol-6-yl)-1,2,3,6-tetrahydro-[1,1'-biphenyl]-1-carboxylate (5 mg, 1.33 mmol) as a solution in MeOH (20 mL). 20% Pd/C (~100 mg) was added under a funnel of nitrogen. The reaction was refluxed overnight. The reaction was cooled, filtered through celite and condensed (420 mg, 84%). LCMS indicated a mixture of 2 diastereomers in an approximately 1:1 ratio. The material was used without further purification.

Step 3: (1r,4r)-1-(3-fluoro-2-methylphenyl)-N-hydroxy-4-(1-methyl-1H-indazol-6-yl)cyclohexanecarboxamide Following Method C (iii) from (1s,4s)-methyl 1-(3-fluoro-2-methylphenyl)-4-(1-methyl-1H-indazol-6-yl)cyclohexanecarboxylate and (1 r,4r)-methyl 1-(3-fluoro-2-methylphenyl)-4-(1-methyl-1H-indazol-6-yl)cyclohexanecarboxylate (420 mg, 1.1 mmol). After 3 d LCMS indicated that one diastereomer had hydrolysed and one remained unchanged. Additional $LiOH.H_2O$ (230 mg, 5.5 mmol) and solvents were added (2 mL THF, 2 mL MeOH, 2 mL water) and heating continued at 80° C. for 2 d. No further reaction was observed by LCMS. The reaction was cooled, condensed and the residue partitioned between water (30 mL) and ether (50 mL) and the water extracted again with EtOAc (50 mL). The combined organic layers were condensed to give unreacted (1 s,4s)-methyl 1-(3-fluoro-2-methylphenyl)-4-(1-methyl-1H-indazol-6-yl)cyclohexanecarboxylate (220 mg). The aqueous layer was acidified to pH4 by dropwise addition of c.HCl, causing a white precipitate to form. The suspension was extracted with EtOAc (3×5 mL). The combined organic layers were filtered through a phase separation cartridge and condensed to give (1r,4r)-1-(3-fluoro-2-methylphenyl)-4-(1-methyl-1H-indazol-6-yl)cyclohexanecarboxylic acid (200 mg). This was subjected to Method D and subsequent purification by preparative HPLC gave the title compound as an off white solid (61 mg). LCMS (ES+) 382 (M+H)+, RT 3.55 min (Analytical method 1); $^1$H NMR δ (ppm)(DMSO-$d_6$): 9.89 (1H, s), 8.63 (1H, d, J=1.5 Hz), 7.93 (1H, s), 7.61 (1H, d, J=8.4 Hz), 7.38 (1H, d, J=7.9 Hz), 7.33-7.27 (2H, m), 7.09 (1H, dd, J=8.9, 8.9 Hz), 6.91 (1H, dd, J=1.1, 8.4 Hz), 3.98 (3H, s), 2.82-2.74 (1H, m), 2.44 (2H, d, J=13.7 Hz), 2.17 (1H, d, J=4.1 Hz), 2.16-2.08 (4H, m), 1.84 (2H, d, J=10.9 Hz), 1.57-1.52 (2H, m).

Step 4: (1s,4s)-1-(3-fluoro-2-methylphenyl)-N-hydroxy-4-(1-methyl-1H-indazol-6-yl)cyclohexanecarboxamide Trimethylaluminium (2 M in heptanes, 1.80 mL, 3.6 mmol) was added cautiously to a stirred suspension of hydroxylamine hydrochloride (0.27 g, 3.95 mmol) in DCM (8 mL) at r.t. under nitrogen. After 1 h a solution of (1 s,4s)-methyl 1-(3-fluoro-2-methylphenyl)-4-(1-methyl-1H-indazol-6-yl)cyclohexanecarboxylate (220 mg, 0.58 mmol) in DCM (4 mL) was added dropwise. The reaction was stirred at r.t. for 30 min after which time LCMS indicated complete conversion to product. The reaction was quenched by the dropwise addition of saturated ammonium chloride solution (1 mL) and water (2.5 mL) and stirred for 30 min. The DCM was removed in vacuo and the resulting slurry diluted with MeOH. The solid was removed by filtration and rinsed with MeOH. The filtrate was concentrated and partitioned between $H_2O$ and EtOAc. The aqueous portion was washed with EtOAc (2×20 mL), and the combined organics dried ($MgSO_4$), filtered and concentrated. Purification by preparative HPLC gave the title compound as a white solid (5 mg). LCMS (ES+) 382 (M+H)+, RT 3.87 min (Analytical method 1); $^1$H NMR δ (ppm)(DMSO-$d_6$): 10.15 (1H, s), 8.67 (1H, s), 7.96 (1H, s), 7.68 (1H, d, J=8.4 Hz), 7.38 (1H, s), 7.33-7.24 (2H, m), 7.06 (2H, dd, J=8.8, 17.9 Hz), 4.02 (3H, s), 2.78-2.67 (1H, m), 2.60-2.50 (1H, m, obscured by DMSO), 2.34-2.29 (1H, m), 2.27 (3H, d, J=2.8 Hz), 2.13-2.06 (2H, m), 1.85-1.72 (4H, m).

Example 105

(±)-2-(3-fluoro-2-methylphenyl)-N-hydroxy-8-oxaspiro[4.5]decane-2-carboxamide

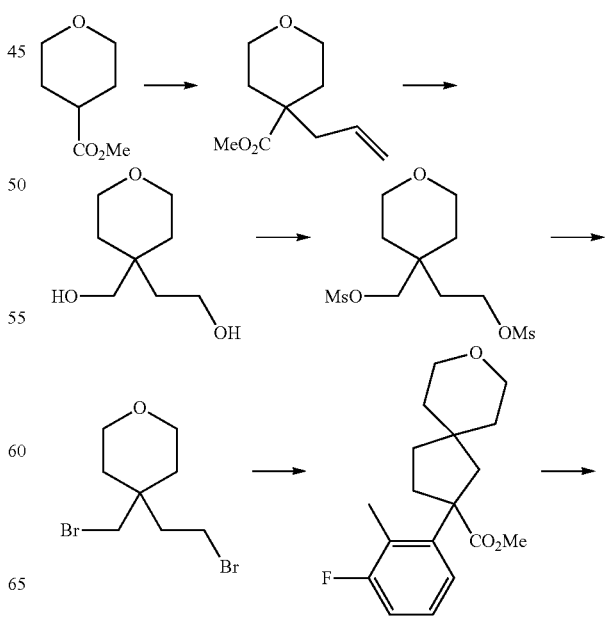

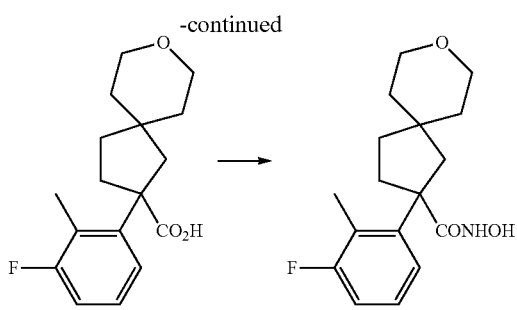

Step 1: methyl 4-allyltetrahydro-2H-pyran-4-carboxylate

A solution of LiHMDS (1 M in hexane, 25 mL, 25 mmol) in dry THF (25 mL) was cooled to −78° C. under $N_2$. A solution of methyl tetrahydro-2H-pyran-4-carboxylate (3.0 g, 20.8 mmol) in dry THF (10 mL) was added dropwise, maintaining the temperature below −7° C. The mixture was stirred at −78° C. for 1 h then a solution of allyl bromide (2.0 mL, 22.9 mmol) in dry THF (2 mL) was added over 15 min. The reaction mixture was stirred at −78° C. for 1.5 h then allowed to warm to r.t. over 16 h. The mixture was then cooled to −78° C. and quenched by the addition of sat. aq. $NH_4Cl$. After warming to r.t. the mixture was diluted with water and extracted with EtOAc. The organic layer was washed with 1 M HCl, sat. aq. $NaHCO_3$ and brine, dried (phase separation cartridge) and concentrated to give the title compound as a pale yellow oil (3.66 g).

Step 2: 2-(4-(hydroxymethyl)tetrahydro-2H-pyran-4-yl)ethanol

A solution of methyl 4-allyltetrahydro-2H-pyran-4-carboxylate (4.0 g, 21.7 mmol) in methanol (1 mL) at −78° C. was sparged with ozone for approximately 3 min whereupon the reaction mixture turned blue. The mixture was purged with oxygen and nitrogen gases before warming to 0° C. and treating with $NaBH_4$ (1.64 g, 43.4 mmol). Once gas evolution ceased the reaction was allowed to warm to r.t. and diluted with water. The mixture was extracted with DCM (3×); the combined extracts were dried (phase separation cartridge) and concentrated to yield a white solid, identified as 2,8-dioxaspiro[4.5]decan-1-one.

This white solid (0.5 g, 3.2 mmol) was dissolved in MeOH (10 mL) and treated with $NaBH_4$ (0.24 g). The reaction was heated to 40° C. for 2 h. TLC analysis indicated incomplete reaction, so further $NaBH_4$ (0.24 g) was added and heating at 04° C. continued for a further 1 h. After cooling to r.t. the reaction was acidified to pH 2 with 1 M HCl and extracted with DCM (3×). The combined extracts were dried (phase separation cartridge) and concentrated to give the title compound (274 mg, 53%).

Step 3: (4-(2-((methylsulfonyl)oxy)ethyl)tetrahydro-2H-pyran-4-yl)methyl methanesulfonate A solution of 2-(4-(hydroxymethyl)tetrahydro-2H-pyran-4-yl)ethanol (274 mg, 1.71 mmol) and $Et_3N$ (0.525 mL, 3.76 mmol) in DCM (10 mL) at 0° C. was treated with methanesulfonyl chloride (0.291 mL, 3.76 mmol), added dropwise. The mixture was stirred at r.t. for 1 h. The mixture was washed with 1 M HCl, dried (phase separation cartridge) and concentrated. The residue was purified by silica column chromatography (gradient elution, 0-100% EtOAc in iso-hexane) to give the title compound as a colorless gum (150 mg).

Step 4: 4-(2-bromoethyl)-4-(bromomethyl)tetrahydro-2H-pyran

A suspension of (4-(2-((methylsulfonyl)oxy)ethyl)tetrahydro-2H-pyran-4-yl)methyl methanesulfonate (484 mg, 1.53 mmol) and LiBr (797 mg, 9.18 mmol) in dry DMF (2 mL) was heated to 105° C. for 1 h. Further LiBr (797 mg) was added and heating resumed for 1.5 h. After cooling to r.t. the mixture was diluted with water and extracted with $Et_2O$ (4×). The combined extracts were washed with brine, dried (phase separation cartridge) and concentrated. The residue was purified by silica column chromatography (gradient elution, 0-50% EtOAc in iso-hexane) to give the title compound as a colorless oil (0.229 g).

Step 5: methyl 2-(3-fluoro-2-methylphenyl)-8-oxaspiro[4.5]decane-2-carboxylate A solution of 4-(2-bromoethyl)-4-(bromomethyl)tetrahydro-2H-pyran (303 mg, 1.06 mmol), methyl 2-(3-fluoro-2-methylphenyl)acetate (193 mg, 1.06 mmol) and NaH (60 wt % in oil, 106 mg, 2.65 mmol) in dry DMF (5 mL) was stirred at r.t. for 2 days. The reaction was quenched with water and extracted with EtOAc (3×). The combined extracts were dried ($Na_2SO_4$) and concentrated. The residue was purified by silica column chromatography (gradient elution, 0-50% EtOAc in iso-hexane) to give the title compound as a colorless oil (0.147 mg).

Steps 6-7: 2-(3-Fluoro-2-methylphenyl)-N-hydroxy-8-oxaspiro[4.5]decane-2-carboxamide Following Methods C and D from methyl 2-(3-fluoro-2-methylphenyl)-8-oxaspiro[4.5]decane-2-carboxylate (139 mg, 0.48 mmol). The title compound was obtained as a white solid (67 mg). LCMS (ES+) 38 (M+H)$^+$, RT 9.33 min (Analytical method 3); $^1$H NMR δ (ppm)(DMSO-d$_6$): 9.90 (1H, s), 8.63 (1H, s), 7.27-7.20 (2H, m), 7.09-7.02 (1H, m), 3.59 (2H, t, J=5.4 Hz), 3.50 (2H, tt, J=17.1, 5.7 Hz), 2.88 (1H, d, J=13.4 Hz), 2.42-2.35 (1H, m), 2.3-2.23 (1H, m), 2.15 (3H, d, J=2.8 Hz), 1.68-1.5 (5H, m), 1.32 (2H, t, J=5.1 Hz).

Example 106

N-hydroxy-1-phenylcycloheptanecarboxamide

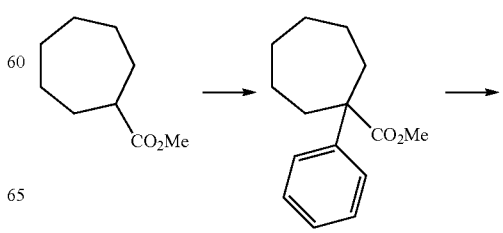

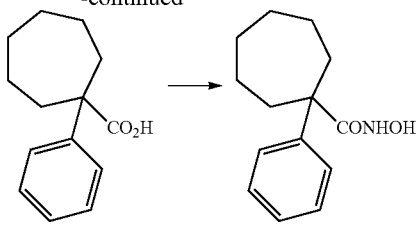

Step 1: methyl 1-phenylcycloheptanecarboxylate n-BuLi (1.6 M in hexane, 2.5 mL, 4.03 mmol) was added to a solution of dicyclohexyl amine (0.73 g, 0.80 mL, 4.03 mmol) in toluene (4 mL) under nitrogen at r.t. and the solution was stirred for 10 min. To this solution at r.t. was added a solution of methyl cycloheptanecarboxylate (0.60 g, 3.85 mmol) in toluene (2 mL) and the combined solution was stirred at r.t. for 5 min. In a second reaction flask Pd(OAc)$_2$ (11 mg, 0.048 mmol), P(tBu)3.HBF4 (28 mg, 0.096 mmol), bromobenzene (0.30 g, 0.20 mL, 1.92 mmol) and toluene (4 mL) were combined and brought rapidly to 100° C. The first reaction solution was added to the catalyst mixture via syringe. The cloudy brown reaction was stirred at 95° C. for 1 h and then allowed to stir at r.t. overnight. The reaction was partitioned between water and DCM (2×). The organic layers were combined, dried over MgSO$_4$ and condensed to give an oil which was purified by gradient column chromatography, eluting with 2-10% EtOAc in i-hex, to give the title compound as a colourless oil (0.60 g) which contained approximately 40 mol % ester starting material.

Step 2: 1-phenylcycloheptanecarboxylic acid

To a solution of methyl 1-phenylcycloheptanecarboxylate (contains some methyl cycloheptanecarboxylate, 0.59 g, 2.54 mmol) in EtOH (4 mL) was added a solution of KOH (1.1 g) in water (1.1 mL) and the resulting mixture refluxed for 3 h. The reaction was cooled, condensed, diluted with water and extracted with ether. The organic layer was dried over MgSO$_4$ and condensed to give the title compound as a colourless gum (0.42 g) containing approximately 40 mol % cycloheptane carboxylic acid; $^1$H NMR δ (ppm)(CDCl$_3$) 10.50 (1 H, br s), 7.39-7.27 (3 H, m), 7.26-7.16 (2 H, m), 2.49-2.35 (2 H, m), 2.12-2.02 (2 H, m), 1.80-1.45 (8H, m).

Step 3: N-hydroxy-1-phenylcycloheptanecarboxamide

Following Method D(ii) from 1-phenylcycloheptanecarboxylic acid (0.42 g, 1.93 mmol) followed by gradient column chromatography, eluting with 0-100% EtOAc in iso-hexane, gave the title compound as a white solid (0.23 g, 53%). LCMS (ES+) 234 (M+H)$^+$; RT 3.49 min (Analytical method 1); $^1$H NMR δ (ppm)(CDCl$_3$) 7.61 (1 H, s), 7.40-7.31 (4 H, m), 7.30-7.26 (2 H, m), 2.41-2.34 (2 H, m), 2.25-2.13 (2 H, m), 1.83-1.75 (2 H, m), 1.67-1.33 (6 H, m).

Example 107

1-(3-Fluoro-2-methylphenyl)-N-hydroxycycloheptanecarboxamide

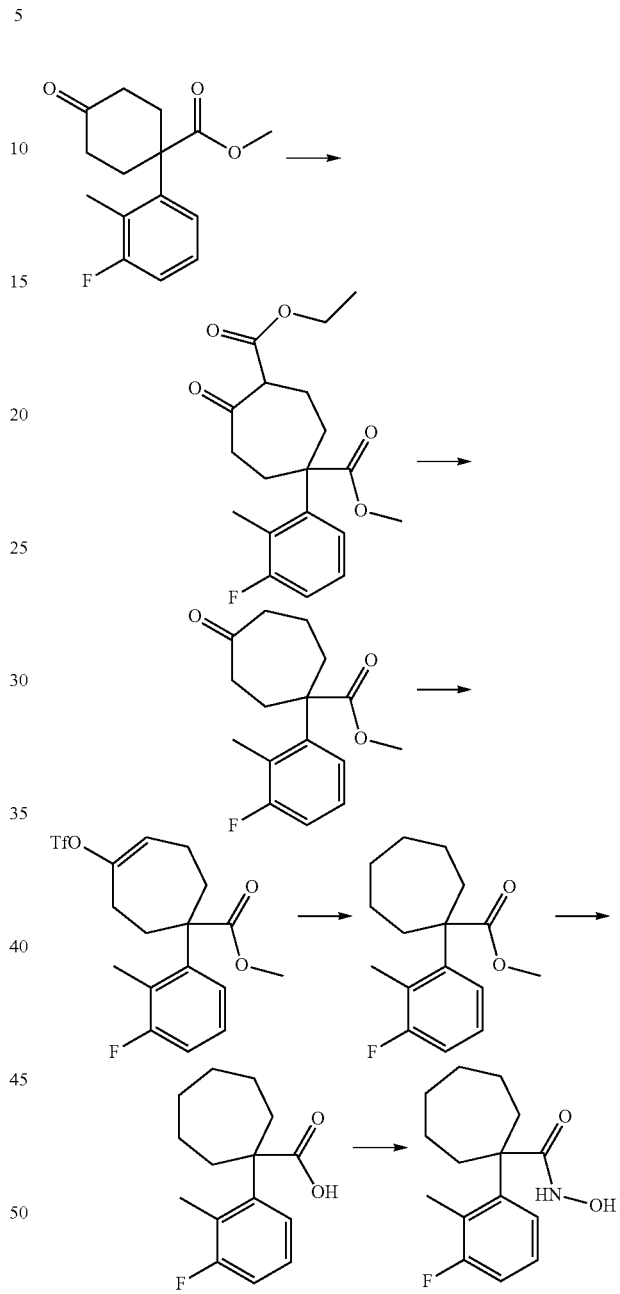

Step 1: 4-Ethyl-1-methyl 1-(3-fluoro-2-methylphenyl)-5-oxocycloheptane-1,4-dicarboxylate To a solution of methyl 1-(3-fluoro-2-methylphenyl)-4-oxocyclohexanecarboxylate (500 mg, 1.9 mmol) in DCM (20 mL) at 0° C. was added boron trifluoride diethyletherate (330 mg, 2.3 mmol) followed by drop wise addition of ethyldiazoacetate (260 mg, 2.3 mmol). The reaction mixture was stirred at 0° C. for 3 h. Reaction mixture quenched with saturated NaHCO$_3$ solution layers separated organics collected solvent removed. The crude product was purified by flash column chromatography to give the title compound as a clear oil (350 mg, 54%). $^1$H NMR δ (ppm)(CDCl3): 12.75 (1 H, s), 7.22-7.09 (2 H, m), 6.96 (1H, t, J=7.8 Hz), 4.26-4.10 (2 H, m), 3.69 (3 H, s), 2.77-2.68 (1 H, m), 2.65-2.55 (2 H, m), 2.54-2.40 (1 H, m), 2.35-2.23 (2 H, m), 2.22-2.18 (2 H, m), 2.14 (3 H, d, J=2.6 Hz), 1.35 (3 H, t, J=12.6 Hz).

Step 2: Methyl 1-(3-fluoro-2-methylphenyl)-4-oxo-cycloheptanecarboxylate

To a solution of 4-ethyl-1-methyl 1-(3-fluoro-2-methylphenyl)-5-oxocycloheptane-1,4-dicarboxylate (345 mg, 0.98 mmol) in methanol (10 mL) was added 15% aq. NaOH solution (3 mL). The reaction mixture was heated to 80° C. for 24 h. Reaction mixture was cooled to r.t. acidified with HCl (5 M sol) and extracted with DCM (3×40 mL). The solvent was removed in vacuo. The crude product was purified by flash column chromatography to give the title compound as a clear oil (250 mg, 94%).

Step 3: Methyl 4-(((1,1-difluoroethyl)sulfonyl)oxy)-1-(3-fluoro-2-methylphenyl)cyclohept-4-enecarboxylate Methyl 1-(3-fluoro-2-methylphenyl)-4-oxocycloheptanecarboxylate (250 mg, 0.95 mmol) and THF (30 mL) were combined under a nitrogen atmosphere and cooled with an ice bath. NaHMDS (1 M in THF) (1.2 mL, 1.2 mmol) was added dropwise followed after 20 min by N-(5-chloropyridin-2-yl)-1,1,1-trifluoro-N-((trifluoromethyl)sulfonyl)methanesulfonamide (500 mg, 1.27 mmol). Reaction mixture was allowed to warm to room temperature and stirred for 3 h, then diluted with DCM, washed with water, evaporated to dryness onto silica and purified by flash chromatography to give the title compound as a clear oil (280 mg, 69%). $^1$H NMR δ (ppm)(CDCl$_3$): 7.17-7.12 (1 H, m), 7.02-6.90 (2 H, m), 5.92 (1H, d, J=6.4 Hz), 3.69 (3 H, s), 2.49-2.15 (12 H, m).

Step 4: Methyl-1-(3-fluoro-2-methylphenyl)cycloheptanecarboxylic acid

To a solution of methyl 4-(((1,1-difluoroethyl)sulfonyl)oxy)-1-(3-fluoro-2-methylphenyl)cyclohept-4-enecarboxylate (280 mg, 0.66 mmol) in ethanol (2 mL) was added ammonium formate (125 mg, 2.0 mmol), and palladium on charcoal (10%, 10 mg). The reaction mixture was heated to 65° C. for 2 h. Reaction mixture was cooled to r.t. and filtered through celite, washing with EtOH (3×10 mL). The solvent was removed in vacuo and the resulting solid was partitioned between water and DCM (3×20 mL). The combined organics were dried (MgSO$_4$), filtered (phase separation cartridge) and the solvent removed to yield the title compound as a pale yellow oil (0.150 g, 86.2%). $^1$H NMR δ (ppm)(CDCl$_3$): 7.12-7.02 (1 H, m), 7.00-6.99 (1 H, m), 6.90-6.81 (1 H, m), 3.69 (3 H, s), 2.47-2.35 (1 H, m), 2.34 (3 H, d, J=2.6 Hz), 2.28-2.20 (1 H, m), 2.12-1.90 (6 H, m), 1.84-1.67 (4 H, m).

Step 5: 1-(3-Fluoro-2-methylphenyl)cycloheptanecarboxylic acid

Following Method C from methyl-1-(3-fluoro-2-methylphenyl)cycloheptanecarboxylic acid (150 mg, 0.56 mmol) to give the title compound as a white solid (115 mg, 81%) used crude in next step. LCMS (ES+) consistent with target (M+H)$^+$.

Step 5: 1-(3-Fluoro-2-methylphenyl)-N-hydroxycycloheptanecarboxamide

To a solution of 1-(3-fluoro-2-methylphenyl)cycloheptanecarboxylic acid (115 mg, 0.46 mmol) in DCM (20 mL) was added oxalyl chloride (0.127 g, 1.0 mmol), and DMF (1 drop). Reaction mixture was stirred for 1 h solvent was removed in vacuo and the resulting solid was dissolved in THF (5 mL) and added drop wise to a vigorously stirred solution of hydroxylamine (50% in water). Stirred for 1 h partitioned between water and DCM (3×20 mL). The combined organics were dried (MgSO$_4$), filtered (phase separation cartridge) and concentrated. Purification by preparative HPLC gave the title compound as a yellow oil (8 mg, 66%). LCMS (ES+) 266 (M+H)$^+$, RT 3.73 min (Analytical method 1); $^1$H NMR δ (ppm)(DMSO-d$_6$): 10.21 (1H, s), 8.56 (1H, s), 7.18-7.11 (1H, m), 7.4-6.97 (2H, m), 2.29 (3H, d, J=3.0 Hz), 2.06-2.02 (2H, m), 1.89-1.80 (4H, m), 1.70-1.51 (6H, m).

Example 108

Analysis of Inhibition of HDAC4 with Class IIa Histone Deacetylase (HDAC) Inhibitors The potency of Class IIa Histone Deacetylase (HDAC) inhibitors is quantified by measuring the Histone Deacetylase 4 (HDAC4) catalytic domain enzymatic activity using the fluorogenic substrate, Boc-Lys(Tfa)-AMC. The substrate is deacetylated to Boc-Lys-AMC by HDAC4. Cleavage by trypsin results in the release of the fluorophore AMC from the deacetylated substrate. The fluorescence of the sample is directly related to the histone deacetylase activity in the sample.

Serially dilute HDAC inhibitor compounds. Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% dimethyl sulfoxide (DMSO). Stocks of 6 µl aliquots of the 10 mM compound in DMSO are prepared and stored at −2° C. From one stock aliquot of each compound to be tested and the reference compound, a 16-point serial dilution is prepared according to Table 1 using a 125 µl 16-channel Matrix multi-channel pipette (Matrix Technologies Ltd).

TABLE 1

Serial Dilution of Compounds

| Diluted Solutions | Well | Concentration (µM) | Dilution ratio | Volumes |
|---|---|---|---|---|
| Concentration 1 | A | 10000 | — | 60 µl 10 mM Test compound/ reference control |
| Concentration 2 | B | 5000 | 1:2 | 30 µl A + 30 µl DMSO |
| Concentration 3 | C | 2500 | 1:2 | 30 µl B + 30 µl DMSO |
| Concentration 4 | D | 1000 | 1:2.5 | 30 µl C + 45 µl DMSO |
| Concentration 5 | E | 500 | 1:2 | 30 µl D + 30 µl DMSO |

TABLE 1-continued

Serial Dilution of Compounds

| Diluted Solutions | Well | Concentration (μM) | Dilution ratio | Volumes |
|---|---|---|---|---|
| Concentration 6 | F | 250 | 1:2 | 30 μl E + 30 μl DMSO |
| Concentration 7 | G | 125 | 1:2 | 30 μl F + 30 μl DMSO |
| Concentration 8 | H | 62.5 | 1:2 | 30 μl G + 30 μl DMSO |
| Concentration 9 | I | 31.25 | 1:2 | 30 μl H + 30 μl DMSO |
| Concentration 10 | J | 15.63 | 1:2 | 30 μl I + 30 μl DMSO |
| Concentration 11 | K | 7.81 | 1:2 | 30 μl J + 30 μl DMSO |
| Concentration 12 | L | 3.91 | 1:2 | 30 μl K + 30 μl DMSO |
| Concentration 13 | M | 1.95 | 1:2 | 30 μl L + 30 μl DMSO |
| Concentration 14 | N | 0.98 | 1:2 | 30 μl M + 30 μl DMSO |
| Concentration 15 | O | 0.49 | 1:2 | 30 μl N + 30 μl DMSO |
| Concentration 16 | P | 0.24 | 1:2 | 30 μl O + 30 μl DMSO |

2 μl (200×) of each diluted solution and each control (full activity: 100% DMSO alone or full inhibition 1 mM) is stamped into V-bottomed polypropylene 384-well compound plates using either the Bravo (384-well head from Agilent) or 12.5 μl 16-channel Matrix multi-channel pipette (Matrix Technologies Ltd). Each well with the 200× compound solution is diluted 1:20 by the addition of 38 μl assay buffer+DMSO (10.5% DMSO, 45 mM Tris-HCl, 123 mM NaCl, 2.4 mM KCl, and 0.9 mM $MgCl_2$ at pH 8.0 and equilibrated to r.t.).

Prepare HDAC4 catalytic domain enzyme (0.2 μg/mL). The HDAC4 catalytic domain enzyme is human catalytic domain HDAC4 protein (amino acids 648-1032) with a C-terminal 6× histidine tag, produced by BioFocus. A working solution of enzyme is prepared from a 500 μg/mL stock aliquot of HDAC4 catalytic domain (thawed on ice) diluted to 0.2 μg/mL with assay buffer (50 mM Tris-HCl, 137 mM NaCl, 2.7 mM KCl, and 1 mM $MgCl_2$ at pH 8 and equilibrated to r.t.) just prior to the addition of the enzyme to the assay.

Prepare 5× (5 μM) Boc-Lys(Tfa)-AMC Substrate. 5× (50 μM) substrate is prepared just prior to the addition to the assay. A 1 mM substrate stock is made by diluting a 100 mM Boc-Lys(Tfa)-AMC in DMSO solution 1:100 by adding it drop-wise to assay buffer (equilibrated to r.t.) while vortexing at slow speed to prevent precipitation. The 5× substrate is prepared by diluting the 1 mM substrate solution 1:20 by adding it drop-wise to assay buffer (equilibrated to r.t.) while vortexing at slow speed to prevent precipitation.

Prepare 3× (30 μM) Developer/Stop Solution. 3× (30 μM) Developer/Stop Solution is prepared just prior to addition to the plate by diluting a stock solution of 1 mM reference compound 1:333 in 25 mg/mL trypsin (PAA Laboratories Ltd.) equilibrated to r.t.

Assay. 5 μl of each solution of 1:20 diluted compound from above is transferred to a clear bottomed, black, 384-well assay plate using the Bravo or the Janus (384-well MDT head from Perkin Elmer). Using a 16-channel Matrix multi-channel pipette, 35 μl of the working solution of HDAC4 catalytic domain enzyme (0.2 μg/mL in assay buffer) is transferred to the assay plate. The assay is then started by adding 10 μl of 5× (50 μM) substrate to the assay plates using either the Bravo, Janus or 16-channel Matrix multi-channel pipette. The assay plate is then shaken for two minutes on an orbital shaker at 900 rpm (rotations per minute). Next the plate is incubated for 15 minutes at 37° C. The reaction is stopped by adding 25 μl of 3× (3 μM) developer/stop solution to the assay plates using either the Bravo, Janus or a 16-channel Matrix multi-channel pipette. Assay plates are then shaken for 5 minutes on an orbital shaker at 1200 rpm. Next, the assay plates are incubated at 37° C. for 1 hour in a tissue culture incubator. Finally, the fluorescence is measured (Excitation: 355 nm, Emission: 460 nm) using PerkinElmer EnVision in top read mode.

Example 109

Analysis of Inhibition of HDAC5 with Class IIa Histone Deacetylase (HDAC) Inhibitors The potency of Class IIa Histone Deacetylase (HDAC) inhibitors is quantified by measuring the Histone Deacetylase 5 (HDAC5) enzymatic activity using the fluorogenic substrate, Boc-Lys(Tfa)-AMC. The substrate is deacetylated to Boc-Lys-AMC by HDAC5. Cleavage by trypsin results in the release of the fluorophore AMC from the deacetylated substrate. The fluorescence of the sample is directly related to the histone deacetylase activity in the sample.

Serially dilute HDAC inhibitor compounds. Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 6 μl aliquots of the 10 mM compound in DMSO are prepared and stored at −2° C. From one stock aliquot of each compound to be tested and the reference compound, a 16-point serial dilution is prepared according to Table 1 using a 125 μl 16-channel Matrix multi-channel pipette.

2 μl (200×) of each diluted solution and each control (full activity: 100% DMSO alone or full inhibition 1 mM) is stamped into V-bottom polypropylene 384-well compound plates using either Bravo, Janus, or a 12.5 μl 16-channel Matrix multi-channel pipette. Each well with the 2 μl of the 200×stamped compound solution is diluted 1:2 by the addition of 38 μl assay buffer+DMSO (10.5% DMSO, 45 mM Tris-HCl, 123 mM NaCl, 2.4 mM KCl, and 0.9 mM $MgCl_2$ at pH 8.0 and equilibrated to 37° C.).

Prepare HDAC5 catalytic domain enzyme (0.57 μg/mL). The HDAC5 catalytic domain enzyme is human HDAC5 catalytic domain (GenBank Accession No. NM_001015053), amino acids 657-1123 with a C-terminal His tag and can be obtained from BPS BioScience. The protein is 51 kDa and is expressed in a baculovirus expression system. A working solution of enzyme is prepared from a 1.65 mg/mL stock aliquot of HDAC5 catalytic domain (thawed on ice) diluted to 0.57 μg/mL with assay buffer (50 mM Tris-HCl, 137 mM NaCl, 2.7 mM KCl, and 1 mM $MgCl_2$ at pH 8 and equilibrated to 37° C.) just prior to the addition of the enzyme to the assay.

Prepare 5× (40 μM) Boc-Lys(Tfa)-AMC Substrate. 5× (4 μM) substrate is prepared just prior to the addition to the assay. The 5× substrate is prepared by diluting the 100 mM Boc-Lys(Tfa)-AMC in DMSO solution 1:2500 by adding it drop-wise to assay buffer (equilibrated to 37° C.) while vortexing at slow speed to prevent precipitation.

Prepare 3× (30 μM) Developer/Stop Solution. 3× (30 μM) Developer/Stop Solution is prepared just prior to addition to the plate by diluting a stock solution of 10 mM reference compound 1:333 in 25 mg/mL trypsin equilibrated to 37° C.

Assay. 5 µl of each solution of the 1:20 diluted inhibitor compounds and controls from above is transferred to a clear bottomed, black, 384-well assay plate using the Bravo or Janus. Using a 16-channel Matrix multi-channel pipette, 35 µl of the working solution of the HDAC5 catalytic domain enzyme (0.57 µg/mL in assay buffer) is transferred to the assay plate. The assay is then started by adding 10 µl of 5× (40 µM) substrate to the assay plates using either the Bravo, Janus or 16-channel Matrix multi-channel pipette. The assay plate is then shaken for one minute on an orbital shaker at 900 rpm. Next, the plates are incubated for 15 minutes at 37° C. The reaction is stopped by adding 25 µl of 3×(30 µM) developer/stop solution to the assay plates using either the Bravo, Janus or a 16-channel Matrix multi-channel pipette. Assay plates are then shaken for 2 minutes on an orbital shaker at 900 rpm. Next, the assay plates are incubated at 37° C. for 1 hour in a tissue culture incubator followed by shaking for 1 minute at the maximum rpm on an orbital shaker before reading on the EnVision. Finally, the fluorescence is measured (Excitation: 355 nm, Emission: 460 nm) using PerkinElmer EnVision in top read mode.

Example 110

Analysis of Inhibition of HDAC7 with Class IIa Histone Deacetylase (HDAC) Inhibitors The potency of Class IIa Histone Deacetylase (HDAC) inhibitors is quantified by measuring the Histone Deacetylase 7 (HDAC7) enzymatic activity using the fluorogenic substrate, Boc-Lys(Tfa)-AMC. The substrate is deacetylated to Boc-Lys-AMC by HDAC7. Cleavage by trypsin results in the release of the fluorophore AMC from the deacetylated substrate. The fluorescence of the sample is directly related to the histone deacetylase activity in the sample.

Serially dilute HDAC inhibitor compounds. Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 60 µl aliquots of the 10 mM compound in DMSO are prepared and stored at −20° C. From one stock aliquot of each compound to be tested and the reference compound, a 16-point serial dilution is prepared according to Table 1 using a 125 µl 16-channel Matrix multi-channel pipette.

2 µl (200×) of each diluted solution and each control (full activity: 100% DMSO alone or full inhibition 1 mM) is stamped into V-bottom polypropylene 384-well compound plates using either the Bravo, Janus, or a 12.5 µl 16-channel Matrix multi-channel pipette. Each well with the 2× compound solution is diluted 1:20 by the addition of 38 µl assay buffer+DMSO (10.5% DMSO, 45 mM Tris-HCl, 123 mM NaCl, 2.4 mM KCl, and 0.9 mM MgCl$_2$ at pH 8.0 and equilibrated to 37° C.).

Prepare HDAC7 enzyme (71 ng/mL). The HDAC7 enzyme is human HDAC7 (GenBank Accession No. AY302468) amino acids 518-end with a N-terminal Glutathione S-transferase (GST) tag and can be obtained from BPS BioScience. The protein is 78 kDa and is expressed in a baculovirus expression system. A working solution of enzyme is prepared from a 0.5 mg/mL stock aliquot of HDAC7 (thawed on ice) diluted to 71 ng/mL with assay buffer (50 mM Tris-HCl, 137 mM NaCl, 2.7 mM KCl, and 1 mM MgCl$_2$ at pH 8 and equilibrated to 37° C.) just prior to the addition of enzyme to the assay.

Prepare 5× (50 µM) Boc-Lys(Tfa)-AMC substrate. 5× (50 µM) substrate is prepared just prior to the addition to the assay. The 5× substrate is prepared by diluting a 100 mM Boc-Lys(Tfa)-AMC in DMSO solution 1:2000 by adding it drop-wise to assay buffer (equilibrated to 37° C.) while vortexing at slow speed to prevent precipitation.

Prepare 3× (30 µM) Developer/Stop Solution. 3× (30 µM) Developer/Stop Solution is prepared just prior to addition to the plate by diluting a stock solution of 10 mM reference compound 1:333 in 25 mg/mL trypsin equilibrated to 37° C.

Assay. 5 µl of each solution of 1:20 diluted compound from above is transferred to a clear bottomed, black, 384-well assay plate using the Bravo or Janus. Using a 16-channel Matrix multi-channel pipette, 35 µl of the working solution of the HDAC7 enzyme (71 ng/mL in assay buffer) is transferred to the assay plate. The assay is then started by adding 10 µl of 5× (50 µM) substrate to the assay plate using either the Bravo, Janus or 16-channel Matrix multi-channel pipette. The assay plate is then shaken for one minute on an orbital shaker at 900 rpm. Next, the plate is incubated for 15 minutes at 37° C. The reaction is then stopped by adding 25 µl of 3× (30 µM) developer/stop solution to the assay plates using either the Bravo, Janus or a 16-channel Matrix multi-channel pipette. The assay plate is then shaken for 2 minutes on an orbital shaker at 900 rpm. Next, the assay plate is incubated at 37° C. for 1 hour in a tissue culture incubator followed by shaking for 1 minute at maximum rpm on an orbital shaker. Finally, the fluorescence is measured (Excitation: 355 nm, Emission: 460 nm) using PerkinElmer EnVision in top read mode.

Example 111

Analysis of Inhibition of HDAC9 with Class IIa Histone Deacetylase (HDAC) Inhibitors The potency of Class IIa Histone Deacetylase (HDAC) inhibitors is quantified by measuring the Histone Deacetylase 9 (HDAC9) enzymatic activity using the fluorogenic substrate, Boc-Lys(Tfa)-AMC. The substrate is deacetylated to Boc-Lys-AMC by HDAC9. Cleavage by trypsin results in the release of the fluorophore AMC from the deacetylated substrate. The fluorescence of the sample is directly related to the histone deacetylase activity in the sample.

Serially dilute HDAC inhibitor compounds. Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 1% DMSO. Stocks of 60 µl aliquots of the 10 mM compound in DMSO are prepared and stored at −20° C. From one stock aliquot of each compound to be tested and the reference compound, a 16-point serial dilution is prepared according to Table 1 using a 125 µl 16-channel Matrix multi-channel pipette.

2 µl (200×) of each diluted solution and each control (full activity: 100% DMSO alone or full inhibition 1 mM) is stamped into V-bottom polypropylene 384-well compound plates using either the Bravo, Janus, or 12.5 µl 16-channel Matrix multi-channel pipette. Each well with the stamped 200×compound solution is diluted 1:20 by the addition of 38

µl assay buffer+DMSO (10.5% DMSO, 45 mM Tris-HCl, 123 mM NaCl, 2.4 mM KCl, and 0.9 mM $MgCl_2$ at pH 8.0 and equilibrated to 37° C.).

Prepare HDAC9 enzyme (0.57 µg/mL). The HDAC9 enzyme is human HDAC9 (GenBank Accession No. NM_178423) amino acids 604-1066 with a C-terminal His tag and can be obtained from BPS BioScience. The protein is 50.7 kDa and is expressed in a baculovirus expression system. A working solution of enzyme is prepared from a 0.5 mg/mL stock aliquot of HDAC9 (thawed on ice) diluted to 0.57 µg/mL with assay buffer (50 mM Tris-HCl, 137 mM NaCl, 2.7 mM KCl, and 1 mM $MgCl_2$ at pH 8 and equilibrated to 37° C.) just prior to the addition of enzyme to the assay.

Prepare 5× (125 µM) Boc-Lys(Tfa)-AMC substrate. 5× (125 µM) substrate is prepared just prior to the addition to the assay. The 5× substrate is prepared by diluting a 100 mM Boc-Lys(Tfa)-AMC in DMSO solution 1:800 by adding it drop-wise to assay buffer (equilibrated to 37° C.) while vortexing at slow speed to prevent precipitation.

Prepare 3× (30 µM) Developer/Stop Solution. 3× (30 µM) Developer/Stop Solution is prepared just prior to addition to the plate by diluting a stock solution of 10 mM reference compound 1:333 in 25 mg/mL trypsin equilibrated to 37° C.

Assay. 5 µl of each solution of 1:20 diluted compound from above is transferred to a clear bottomed, black, 384-well assay plate using the Bravo or Janus. Using a 16-channel Matrix multi-channel pipette, 35 µl of the working solution of the HDAC9 enzyme (0.57 µg/mL in assay buffer) is transferred to the assay plate. The assay is then started by adding 10 µl of 5× (125 µM) substrate to the assay plate using either the Bravo, Janus or 16-channel Matrix multi-channel pipette. The assay plate is then shaken for one minute on an orbital shaker at 900 rpm. Next, the plate is incubated for 15 minutes at 37° C. The reaction is stopped by adding 25 µl of 3× developer/stop solution to the assay plates using either the Bravo, Janus or a 16-channel Matrix multi-channel pipette. The assay plate is then shaken for 2 minutes on an orbital shaker at 900 rpm. Next, the assay plate is incubated at 37° C. for 1 hour in a tissue culture incubator followed by shaking for 1 minute at maximum rpm on an orbital shaker before reading on the enVision. Finally, the fluorescence is measured (Excitation: 355 nm, Emission: 460 nm) using PerkinElmer EnVision in top read mode.

Example 112

Analysis of Inhibition of Cellular HDAC Activity with Class IIa Histone Deacetylase (HDAC) Inhibitors The potency of Class IIa Histone Deacetylase (HDAC) inhibitors is quantified by measuring the cellular histone deacetylase enzymatic activity using the fluorogenic substrate, Boc-Lys(Tfa)-AMC. After penetration in Jurkat E6-1 cells, the substrate is deacetylated to Boc-Lys-AMC. After cell lysis and cleavage by trypsin, the fluorophore AMC is released from the deacetylated substrate only. The fluorescence of the sample is directly related to the histone deacetylase activity in the sample.

Jurkat E6.1 cell culture and plating. Jurkat E6.1 cells are cultured according to standard cell culture protocols in Jurkat E6.1 Growth Media (RPMI without phenol red, 10% FBS, 1 mM HEPES, and 1 mM Sodium Pyruvate). Jurkat E6.1 cells are counted using a Coulter Counter and resuspended in Jurkat E6.1 growth media at a concentration of 75,000 cells/35 µl. 35 µl or 75,000 cells is seeded into Greiner microtitre assay plates. The plates are then incubated at 37° C. and 5% $CO_2$ while other assay components are being prepared.

Serially dilute HDAC inhibitor compounds. Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 1% DMSO. Stocks of 70 µl aliquots of the 10 mM compound in DMSO are prepared and stored at −20° C. From one stock aliquot of each compound to be tested and the reference compound, a 16-point serial dilution is prepared according to Table 1 using a 125 µl 16-channel Matrix multi-channel pipette.

2 µl (200×) of each diluted solution and each control (full activity: 100% DMSO alone or full inhibition 1 mM) is stamped into V-bottom polypropylene 384-well compound plates using either the Bravo, Janus, or 12.5 µl 16-channel Matrix multi-channel pipette. Each well with the 200× compound solution is diluted 1:20 by the addition of 38 µl Jurkat assay buffer+DMSO (9.5% DMSO, RPMI without phenol red, 0.09% FBS, 9 mM Hepes, and 0.9 mM Sodium Pyruvate equilibrated to r.t.)

Prepare 5× (500 µM) Boc-Lys(Tfa)-AMC substrate. 5× (500 µM) substrate is prepared just prior to the addition to the assay. The 5× substrate is prepared by diluting a 100 mM Boc-Lys(Tfa)-AMC in DMSO solution 1:200 by adding it drop-wise to Jurkat assay medium (RPMI without phenol red, 0.1% FBS, 10 mM Hepes, and 1 mM Sodium Pyruvate equilibrated to 37° C.) while vortexing at slow speed to prevent precipitation.

Prepare 3× Lysis Buffer. 10 mL of 3× lysis buffer is prepared with 8.8 mL of 3× stock lysis buffer (50 mM Tris-HCl, pH 8.0, 137 mM NaCl, 2.7 mM KCl, 1 mM $MgCl_2$, 1% Nonidet P40 Substitute equilibrated to r.t.) and 1.2 mL of 3 mg/mL Trypsin equilibrated to r.t.

Assay. 5 µl of each solution of 1:20 diluted compound from above is transferred to the Greiner microtitre assay plates with 75,000 cells/well using the Bravo. Cells are then incubated for 2 hours at 37° C. and 5% $CO_2$. The assay is then started by adding 10 µl of 5× (500 µM) substrate to the assay plate using either the Bravo or 16-channel Matrix multi-channel pipette. The cells are then incubated for 3 hours at 37° C. and 5% $CO_2$. Next, 25 µl of 3× lysis buffer is added to each well using either the 125 µl 16 channel pipette or the Bravo. The assay plate is then incubated overnight (15-16 hours) at 37° C. and 5% $CO_2$. The following day, the plates are shaken on an orbital shaker for 1 minute at 900 rpm. Finally the top read fluorescence (Excitation: 355 nm, Emission: 460 nm) is measured using PerkinElmer EnVision.

Using the synthetic methods similar to those described above and the assay protocols described above, the following compounds were synthesized and tested.

| Example # | Structure | Name | Biochemical HDAC4 IC$_{50}$ μM | Cell IC$_{50}$ μM |
|---|---|---|---|---|
| 1 | 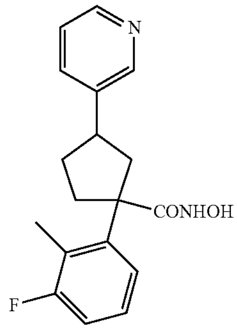 | 1-(3-Fluoro-2-methylphenyl)-N-hydroxy-3-(pyridin-3-yl)cyclopentanecarboxamide | 0.19 | 1.23 |
| 2 | D1, rac | (±)-(1S*,3R*)-1-(3-Fluoro-2-methylphenyl)-N-hydroxy-3-(pyrimidin-5-yl)cyclopentanecarboxamide | 0.29 | 1.91 |
| 3 | D2, rac | (±)-(1S*,3S*)-1-(3-Fluoro-2-methylphenyl)-N-hydroxy-3-(pyrimidin-5-yl)cyclopentanecarboxamide | 0.39 | 1.60 |
| 4 | D1 | (1R*,3S*)-1-(3-Fluoro-2-methylphenyl)-N-hydroxy-3-phenylcyclopentanecarboxamide | 0.04 | 0.44 |

-continued

| Example # | Structure | Name | Biochemical HDAC4 IC$_{50}$ μM | Cell IC$_{50}$ μM |
|---|---|---|---|---|
| 5 | D2 | (1S*,3R*)-1-(3-Fluoro-2-methylphenyl)-N-hydroxy-3-phenylcyclopentanecarboxamide | 1.1 | 7.85 |
| 6 | D3 | (1S*,3S*)-1-(3-Fluoro-2-methylphenyl)-N-hydroxy-3-phenylcyclopentanecarboxamide | 0.10 | 0.61 |
| 7 | D4 | (1R*,3R*)-1-(3-Fluoro-2-methylphenyl)-N-hydroxy-3-phenylcyclopentanecarboxamide | 0.05 | 1.12 |
| 8 | 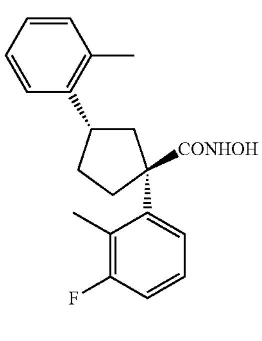 | (±)-(1S*,3S*)-1-(3-Fluoro-2-methylphenyl)-N-hydroxy-3-(o-tolyl)cyclopentanecarboxamide | 0.17 | 0.48 |

| Example # | Structure | Name | Biochemical HDAC4 IC$_{50}$ μM | Cell IC$_{50}$ μM |
|---|---|---|---|---|
| 9 | D1 | (1S,3S*)-1-(3-Fluoro-2-methyl-phenyl)-3-(5-fluoropyridin-3-yl)-N-hydroxycyclopentanecarboxamide | 0.15 | 1.28 |
| 10 | D2 | (1S,3R*)-1-(3-Fluoro-2-methyl-phenyl)-3-(5-fluoropyridin-3-yl)-N-hydroxycyclopentanecarboxamide | 0.14 | 1.39 |
| 11 | D1 | (1S,3S*)-1-(3-Fluoro-2-methylphenyl)-3-(5-fluoropyridin-2-yl)-N-hydroxycyclopentanecarboxamide | 0.20 | 1.83 |

| Example # | Structure | Name | Biochemical HDAC4 IC$_{50}$ μM | Cell IC$_{50}$ μM |
|---|---|---|---|---|
| 12 | D2 | (1S,3R*)-1-(3-Fluoro-2-methylphenyl)-3-(5-fluoropyridin-2-yl)-N-hydroxycyclopentanecarboxamide | 0.24 | 2.37 |
| 13 | D1 | (1r,4r)-4-(5-Fluoropyridin-3-yl)-N-hydroxy-1-phenylcyclohexanecarboxamide | 6.4 | 48.8 |
| 14 | D2 | (1s,4s)-4-(5-Fluoropyridin-3-yl)-N-hydroxy-1-phenylcyclohexanecarboxamide | >50 | >50 |
| 15 | 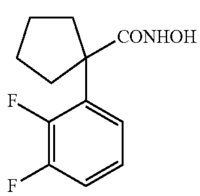 | 1-(2,3-Difluorophenyl)-N-hydroxycyclopentanecarboxamide | 2.5 | 18.5 |
| 16 | 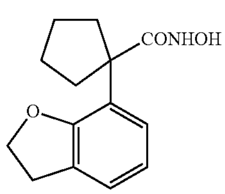 | 1-(2,3-Dihydrobenzofuran-7-yl)-N-hydroxycyclopentanecarboxamide | >50 | >50 |

-continued

| Example # | Structure | Name | Biochemical HDAC4 IC$_{50}$ μM | Cell IC$_{50}$ μM |
|---|---|---|---|---|
| 17 | 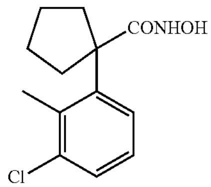 | 1-(3-Chloro-2-methylphenyl)-N-hydroxycyclopentanecarboxamide | 0.28 | 2.53 |
| 18 | 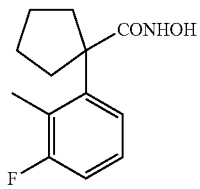 | 1-(3-Fluoro-2-methylphenyl)-N-hydroxycyclopentanecarboxamide | 0.27 | 1.70 |
| 19 | 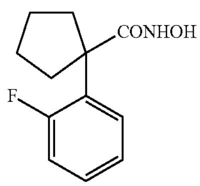 | 1-(2-Fluorophenyl)-N-hydroxycyclopentanecarboxamide | 4.6 | 44.7 |
| 20 | 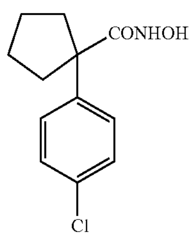 | 1-(4-Chlorophenyl)-N-hydroxycyclopentanecarboxamide | 24.0 | >50 |
| 21 | 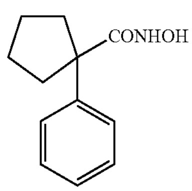 | N-Hydroxy-1-phenylcyclopentanecarboxamide | 11.4 | >50 |
| 22 | 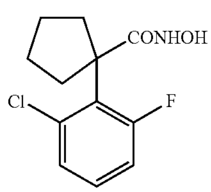 | 1-(2-Chloro-6-fluorophenyl)-N-hydroxycyclopentanecarboxamide | 2.5 | 15.6 |
| 23 | 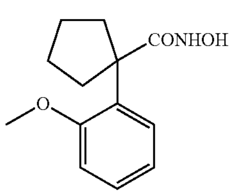 | N-Hydroxy-1-(2-methoxyphenyl)cyclopentanecarboxamide | >50 | >50 |

-continued

| Example # | Structure | Name | Biochemical HDAC4 IC$_{50}$ μM | Cell IC$_{50}$ μM |
|---|---|---|---|---|
| 24 | 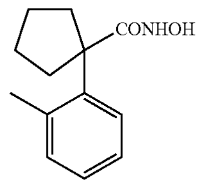 | N-Hydroxy-1-o-tolylcyclopentanecarboxamide | 0.73 | 8.12 |
| 25 | 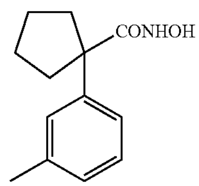 | N-Hydroxy-1-m-tolylcyclopentanecarboxamide | 8.2 | 43.7 |
| 26 | 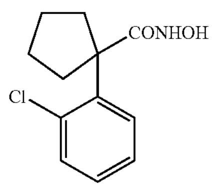 | 1-(2-Chlorophenyl)-N-hydroxycyclopentanecarboxamide | 1.90 | 15.1 |
| 27 | 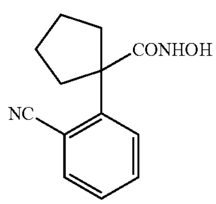 | 1-(2-Cyanophenyl)-N-hydroxycyclopentanecarboxamide | >50 | >50 |
| 28 | 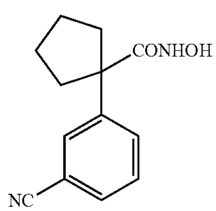 | 1-(3-Cyanophenyl)-N-hydroxycyclopentanecarboxamide | >50 | >50 |
| 29 | 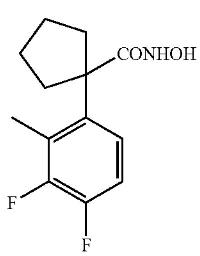 | 1-(3,4-Difluoro-2-methylphenyl)-N-hydroxycyclopentanecarboxamide | 0.15 | 1.41 |
| 30 | 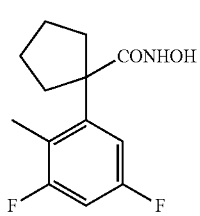 | 1-(3,5-Difluoro-2-methylphenyl)-N-hydroxycyclopentanecarboxamide | 0.33 | 2.63 |

-continued

| Example # | Structure | Name | Biochemical HDAC4 IC$_{50}$ μM | Cell IC$_{50}$ μM |
|---|---|---|---|---|
| 31 | (structure) | 1-(2-Chloro-6-methylphenyl)-N-hydroxycyclopentanecarboxamide | 0.91 | 8.1 |
| 32 | (structure) | 1-(2-Ethylphenyl)-N-hydroxycyclopentanecarboxamide | 1.1 | 6.5 |
| 33 | (structure) | N-Hydroxy-1-(3-methoxy-2-(trifluoromethyl)phenyl)cyclopentanecarboxamide | >50 | >50 |
| 34 | (structure) | N-Hydroxy-1-(2-(trifluoromethyl)phenyl)cyclopentanecarboxamide | 11 | 46 |
| 35 | (structure) | 1-(4-Fluoro-2-methylphenyl)-N-hydroxycyclopentanecarboxamide | 0.57 | 5.6 |
| 36 | (structure) | 1-(5-Fluoro-2-methylphenyl)-N-hydroxycyclopentanecarboxamide | 0.83 | 7.5 |
| 37 | (structure) | 1-(2-Fluoro-6-methylphenyl)-N-hydroxycyclopentanecarboxamide | 1.5 | 12 |

| Example # | Structure | Name | Biochemical HDAC4 IC$_{50}$ μM | Cell IC$_{50}$ μM |
|---|---|---|---|---|
| 38 | 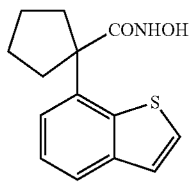 | 1-(Benzo[b]thiophen-7-yl)-N-hydroxycyclopentanecarboxamide | 0.61 | 4.6 |
| 39 | D1 | (1R,3S*)-1-(3-Fluoro-2-methylphenyl)-3-(5-fluoropyridin-3-yl)-N-hydroxycyclopentanecarboxamide | 0.72 | 8.4 |
| 40 | D2 | (1R,3R*)-1-(3-Fluoro-2-methylphenyl)-3-(5-fluoropyridin-3-yl)-N-hydroxycyclopentanecarboxamide | 3.6 | 8.4 |
| 41 | D1 | (1S,3R)-3-(5-Fluoropyridin-3-yl)-N-hydroxy-1-phenylcyclopentanecarboxamide | 1.9 | 13 |

-continued

| Example # | Structure | Name | Biochemical HDAC4 IC$_{50}$ μM | Cell IC$_{50}$ μM |
|---|---|---|---|---|
| 42 | D2 | (1S,3S)-3-(5-Fluoropyridin-3-yl)-N-hydroxy-1-phenylcyclopentanecarboxamide | 1.4 | 7.2 |
| 43 | 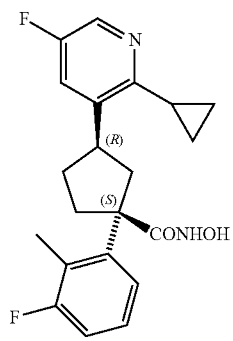 | (1S,3R)-3-(2-Cyclopropyl-5-fluoropyridin-3-yl)-1-(3-fluoro-2-methylphenyl)-N-hydroxycyclopentanecarboxamide | 0.24 | 0.61 |
| 44 | D1 | (1S,3S*)-1-(3-Fluoro-2-methylphenyl)-3-(5-fluoro-6-methoxypyridin-3-yl)-N-hydroxycyclopentanecarboxamide | 0.33 | 1.7 |
| 45 | 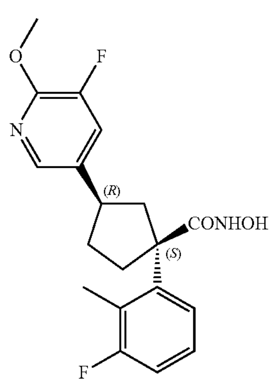 | (1S,3R*)-1-(3-Fluoro-2-methylphenyl)-3-(5-fluoro-6-methoxypyridin-3-yl)-N-hydroxycyclopentanecarboxamide | 0.19 | 0.42 |

-continued

| Example # | Structure | Name | Biochemical HDAC4 IC$_{50}$ μM | Cell IC$_{50}$ μM |
|---|---|---|---|---|
| 46 | 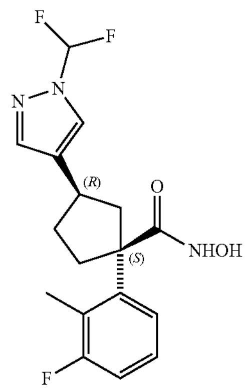 | (1S,3R*)-3-(1-(Difluoromethyl)-1H-pyrazol-4-yl)-1-(3-fluoro-2-methylphenyl)-N-hydroxycyclopentanecarboxamide | 0.095 | 0.54 |
| 47 | 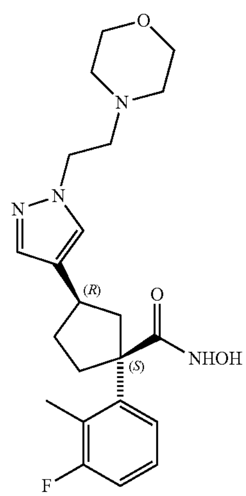 | (1S,3R*)-1-(3-Fluoro-2-methylphenyl)-N-hydroxy-3-(1-(2-morpholinoethyl)-1H-pyrazol-4-yl)cyclopentanecarboxamide | 0.14 | 0.83 |
| 48 | 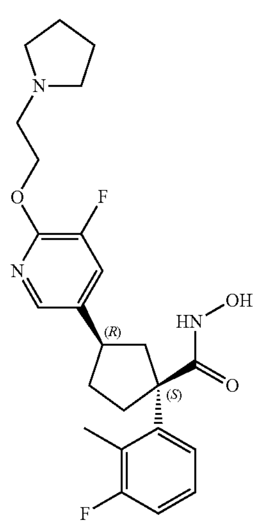 | (1S,3R*)-1-(3-Fluoro-2-methylphenyl)-3-(5-fluoro-6-(2-(pyrrolidin-1-yl)ethoxy)pyridin-3-yl)-N-hydroxycyclopentanecarboxamide | 0.32 | 0.75 |

-continued

| Example # | Structure | Name | Biochemical HDAC4 IC$_{50}$ μM | Cell IC$_{50}$ μM |
|---|---|---|---|---|
| 49 | D1 | (1S,3R*)-1-(3-Fluoro-2-methylphenyl)-N-hydroxy-3-(1-methyl-1H-pyrazol-5-yl)cyclopentanecarboxamide | 0.17 | 0.40 |
| 50 | D2 | (1S,3S*)-1-(3-Fluoro-2-methylphenyl)-N-hydroxy-3-(1-methyl-1H-pyrazol-5-yl)cyclopentanecarboxamide | 0.25 | 1.8 |
| 51 | 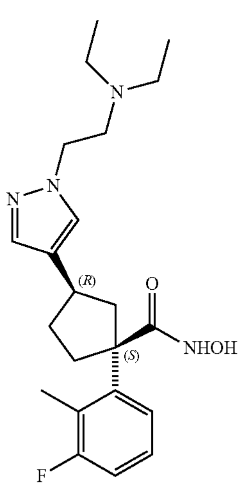 | (1S,3R*)-3-(1-(2-(Diethylamino)ethyl)-1H-pyrazol-4-yl)-1-(3-fluoro-2-methylphenyl)-N-hydroxycyclopentanecarboxamide | 0.082 | 0.29 |

-continued

| Example # | Structure | Name | Biochemical HDAC4 IC$_{50}$ μM | Cell IC$_{50}$ μM |
|---|---|---|---|---|
| 52 | D1 | N-((R)-1-(Dipropylamino)propan-2-yl)-4-((1R*,3S)-3-(3-fluoro-2-methylphenyl)-3-(hydroxycarbamoyl)cyclopentyl)benzamide | 0.20 | 0.18 |
| 53 | D2 | N-((R)-1-(Dipropylamino)propan-2-yl)-4-((1S*,3S)-3-(3-fluoro-2-methylphenyl)-3-(hydroxycarbamoyl)cyclopentyl)benzamide | 0.16 | 0.15 |
| 54 | D1 | (1S,3R*)-3-(1-(Difluoromethyl)-1H-indazol-6-yl)-1-(3-fluoro-2-methylphenyl)-N-hydroxycyclopentanecarboxamide | 0.072 | 0.11 |

| Example # | Structure | Name | Biochemical HDAC4 IC$_{50}$ μM | Cell IC$_{50}$ μM |
|---|---|---|---|---|
| 55 | D2 | (1S,3S*)-3-(1-(Difluoromethyl)-1H-indazol-6-yl)-1-(3-fluoro-2-methylphenyl)-N-hydroxycyclopentanecarboxamide | 0.046 | 0.16 |
| 56 | 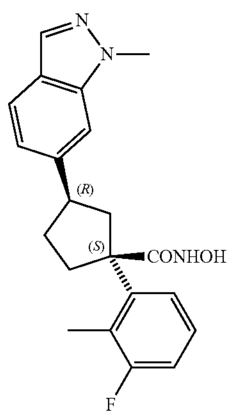 | (1S,3R*)-1-(3-Fluoro-2-methylphenyl)-N-hydroxy-3-(1-methyl-1H-indazol-6-yl)cyclopentanecarboxamide | 0.14 | 0.23 |
| 57 | D1 | (1S,3R*)-1-(3-Fluoro-2-methylphenyl)-N-hydroxy-3-(imidazo[1,2-a]pyridin-7-yl)cyclopentanecarboxamide | 0.098 | 0.18 |

| Example # | Structure | Name | Biochemical HDAC4 IC$_{50}$ μM | Cell IC$_{50}$ μM |
|---|---|---|---|---|
| 58 | D2 | (1S,3S*)-1-(3-Fluoro-2-methylphenyl)-N-hydroxy-3-(imidazo[1,2-a]pyridin-7-yl)cyclopentanecarboxamide | 0.082 | 0.30 |
| 59 | 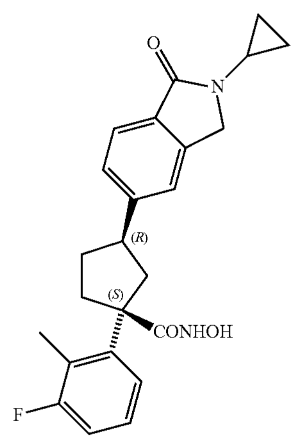 | (1S,3R*)-3-(2-Cyclopropyl-1-oxoisoindolin-5-yl)-1-(3-fluoro-2-methylphenyl)-N-hydroxycyclopentanecarboxamide | 0.14 | 0.19 |
| 60 | 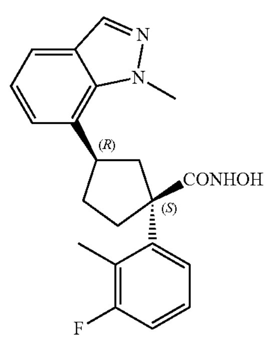 | (1S,3R*)-1-(3-Fluoro-2-methylphenyl)-N-hydroxy-3-(1-methyl-1H-indazol-7-yl)cyclopentanecarboxamide | 0.36 | 0.81 |
| 61 | 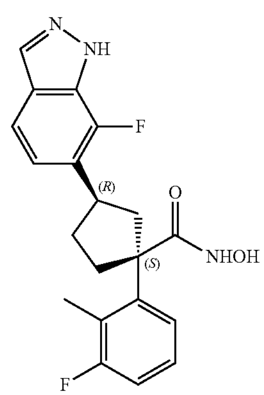 | (1S,3R*)-3-(7-Fluoro-1H-indazol-6-yl)-1-(3-fluoro-2-methylphenyl)-N-hydroxycyclopentanecarboxamide | 0.073 | 0.081 |

| Example # | Structure | Name | Biochemical HDAC4 IC$_{50}$ μM | Cell IC$_{50}$ μM |
|---|---|---|---|---|
| 62 | 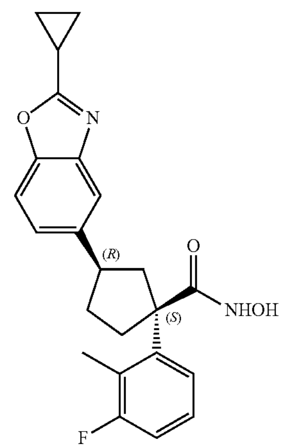 | (1S,3R*)-3-(2-Cyclopropylbenzo[d]oxazol-5-yl)-1-(3-fluoro-2-methylphenyl)-N-hydroxycyclopentanecarboxamide | 0.28 | 0.41 |
| 63 | D1 | (1S,3R*)-1-(3-Fluoro-2-methylphenyl)-N-hydroxy-3-(1-methyl-1H-indazol-5-yl)cyclopentanecarboxamide | 0.11 | 0.14 |
| 64 | D2 | (1S,3S*)-1-(3-Fluoro-2-methylphenyl)-N-hydroxy-3-(1-methyl-1H-indazol-5-yl)cyclopentanecarboxamide | 0.10 | 0.22 |

-continued

| Example # | Structure | Name | Biochemical HDAC4 IC$_{50}$ μM | Cell IC$_{50}$ μM |
|---|---|---|---|---|
| 65 | D1 | (1S,3R*)-3-(2-(Difluoromethyl)-2H-indazol-6-yl)-1-(3-fluoro-2-methylphenyl)-N-hydroxycyclopentanecarboxamide | 0.11 | 0.099 |
| 66 | D2 | (1S,3S*)-3-(2-(Difluoromethyl)-2H-indazol-6-yl)-1-(3-fluoro-2-methylphenyl)-N-hydroxycyclopentanecarboxamide | 0.22 | 0.19 |
| 67 | D1 | (1S,3R*)-3-(3-Fluoro-1-methyl-1H-indazol-6-yl)-1-(3-fluoro-2-methylphenyl)-N-hydroxycyclopentanecarboxamide | 0.40 | 0.36 |

-continued
| Example # | Structure | Name | Biochemical HDAC4 IC$_{50}$ μM | Cell IC$_{50}$ μM |
|---|---|---|---|---|
| 68 | 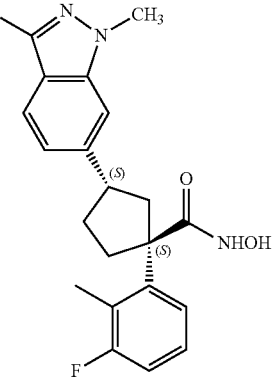 D2 | (1S,3S*)-3-(3-Fluoro-1-methyl-1H-indazol-6-yl)-1-(3-fluoro-2-methylphenyl)-N-hydroxycyclopentanecarboxamide | 0.32 | 0.21 |
| 69 | 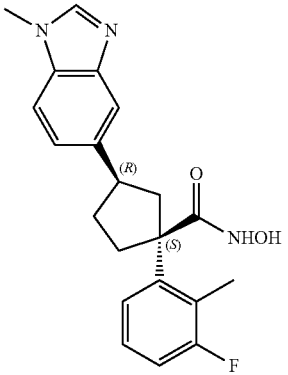 | (1S,3R*)-1-(3-Fluoro-2-methylphenyl)-N-hydroxy-3-(1-methyl-1H-benzo[d]imidazol-5-yl)cyclopentanecarboxamide | 0.090 | 0.20 |
| 70 | 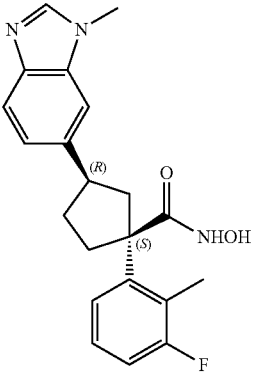 D1 | (1S,3R*)-1-(3-Fluoro-2-methylphenyl)-N-hydroxy-3-(1-methyl-1H-benzo[d]imidazol-6-yl)cyclopentanecarboxamide | 0.11 | 0.13 |

-continued

| Example # | Structure | Name | Biochemical HDAC4 IC$_{50}$ μM | Cell IC$_{50}$ μM |
|---|---|---|---|---|
| 71 | D2 | (1S,3S*)-1-(3-Fluoro-2-methylphenyl)-N-hydroxy-3-(1-methyl-1H-benzo[d]imidazol-6-yl)cyclopentanecarboxamide | 0.059 | 0.11 |
| 72 | D1 | (1S,3R*)-1-(3-Fluoro-2-methylphenyl)-N-hydroxy-3-(1-methyl-1H-benzo[d]imidazol-6-yl)cyclopentanecarboxamide | 0.30 | 0.47 |
| 73 | D2 | (1S,3S*)-1-(3-Fluoro-2-methylphenyl)-N-hydroxy-3-(1-methyl-1H-benzo[d]imidazol-6-yl)cyclopentanecarboxamide | 0.27 | 0.41 |

| Example # | Structure | Name | Biochemical HDAC4 IC$_{50}$ μM | Cell IC$_{50}$ μM |
|---|---|---|---|---|
| 74 | 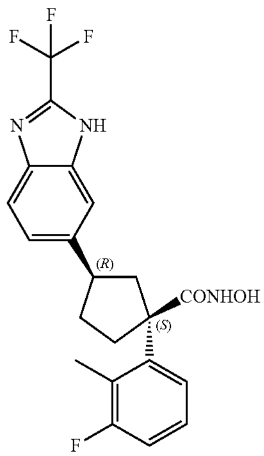 | (1S,3R*)-1-(3-Fluoro-2-methylphenyl)-N-hydroxy-3-(2-(trifluoromethyl)-1H-benzo[d]imidazol-6-yl)cyclopentanecarboxamide | 0.074 | 0.11 |
| 75 | D1 | (1S,3S*)-3-(Benzo[d]thiazol-2-yl)-1-(3-fluoro-2-methylphenyl)-N-hydroxycyclopentanecarboxamide | 0.080 | 0.16 |
| 76 | D2 | (1S,3R*)-3-(Benzo-[d]thiazol-2-yl)-1-(3-fluoro-2-methylphenyl)-N-hydroxycyclopentanecarboxamide | 0.16 | 0.24 |

| Example # | Structure | Name | Biochemical HDAC4 IC$_{50}$ µM | Cell IC$_{50}$ µM |
|---|---|---|---|---|
| 77 | D1 | (1S,3S*)-3-(2-Cyclopropylbenzo[d]thiazol-6-yl)-1-(3-fluoro-2-methylphenyl)-N-hydroxycyclopentanecarboxamide | 0.31 | 0.42 |
| 78 | D2 | (1S,3R*)-3-(2-Cyclopropylbenzo[d]thiazol-6-yl)-1-(3-fluoro-2-methylphenyl)-N-hydroxycyclopentanecarboxamide | 0.34 | 0.42 |
| 79 | D1 | (1S,3S*)-3-(2-Cyclopropylbenzo[d]thiazol-5-yl)-1-(3-fluoro-2-methylphenyl)-N-hydroxycyclopentanecarboxamide | 0.29 | 0.38 |

| Example # | Structure | Name | Biochemical HDAC4 IC$_{50}$ μM | Cell IC$_{50}$ μM |
|---|---|---|---|---|
| 80 | D2 | (1S,3R*)-3-(2-Cyclopropylbenzo[d]thiazol-5-yl)-1-(3-fluoro-2-methylphenyl)-N-hydroxycyclopentanecarboxamide | 0.33 | 0.38 |
| 81 | 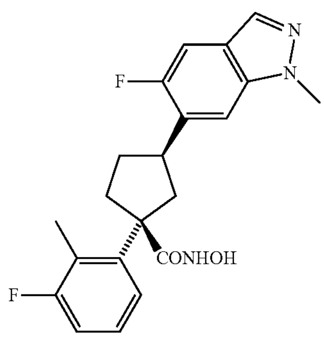 | (1S,3R)-3-(5-Fluoro-1-methyl-1H-indazol-6-yl)-1-(3-fluoro-2-methylphenyl)-N-hydroxycyclopentanecarboxamide | 0.15 | 0.58 |
| 82 | D1 | (1S,3S*)-3-(7-Fluoro-1-methyl-1H-indazol-6-yl)-1-(3-fluoro-2-methylphenyl)-N-hydroxycyclopentanecarboxamide | 0.11 | 0.25 |
| 83 | D2 | (1S,3R*)-3-(7-Fluoro-1-methyl-1H-indazol-6-yl)-1-(3-fluoro-2-methylphenyl)-N-hydroxycyclopentanecarboxamide | 0.055 | 0.059 |

| Example # | Structure | Name | Biochemical HDAC4 IC$_{50}$ μM | Cell IC$_{50}$ μM |
|---|---|---|---|---|
| 84 | D1 | (1S,3S*)-1-(3-Fluoro-2-methylphenyl)-N-hydroxy-3-(quinolin-6-yl)cyclopentanecarboxamide | 0.048 | 0.18 |
| 85 | D2 | (1S,3R*)-1-(3-Fluoro-2-methylphenyl)-N-hydroxy-3-(quinolin-6-yl)cyclopentanecarboxamide | 0.062 | 0.12 |
| 86 | 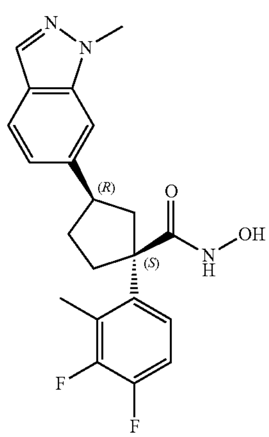 | (1S,3R*)-1-(3,4-Difluoro-2-methylphenyl)-N-hydroxy-3-(1-methyl-1H-indazol-6-yl)cyclopentanecarboxamide | 0.090 | 0.16 |
| 87 | D1 | (1S,3R*)-1-(3-Fluoro-2-methylphenyl)-N-hydroxy-3-(pyrrolidin-1-yl)cyclopentanecarboxamide | 20 | >50 |

| Example # | Structure | Name | Biochemical HDAC4 IC$_{50}$ μM | Cell IC$_{50}$ μM |
|---|---|---|---|---|
| 88 | D2 | (1S,3S*)-1-(3-Fluoro-2-methylphenyl)-N-hydroxy-3-(pyrrolidin-1-yl)cyclopentanecarboxamide | >50 | >50 |
| 89 | D1 | (1S,3R*)-1-(3-Fluoro-2-methylphenyl)-N-hydroxy-3-morpholinocyclopentanecarboxamide | 1.1 | 7.3 |
| 90 | D2 | (1S,3S*)-1-(3-Fluoro-2-methylphenyl)-N-hydroxy-3-morpholinocyclopentanecarboxamide | 2.5 | 24 |
| 91 | 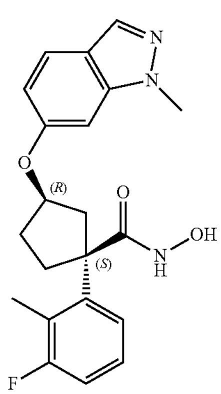 | (1S,3R)-1-(3-Fluoro-2-methylphenyl)-N-hydroxy-3-((1-methyl-1H-indazol-6-yl)oxy)cyclopentanecarboxamide | 0.29 | 1.6 |

| Example # | Structure | Name | Biochemical HDAC4 IC$_{50}$ μM | Cell IC$_{50}$ μM |
|---|---|---|---|---|
| 92 | 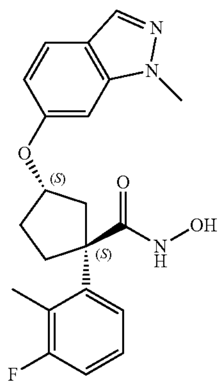 | (1S,3S)-1-(3-Fluoro-2-methylphenyl)-N-hydroxy-3-((1-methyl-1H-indazol-6-yl)oxy)cyclopentanecarboxamide | 0.14 | 0.47 |
| 93 | 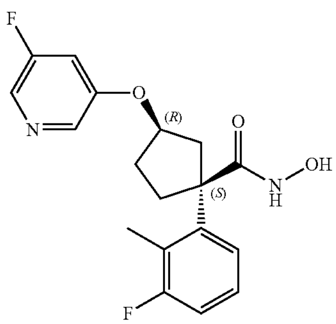 | (1S,3R)-1-(3-Fluoro-2-methylphenyl)-3-((5-fluoropyridin-3-yl)oxy)-N-hydroxycyclopentanecarboxamide | 0.2 | 1.9 |
| 94 | 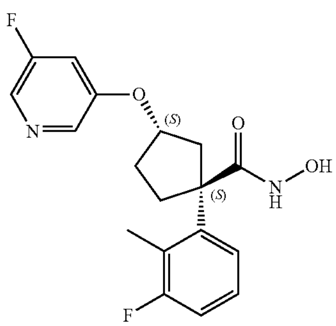 | (1S,3S)-1-(3-Fluoro-2-methylphenyl)-3-((5-fluoropyridin-3-yl)oxy)-N-hydroxycyclopentanecarboxamide | 0.16 | 0.83 |
| 95 | 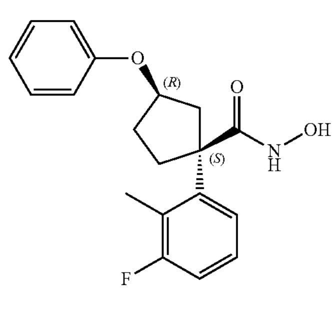 | (1S,3R)-1-(3-Fluoro-2-methylphenyl)-N-hydroxy-3-phenoxycyclopentanecarboxamide | 0.16 | 1.5 |

| Example # | Structure | Name | Biochemical HDAC4 IC$_{50}$ μM | Cell IC$_{50}$ μM |
|---|---|---|---|---|
| 96 | 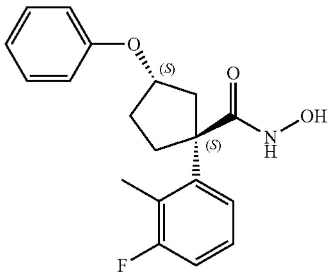 | (1S,3S)-1-(3-Fluoro-2-methylphenyl)-N-hydroxy-3-phenoxycyclopentanecarboxamide | 0.13 | 0.26 |
| 97 | 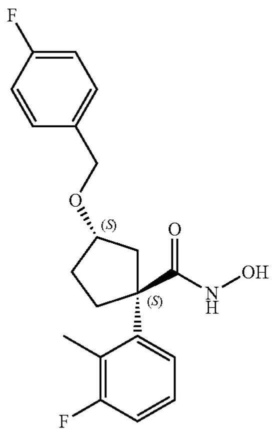 | (1S,3S)-1-(3-Fluoro-2-methylphenyl)-3-((4-fluorobenzyl)oxy)-N-hydroxycyclopentanecarboxamide | 0.24 | 0.66 |
| 98 | 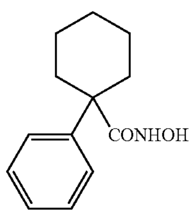 | 1-Phenyl-N-hydroxycyclohexylcarboxamide | >50 | >50 |
| 99 | 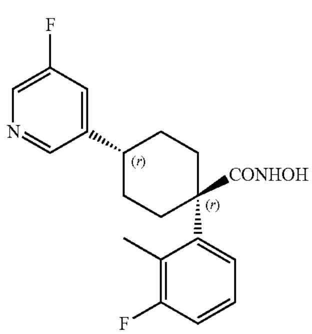 | (1r,4r)-1-(3-Fluoro-2-methylphenyl)-4-(5-fluoropyridin-3-yl)-N-hydroxycyclohexanecarboxamide | 4.1 | 38 |

D1

-continued

| Example # | Structure | Name | Biochemical HDAC4 IC$_{50}$ μM | Cell IC$_{50}$ μM |
|---|---|---|---|---|
| 100 | D2 | (1s,4s)-1-(3-Fluoro-2-methylphenyl)-4-(5-fluoropyridin-3-yl)-N-hydroxycyclohexanecarboxamide | 0.66 | 0.37 |
| 101 | 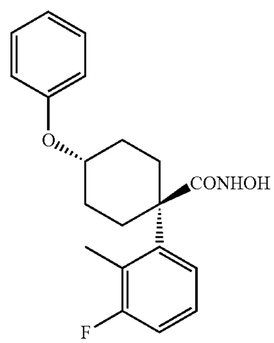 | (1r,4r)-1-(3-Fluoro-2-methylphenyl)-N-hydroxy-4-phenoxycyclohexanecarboxamide | 0.68 | 0.54 |
| 102 | 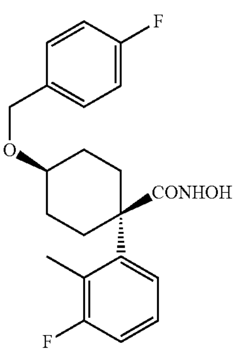 | (1s,4s)-1-(3-Fluoro-2-methylphenyl)-4-((4-fluorobenzyl)oxy)-N-hydroxycyclohexanecarboxamide | 14 | 49 |
| 103 | 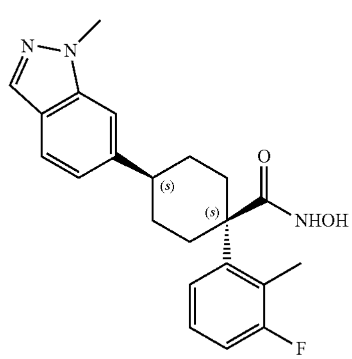 | (1s,4s)-1-(3-Fluoro-2-methylphenyl)-N-hydroxy-4-(1-methyl-1H-indazol-6-yl)cyclohexanecarboxamide | 4.2 | 26 |

-continued

| Example # | Structure | Name | Biochemical HDAC4 IC$_{50}$ μM | Cell IC$_{50}$ μM |
|---|---|---|---|---|
| 104 | 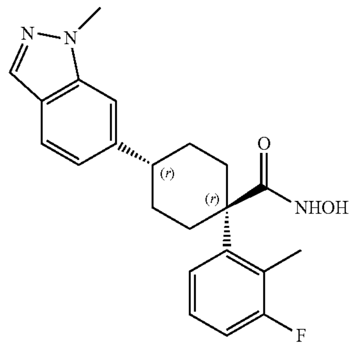 | (1r,4r)-1-(3-Fluoro-2-methylphenyl)-N-hydroxy-4-(1-methyl-1H-indazol-6-yl)cyclohexanecarboxamide | 0.95 | 0.65 |
| 105 | 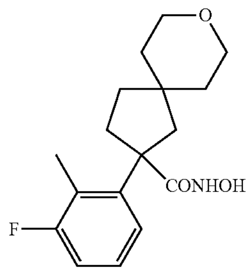 | (±)-2-(3-Fluoro-2-methylphenyl)-N-hydroxy-8-oxaspiro[4.5]decane-2-carboxamide | 1.4 | 12 |
| 106 | 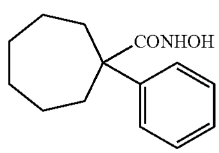 | N-Hydroxy-1-phenylcycloheptanecarboxamide | 6.9 | 41.1 |
| 107 | 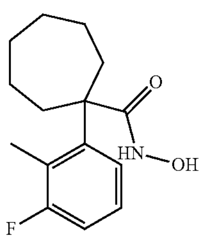 [SMILES: Cc1c(F)cccc1C1(C(=O)NO)CCCCCC1] | 1-(3-Fluoro-2-methylphenyl)-N-hydroxycycloheptanecarboxamide | >50 | >50 |

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed:

1. A compound of Formula I, or a pharmaceutically acceptable salt thereof,

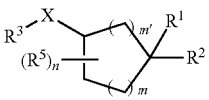

Formula I wherein:
$R^1$ is —C(O)NH(OH) or —N(OH)C(O)$R^4$;
$R^2$ is aryl, heteroaryl, or heterocycloalkyl, each of which is optionally substituted with 1 to 3 substituents independently selected from halo, alkyl, cycloalkyl, haloalkyl, hydroxyl, alkoxy, and nitrile;
X is absent, —O—, —N$R^6$—, or —[C($R^7R^8$)]$_p$—;
$R^3$ is alkyl, cycloalkyl, heterocycloalkyl, aryl, heteroaryl, aralkyl, or heteroaralkyl, each of which is optionally substituted with 1 to 3 substituents independently selected from halo, —CONR$^b$R$^c$, alkyl, alkyl substituted with —NR$^b$R$^c$, cycloalkyl, haloalkyl, hydroxyl, alkoxy, haloalkoxy, alkoxy substituted with —NR$^b$R$^c$, aryl, heteroaryl, and nitrile;

R$^4$ is hydrogen, lower alkyl or lower haloalkyl;

for each occurrence, R$^5$ is independently selected from halo, lower alkyl, lower haloalkyl, and hydroxyl; or R$^3$ taken together with R$_5$, and any intervening atoms, forms a 3- to 7-membered heterocycloalkyl or cycloalkyl ring;

m and m' are independently selected from 1, 2, and 3, provided that m+m'≤4;

n is 0, 1, 2 or 3;

p is 1 or 2;

R$^6$ is hydrogen, lower alkyl, cycloalkyl, or lower haloalkyl; and for each occurrence, R$^7$ and R$^8$ are each independently selected from hydrogen, halo, lower alkyl, and lower haloalkyl, R$^b$ is selected from H, C$_1$-C$_6$ alkyl, aryl, and heteroaryl; and R$^c$ is selected from hydrogen and C$_1$-C$_4$ alkyl; or R$^b$ and R$^c$, and the nitrogen to which they are attached, form a heterocycloalkyl group; and where for R$^b$ and R$^c$, each C$_1$-C$_6$ alkyl, aryl, heterocycloalkyl, and heteroaryl is unsubstituted or substituted with one or more substituents independently selected from C$_1$-C$_4$ alkyl, C$_3$-C$_6$ cycloalkyl, aryl, heteroaryl, aryl-C$_1$-C$_4$ alkyl-, heteroaryl-C$_1$-C$_4$ alkyl-, C$_1$-C$_4$ haloalkyl-, —OC$_1$-C$_4$ alkyl, —OC$_1$-C$_4$ alkylphenyl, —C$_1$-C$_4$ alkyl-OH, —C$_1$-C$_4$ alkyl-O—C$_1$-C$_4$ alkyl, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substituent for heteroaryl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ phenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

2. The compound of claim 1, or a pharmaceutically acceptable salt thereof, wherein the compound of Formula I is a compound of Formula II:

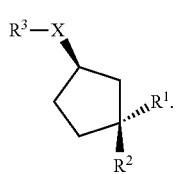

Formula II

3. The compound of claim 1, or a pharmaceutically acceptable salt thereof, wherein m is 1.

4. The compound of claim 1, or a pharmaceutically acceptable salt thereof, wherein m is 2.

5. The compound of claim 1, or a pharmaceutically acceptable salt thereof, wherein m is 3.

6. The compound of claim 5, or a pharmaceutically acceptable salt thereof, wherein m' is 1.

7. The compound of claim 5, or a pharmaceutically acceptable salt thereof, wherein m' is 2.

8. The compound of claim 5, or a pharmaceutically acceptable salt thereof, wherein m' is 3.

9. The compound of claim 1, or a pharmaceutically acceptable salt thereof, wherein R$^1$ is —C(O)NH(OH).

10. The compound of claim 1, or a pharmaceutically acceptable salt thereof, wherein R$^1$ is —N(OH)C(O)R$^4$.

11. The compound of claim 10, or a pharmaceutically acceptable salt thereof, wherein R$^4$ is hydrogen or lower alkyl.

12. The compound of claim 11, or a pharmaceutically acceptable salt thereof, wherein R$^4$ is lower alkyl.

13. The compound of claim 1, or a pharmaceutically acceptable salt thereof, wherein n is 1.

14. The compound of claim 1, or a pharmaceutically acceptable salt thereof, wherein n is 2.

15. The compound of claim 1, or a pharmaceutically acceptable salt thereof, wherein n is 3.

16. The compound of claim 1, or a pharmaceutically acceptable salt thereof, wherein, for each occurrence, R$^5$ is independently selected from halo and lower alkyl.

17. The compound of claim 1, or a pharmaceutically acceptable salt thereof, wherein n is 0.

18. The compound of claim 1, or a pharmaceutically acceptable salt thereof, wherein R$^2$ is phenyl optionally substituted with 1 to 3 substituents independently selected from halo, alkyl, cycloalkyl, haloalkyl, hydroxyl, alkoxy, and nitrile.

19. The compound of claim 18, or a pharmaceutically acceptable salt thereof, wherein R$^2$ is phenyl optionally substituted with 1 to 3 substituents independently selected from halo, alkyl, and haloalkyl.

20. The compound of claim 19, or a pharmaceutically acceptable salt thereof, wherein R$^2$ is 3-fluoro-2-methylphenyl or 2-methylphenyl.

21. The compound of claim 1, or a pharmaceutically acceptable salt thereof, wherein R$^2$ is heteroaryl optionally substituted with 1 to 3 substituents independently selected from halo, alkyl, and haloalkyl.

22. The compound of claim 21, or a pharmaceutically acceptable salt thereof, wherein R$^2$ is pyridinyl optionally substituted with 1 to 3 substituents independently selected from halo, alkyl, and haloalkyl.

23. The compound of claim 22, or a pharmaceutically acceptable salt thereof, wherein R$^2$ is 2-methylpyridin-3-yl.

24. The compound of claim 1, or a pharmaceutically acceptable salt thereof, wherein p is 1.

25. The compound of claim 1, or a pharmaceutically acceptable salt thereof, wherein p is 2.

26. The compound of claim 1, or a pharmaceutically acceptable salt thereof, wherein, for each occurrence, R$^7$ and R$^8$ are each independently selected from hydrogen, halo, and lower alkyl.

27. The compound of claim 1, or a pharmaceutically acceptable salt thereof, wherein X is absent.

28. The compound of claim 1, or a pharmaceutically acceptable salt thereof, wherein X is —O—.

29. The compound of claim 1, or a pharmaceutically acceptable salt thereof, wherein X is —NR$^6$—.

30. The compound of claim 29, or a pharmaceutically acceptable salt thereof, wherein R$^6$ is hydrogen, lower alkyl, or cycloalkyl.

31. The compound of claim 1, or a pharmaceutically acceptable salt thereof, wherein R$^3$ is alkyl, cycloalkyl, heterocycloalkyl, aryl, heteroaryl, aralkyl, or heteroaralkyl, each of which is optionally substituted with 1 to 3 substituents independently selected from halo, —CONR$^b$R$^c$, alkyl, alkyl substituted with —NR$^b$R$^c$, cycloalkyl, haloalkyl, hydroxyl, alkoxy, alkoxy substituted with —NR$^b$R$^c$, and nitrile.

32. The compound of claim 31, or a pharmaceutically acceptable salt thereof, wherein R$^3$ is aryl optionally substituted with 1 to 3 substituents independently selected from halo, alkyl, cycloalkyl, haloalkyl, hydroxyl, alkoxy, and nitrile.

33. The compound of claim 32, or a pharmaceutically acceptable salt thereof, wherein R$^3$ is phenyl, 2-methylphenyl, 3,4-dihydro-2H-benzo[b][1,4]oxazin-6-yl, 4,4-difluoro-1,2,3,4-tetrahydroquinolin-7-yl, or 4,4,8-trifluoro-1,2,3,4-tetrahydroquinolin-6-yl.

34. The compound of claim 31, or a pharmaceutically acceptable salt thereof, wherein R$^3$ is heteroaryl optionally substituted with 1 to 3 substituents independently selected from halo, alkyl, cycloalkyl, haloalkyl, hydroxyl, alkoxy, and nitrile.

35. The compound of claim 34, or a pharmaceutically acceptable salt thereof, wherein R$^3$ is 6-methylpyridin-3-yl, 5-fluoropyridin-3-yl, 5-(trifluoromethyl)pyrimidin-2-yl, 5-methylpyrimidin-2-yl, pyrimidin-2-yl, 2-(trifluoromethyl)pyrimidin-5-yl, 2-methylpyrimidin-5-yl, pyrimidin-5-yl, 2-(trifluoromethyl)pyrimidin-4-yl, 2-methylpyrimidin-4-yl, pyrimidin-4-yl, 6-(trifluoromethyl)pyridazin-4-yl, 6-methylpyridazin-4-yl, pyridazin-4-yl, 6-cyclopropylpyridazin-4-yl, pyrazin-2-yl, 5-(trifluoromethyl)pyrazin-2-yl, 5-methylpyrazin-2-yl, 3-cyclopropylpyrazin-2-yl, 1-(2,2,2-trifluoroethyl)-1H-pyrazol-4-yl, 2-cyclopropyloxazol-5-yl, 2-cyclopropylthiazol-5-yl, 2-methylbenzo[d]oxazol-5-yl, 1H-pyrrolo[2,3-b]pyridin-6-yl, imidazo[1,2-a]pyridin-7-yl, 1H-indazol-6-yl, or 2-oxo-1,2-dihydropyridin-3-yl.

36. The compound of claim 1, or a pharmaceutically acceptable salt thereof, wherein R$^3$ is heterocycloalkyl optionally substituted with 1 to 3 substituents independently selected from halo, alkyl, cycloalkyl, haloalkyl, hydroxyl, alkoxy, aryl, heteroaryl, and nitrile.

37. The compound of claim 36, or a pharmaceutically acceptable salt thereof, wherein R$^3$ is 1H-pyrrolo[3,4-c]pyridin-2(3H)-yl, 3,4-dihydroisoquinolin-2(1H)-yl, 4-cyclopropylpiperazin-1-yl, 1-(2,2,2-trifluoroethyl)piperidin-4-yl, or 1-cyclopropylpiperidin-4-yl.

38. A compound selected from:
1-(3-fluoro-2-methylphenyl)-N-hydroxy-3-(pyridin-3-yl)cyclopentanecarboxamide;
(±)-(1S*,3R*)-1-(3-fluoro-2-methylphenyl)-N-hydroxy-3-(pyrimidin-5-yl)cyclopentanecarboxamide;
(±)-(1S*,3S*)-1-(3-fluoro-2-methylphenyl)-N-hydroxy-3-(pyrimidin-5-yl)cyclopentanecarboxamide;
(1R*,3S*)-1-(3-fluoro-2-methylphenyl)-N-hydroxy-3-phenylcyclopentanecarboxamide;
(1S*,3R*)-1-(3-fluoro-2-methylphenyl)-N-hydroxy-3-phenylcyclopentanecarboxamide;
(1S*,3S*)-1-(3-fluoro-2-methylphenyl)-N-hydroxy-3-phenylcyclopentanecarboxamide;
(1R*,3R*)-1-(3-fluoro-2-methylphenyl)-N-hydroxy-3-phenylcyclopentanecarboxamide;
(±)-(1S*,3S*)-1-(3-fluoro-2-methylphenyl)-N-hydroxy-3-(o-tolyl)cyclopentanecarboxamide;
(1S,3S*)-1-(3-fluoro-2-methyl-phenyl)-3-(5-fluoropyridin-3-yl)-N-hydroxycyclopentanecarboxamide;
(1S,3R*)-1-(3-fluoro-2-methyl-phenyl)-3-(5-fluoropyridin-3-yl)-N-hydroxycyclopentanecarboxamide;
(1S,3S*)-1-(3-fluoro-2-methylphenyl)-3-(5-fluoropyridin-2-yl)-N-hydroxycyclopentane carboxamide;
(1S,3R*)-1-(3-fluoro-2-methylphenyl)-3-(5-fluoropyridin-2-yl)-N-hydroxycyclopentane carboxamide;
(1r,4r)-4-(5-fluoropyridin-3-yl)-N-hydroxy-1-phenylcyclohexanecarboxamide;
(1s,4s)-4-(5-fluoropyridin-3-yl)-N-hydroxy-1-phenylcyclohexanecarboxamide;
1-(2,3-difluorophenyl)-N-hydroxycyclopentanecarboxamide;
1-(2,3-dihydrobenzofuran-7-yl)-N-hydroxycyclopentanecarboxamide;
1-(3-chloro-2-methylphenyl)-N-hydroxycyclopentanecarboxamide;
1-(3-fluoro-2-methylphenyl)-N-hydroxycyclopentanecarboxamide;
N-hydroxy-1-phenylcyclopentanecarboxamide;
1-(2-chloro-6-fluorophenyl)-N-hydroxycyclopentanecarboxamide;
N-hydroxy-1-(2-methoxyphenyl)cyclopentanecarboxamide;
N-hydroxy-1-o-tolylcyclopentanecarboxamide;
N-hydroxy-1-m-tolylcyclopentanecarboxamide;
1-(2-cyanophenyl)-N-hydroxycyclopentanecarboxamide;
1-(3-cyanophenyl)-N-hydroxycyclopentanecarboxamide;
1-(3,4-difluoro-2-methylphenyl)-N-hydroxycyclopentanecarboxamide;
1-(3,5-difluoro-2-methylphenyl)-N-hydroxycyclopentanecarboxamide;
1-(2-chloro-6-methylphenyl)-N-hydroxycyclopentanecarboxamide;
1-(2-ethylphenyl)-N-hydroxycyclopentanecarboxamide;
N-hydroxy-1-(3-methoxy-2-(trifluoromethyl)phenyl)cyclopentanecarboxamide;
N-hydroxy-1-(2-(trifluoromethyl)phenyl)cyclopentanecarboxamide;
1-(4-fluoro-2-methylphenyl)-N-hydroxycyclopentanecarboxamide;
1-(5-fluoro-2-methylphenyl)-N-hydroxycyclopentanecarboxamide;
1-(2-fluoro-6-methylphenyl)-N-hydroxycyclopentanecarboxamide;
1-(benzo[b]thiophen-7-yl)-N-hydroxycyclopentanecarboxamide;
(1R,3S*)-1-(3-fluoro-2-methylphenyl)-3-(5-fluoropyridin-3-yl)-N-hydroxycyclopentanecarboxamide;
(1R,3R*)-1-(3-fluoro-2-methylphenyl)-3-(5-fluoropyridin-3-yl)-N-hydroxycyclopentanecarboxamide;
(1S,3R)-3-(5-fluoropyridin-3-yl)-N-hydroxy-1-phenylcyclopentanecarboxamide;
(1S,3S)-3-(5-fluoropyridin-3-yl)-N-hydroxy-1-phenylcyclopentanecarboxamide;
(1S,3R)-3-(2-cyclopropyl-5-fluoropyridin-3-yl)-1-(3-fluoro-2-methylphenyl)-N-hydroxycyclopentanecarboxamide;
(1S,3S*)-1-(3-fluoro-2-methylphenyl)-3-(5-fluoro-6-methoxypyridin-3-yl)-N-hydroxycyclopentanecarboxamide;
(1S,3R*)-1-(3-fluoro-2-methylphenyl)-3-(5-fluoro-6-methoxypyridin-3-yl)-N-hydroxycyclopentanecarboxamide;
(1S,3R*)-3-(1-(Difluoromethyl)-1H-pyrazol-4-yl)-1-(3-fluoro-2-methylphenyl)-N-hydroxy cyclopentane carboxamide;
(1S,3R*)-1-(3-fluoro-2-methylphenyl)-N-hydroxy-3-(1-(2-morpholinoethyl)-1H-pyrazol-4-yl)cyclopentanecarboxamide;
(1S,3R*)-1-(3-Fluoro-2-methylphenyl)-3-(5-fluoro-6-(2-(pyrrolidin-1-yl)ethoxy)pyridin-3-yl)-N-hydroxycyclopentanecarboxamide;

(1S,3R*)-1-(3-Fluoro-2-methylphenyl)-N-hydroxy-3-(1-methyl-1H-pyrazol-5-yl)cyclopentane carboxamide;
(1S,3S*)-1-(3-Fluoro-2-methylphenyl)-N-hydroxy-3-(1-methyl-1H-pyrazol-5-yl)cyclopentanecarboxamide;
(1S,3R*)-3-(1-(2-(diethylamino)ethyl)-1H-pyrazol-4-yl)-1-(3-fluoro-2-methylphenyl)-N-hydroxycyclopentanecarboxamide;
N-((R)-1-(dipropylamino)propan-2-yl)-4(1R*,3S)-3-(3-fluoro-2-methylphenyl)-3-(hydroxycarbamoyl)cyclopentyl)benzamide;
N-((R)-1-(dipropylamino)propan-2-yl)-4S*,3S)-3-(3-fluoro-2-methylphenyl)-3-(hydroxycarbamoyl)cyclopentyl)benzamide;
(1S,3R*)-3-(1-(difluoromethyl)-1H-indazol-6-yl)-1-(3-fluoro-2-methylphenyl)-N-hydroxycyclopentanecarboxamide;
(1S,3S*)-3-(1-(difluoromethyl)-1H-indazol-6-yl)-1-(3-fluoro-2-methylphenyl)-N-hydroxycyclopentanecarboxamide;
(1S,3R*)-1-(3-fluoro-2-methylphenyl)-N-hydroxy-3-(1-methyl-1H-indazol-6-yl)cyclopentanecarboxamide;
(1S,3R*)-1-(3-fluoro-2-methylphenyl)-N-hydroxy-3-(imidazo[1,2-a]pyridin-7-yl)cyclopentanecarboxamide;
(1S,3S*)-1-(3-fluoro-2-methylphenyl)-N-hydroxy-3-(imidazo[1,2-a]pyridin-7-yl)cyclopentanecarboxamide;
(1S,3R*)-3-(2-cyclopropyl-1-oxoisoindolin-5-yl)-1-(3-fluoro-2-methylphenyl)-N-hydroxycyclopentanecarboxamide;
(1S,3R*)-1-(3-fluoro-2-methylphenyl)-N-hydroxy-3-(1-methyl-1H-indazol-7-yl)cyclopentanecarboxamide;
(1S,3R*)-3-(7-fluoro-1H-indazol-6-yl)-1-(3-fluoro-2-methylphenyl)-N-hydroxycyclopentanecarboxamide;
(1S, 3R*)-3-(2-Cyclopropylbenzo[d]oxazol-5-yl)-1-(3-fluoro-2-methylphenyl)-N-hydroxycyclopentanecarboxamide;
(1S,3R*)-1-(3-fluoro-2-methylphenyl)-N-hydroxy-3-(1-methyl-1H-indazol-5-yl) cyclopentanecarboxamide;
(1S,3S*)-1-(3-fluoro-2-methylphenyl)-N-hydroxy-3-(1-methyl-1H-indazol-5-yl) cyclopentanecarboxamide;
(1S,3R*)-3-(2-(difluoromethyl)-2H-indazol-6-yl)-1-(3-fluoro-2-methylphenyl)-N-hydroxycyclopentanecarboxamide;
(1S,3S*)-3-(2-(difluoromethyl)-2H-indazol-6-yl)-1-(3-fluoro-2-methylphenyl)-N-hydroxycyclopentanecarboxamide;
(1S,3R*)-3-(3-fluoro-1-methyl-1H-indazol-6-yl)-1-(3-fluoro-2-methylphenyl)-N-hydroxycyclopentanecarboxamide;
(1S,3S*)-3-(3-fluoro-1-methyl-1H-indazol-6-yl)-1-(3-fluoro-2-methylphenyl)-N-hydroxycyclopentanecarboxamide;
(1S,3R*)-1-(3-fluoro-2-methylphenyl)-N-hydroxy-3-(1-methyl-1H-benzo[d]imidazol-5-yl )cyclopentanecarboxamide;
(1S,3R*)-1-(3-fluoro-2-methylphenyl)-N-hydroxy-3-(1-methyl-1H-benzo[d]imidazol-6-yl)cyclopentanecarboxamide;
(1S,3S*)-1-(3-fluoro-2-methylphenyl)-N-hydroxy-3-(1-methyl-1H-benzo[d]imidazol-6-yl)cyclopentanecarboxamide;
(1S,3R*)-1-(3-fluoro-2-methylphenyl)-N-hydroxy-3-(2-(trifluoromethyl)-1H-benzo[d]imidazol-6-yl)cyclopentanecarboxamide;
(1S,3S*)-3-(benzo[d]thiazol-2-yl)-1-(3-fluoro-2-methylphenyl)-N-hydroxycyclopentanecarboxamide;
(1S,3R*)-3-(benzo [d]thiazol -2 -yl)- 1-(3-fluoro-2-methylphenyl)-N-hydroxycyclopentanecarboxamide;
(1S,3S*)-3-(2-cyclopropylbenzo[d]thiazol-6-yl)-1-(3-fluoro-2-methylphenyl)-N-hydroxycyclopentanecarboxamide;
(1S,3R*)-3 - (2 -cyclopropylbenzo[d]thiazol -6 -yl)- 1 -(3-fluoro-2-methylphenyl)-N-hydroxycyclopentanecarboxamide;
(1S,3S*)-3-(2-cyclopropylbenzo[d]thiazol-5-yl)-1-(3-fluoro-2-methylphenyl)-N-hydroxycyclopentanecarboxamide;
(1S,3R*)-3 -(2-cyclopropylbenzo[d]thiazol-5-yl)- 1-(3-fluoro-2-methylphenyl)-N-hydroxycyclopentanecarboxamide;
(1S,3R)-3-(5-fluoro-1-methyl-1H-indazol-6-yl)-1-(3-fluoro-2-methylphenyl)-N-hydroxycyclopentanecarboxamide;
(1S,3S*)-3-(7-fluoro-1-methyl-1H-indazol-6-yl)-1-(3-fluoro-2-methylphenyl)-N-hydroxycyclopentanecarboxamide;
(1S,3R*)-3-(7-fluoro-1-methyl-1H-indazol-6-yl)-1-(3-fluoro-2-methylphenyl)-N-hydroxycyclopentanecarboxamide;
(1S,3S*)-1-(3-fluoro-2-methylphenyl)-N-hydroxy-3-(quinolin-6-yl)cyclopentanecarboxamide;
(1S,3R*)-1-(3-fluoro-2-methylphenyl)-N-hydroxy-3-(quinolin-6-yl)cyclopentanecarboxamide;
(1S,3R*)-1-(3,4-difluoro-2-methylphenyl)-N-hydroxy-3-(1-methyl-1H-indazol-6-yl)cyclopentanecarboxamide;
(1S,3R*)-1-(3-fluoro-2-methylphenyl)-N-hydroxy-3-(pyrrolidin-1-yl)cyclopentanecarboxamide;
(1S,3S*)-1-(3-fluoro-2-methylphenyl)-N-hydroxy-3-(pyrrolidin-1-yl)cyclopentanecarboxamide;
(1S,3R*)-1-(3-fluoro-2-methylphenyl)-N-hydroxy-3-morpholinocyclopentanecarboxamide;
(1S,3S*)-1-(3-fluoro-2-methylphenyl)-N-hydroxy-3-morpholinocyclopentanecarboxamide;
(1S,3R)-1-(3-fluoro-2-methylphenyl)-N-hydroxy-3-((1-methyl-1H-indazol-6-yl)oxy)cyclopentanecarboxamide;
(1S,3S)-1-(3-fluoro-2-methylphenyl)-N-hydroxy-3-((1-methyl-1H-indazol-6-yl)oxy)cyclopentanecarboxamide;
(1S,3R)-1-(3-fluoro-2-methylphenyl)-3-((5-fluoropyridin-3-yl)oxy)-N-hydroxycyclopentanecarboxamide;
(1S,3S)-1-(3-fluoro-2-methylphenyl)-3-((5-fluoropyridin-3-yl)oxy)-N-hydroxycyclopentanecarboxamide;
(1S,3R)-1-(3-fluoro-2-methylphenyl)-N-hydroxy-3-phenoxycyclopentanecarboxamide;
(1S,3S)-1-(3-fluoro-2-methylphenyl)-N-hydroxy-3-phenoxycyclopentanecarboxamide;
(1S,3S)-1-(3-fluoro-2-methylphenyl)-3((4-fluorobenzyl)oxy)-N-hydroxycyclopentanecarboxamide;
1-phenyl-N-hydroxycyclohexylcarboxamide;
(1r,4r)-1-(3-fluoro-2-methylphenyl)-4-(5-fluoropyridin-3-yl)-N-hydroxycyclohexanecarboxamide;
(1s,4s)-1-(3-fluoro-2-methylphenyl)-4-(5-fluoropyridin-3-yl)-N-hydroxycyclohexanecarboxamide;
(1r,4-1-(3-fluoro-2-methylphenyl)-N-hydroxy-4-phenoxycyclohexanecarboxamide;
(1s,4s)-1-(3-fluoro-2-methylphenyl)-4((4-fluorobenzyl)oxy)-N-hydroxycyclohexanecarboxamide;
(1s,4s)-1-(3-fluoro-2-methylphenyl)-N-hydroxy-4-(1-methyl-1H-indazol-6-yl)cyclohexanecarboxamide;
(1r,4r)-1-(3-fluoro-2-methylphenyl)-N-hydroxy-4-(1-methyl-1H-indazol-6-yl)cyclohexanecarboxamide;

(±)-2-(3-fluoro-2-methylphenyl)-N-hydroxy-8-oxaspiro[4.5]decane-2-carboxamide;
N-hydroxy-1-phenylcycloheptanecarboxamide; and
1-(3-fluoro-2-methylphenyl)-N-hydroxycycloheptanecarboxamide,
or a pharmaceutically acceptable salt thereof.

39. A pharmaceutically acceptable composition comprising a pharmaceutically acceptable carrier and at least one compound of claim 1, or a pharmaceutically acceptable salt thereof.

40. A pharmaceutical composition of claim 39, wherein the composition is formulated as a tablet, a capsule, a powder, a liquid, a suspension, a suppository, or an aerosol.

41. The compound of claim 1, or a pharmaceutically acceptable salt thereof, wherein the compound of Formula I is a compound of Formula III:

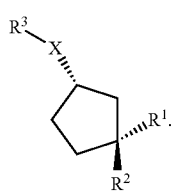

Formula III

42. The compound of claim 1, or a pharmaceutically acceptable salt thereof, wherein the compound of Formula I is a compound of Formula IV:

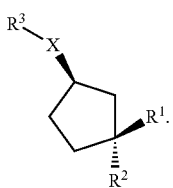

Formula IV

43. The compound of claim 1, or a pharmaceutically acceptable salt thereof, wherein the compound of Formula I is a compound of Formula V:

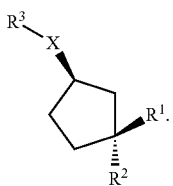

Formula V

* * * * *